US010123983B2

(12) United States Patent
O'Keefe et al.

(10) Patent No.: US 10,123,983 B2
(45) Date of Patent: Nov. 13, 2018

(54) DNA METHYLTRANSFERASES FOR THE TREATMENT AND PREVENTION OF ARTHRITIS

(71) Applicant: Washington University, St. Louis, MO (US)

(72) Inventors: Regis J. O'Keefe, St. Louis, MO (US); Jie Shen, St. Louis, MO (US); Audrey McAlinden, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/265,009

(22) Filed: Sep. 14, 2016

(65) Prior Publication Data
US 2017/0071889 A1 Mar. 16, 2017

Related U.S. Application Data

(60) Provisional application No. 62/218,186, filed on Sep. 14, 2015.

(51) Int. Cl.
*A61K 31/197* (2006.01)
*A61K 48/00* (2006.01)
*C12N 9/10* (2006.01)
*A61K 39/00* (2006.01)
*A01K 67/027* (2006.01)

(52) U.S. Cl.
CPC ........ *A61K 31/197* (2013.01); *A61K 39/0011* (2013.01); *A61K 48/005* (2013.01); *C12N 9/1007* (2013.01); *A01K 67/0276* (2013.01); *A01K 2217/075* (2013.01); *A01K 2227/105* (2013.01); *A01K 2267/0325* (2013.01); *A61K 2039/5158* (2013.01); *A61K 2039/55522* (2013.01)

(58) Field of Classification Search
None
See application file for complete search history.

(56) References Cited

U.S. PATENT DOCUMENTS 7,189,747 B2* 3/2007 Schrier .................. A61K 31/00
514/364
2013/0129668 A1 5/2013 Firestein et al.

OTHER PUBLICATIONS

CAPLUS:528030.*
Pearson, W. et al. chapter 32 in Bagchi, D et al., eds., Arthritis: Pathophysiology, Prevention, and Therapeutics. CRC Press-Taylor & Francis Group 2011.*
Connelly, A. Erin et al J. Medicinal Food 2014 vol. 17 pp. 1361-1367.*
Anderson, D. et al., "Post-Traumatic Osteoarthritis: Improved Understanding and Opportunities for Early Intervention," J. Orthop. Res., Jun. 2011, pp. 802-809, vol. 29, Wiley Online Library, with Author Manuscript, available in PMC Jun. 1. 2012, pp. 1-16.
ArcOGEN Consortium and arcOGEN Collaborators, "Identification of new susceptibility loci for osteoarthritis (arcOGEN): a genome-wide association study," Lancet, Sep. 1, 2012, pp. 815-823, vol. 380.
Baron, U. et al., "Co-regulation of two gene activities by tetracycline via a bidirectional promoter," Nucleic Acid Res., 1995, pp. 3605-3606, vol. 23, No. 17, Oxford University Press.
Barter, M. et al., "Epigenetic mechanisms in cartilage and osteoarthritis: DNA methylation, histone modifications and microRNAs," Osteoarthritis and Cartilage, 2012, pp. 339-349, vol. 20, Elsevier Ltd.
Barter, M. et al., "Epigenetic Mechanisms and Non-coding RNAs in Osteoarthritis," Curr. Rheumatol. Rep., 2013, pp. 1-9, vol. 15, No. 353, Springer Science+Business Media, New York, New York.
Baumann, K., "A metabolic switch," Mol. Cell Biol., Feb. 2013, 1 pg., vol. 14, Macmillan Publishers Limited.
Belteki, G. et al., "Conditional and inducible transgene expression in mice through the combinatorial use of Cre-mediated recombination and tetracycline induction," Nucleic Acid Res., 2005, pp. 1-10, vol. 33, No. 5, , e51, Oxford University Press.
Bijlsma, J. et al., "Osteoarthritis: an update with relevance for clinical practice," Lancet, Jun. 18, 2011, pp. 2115-2126, vol. 377.
Bijsterbosch, J. et al., "Association study of candidate genes for the progression of hand osteoarthritis," Osteoarthritis and Cartilage, 2013, pp. 565-569, vol. 21, Elsevier Ltd.
Blaney Davidson, E. et al., "Increase in ALK1/ALK5 Ratio as a Cause for Elevated MMP-13 Expression in Osteoarthritis in Humans and Mice," J. Immunol., 2009, pp. 7937-7945, vol. 182, with 2010, 1 pg., Corrections.
Challen, G. et al., "Dnmt3a is essential for hematopoietic stem cell differentiation," NIH Public Access, Author Manuscript, available in PMC Apr. 28, 2013, pp. 1-24, Published in final edited form as: Nat. Genet., 2012, pp. 23-31, vol. 44, No. 1, Nature America, Inc.
Chen, M. et al., "Promoter Hypermethylation Mediated Downregulation of FBP1 in Human Hepatocellular Carcinoma and Colon Cancer," PLoS ONE, Oct. 2011, pp. 1-8, vol. 6, No. 10, e25564.
Cutler, D. et al., "The Potential for Cost Savings through Bundled Episode Payments," NIH Public Access, Author Manuscript, available in PMC Apr. 12, 2012, pp. 1-4, Published in final edited form as: N. Engl. J. Med., Mar. 22, 2012, pp. 1075-1077, vol. 366, No. 12.
Delgado-Calle, J. et al., "Genome-Wide Profiling of Bone Reveals Differentially Methylated Regions in Osteoporosis and Osteoarthritis," Arthritis and Rheumatism, Jan. 2013, pp. 197-205, vol. 65, No. 1.
Den Hollander, W. et al., "Knee and hip articular cartilage have distinct epigenomic landscapes: implications for future cartilage regeneration approaches," Ann. Rheum. Dis., 2014, pp. 2208-2212, vol. 73.

(Continued)

*Primary Examiner* — Heidi Reese
(74) *Attorney, Agent, or Firm* — Polsinelli PC

(57) ABSTRACT

The present disclosure is directed to compositions and methods for treating osteoarthritis comprising increasing the expression of Dnmt3b and/or inhibiting aminobutyrate aminotransferase.

21 Claims, 85 Drawing Sheets
(60 of 85 Drawing Sheet(s) Filed in Color)
Specification includes a Sequence Listing.

(56) References Cited

OTHER PUBLICATIONS

Dodge, J. et al., "Inactivation of Dnmt3b in Mouse Embryonic Fibroblasts Results in DNA Hypomethylation, Chromosomal Instability, and Spontaneous Immortalization," J. Biol. Chem., May 6, 2005, pp. 17986-17991, vol. 280, No. 18.
Eijkelenboom, A. et al., "FOXOs: signalling integrators for homeostasis maintenance," Mol. Cell Biol., Feb. 2013, pp. 83-97, vol. 14, Macmillan Publishers Limited.
Evangelou, E. et al., "A meta-analysis of genome-wide association studies identifies novel variants associated with osteoarthritis of the hip," Ann. Rheum. Dis., 2014, pp. 2130-2136, vol. 73.
Felson, D., "Osteoarthritis of the Knee," N. Engl. J. Med., 2006, pp. 841-848, vol. 354, Massachusetts Medical Society.
Fernandez-Tajes, J. et al., "Genome-wide DNA methylation analysis of articular chondrocytes reveals a cluster of osteoarthritic patients," Ann. Rheum. Dis., 2014, pp. 668-677, vol. 73.
Glasson, S. et al., "Deletion of active ADAMTS5 prevents cartilage degradation in a murine model of osteoarthritis," Nature, Mar. 31, 2005, pp. 644-648, vol. 434, Nature Publishing Group, with Corrections & Amendments, Nature, Mar. 1, 2007, p. 102, vol. 446, Nature Publishing Group.
Glasson, S. et al., "The surgical destabilization of the medial meniscus (DMM) model of osteoarthritis in the 129/SvEv mouse," OsteoArthritis and Cartilage, 2007, pp. 1061-1069, vol. 15, Elsevier Ltd.
Glasson, S. et al., "The OARSI histopathology initiative— recommendations for histological assessments of osteoarthritis in the mouse," Osteoarthritis and Cartilage, 2010, pp. S17-S23, vol. 18, Elsevier Ltd.
Goldring, M. et al., "Epigenomic and microRNA-mediated regulation in cartilage development, homeostasis, and osteoarthritis," Trends Mol. Med., Feb. 2012, pp. 109-118, vol. 18, No. 2, Elsevier Ltd., with Author Manuscript, NIH Public Access, available in PMC Feb. 1, 2013, pp. 1-19, Elsevier Ltd.
Goldring, M. et al., "Emerging targets in osteoarthritis therapy," Curr. Opin. Pharmacol., 2015, pp. 51-63, vol. 22.
Gosset, M. et al., "Primary culture and phenotyping of murine chondrocytes," Nature Protocols, 2008, pp. 1253-1260, vol. 3, No. 8, Nature Publishing Group.
Grayson, D. et al., "The Dynamics of DNA Methylation in Schizophrenia and Related Psychiatric Disorders," Neuropsychopharmacology, 2013, pp. 138-166, vol. 38, Nature Publishing Group.
Greene, M. et al., "Aging-related inflammation in osteoarthritis," Osteoarthritis and Cartilage, 2015, pp. 1966-1971, vol. 23, Elsevier Ltd.
Gross, D. et al., "The role of FoxO in the regulation of metabolism," Oncogene, 2008, pp. 2320-2336, vol. 27, Nature Publishing Group.
Gu, J. et al., "Mapping of Variable DNA Methylation Across Multiple Cell Types Defines a Dynamic Regulatory Landscape of the Human Genome," G3 (Genes, Genomes, Genetics), Apr. 2016, pp. 973-986, vol. 6.
Haseeb, A. et al., "Modulation of Ten-Eleven Translocation 1 (TET1), Isocitrate Dehydrogenase (IDH) Expression, alpha-Ketoglutarate (alpha-KG), and DNA Hydroxymethylation Levels by Interleukin-1beta in Primary Human Chondrocytes," J. Biol. Chem., Mar. 7, 2014, pp. 6877-6885, vol. 289, No. 10, The American Society for Biochemistry and Molecular Biology, Inc., U.S.A.
Hata, K. et al., "Dnmt3L cooperates with the Dnmt3 family of de novo DNA methyltransferases to establish maternal imprints in mice," Development, 2002, pp. 1983-1993, vol. 129, The Company of Biologists Limited, Great Britain.
Heinz, S. et al., "Simple Combinations of Lineage-Determining Transcription Factors Prime cis-Regulatory Elements Required for Macrophage and B Cell Identities," Mol. Cell, May 28, 2010, pp. 576-589, vol. 38, Elsevier Inc.
Henry, S. et al., "Generation of Aggrecan-CreERT2 Knockin Mice for Inducible Cre Activity in Adult Cartilage," Genesis, Dec. 2009, pp. 805-814, vol. 47, No. 12, Wiley-Liss, Inc., with Author Manuscript, NIH Public Access, available in PMC Mar. 13, 2014, pp. 1-16.
Hirata, M. et al., "C/EBPbeta and RUNX2 cooperate to degrade cartilage with MMP-13 as the target and HIF-2alpha as the inducer in chondrocytes," Human Mol. Genet., 2012, pp. 1111-1123, vol. 21, No. 5, Oxford University Press.
Hitchler, M. et al., "Metabolic defects provide a spark for the epigenetic switch in cancer," NIH Public Access, Author Manuscript, available in PMC Jul. 15, 2010, pp. 1-30, Published in final edited form as: Free Radic. Biol. Med., Jul. 15, 2009, pp. 115-127, vol. 47, No. 2, Elsevier Inc.
Hootman, J. et al., "Projections of US Prevalence of Arthritis and Associated Activity Limitations," Arthritis and Rheumatism, Jan. 2006, pp. 226-229, vol. 54, No. 1.
Hunter, D. et al., "The individual and socioeconomic impact of osteoarthritis," J. Nat. Rev. Rheumatol., Jul. 2014, pp. 437-441, vol. 10, Macmillan Publishers Limited.
Imagawa, K. et al., "Association of Reduced Type IX Collagen Gene Expression in Human Osteoarthritic Chondrocytes With Epigenetic Silencing by DNA Hypermethylation," Arthritis & Rheumatology, Nov. 2014, pp. 3040-3051, vol. 66, No. 11, Wiley Periodicals, Inc.
Jeffries, M. et al., "Genome-Wide DNA Methylation Study Identifies Significant Epigenomic Changes in Osteoarthritic Cartilage," Arthritis & Rheumatology, Oct. 2014, pp. 2804-2815, vol. 66, No. 10.
Kaelin, W. et al., "Influence of Metabolism on Epigenetics and Disease," NIH Public Access, Author Manuscript, available in PMC Sep. 28, 2013, pp. 1-28, Published in final edited form as: Cell, Mar. 28, 2013, pp. 56-69, vol. 153, No. 1, Elsevier Inc.
Kamekura, S. et al., "Osteoarthritis development in novel experimental mouse models induced by knee joint instability," OsteoArthritis and Cartilage, 2005, pp. 632-641, vol. 13, Elsevier Ltd.
Kim, J. et al., "Epigenetic mechanisms in mammals," Cell. Mol. Life Sci., 2009, pp. 596-612, vol. 66, Birkhauser Verlag, Basel.
Kim, K. et al., "Changes in the Epigenetic Status of the SOX-9 Promoter in Human Osteoarthritic Cartilage," J. Bone Mineral Res., May 2013, pp. 1050-1060, vol. 28, No. 5.
Kim, J-H. et al., "Regulation of the Catabolic Cascade in Osteoarthritis by the Zinc-ZIP8-MTF1 Axis," Cell, Feb. 13, 2014, pp. 730-743, vol. 156, Elsevier Inc.
Klose, R. et al., "JmjC-domain-containing proteins and histone demethylation," Genetics, Sep. 2006, pp. 715-727, vol. 7, Nature Publishing Group.
Kousteni, S., "FoxO1, the transcriptional chief of staff of energy metabolism," Bone, 2012, pp. 437-443, vol. 50, Elsevier Inc.
Lei, H. et al., "De novo DNA cytosine methyltransferase activities in mouse embryonic stem cells," Development, 1996, pp. 3195-3205, vol. 122, The Company of Biologists Limited, Great Britain.
Li, E. et al., "Targeted Mutation of the DNA Methyltransferase Gene Results in Embryonic Lethality," Cell, Jun. 12, 1992, pp. 915-926, vol. 69, Cell Press.
Li, C. et al., "Identifying disease related sub-pathways for analysis of genome-wide association studies," Gene, 2012, pp. 101-109, vol. 503, Elsevier B.V.
Lin, A. et al., "Modulating hedgehog signaling can attenuate the severity of osteoarthritis," Nat. Med., Dec. 2009, pp. 1421-1425, vol. 15, No. 12, with 1 pg. continuation, and Errata & Corrigenda, Jan. 2010, p. 129, vol. 16, No. 1.
Little, C. et al., "Matrix Metalloproteinase-13 Deficient Mice Are Resistant to Osteoarthritic Cartilage Erosion but Not Chondrocyte Hypertrophy or Osteophyte Development," NIH Public Access Author Manuscript, available in PMC Dec. 1, 2010, pp. 1-18, Published in final edited form as: Arthritis Rheum., Dec. 2009, pp. 3723-3733, vol. 60, No. 12.
Liu, X. et al., "Warburg effect revisited: an epigenetic link between glycolysis and gastric carcinogenesis," Oncogene, 2010, pp. 442-450, vol. 29, Macmillan Publishers Limited.
Lorenzo, P. et al., "Altered patterns and synthesis of extracellular matrix macromolecules in early osteoarthritis," Matrix Biol., 2004, pp. 381-391, vol. 23, Elsevier.

(56) References Cited

OTHER PUBLICATIONS

Loughlin, J. et al., "Functional variants within the secreted frizzled-related protein 3 gene are associated with hip osteoarthritis in females," PNAS, Jun. 29, 2004, pp. 9757-9762, vol. 101, No. 26.
Loughlin, J. et al., "Epigenetics of articular cartilage in knee and hip OA," Rheumatology, Jan. 2015, pp. 1-2, vol. 11, Macmillan Publishers Limited.
Love, M. et al., "Moderated estimation of fold change and dispersion for RNA-seq data with DESeq2," Genome Biol., 2014, pp. 1-21, vol. 15, No. 550.
Lv, L. et al., "Acetylation Targets the M2 Isoform of Pyruvate Kinase for Degradation through Chaperone-Mediated Autophagy and Promotes Tumor Growth," HHS Public Access, Author Manuscript, available in PMC May 25, 2016, pp. 1-23, Published in final edited form as: Mol. Cell, Jun. 24, 2011, pp. 719-730, vol. 42, No. 6.
Maunakea, A. et al., "Conserved role of intragenic DNA methylation in regulating alternative promoters," Nature, Jul. 8, 2010, pp. 253-257, vol. 466, with 3 pgs. of Methods, Macmillan Publishers Limited.
Mclean, C. et al., "Great improves functional interpretation of cis-regulatory regions," Nat. Biotechnol., May 2010, pp. 495-501, vol. 28, No. 5, with 2 pgs. of Online Methods, Nature America, Inc.
Mirando, A. et al., "RBP-Jk-Dependent Notch Signaling Is Required for Murine Articular Cartilage and Joint Maintenance," Arthritis & Rhuematism, Oct. 2013, pp. 2623-2633, vol. 65, No. 10.
Mooney, R. et al., "High-fat diet accelerates progression of osteoarthritis after meniscal/ligamentous injury," Arthritis Research & Therapy, 2011, pp. 1-10, vol. 13, No. R198.
Munger, J. et al., "Systems-level metabolic flux profiling identifies fatty acid synthesis as a target for antiviral therapy," Nat. Biotechnol., Oct. 2008, pp. 1179-1186, vol. 26, No. 10, with Author Manuscript, NIH Public Access, available in PMC Feb. 22, 2010, pp. 1-21.
Neves-Costa, A. et al., "TET1 is a negative transcriptional regulator of IL-1beta in the THP-1 cell line," Mol. Immunol., 2013, pp. 264-270, vol. 54, Elsevier Ltd.
Okano, M et al., "DNA Methyltransferases Dnmt3a and Dnmt3b Are Essential for De Novo Methylation and Mammalian Development," Cell, Oct. 29, 1999, pp. 247-257, vol. 99, Cell Press.
Osei, Y. et al., "Screening and sequence determination of a cDNA encoding the human brain 4-aminobutyrate aminotransferase," Gene, 1995, pp. 185-187, vol. 155, Elsevier Science B.V.
Ovchinnikov, D. et al., "Col2a1-Directed Expression of Cre Recombinase in Differentiating Chondrocytes in Transgenic Mice," Genesis, 2000, pp. 145-146, vol. 26, Wiley-Liss, Inc.
Panoutsopoulou, K. et al., "Advances in osteoarthritis genetics," J. Med. Genet., 2013, pp. 715-724, vol. 50.
Park, Y. et al., "Differential methylation analysis for BS-seq data under general experimental design," Bioinformatics, 2016, pp. 1446-1453, vol. 32, No. 10, Oxford University Press.
Pellock, J., "Balancing clinical benefits of vigabatrin with its associated risk of vision loss," Acta Neurol. Scand., 2011, pp. 83-91, vol. 124, Suppl. 192, John Wiley & Sons A/S.
Pollesello, P. et al., "Energy State of Chondrocytes Assessed by 31P-NMR Studies of Preosseous Cartilage," Biochem. Biophys. Res. Comm., Oct. 15, 1991, pp. 216-222, vol. 180, No. 1, Academic Press, Inc.
Reynard, L. et al., "Insights from human genetic studies into the pathways involved in osteoarthritis," J. Nat. Rev. Rheumatol., Oct. 2013, pp. 573-583, vol. 9, Macmillan Publishers Limited.
Reynard, L. et al., "CpG methylation regulates allelic expression of GDF5 by modulating binding of SP1 and SP3 repressor proteins to the osteoarthritis susceptibility SNP rs143383," Hum. Genet., 2014, pp. 1059-1073, vol. 133, Springer.
Rodriguez-Fontenla, C. et al., "Assessment of Osteoarthritis Candidate Genes in a Meta-Analysis of Nine Genome-Wide Association Studies," Arthritis & Rheumatology, Apr. 2014, pp. 940-949, vol. 66, No. 4, Wiley Periodicals, Inc.
Rushton, M. et al., "Characterization of the Cartilage DNA Methylome in Knee and Hip Osteoarthritis," Arthritis & Rheumatology, Sep. 2014, pp. 2450-2460, vol. 66, No. 9, Wiley Periodicals, Inc.
Rushton, M. et al., "Methylation quantitative trait locus analysis of osteoarthritis links epigenetics with genetic risk," Hum. Mol. Genet., 2015, pp. 7432-7444, vol. 24, No. 25, Oxford University Press.
Rushton, M. et al., "Differential DNA methylation and expression of inflammatory and zinc transporter genes defines subgroups of osteoarthritis hip patients," Ann. Rheum. Dis., 2015, pp. 1778-1782, vol. 74.
Sampson, E. et al., "Establishment of an Index with Increased Sensitivity for Assessing Murine Arthritis," NIH Public Access Author Manuscript, available in PMC Aug. 1, 2012, pp. 1-16, Published in final edited form as: J. Orthop. Res., Aug. 2011, pp. 1145-1151, vol. 29, No. 8.
Serra, R. et al., "Expression of a Truncated, Kinase-Defective TGF-beta Type II Receptor in Mouse Skeletal Tissue Promotes Terminal Chondrocyte Differentiation and Osteoarthritis," J. Cell Biol., Oct. 20, 1997, pp. 541-552, vol. 139, No. 2, The Rockefeller University Press.
Shen, J. et al., "Deletion of the Transforming Growth Factor beta Receptor Type II Gene in Articular Chondrocytes Leads to a Progressive Osteoarthritis-like Phenotype in Mice," NIH Public Access Author Manuscript, available in PMC Feb. 19, 2014, pp. 1-18, Published in final edited form as: Arthritis Rheum., Dec. 2013, pp. 3107-3119, vol. 65, No. 12.
Smith, Z. et al., "DNA methylation: roles in mammalian development," J. Nat. Rev. Genetics, Mar. 2013, pp. 205-220, vol. 14, Macmillan Publishers Limited.
Stanton, H. et al., "ADAMTS5 is the major aggrecanase in mouse cartilage in vivo and in vitro," Nature, Mar. 31, 2005, pp. 648-652, vol. 434, Nature Publishing Group.
Subramaniam, D. et al., "DNA methyltransferases: a novel target for prevention and therapy," Frontiers in Oncology, Cancer Molecular Targets and Therapeutics, May 2014, pp. 1-13, vol. 4, Article 80.
Takubo, K. et al., "Regulation of Glycolysis by Pdk Functions as a Metabolic Checkpoint for Cell Cycle Quiescence in Hematopoietic Stem Cells," Cell Stem Cell, Jan. 3, 2013, pp. 49-61, vol. 12, Elsevier Inc.
Tannahill, G. et al., "Succinate is an inflammatory signal that induces IL-1beta through HIF-1alpha," Nature, Apr. 11, 2013, pp. 238-242, vol. 496, with 1 pg. of Methods, Macmillan Publishers Limited.
Taylor, S. et al., "A Global Increase in 5-Hydroxymethylcytosine Levels Marks Osteoarthritic Chondrocytes," Arthritis & Rheumatology, Jan. 2014, pp. 90-100, vol. 66, No. 1.
Thijssen, E. et al., "Obesity and osteoarthritis, more than just wear and tear: pivotal roles for inflamed adipose tissue and dyslipidaemia in obesity-induced osteoarthritis," Rheumatology, 2015, pp. 588-600, vol. 54.
Tolman, J. et al., "Vigabatrin: a comprehensive review of drug properties including clinical updates following recent FDA approval," Expert Opin. Pharmacother., 2009, pp. 3077-3089, vol. 10, No. 18, Informa UK Ltd.
Tsolis, K. et al., "Comparative proteomic analysis of hypertrophic chondrocytes in osteoarthritis," Clinical Proteomics, 2015, pp. 1-16, vol. 12, No. 12.
Valdes, A. et al., "Genetic Variation in the SMAD3 Gene Is Associated With Hip and Knee Osteoarthritis," Arthritis & Rheumatism, Aug. 2010, pp. 2347-2352, vol. 62, No. 8.
Valdes, A. et al., "The GDF5 rs143383 polymorphism is associated with osteoarthritis of the knee with genome-wide statistical significance," Ann. Rheum. Dis., May 2011, pp. 873-875, vol. 70, No. 5.
Van Den Berg, W., "Osteoarthritis year 2010 in review: pathomechanisms," Osteoarthritis and Cartilage, 2011, pp. 338-341, vol. 19, Elsevier Ltd.
Villalvilla, A. et al., "Lipid Transport and Metabolism in Healthy and Osteoarthritic Cartilage," Int. J. Mol. Sci., 2013, pp. 20793-20808, vol. 14.
Wang, M. et al., "Recent progress in understanding molecular mechanisms of cartilage degeneration during Osteoarthritis," Ann. N.Y. Acad. Sci., 2011, pp. 61-69, vol. 1240, with NIH Public Access Author Manuscript, available in PMC Jun. 4, 2013, pp. 1-11.

(56) References Cited

OTHER PUBLICATIONS

Wang, M. et al., "Conditional Activation of beta-Catenin Signaling Leads to Severe Defects in Intervertebral Disc Tissue," NIH Public Access Author Manuscript, available in PMC Aug. 1, 2013, pp. 1-17, Published in final edited form as: Arthritis Rheum., Aug. 2012, pp. 2611-2623, vol. 64, No. 8.

Wang, X. et al., "Metabolic triggered inflammation in osteoarthritis," Osteoarthritis and Cartilage, 2015, pp. 22-30, vol. 23, Elsevier Ltd.

Wolf, A. et al., "Developmental profile and regulation of the glycolytic enzyme hexokinase 2 in normal brain and glioblastoma multiforme," Neurobiology of Disease, 2011, pp. 84-91, vol. 44, Elsevier Inc.

Wu, H. et al., "Dual functions of Tet1 in transcriptional regulation in mouse embryonic stem cells," NIH Public Access Author Manuscript, available in PMC Jan. 8, 2013, pp. 1-13, Published in final edited form as: Nature, May 19, 2011, pp. 389-393, vol. 473, No. 7347.

Xu, W. et al., "Oncometabolite 2-Hydroxyglutarate Is a Competitive Inhibitor of alpha-Ketoglutarate-Dependent Dioxygenases," NIH Public Access Author Manuscript, available in PMC Dec. 2, 2011, pp. 1-25, Published in final edited form as: Cancer Cell., Jan. 18, 2011, pp. 17-30, vol. 19, No. 1.

Yang, X. et al., "TGF-beta/Smad3 Signals Repress Chondrocyte Hypertrophic Differentiation and Are Required for Maintaining Articular Cartilage," J. Cell Biol., Apr. 2, 2001, pp. 35-46, vol. 153, No. 1.

Yu, W-M. et al., "Metabolic Regulation by the Mitochondrial Phosphatase PTPMT1 Is Required for Hematopoietic Stem Cell Differentiation," NIH Public Access Author Manuscript, available in PMC Jan. 3, 2014, pp. 1-23, Published in final edited form as: Cell Stem Cell., Jan. 3, 2013, pp. 62-74, vol. 12, No. 1.

Zhang, Q. et al., "Tet2 is required to resolve inflammation by recruiting Hdac2 to specifically repress IL-6," Nature, Sep. 17, 2015, pp. 389-393, vol. 525, with 9 pgs. of Methods, Macmillan Publishers Limited.

\* cited by examiner 3-month-old 27-month-old

Sham

MLI

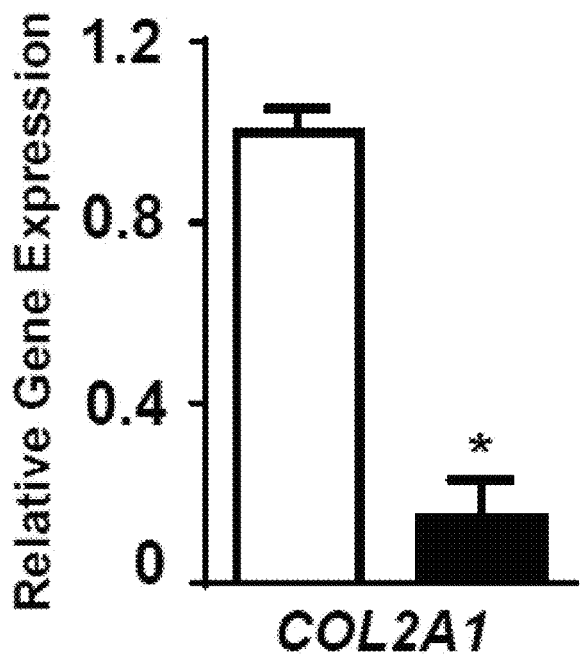
FIG. 3A
FIG. 3B
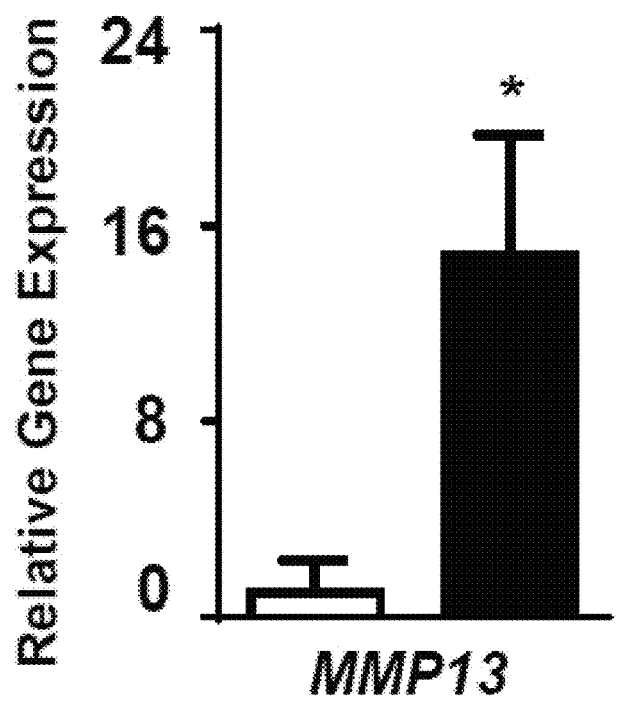

```
Mouse: -182  GGGGGCCCAGGGGAGGCTCCGAGGAGGCA  -153
Human: -169  AGGGGCGGAGGGGAGGCTCCGAGCGATTTC -140
Dog:   -386  CAAGGCTGTCGGGAGGCAGGCAGGGGCAGG -357
Horse: -90   AGGCATTGGCGGGAGGTTTGGGGATGTGCT -61
```

| Associated Network Functions | Score |
|---|---|
| Cell Death and Survival, Cellular Assembly and Organization, Cellular Compromise | 38 |
| Lipid Metabolism, Molecular Transport, Small Molecule Biochemistry | 36 |
| Cell Cycle, Cellular Assembly and Organization, DNA Replication, Recombination, and Repair | 32 |

FIG. 11D

| Enriched pathway | P-value |
|---|---|
| Hepatic Fibrosis/Hepatic Stellate Cell Activation | 1.88E-09 |
| Role of Osteoblasts, Osteoclasts and Chondrocytes in Rheumatoid Arthritis | 2.87E-07 |
| Adipogenesis pathway | 3.73E-05 |

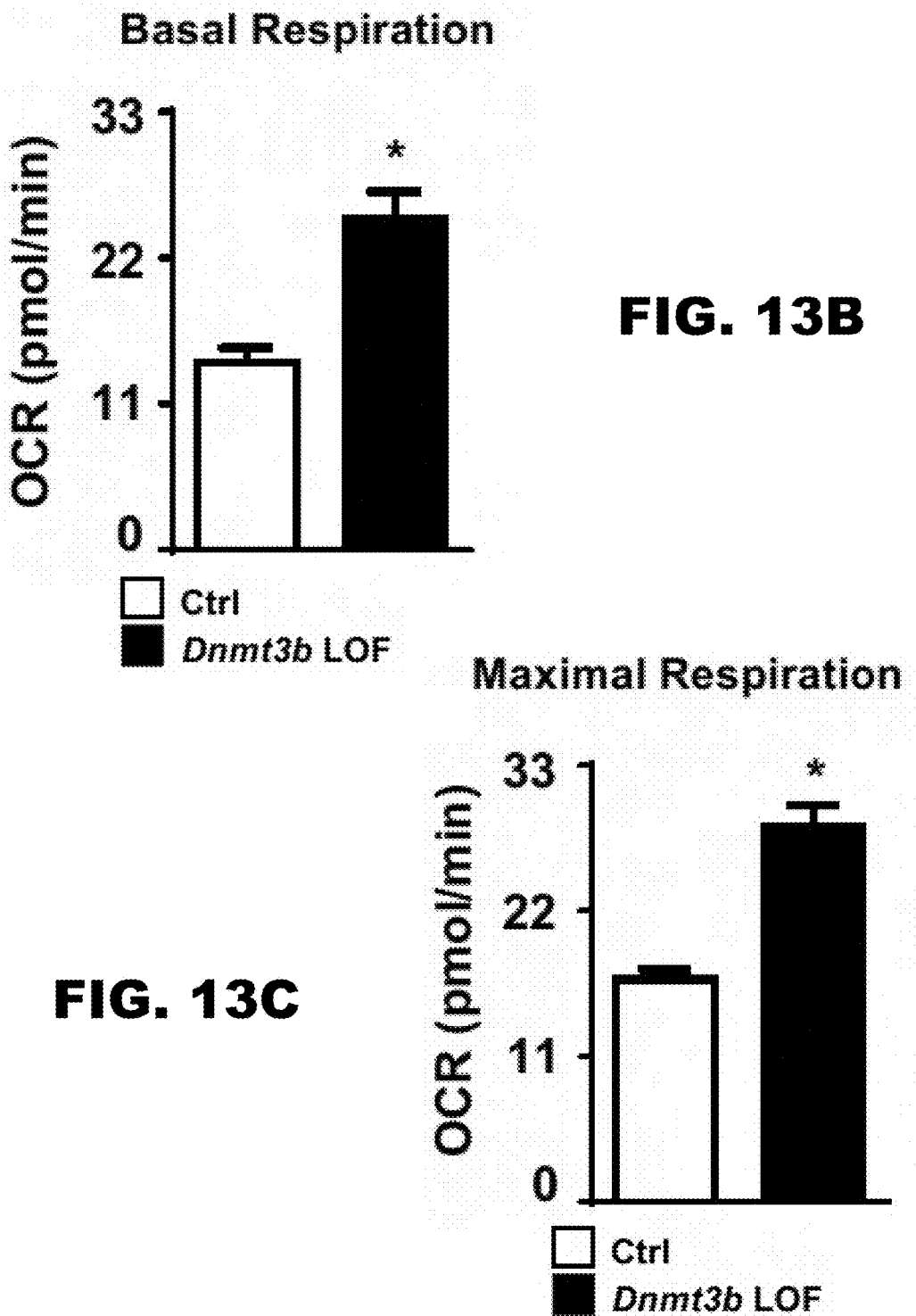

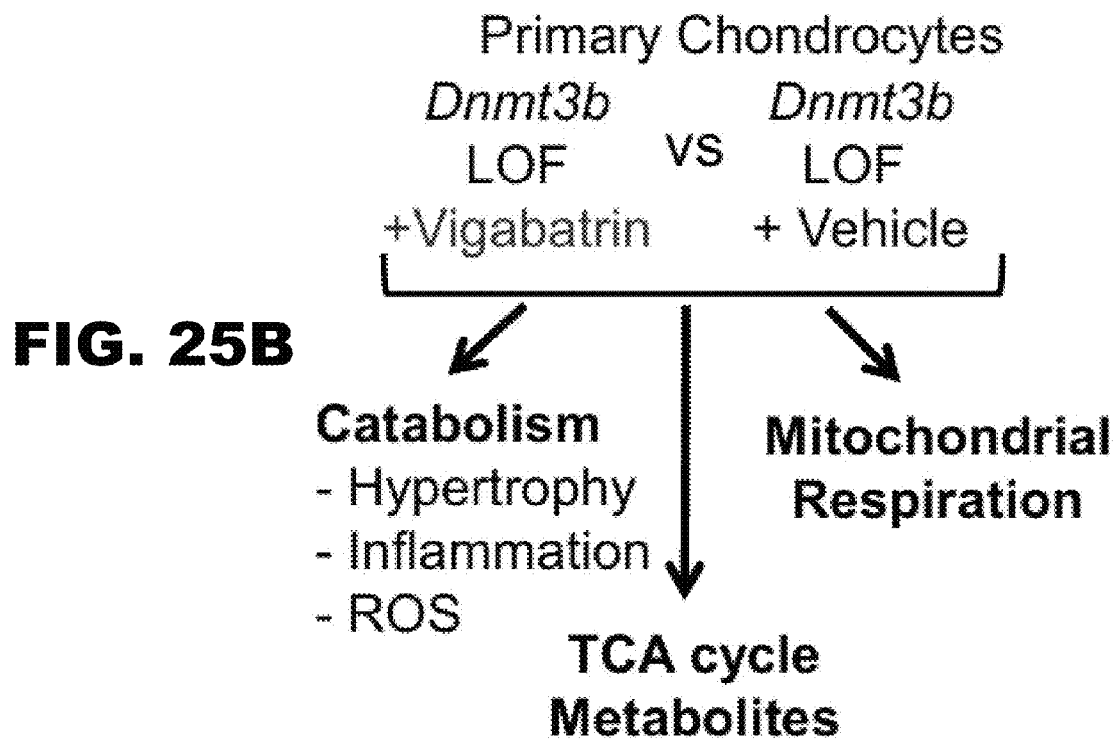

SEQUENCE LISTING

```
<160> NUMBER OF SEQ ID NOS: 37

<210> SEQ ID NO 1
<211> LENGTH: 30
<212> TYPE: DNA
<213> ORGANISM: Mus musculus

<400> SEQUENCE: 1
gggggcccag gggaggctcc cgaggaggca                                      30

<210> SEQ ID NO 2
<211> LENGTH: 30
<212> TYPE: DNA
<213> ORGANISM: Homo sapiens

<400> SEQUENCE: 2
aggggcggag gggaggctcc gagcgatttc                                      30

<210> SEQ ID NO 3
<211> LENGTH: 30
<212> TYPE: DNA
<213> ORGANISM: Canis lupus

<400> SEQUENCE: 3
caaggctgtc gggaggcagg caggggcagg                                      30

<210> SEQ ID NO 4
<211> LENGTH: 30
<212> TYPE: DNA
<213> ORGANISM: Equus caballus

<400> SEQUENCE: 4
aggcattggc gggaggtttg gggatgtgct                                      30

<210> SEQ ID NO 5
<211> LENGTH: 10
<212> TYPE: DNA
<213> ORGANISM: Artificial Sequence
<220> FEATURE:
<223> OTHER INFORMATION: SYNTHESIZED

<400> SEQUENCE: 5
atctggctcc                                                            10

<210> SEQ ID NO 6
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 6
ctggtcatct aggagggtga                                                 20

<210> SEQ ID NO 7
<211> LENGTH: 17
```

```
<212> TYPE: DNA
<213> ORGANISM: Artificial Sequence
<220> FEATURE:
<223> OTHER INFORMATION: SYNTHESIZED

<400> SEQUENCE: 7
cgggcgaggg agatttg                                                  17

<210> SEQ ID NO 8
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 8
gcagagatgg agaacctggt a                                             21

<210> SEQ ID NO 9
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 9
agccttctcg tcatoccct                                                19

<210> SEQ ID NO 10
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 10
atgccttgtt ctcctcttac tg                                            22

<210> SEQ ID NO 11
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 11
tgctgaacgg taccaaacg                                                19

<210> SEQ ID NO 12
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 12
cgtccactgt cactttaata gctc                                          24

<210> SEQ ID NO 13
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 13
```

```
gtagccaggt tcaacgatct g                                              21

<210> SEQ ID NO 14
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 14
agactggtaa tggcatcaag g                                              21

<210> SEQ ID NO 15
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 15
gccatttcat gcttcctgat g                                              21

<210> SEQ ID NO 16
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 16
cctgccaggg cttcagtggc                                                20

<210> SEQ ID NO 17
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 17
caggcagcgc agtgtgagct                                                20

<210> SEQ ID NO 18
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 18
gccgaattgt gtcttggtgg atgaca                                         26

<210> SEQ ID NO 19
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 19
cctggtggaa tgcactgcag aagga                                          25

<210> SEQ ID NO 20
<211> LENGTH: 21
<212> TYPE: DNA
<213> ORGANISM: Artificial Sequence
```

```
<220> FEATURE:
<223> OTHER INFORMATION: SYNTHESIZED

<400> SEQUENCE: 20
aatacccaac tccttgagca c                                              21

<210> SEQ ID NO 21
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 21
tcttcactac tgatcctgac ct                                             22

<210> SEQ ID NO 22
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 22
gagcctgttc ctcgatgtgg                                                20

<210> SEQ ID NO 23
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 23
caaacccacc tgaggctgtt                                                20

<210> SEQ ID NO 24
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 24
tgttgttgtc agggtgagaa tc                                             22

<210> SEQ ID NO 25
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 25
tcttgcttct ggcaaactta ca                                             22

<210> SEQ ID NO 26
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 26
ccggattgag aaggtcatct ac                                             22
```

<210> SEQ ID NO 27
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 27
aagataacaa tcacggcgtt ct                                      22

<210> SEQ ID NO 28
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 28
agatgtggat cagcaagcag                                         20

<210> SEQ ID NO 29
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 29
gcgcaagtta ggttttgtca                                         20

<210> SEQ ID NO 30
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 30
ttgatattcc cctcgtgctt c                                       21

<210> SEQ ID NO 31
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 31
cgagtcctgt cattgtttga tg                                      22

<210> SEQ ID NO 32
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 32
ggcaatagca ggttcacgta ca                                      22

<210> SEQ ID NO 33
<211> LENGTH: 22
<212> TYPE: DNA
<213> ORGANISM: Artificial Sequence
<220> FEATURE:
<223> OTHER INFORMATION: SYNTHESIZED

```
<400> SEQUENCE: 33
cgataacagt cttgccccac tt                                              22

<210> SEQ ID NO 34
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 34
cttgaccact ccaaggaccc                                                 20

<210> SEQ ID NO 35
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 35
cctggaccat agagagactg ga                                              22

<210> SEQ ID NO 36
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 36
tgtagttgag gtcaatgaag gg                                              22

<210> SEQ ID NO 37
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 37
acatcgctca gacaccatg                                                  19
```

US 10,123,983 B2

DNA METHYLTRANSFERASES FOR THE TREATMENT AND PREVENTION OF ARTHRITIS

CROSS REFERENCE TO RELATED APPLICATIONS

This application claims the benefit of U.S. Provisional Application No. 62/218,186, filed Sep. 14, 2015, the disclosure of which is hereby incorporated by reference in its entirety.

GOVERNMENTAL RIGHTS

This invention was made with government support under R01 AR069605-01 awarded by the NIH. The government has certain rights in the invention.

FIELD OF THE INVENTION

The present disclosure is directed to compositions and methods for treating osteoarthritis comprising increasing the expression of Dnmt3b and/or inhibiting aminobutyrate aminotransferase.

BACKGROUND OF THE INVENTION

Osteoarthritis (OA) is the most common form of arthritis and the leading cause for disability in the United States, resulting in an extremely high socioeconomic burden. OA is clinically characterized by articular cartilage degeneration, subchondral bone sclerosis, and osteophyte formation. A variety of risk factors have been identified in the initiation and progression of OA including aging, obesity, traumatic injury, environmental factors and inherent genetic alterations. Despite extensive research to delineate the pathogenic mechanisms of OA, a complete understanding of the factors that initiate OA or accelerate its progression has yet to be achieved. Subsequently, there is no effective disease-modifying treatment for OA except pain relieving medication and surgical replacement of damaged joints.

SUMMARY OF THE INVENTION

In an aspect, the disclosure provides a method to reduce cartilage degradation. The method comprises administering a composition comprising a compound that increases the expression of Dmnt3b and/or a compound that inhibits aminobutyrate aminotransferase.

In another aspect, the disclosure provides a method to increase cartilage area. The method comprises administering a composition comprising a compound that increases the expression of Dmnt3b and/or a compound that inhibits aminobutyrate aminotransferase.

In still another aspect, the disclosure provides a method of treating osteoarthritis (OA) in a subject. The method comprises administering to the subject a composition comprising a compound that increases the expression of Dmnt3b and/or a compound that inhibits aminobutyrate aminotransferase.

In certain embodiments, the compound that increases the expression of Dmnt3b is a vector comprising the Dnmtb3 nucleotide sequence. In other embodiments, the compound that inhibits aminobutyrate aminotransferase is selected from the group consisting of vigabatrin, L-2,4-diaminobutyric acid dihydrochloride, gamma-acetylenic GABA, S(+)-gamma-vinyl-GABA, gabaculine, aminooxyacetic acid, phenelzine, phenylethylidenehydrazine (PEH), rosmarinic acid and valproic acid. In an embodiment, the compounds that inhibits aminobutyrate aminotransferase is vigabatrin. In another embodiment, the subject is at risk of developing osteoarthritis (OA). Specifically, the subject is obese or has had joint surgery. In different embodiments, the composition is administered orally or via intra-articular injection. In certain embodiments, the method further comprises administering standard treatments for OA.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A, FIG. 1B) Dnmt3a is not expressed in chondrocytes from 3 mo WT articular cartilage [(FIG. 1B) represents a magnified image of the boxed region in (FIG. 1A)]. (FIG. 1C) Dnmt3a expression in pancreas tissue (positive control). (FIG. 1D, FIG. 1E, FIG. 1F) Robust expression of Dnmt3b in chondrocytes of 3 mo WT articular cartilage and lower expression in underlying growth plate cartilage; [(FIG. 1E) represents a magnified image of the dashed boxed area of articular cartilage in (FIG. 1D); (FIG. 1F) represents a magnified image of the solid boxed area of growth plate cartilage in (FIG. 1D)]. Dnmt3b expression is also shown in: (FIG. 1G) 3 mo versus 27 mo WT murine knee articular cartilage; (FIG. 1H) 14 wk old murine articular cartilage following MLI surgery compared to cartilage from sham control knees; (FIG. 1I) 14 wk murine articular cartilage in mice fed a high fat diet (HFD) compared to controls (Ctrl) fed a normal diet. (FIG. 1J) Two representative images showing DNMT3B expression in human healthy articular cartilage or osteoarthritic cartilage tissue sections. (FIG. 1K) Reduced DNMT3B expression in human primary OA chondrocytes compared to healthy chondrocytes). (FIG. 1L, FIG. 1M) Induction of human primary chondrocytes (n=3) with IL-1β results in decreased expression of DNMT3B mRNA and protein levels. All scale bars, 100 μm.

FIG. 3A and FIG. 3B depict graphs showing altered anabolic and catabolic gene expression in IL-1β-treated human primary chondrocytes. Reduced COL2A1 (FIG. 3A) and increased MMP13 (FIG. 3B) expression following IL-1β treatment (48 h) of human primary articular chondrocytes isolated from total knee replacement surgeries.

(FIG. 4A) Sequence alignment and conservation of an NF-κB binding site (red) in the promoter region of the Dnmt3b gene of different species. Mouse—SEQ ID NO:1; Human—SEQ ID NO:2; Dog; SEQ ID NO:3; Horse—SEQ ID NO:4. (FIG. 4B) Reduced luciferase expression in IL-1β stimulated (24 h) chondrogenic murine ATDC-5 cells transfected with a luciferase reporter plasmid containing the Dnmt3b promoter sequence when compared to control (Ctrl) untreated cells. Reduced luciferase activity is attenuated when ATDC-5 cells were transfected with a reporter plasmid containing a mutated NF-κB binding site (ATCTGGCTCC; SEQ ID NO:5). (FIG. 4C, FIG. 4D) Pull-down of genomic DNA with an NF-κB antibody (ChIP assay) shows interaction of NF-κB with its binding site in the Dnmt3b promoter region by qPCR (FIG. 4C) and semi-quantitative gel electrophoresis (FIG. 4D) utilizing specific primers to amplify the Dnmt3b promoter region containing the NF-κB binding site. (FIG. 4E, FIG. 4F) Dnmt3b mRNA and protein levels were reduced in murine WT primary articular chondrocytes (extracted from 3 mo murine knee joints) following IL-1β induction (48 h).

(FIG. 5C) Dnmt3b si RNA treatment resulted in increased expression of the catabolic/hypertrophic chondrocyte markers Col10a1, Runx2, and Mmp13, and decreased expression of the anabolic marker, Col2a1 in murine primary chondrocytes. (FIG. 5D) Reduced Dnmt3b expression resulted in increased alkaline phosphatase (ALP) activity in murine primary chondrocytes, but not to the extent resulting from BMP-2 treatment (positive control). (FIG. 5E, FIG. 5F) Dnmt3b siRNA treatment affected the balance of TGF-β and BMP signaling as shown by decreased phospho(p)-Smad2/3 expression and increased p-Smad1/5/8 expression in murine primary chondrocytes, respectively.

(FIG. 6G) OARSI scoring system was used to quantify the ABH/OG stained tissue sections. (FIG. 6H) Articular cartilage area was quantified by histomorphometry. (FIG. 6I) Knee joints from 8 mo Dnmt3b LOF and Ctrl mice were analyzed by microCT. (FIG. 6J) Subchondral bone volume and (FIG. 6K) subchondral bone trabecular connective density were calculated from the microCT images. Arrows in (FIG. 6B) and (FIG. 6C) show areas of proteoglycan loss and cartilage fibrillation, respectively. Arrows in (FIG. 6E) and (FIG. 6F) show osteophyte formation and an area of proteoglycan loss in articular cartilage, respectively. Yellow arrows in (FIG. 6I) denote osteophyte formation. Scale bars, 100 μm.

(FIG. 7A) Fluorescence microscopy shows recombination efficiency in 2 mo Agc1Cre$^{ERT2}$; mT/mG mice followed by tamoxifen injection for 5 days. (FIG. 7B) Dnmt3b protein knock-down in 3 mo articular chondrocytes of Dnmt3b LOF mice compared to Cre+ control (Ctrl) littermates. Scale bars, 100 μm.

(FIG. 8A) qPCR analysis of Dnmts and Tets in 3 mo articular cartilage isolated from Dnmt3b LOF and Cre+ control (Ctrl) mice. (FIG. 8B) Tet activity analysis in chondrocytes from 3 mo Dnmt3b LOF or Ctrl mice.

(FIG. 10A) TUNEL staining and analysis of knee joint articular cartilage tissue sections from 5 mo Dnmt3b LOF and Cre+ control (Ctrl) mice by fluorescence microscopy; (FIG. 10B) Quantification of apoptotic cell numbers from the TUNEL-stained fluorescent images. (FIG. 10C) Reactive oxygen species (ROS) analysis of 2 mo Dnmt3b LOF articular chondrocytes (i.e. chondrocytes from Dnmt3b$^{f/f}$ mice treated with Ad5-Cre for 48 h) compared to control (Ctrl) chondrocytes (Dnmt3b LOF chondrocytes treated with Ad5-GFP for 48 h).

FIG. 11A, FIG. 11B, FIG. 11C, FIG. 11D, FIG. 11E, FIG. 11F, FIG. 11G and FIG. 11H depict graphs and images showing altered epigenomic and transcriptomic signatures in Dnmt3b LOF chondrocytes. (FIG. 11A) PCA plot of samples based on RNA-seq data; (FIG. 11B) Heatmap display of top 25 significantly differentially expressed genes between Dnmt3b LOF and control; (FIG. 11C) Word cloud representing gene frequency of enriched function categories from all differentially expressed genes; (FIG. 11D) Associated network function of all differentially expressed genes by IPA analysis; (FIG. 11E) Global methylation distribution of Dnmt3b LOF and control samples showing there is no global difference; (FIG. 11F) Methylation difference of DMR versus genome as background; (FIG. 11G) Significant overlap of genes nearby DMRs and differentially expressed genes, p-values calculated by hypergeometric test; (FIG. 11H) Enriched pathway of genes nearby DMRs and differentially expressed genes.

(FIG. 12A) Heatmap of sample-to-sample distances using the rlog-transformed values showing more similarity of RNA-seq signal observed in each group; (FIG. 12B) An MA-plot of gene expression changes. The log 2 fold change for a particular comparison is plotted on the y-axis and the average of the counts normalized by size factor is shown on the x-axis. Each gene is represented with a dot. Genes with an adjusted p value below a threshold (here 0.1, the default) are shown in red; (FIG. 12C) Enrichment of differentially expressed genes show enriched function related to cell cycle process, bone development etc; (FIG. 12D) Genes from differentially expressed list are related with TGF/BMP pathway network, green indicates down-regulation and red indicates up-regulation; (FIG. 12E) Genomic feature distributions of DMRs; (FIG. 12F) Enriched transcription factor binding sites found in DMRs using Homer software.

FIG. 13A, FIG. 13B, FIG. 13C, FIG. 13D, FIG. 13E, FIG. 13F, FIG. 13G, FIG. 13H, FIG. 13I, FIG. 13J, FIG. 13K, FIG. 13L, FIG. 13M and FIG. 13N depict graphs showing mitochondria function and cellular homeostasis in Dnmt3b LOF chondrocytes. Primary articular chondrocytes were isolated from 2 mo Dnmt3b$^{f/f}$ mice and infected with Ad5-Cre (Dnmt3b LOF) or Ad5-GFP (Ctrl) for 48 h. (FIG. 13A, FIG. 13B, FIG. 13C) Mitochondrial respiration was measured by the Seahorse XF Extracellular Flux Analyzer. Basal respiration and maximal respiration, as measured by the oxygen consumption rate (OCR) are shown. (FIG. 13D, FIG. 13E, FIG. 13F) TCA metabolite (succinate, fumarate) and NADH analysis by HPLC-MS. (FIG. 13G, FIG. 13H, FIG. 13I) Mitochondrial metabolism analysis was measured in 2 mo WT cells treated with either 1 mM diethyl succinate or vehicle for 48 h by the Seahorse XF Extracellular Flux Analyzer. (FIG. 13J) Chondrocyte gene expression in response to succinate treatment was analyzed by qPCR. (FIG. 13K, FIG. 13L, FIG. 13M) Mitochondrial respiration analysis in BMP-2-treated 2 mo WT chondrocytes in the presence or absence antimycin A+rotenone for 48 h. (FIG. 13N) Analysis of chondrocyte gene expression in response to BMP-2 treatment+/−antimycin A+rotentone (0.1 µM).

(FIG. 17A, FIG. 17B) Alcian blue/hematoxylin/orange G stained sections of Ctrl or Dnmt3b GOF knee joints 12 weeks following sham surgery. Representative images of histological sections from Ctrl or Dnmt3b GOF mice at 8 wk (FIG. 17C, FIG. 17D, FIG. 17E, FIG. 17F) or 12 wk (FIG. 17G, FIG. 17H, FIG. 17I, FIG. 17J) following MLI surgery. (FIG. 17E) and (FIG. 17F) are magnified images of the boxed region in (FIG. 17C) and (FIG. 17D), respectively; (FIG. 17I) and (FIG. 17J) are magnified images of the boxed regions in (FIG. 17G) and (FIG. 17H), respectively. (FIG. 17K) Quantitation of histological assessment by OARSI scoring. (FIG. 17L) Histomorphometric analysis of Ctrl or Dnmt3b GOF cartilage. (FIG. 17M) Gene expression in chondrocytes isolated from 10 wk Ctrl or Dnmt3b GOF chondrocytes. (FIG. 17N, FIG. 17O, FIG. 17P) Mitochondrial respiration in primary articular chondrocytes isolated from 2 mo Col2a1Cre; Rosa-rtTA$^{f/+}$; Dnmt3b-tg mice, treated with vehicle (Ctrl) or doxycycline (Dnmt3b GOF) for 48 h. Mitochondrial respiration was measured by the Seahorse XF Extracellular Flux Analyzer. OCR, oxygen consumption rate. Scale bars, 100 µm.

(FIG. 18A) Schematic representation of the strategy utilized to generate doxycycline (DOX)-inducible Dnmt3b over-expression in murine cartilage tissue. (FIG. 18B, FIG. 18C, FIG. 18D) Genotyping strategy, utilizing three different primer pairs, to confirm recombination. Mouse line #9 was used for breeding and subsequent experimental analyses.

(FIG. 19A) Fluorescence microscopy shows recombination efficiency in 10 wk Col2a1Cre; Rosa-rtTA$^{f/+}$; H2BGFP mice. Scale bar, 100 µm. (FIG. 19B) Confirmation of Dnmt3b protein over-expression in primary articular chondrocytes from 10 wk Dnmt3b GOF or Cre+ control (Ctrl) mice by Western blotting using Dnmt3b or FLAG antibodies.

(FIG. 20A) qPCR confirmation of Abat expression. (FIG. 20B) Enzymatic methylation qPCR of Abat promoter region.

(FIG. 22A) Western blot of primary ACs isolated form sham and MLI cartilage. (FIG. 22B) IHC for Abat in WT articular cartilage 4-weeks post-MLI.

FIG. 25A, FIG. 25B and FIG. 25C depict the experimental design to determine the effects of Dnmt3b loss-of-function on catabolic induction in parimary chondrocytes (FIG. 25A). Experiments are also included to address the potential role of Abat as a mediator of catabolism by altering cell metabolism (i.e. TCA cycle and mitochondrial function), (FIG. 25B, FIG. 25C).

DETAILED DESCRIPTION OF THE INVENTION

Figure 1A:
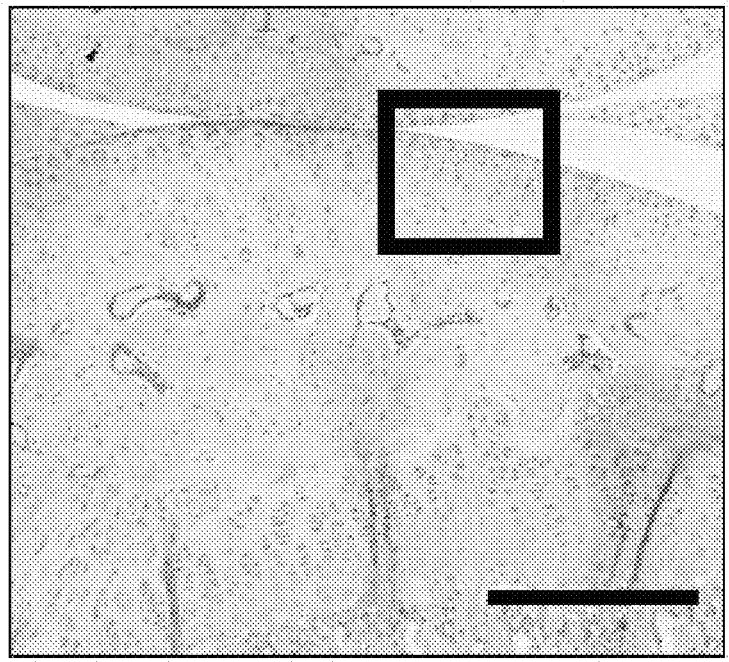
FIG. 1A, FIG. 1B, FIG. 1C, FIG. 1D, FIG. 1E, FIG. 1F, FIG. 1G, FIG. 1H, FIG. 1I, FIG. 1J, FIG. 1K, FIG. 1L and FIG. 1M depict images, graphs and an immunoblot showing Dnmt3b expression in murine and human knee joint cartilage.

Osteoarthritis (OA) is the most common form of arthritis worldwide. It is a complex disease affecting the whole joint but is generally characterized by progressive degradation of articular cartilage. The inventors have discovered that the de novo DNA methyltransferase (Dnmt) 3b, but not Dnmt3a, is present in healthy murine and human articular chondrocytes and expression decreases in OA mouse models and in chondrocytes from human OA patients. Targeted deletion of Dnmt3b in articular chondrocytes results in an early onset and progressive post-natal OA-like pathology. The inventors have also shown that decreases in Dnmt3b result in increased expression of 4-aminobutyrate aminotransferase (Abat) and elevated TCA metabolites and mitochondrial respiration. Importantly, a chondroprotective effect was found following increased expression of Dnmt3b or inhibition of Abat in articular chondrocytes in vitro and in vivo. Accordingly, disclosed herein are compositions and methods for treating osteoarthritis comprising increasing the expression of Dnmt3b and/or inhibiting Abat.

Various aspects of the disclosure are described in more detail below.

I. Compositions

In an aspect, a composition of the disclosure comprises a compound that increases the expression of Dnmt3b. Dnmt3b may also be referred to as DNA (Cytosine-5-)-Methyltransferase 3 Beta, DNA Methyltransferase HsaIIIB, DNA MTase HsaIIIB, EC 2.1.1.37, M.HsaIIIB, ICF1, DNA (Cytosine-5)-Methyltransferase 3B or ICF.

In another aspect, a composition of the disclosure comprises a compound that inhibits aminobutyrate aminotransferase. Aminobutyrate aminotransferase may also be referred to as Abat, 4-aminobutyrate transaminase, EC 2.6.1.19, GABA transaminase or 4-aminobutyrate aminotransferase.

A compound of the disclosure may be modified to improve potency, bioavailability, solubility, stability, handling properties, or a combination thereof, as compared to an unmodified version.

A composition of the disclosure may comprise a compound that increases the expression of Dnmt3b and a compound that inhibits aminobutyrate aminotransferase. Additionally, a composition of the disclosure may comprise one or more additional drug or therapeutically active agent in addition to a compound that increases the expression of Dnmt3b and/or a compound that inhibits aminobutyrate aminotransferase. A composition of the disclosure may further comprise a pharmaceutically acceptable excipient, carrier or diluent. Further, a composition of the disclosure may contain preserving agents, solubilizing agents, stabilizing agents, wetting agents, emulsifiers, sweeteners, colorants, odorants, salts (substances of the present disclosure may themselves be provided in the form of a pharmaceutically acceptable salt), buffers, coating agents or antioxidants.

Other aspects of the disclosure are described in further detail below.

(a) Compound that Increases the Expression of Dnmt3b

The compounds detailed herein include compounds that increase the expression of Dnmt3b. Methods to determine if a compound increases the expression of Dnmt3b are known in the art. For example, Dnmt3b nucleic acid expression, Dnmt3b protein expression, or Dnmt3b activity may be measured as described in more detail below. Dnmt3b is part of the DNA methyltransferase (DNA MTase) family of enzymes which catalyze the transfer of a methyl group to DNA. Dnmt1 is largely responsible for the maintenance of DNA methylation during cell division, whereas Dnmt3a and Dnmt3b predominantly act as de novo DNA methyltransferases responsible for the establishment of unique DNA methylation signatures. Importantly, Dnmt3b expression, but not Dnmt1 or Dnmt3a expression, is significantly reduced in osteoarthritis (OA) chondrocytes relative to healthy chondrocytes. Chondrocytes, the unique cellular component of articular cartilage, maintain the matrix components under normal, low turnover conditions in which the glycosaminoglycans on proteoglycans and other noncollagen molecules can be replaced. During the development of osteoarthritis (OA), the normal, quiescent chondrocytes become activated and undergo a phenotypic shift, resulting in fibrillation and degradation of cartilage matrix, the appearance of chondrocyte clusters, increased cartilage calcification associated with tidemark advancement or duplication, and vascular penetration from the subchondral bone.

A compound with the ability to increase the expression of Dnmt3b in chondrocytes may potentially be used as an osteoarthritic drug. A compound with the ability to increase the expression of Dnmt3b may include, without limitation, a compound, a drug, a small molecule, a peptide, a nucleic acid molecule, a protein, an antibody, and combinations thereof. A nucleic acid molecule may be an antisense oligonucleotide, a ribozyme, a small nuclear RNA (snRNA), a long noncoding RNA (LncRNA), or a nucleic acid molecule which forms triple helical structures. In certain embodiments, a compound with the ability to increase the expression of Dnmt3b may be a nucleic acid comprising Dnmt3b. The nucleic acid comprising Dnmt3b may then be expressed in a chondrocyte. Methods of expressing a nucleic acid in a cell are known in the art. For example, a vector comprising the Dnmt3b nucleotide sequence may be used to express Dnmt3b in a cell. As used herein, a vector is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors. A vector encoding Dnmt3b may be introduced into a cell by transfection. Methods for transfecting nucleic acids are well known to persons skilled in the art. Transfection methods include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, or DreamFect. In other embodiments, a compound with the ability to increase the expression of Dnmt3b may be Dnmt3b protein. In certain embodiments, a compound that increases the expression of Dnmt3b enhances enzymatic activity of Dnmt3b. In other embodiments, a compound that increases the expression of Dnmt3b increases Dnmt3b protein expression. In still other embodiments, a compound that increases the expression of Dnmt3b increases Dnmt3b nucleic acid expression.

Dnmt3b may be encoded by the Dnmt3b gene from *Homo sapiens* or a homolog thereof (GenBank accession number NC_000020.11). In another example, Dnmt3b may be encoded by the Dnmt3b gene from *Mus musculus* or a homolog thereof (GenBank accession number NC_000068.7). Dnmt3b may also be an analogue, active fragment or derivative of Dnmt3b, having an activity as described in the present disclosure. A skilled artisan will appreciate that homologs of Dnmt3b can be found in a variety of species. Non-limiting examples include rat (NC_005102.4), chicken (NC_006107.3), cow (AC_000170.1), chimpanzee (NC_006487.3), Rhesus monkey (NC_007867.1), pig (NC_010459.4), goat (NC_022305.1), gorilla (NC_018444.1), cat (NC_018725.2), sheep (NC_019470.1), rabbit (NC_013672.1), horse (NC_009165.2) and dog (NC_006606.3). It is appreciated that the present disclosure is directed to homologs of Dnmt3b in other organisms and is not limited to the mouse and human homolog. Homologs can be found in other species by methods known in the art. In determining whether a Dnmt3b has significant homology or shares a certain percentage of sequence identity with a sequence of the disclosure, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the disclosure. Equally, BLAST protein searches may be performed with the BLASTX program to obtain amino acid sequences that are homologous to a polypeptide of the disclosure. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details.

A Dnmt3b of the disclosure may be at least 65, 70, 75, 80, 85, 90, or 95% homologous to Dnmt3b provided it has the same activity as the mouse and/or human Dnmt3b. In certain embodiments, a Dnmt3b of the disclosure may be at least 65, 66, 67, 68, 69, or 70% homologous to Dnmt3b provided it has the same activity as the mouse and/or human Dnmt3b. In different embodiments, a Dnmt3b of the disclosure may be at least 71, 72, 73, 74, 75, 76, 77, 78 or 79% homologous to Dnmt3b provided it has the same activity as the mouse and/or human Dnmt3b. In one embodiment, a Dnmt3b of the disclosure may be at least 80, 81, 82, 83, 84, 85, 86, 87, 88, or 89% homologous to Dnmt3b. In another embodiment, a Dnmt3b of the disclosure may be at least 90, 91, 92, 93, 94, 95, 96, 97, 98, 99, or 100% homologous to Dnmt3b. In yet another embodiment, a Dnmt3b may be a truncation or variant that has the same activity as the full length Dnmt3b. Further, if the Dnmt3b is not human, the Dnmt3b may be codon optimized for optimal expression in human. Methods of codon optimizing a nucleic acid are known in the art.

(b) Compound that Inhibits Aminobutyrate Aminotransferase

In another aspect, the compounds detailed herein include compounds that inhibit aminobutyrate aminotransferase (Abat). Methods to determine if a compound inhibits Abat are known in the art. For example, Abat nucleic acid expression, Abat protein expression, or Abat activity may be measured as described in more detail below. Abat utilizes two substrates, 4-aminobutanoate (GABA) and 2-oxoglutarate, to produce two products, succinate semialdehyde and L-glutamate. Abat belongs to the family of transferases, specifically the transaminases, which transfer nitrogenous groups. Abat participates in 5 metabolic pathways: alanine and aspartate metabolism, glutamate metabolism, beta-alanine metabolism, propanoate metabolism, and butanoate metabolism. Importantly, Abat expression is significantly elevated in osteoarthritis (OA) chondrocytes relative to healthy chondrocytes.

A compound with the ability to inhibit Abat in chondrocytes may potentially be used as an osteoarthritic drug. A compound with the ability to inhibit Abat may include, without limitation, a compound, a drug, a small molecule, a peptide, a nucleic acid molecule, a protein, an antibody, and combinations thereof. A nucleic acid molecule may be an antisense oligonucleotide, a ribozyme, a small nuclear RNA (snRNA), a long noncoding RNA (LncRNA), or a nucleic acid molecule which forms triple helical structures. Non-limiting examples of a compound that inhibits Abat include vigabatrin, L-2,4-diaminobutyric acid dihydrochloride, gamma-acetylenic GABA, S(+)-gamma-vinyl-GABA, 3-methyl-GABA, 4-amino-5-hexynoic acid, gabaculine, aminooxyacetic acid, phenelzine, phenylethylidenehydrazine (PEH), rosmarinic acid and valproic acid. In a specific embodiment, a compound that inhibits Abat is vigabatrin. In certain embodiments, a compound that inhibits Abat blocks enzymatic activity of Abat. In other embodiments, a compound that inhibits Abat reduces Abat protein expression. In still other embodiments, a compound that inhibits Abat reduces Abat nucleic acid expression.

i. Nucleic Acid Expression

In an embodiment, Dnmt3b nucleic acid expression may be measured to identify a compound that increases the expression of Dnmt3b. For example, when Dnmt3b nucleic acid expression is increased in the presence of a compound relative to an untreated control, the compound increases the expression of Dnmt3b. In a specific embodiment, Dnmt3b mRNA may be measured to identify a compound that increases the expression of Dnmt3b. In another embodiment, Abat nucleic acid expression may be measured to identify a compound that inhibits Abat. For example, when Abat nucleic acid expression is decreased in the presence of a compound relative to an untreated control, the compound inhibits Abat. In a specific embodiment, Abat mRNA may be measured to identify a compound that inhibits Abat.

Methods for assessing an amount of nucleic acid expression in cells are well known in the art, and all suitable methods for assessing an amount of nucleic acid expression known to one of skill in the art are contemplated within the scope of the disclosure. The term "amount of nucleic acid expression" or "level of nucleic acid expression" as used herein refers to a measurable level of expression of the nucleic acids, such as, without limitation, the level of messenger RNA (mRNA) transcript expressed or a specific variant or other portion of the mRNA, the enzymatic or other activities of the nucleic acids, and the level of a specific metabolite. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of expression of a target nucleic acid comprises, in part, measuring the level of target nucleic acid mRNA expression.

In one embodiment, the amount of nucleic acid expression may be determined by using an array, such as a microarray. Methods of using a nucleic acid microarray are well and widely known in the art. For example, a nucleic acid probe that is complementary or hybridizable to an expression product of a target gene may be used in the array. The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the amount of nucleic acid expression may be determined using PCR. Methods of PCR are well and widely known in the art, and may include quantitative PCR, semi-quantitative PCR, multiplex PCR, or any combination thereof. Specifically, the amount of nucleic acid expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression may be measured by measuring an entire mRNA transcript for a nucleic acid sequence, or measuring a portion of the mRNA transcript for a nucleic acid sequence. For instance, if a nucleic acid array is utilized to measure the amount of mRNA expression, the array may comprise a probe for a portion of the mRNA of the nucleic acid sequence of interest, or the array may comprise a probe for the full mRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. This allows comparisons between assays that are performed on different occasions.

Dnmt3b or Abat nucleic acid expression may be increased or decreased in the presence of a compound relative to an untreated control. In one embodiment, Dnmt3b or Abat nucleic acid expression can be compared using the ratio of the level of expression of Dnmt3b or Abat nucleic acid in the presence of a compound as compared with the expression level of Dnmt3b or Abat nucleic acid in the absence of a compound. For example, a nucleic acid is differentially expressed if the ratio of the level of expression of Dnmt3b or Abat nucleic acid in the presence of a compound as compared with the expression level of Dnmt3b or Abat nucleic acid in the absence of a compound is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment, the increase or decrease in expression is measured using p-value. For instance, when using p-value, a nucleic acid is identified as being differentially expressed between a Dnmt3b or Abat nucleic acid in the presence of a compound and Dnmt3b or Abat nucleic acid in the absence of a compound when the p-value is less than 0.1, preferably less than 0.05, more preferably less than 0.01, even more preferably less than 0.005, the most preferably less than 0.001.

ii. Protein Expression

In another embodiment, Dnmt3b protein expression may be measured to identify a compound that increases the expression of Dnmt3b. For example, when Dnmt3b protein expression is increased in the presence of a compound relative to an untreated control, the compound increases the expression of Dnmt3b. In a specific embodiment, Dnmt3b protein expression may be measured using immunoblot or immunohistochemistry (IHC). In a different embodiment, Abat protein expression may be measured to identify a compound that inhibits Abat. For example, when Abat protein expression is decreased in the presence of a compound relative to an untreated control, the compound inhibits Abat. In a specific embodiment, Abat protein expression may be measured using immunoblot or immunohistochemistry (IHC).

Methods for assessing an amount of protein expression are well known in the art, and all suitable methods for assessing an amount of protein expression known to one of skill in the art are contemplated within the scope of the disclosure. Non-limiting examples of suitable methods to assess an amount of protein expression may include epitope binding agent-based methods and mass spectrometry based methods.

In some embodiments, the method to assess an amount of protein expression is mass spectrometry. By exploiting the intrinsic properties of mass and charge, mass spectrometry (MS) can resolve and confidently identify a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present disclosure, one can use mass spectrometry to look for the level of protein encoded from a target nucleic acid of the disclosure.

In some embodiments, the method to assess an amount of protein expression is an epitope binding agent-based method. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of binding to a target gene protein. Nucleic acids may include RNA, DNA, and naturally occurring or synthetically created derivative.

As used herein, the term "antibody" generally means a polypeptide or protein that recognizes and can bind to an epitope of an antigen. An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody and a humanized antibody. The techniques for preparing and using various antibody-based constructs and fragments are well known in the art. Means for preparing and characterizing antibodies are also well known in the art (See, e.g. Antibodies: A Laboratory Manual, Cold Spring Harbor Laboratory, 1988; herein incorporated by reference in its entirety).

As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in it binding to a polypeptide, may be synthesized and/or identified by in vitro evolution methods. Means for preparing and characterizing aptamers, including by in vitro evolution methods, are well known in the art (See, e.g. U.S. Pat. No. 7,939,313; herein incorporated by reference in its entirety).

In general, an epitope binding agent-based method of assessing an amount of protein expression comprises contacting a sample comprising a polypeptide with an epitope binding agent specific for the polypeptide under conditions effective to allow for formation of a complex between the epitope binding agent and the polypeptide. Epitope binding agent-based methods may occur in solution, or the epitope binding agent or sample may be immobilized on a solid surface. Non-limiting examples of suitable surfaces include microtitre plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen present. After this time, the complex will be washed and the complex may be detected by any method well known in the art. Methods of detecting the epitope binding agent-polypeptide complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, and luciferase). Methods of detecting an epitope binding agent-polypeptide complex based on the detection of a label or marker are well known in the art.

In some embodiments, an epitope binding agent-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In some embodiments, the epitope binding agent-based method is an ELISA. In other embodiments, the epitope binding agent-based method is a radioimmunoassay. In still other embodiments, the epitope binding agent-based method is an immunoblot or Western blot. In alternative embodiments, the epitope binding agent-based method is an array. In another embodiment, the epitope binding agent-based method is flow cytometry. In different embodiments, the epitope binding agent-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

Dnmt3b or Abat protein expression may be increased or decreased in the presence of a compound relative to an untreated control. In one embodiment, Dnmt3b or Abat protein expression can be compared using the ratio of the level of expression of Dnmt3b or Abat protein in the presence of a compound as compared with the expression level of Dnmt3b or Abat protein in the absence of a compound. For example, a protein is differentially expressed if the ratio of the level of expression of Dnmt3b or Abat protein in the presence of a compound as compared with the expression level of Dnmt3b or Abat protein in the absence of a compound is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment, the increase or decrease in expression is measured using p-value. For instance, when using p-value, a protein is identified as being differentially expressed between Dnmt3b or Abat protein in the presence of a compound and Dnmt3b or Abat protein in the absence of a compound when the p-value is less than 0.1, preferably less than 0.05, more preferably less than 0.01, even more preferably less than 0.005, the most preferably less than 0.001.

iii. Dnmt3b /Abat Activity

In an embodiment, Dnmt3b activity may be measured to identify a compound that increases the expression of Dmnt3b. For example, methylation may be measured. In another embodiment, downstream effectors of Dnmt3b may be measured. For example, Col2a1, Col10a1, Runx2 and/or Mmp13 nucleic acid expression levels may be measured. A compound that increases the expression of Dnmt3 may increase the expression of Col2a1. Alternatively, a compound that increases the expression of Dnmt3 may decrease the expression of Col10a1, Runx2 and Mmp13. In another example, the TGFβ pathway and/or BMP pathway may be measured. A compound that increases the TGFβ pathway may increase the expression of Dnmt3b. Alternatively, a compound that decreases the BMP pathway may increase the expression of Dnmt3b. In a different example, cartilage area may be measured. A compound that increases the expression of Dnmt3 may increase cartilage area.

In another embodiment, Abat activity may be measured to identify a compound that inhibits Abat. For example, the production of succinate, glutamate, NADH and/or fumarate may be measured. A compound that inhibits Abat may decrease the production of succinate, glutamate, NADH and/or fumarate. In another example, mitochondrial respiration may be measured. A compound that inhibits Abat may decrease mitochondrial respiration.

(c) Components of the Composition

The present disclosure also provides pharmaceutical compositions. The pharmaceutical composition comprises a compound that increases the expression of Dmnt3b and/or a compound that inhibits aminobutyrate aminotransferase, as an active ingredient(s), and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition a compound that increases the expression of Dmnt3b and/or a compound that inhibits aminobutyrate aminotransferase is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present disclosure. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery a compound that increases the expression of Dmnt3b and/or a compound that inhibits aminobutyrate aminotransferase in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a compound that increases the expression of Dmnt3b and/or a compound that inhibits aminobutyrate aminotransferase may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a compound that increases the expression of Dmnt3b and/or a compound that inhibits aminobutyrate aminotransferase (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the disclosure may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the disclosure generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. A compound that increases the expression of Dmnt3b and/or a compound that inhibits aminobutyrate aminotransferase may be encapsulated in a microemulsion by any method generally known in the art.

In yet another embodiment, a compound that increases the expression of Dmnt3b and/or a compound that inhibits aminobutyrate aminotransferase may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the disclosure therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the disclosure. Generally, the size of dendrimers may range from about 1 nm to about 100 nm.

II. Methods

In an aspect, the disclosure provides a method to reduce cartilage degradation. The method comprises administering a composition comprising a compound that increases the expression of Dmnt3b and/or a compound that inhibits aminobutyrate aminotransferase. Cartilage degradation may be measured via methods standard in the art. For example, cartilage area may be measured, OARSI scoring may be conducted, imaging may be done to evaluate bone volume. Additionally, inflammation, TCA cycle metabolites and/or mitochondrial respiration may be measured. Cartilage degradation may be reduced by increasing the expression of Dmnt3b in chondrocytes and/or inhibiting the activity of aminobutyrate aminotransferase (Abat) in chondrocytes.

In another aspect, the disclosure provides a method to increase cartilage area. The method comprises administering a composition comprising a compound that increases the expression of Dmnt3b and/or a compound that inhibits aminobutyrate aminotransferase. Cartilage area may be measured via methods standard in the art. For example, cartilage area may be directly measured. Alternatively, additional tests may be conducted as a surrogate for increased cartilage area. For example, OARSI scoring may be conducted, imaging may be done to evaluate bone volume and/or inflammation, TCA cycle metabolites and/or mitochondrial respiration may be measured. Cartilage area may be increased by increasing the expression of Dmnt3b in chondrocytes and/or inhibiting the activity of aminobutyrate aminotransferase (Abat) in chondrocytes.

In a different aspect, the disclosure provides a method of treating or preventing arthritis in a subject. The method comprises administering to the subject a composition comprising a compound that increases the expression of Dmnt3b and/or a compound that inhibits aminobutyrate aminotransferase. As used herein, "arthritis" means "joint inflammation," and describes different diseases and conditions that affect joints, the tissues that surround joints, and other connective tissue. Two of the most common forms of arthritis are osteoarthritis and rheumatoid arthritis. Common arthritis joint symptoms include swelling, pain, stiffness and decreased range of motion. Symptoms may come and go and can be mild, moderate or severe. Symptoms stay about the same for years, but may progress or get worse over time. Severe arthritis can result in chronic pain, inability to do daily activities and make it difficult to walk or climb stairs. Arthritis can cause permanent joint changes. Some types of arthritis also affect the heart, eyes, lungs, kidneys and skin as well as the joints. Arthritis may be degenerative arthritis such as osteoarthritis, inflammatory arthritis such as rheumatoid arthritis and psoriatic arthritis, infectious arthritis sometimes caused by *Salmonella* and *Shigella* (food poisoning or contamination), *Chlamydia* and *Gonorrhea* (sexually transmitted diseases) and hepatitis C virus (a blood-to-blood infection, often through shared needles or transfusions), and metabolic arthritis such as gout due to uric acid. Non-limiting examples of types of arthritis include adult-onset Still's disease, ankylosing spondylitis, back pain, Behçet's disease, bursitis, calcium pyrophosphate deposition disease (CPPD), carpal tunnel syndrome, chondromalacia patella, chronic fatigue syndrome, complex regional pain syndrome, cryopyrin-associated periodic syndromes (CAPS), degenerative disc disease, developmental-dysplasia of hip, Ehlers-Danlos, familial Mediterranean fever, fibromyalgia, fifth disease, giant cell arteritis, gout, hemochromatosis, infectious arthritis, inflammatory arthritis, inflammatory bowel disease, juvenile arthritis, juvenile dermatomyositis (JD), juvenile idiopathic arthritis (JIA), juvenile scleroderma, Kawasaki disease, lupus, lupus in children & teens, Lyme disease, mixed connective tissue disease, myositis (inc. polymyositis, dermatomyositis), osteoarthritis, osteoporosis, Pagets, palindromic rheumatism, patellofemoral pain syndrome, pediatric rheumatic diseases, pediatric SLE, polymyalgia rheumatic, pseudogout, psoriatic arthritis, Raynaud's phenomenon, reactive arthritis, reflex sympathetic dystrophy, Reiter's syndrome, rheumatic fever, rheumatism, rheumatoid arthritis, scleroderma, Sjögren's disease, spinal stenosis, spondyloarthritis, systemic juvenile idiopathic arthritis, systemic lupus erythematosus, systemic lupus erythematosus in children & teens, systemic sclerosis, temporal arteritis, tendinitis, vasculitis and Wegener's granulomatosis. A composition of the disclosure may treat a prevent arthritis by alleviating signs or symptoms associated with arthritis. A skilled artisan would be able to determine signs and symptoms associated with the various type of arthritis.

In still another aspect, the disclosure provides a method of treating osteoarthritis in a subject. The method comprises administering to the subject a composition comprising a compound that increases the expression of Dmnt3b and/or a compound that inhibits aminobutyrate aminotransferase. The subject may be a subject diagnosed with osteoarthritis (OA) or a subject at risk for developing OA. If the subject is at risk for developing OA, a method of the disclosure may prevent or delay the development of OA in a subject. A subject may be diagnosed with OA if they are exhibiting signs and symptoms of OA including, but not limited to, pain, tenderness, stiffness, loss of flexibility, grating sensation and/or bone spurs. Additionally, tests may be conducted to diagnose a subject with OA. Non-limiting examples of tests include imaging tests such as X-rays and MRI and lab tests such as blood tests and joint fluid analysis. A subject may be at risk for developing OA if they are of older age, female, obese, have sustained joint injuries, have an occupation that involves repetitive stress on a particular joint, have a family history of OA, have bone deformities, have had joint surgery, and/or have other diseases such as diabetes or other rheumatic diseases such as gout and rheumatoid arthritis. By "treat or prevent" is meant reducing the signs and symptoms of OA such as feelings of pain, tenderness, stiffness, loss of flexibility, grating sensation and/or bone spurs, increasing cartilage area, reducing cartilage degradation, decreasing inflammation of the joint, decreasing OARSI score, decreasing TCA cycle metabolites and/or mitochondrial respiration in chondrocytes, increasing methylation in chondrocytes, decreasing Abat activity in chondrocytes, and/or increasing Dnmt3b expression in chondrocytes.

In a specific embodiment, the disclosure provides a method of treating or preventing osteoarthritis, the method comprising administering a composition comprising vigabatrin.

In certain embodiments, a method of the disclosure may be combined with methods standard in the art for treating OA. Standard methods for treating OA include, but are not limited to, administration of acetaminophen and/or non-steroidal anti-inflammatory drugs (NSAIDs), physical therapy, occupational therapy, braces or shoe inserts, a chronic pain class, cortisone shots, lubrication injections, realigning bones and/or joint replacement. Additionally, methods of the disclosure may be used in combination with lifestyle changes such as exercise, weight loss, hot and cold pain management, application of over-the-counter pain creams and/or assistive devices. Further, methods of the disclosure may be used in combination with alternative medicine, including, but not limited to, acupuncture, use of glucosamine and chondroitin, use of avocado-soybean unsaponifiables, and/or tai chi and yoga.

Additionally, the disclosure provides a method to detect osteoarthritis. The method comprises detecting the presence of Dnmt3b and/or Abat. Dnmt3b and/or Abat may be detected ex vivo by biopsying a suspected site of OA and detecting the presence of Dnmt3b and/or Abat via imaging (such as IHC), protein expression methods (such as immunoblot) and/or nucleic acid expression (such as PCR). When the Dnmt3b is decreased relative to Dnmt3b found in a healthy individual, the subject may have OA. Alternatively, when the Abat is increased relative to Abat found in a healthy individual, the subject may have OA. Dnmt3b or Abat may be increased or decreased relative to a healthy control. In one embodiment, Dnmt3b or Abat can be compared using the ratio of the level of expression of Dnmt3b or Abat in the biological sample as compared with the expression level of Dnmt3b or Abat in a healthy control. For example, Dnmt3b or Abat is differentially expressed if the ratio of the level of expression of Dnmt3b or Abat in the biological sample as compared with the expression level of Dnmt3b or Abat in the healthy individual is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment, the increase or decrease in expression is measured using p-value. For instance, when using p-value, Dnmt3b or Abat is identified as being differentially expressed between Dnmt3b or Abat in the biological sample and Dnmt3b or Abat in the healthy individual when the p-value is less than 0.1, preferably less than 0.05, more preferably less than 0.01, even more preferably less than 0.005, the most preferably less than 0.001.

The composition is described in Section I, the subject and administration are described below.

(a) Subject

A method of the disclosure may be used to treat or prevent OA in a subject that is a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In certain embodiments, the animal is a laboratory animal. Non-limiting examples of a laboratory animal may include rodents, canines, felines, and non-human primates. In other embodiments, the animal is a rodent. Non-limiting examples of rodents may include mice, rats, guinea pigs, etc. In a specific embodiment, the subject is a human.

The human subject may be of any age. However, since OA may be associated with aging, a human subject may be an older human subject. In some embodiments, the human subject may be about 20, 25, 30, 40, 45, 50, 55, 60, 65, 70, 75, 80, 85, 90, 95 years of age or older. In some preferred embodiments, the human subject is 30 years of age or older. In other preferred embodiments, the human subject is 40 years of age or older. In other preferred embodiments, the human subject is 45 years of age or older. In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

(b) Administration

In certain aspects, a therapeutically effective amount of a composition of the disclosure may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. For example, if the disease or condition is osteoarthritis, the composition may be administered via intra-articular injection. It is within the skill of one in the art, to determine the route of administration based on the disease or condition to be treated. In a specific embodiment, a composition of the disclosure is administered orally.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the peptides useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

For therapeutic applications, a therapeutically effective amount of a composition of the disclosure is administered to a subject. A "therapeutically effective amount" is an amount of the therapeutic composition sufficient to produce a measurable response (e.g., a reduction in symptoms, a decrease in joint inflammation, an increase in cartilage area). Actual dosage levels of active ingredients in a therapeutic composition of the disclosure can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, OA locations and longevity, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The timing of administration of the treatment relative to the disease itself and duration of treatment will be determined by the circumstances surrounding the case. Treatment could begin in a hospital or clinic itself, or at a later time after discharge from the hospital or after being seen in an outpatient clinic.

Duration of treatment could range from a single dose administered on a one-time basis to a life-long course of therapeutic treatments. The duration of treatment can and will vary depending on the subject and the disease or disorder to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The frequency of dosing may be once, twice, three times or more daily or once, twice, three times or more per week or per month, or as needed as to effectively treat the symptoms or disease. In certain embodiments, the frequency of dosing may be once, twice or three times daily. For example, a dose may be administered every 24 hours, every 12 hours, or every 8 hours. In other embodiments, the frequency of dosing may be once, twice or three times weekly. For example, a dose may be administered every 2 days, every 3 days or every 4 days. In a different embodiment, the frequency of dosing may be one, twice, three or four times monthly. For example, a dose may be administered every 1 week, every 2 weeks, every 3 weeks or every 4 weeks.

Although the foregoing methods appear the most convenient and most appropriate and effective for administration of a composition of the disclosure, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Introduction to Examples 1-5

Osteoarthritis (OA) is the most common arthritic condition, clinically characterized by articular cartilage degeneration, subchondral bone sclerosis, synovitis and osteophyte formation[1]. OA risk factors include age, gender, obesity, prior joint injury, mechanics (e.g. joint malalignment) and inherent genetic alterations[2,3]. Currently, there are still no effective disease-modifying treatments for OA except pain relief medication and surgical replacement of damaged joints[4-6].

At the tissue level, disruption of cartilage homeostasis in OA results in enhanced catabolism resulting in extracellular matrix (ECM) degradation. Many of the cellular and molecular changes in OA have been identified in studies utilizing murine models of OA or from analysis of human cartilage/chondrocytes from OA patients[3,7,8]. As a result, there is the potential for development of new therapeutic approaches to target factors involved in inflammation, oxidative stress and autophagy to name a few[9]. In addition to altered cellular and molecular pathways, a number of gene polymorphisms have been reported in human OA (e.g. GDF5, SMAD3)[10,11] and there are now several, robustly replicated, significant OA loci that have been identified by large-scale genome wide association studies (GWAS)[12-14]. However, many candidate gene studies for OA have identified false associations due to relatively small sample sizes. For example, one study carried out meta-analysis from nine GWAS and showed that only 2 out of 199 potential candidate genes (COL11A1 and VEGF) were associated with OA in human patients[15]. The OA loci discovered to date explain only a small fraction of the heritability of OA estimated by epidemiological studies.

DNA methylation is a well-characterized epigenetic mechanism involving the addition of a methyl group (CH3) from the methyl donor S-adenosyl methionine (SAM) to a cytosine within CpG sites to form 5-methylcytosine (5mC). Methylation within promoters, enhancers or gene bodies can significantly alter gene expression profiles[19,20]. Of the three catalytic DNA methyltransferase enzymes, DNMT3A and DNMT3B are known as the de novo methyltransferases and are predominantly responsible for the establishment of unique methylation patterns during development[21]. DNMT1, however, is largely responsible for maintaining the DNA methylation signatures created by these de novo enzymes during cell division. This study was designed to address the potential role of the de novo Dnmt3 enzymes in regulating murine articular cartilage homeostasis. The inventors show that Dnmt3b loss-of-function is associated with an OA-like pathology in mice due, in part, to alterations in cellular metabolism. Importantly, the inventors also show reduced DNMT3B expression in human OA chondrocytes and that Dnmt3b gain-of-function mice are protected from developing OA. These findings may lead to the discovery of novel therapeutic targets to treat OA.

Example 1

Figure 1B:
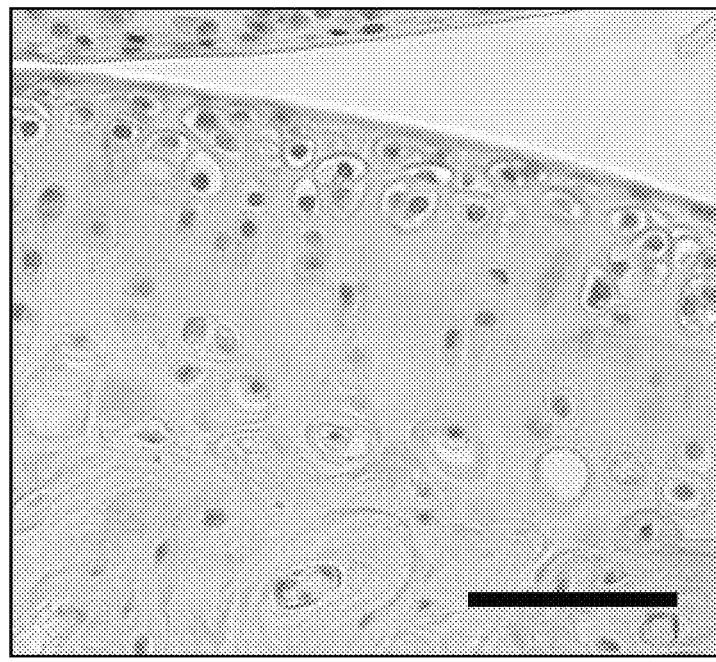
Figure 1C:
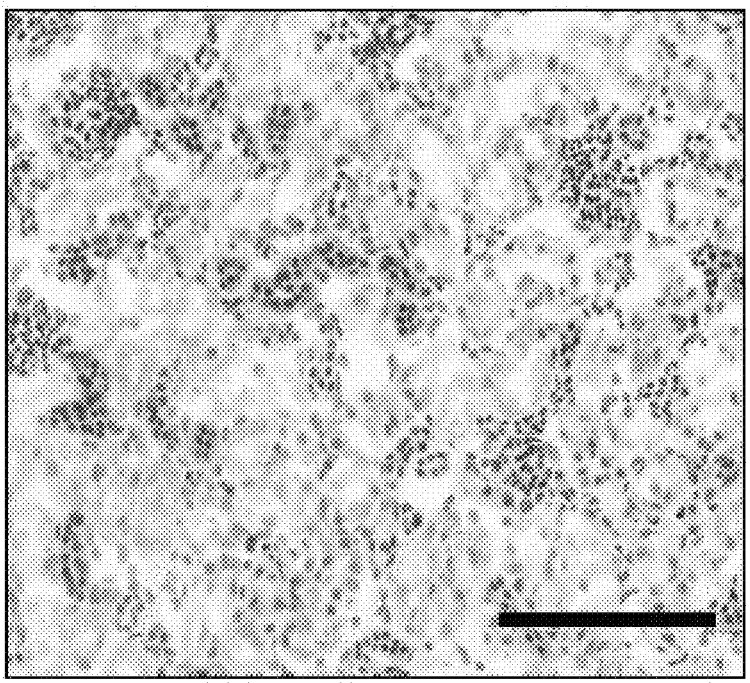
Figure 1D:
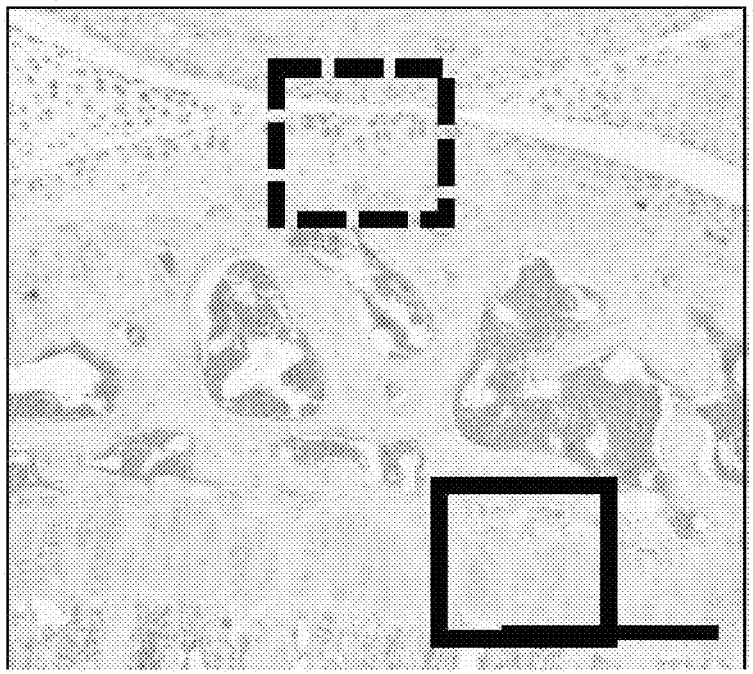
Figure 1E:
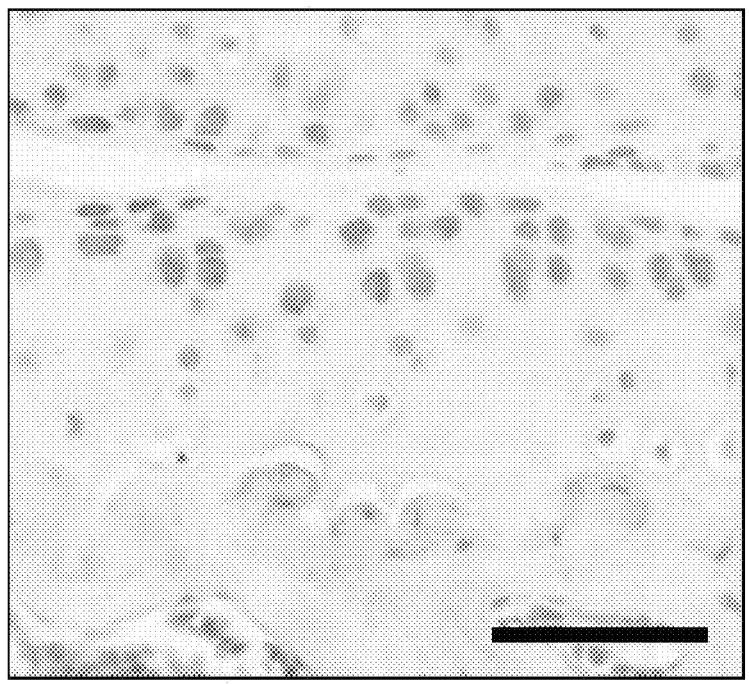
Figure 1F:
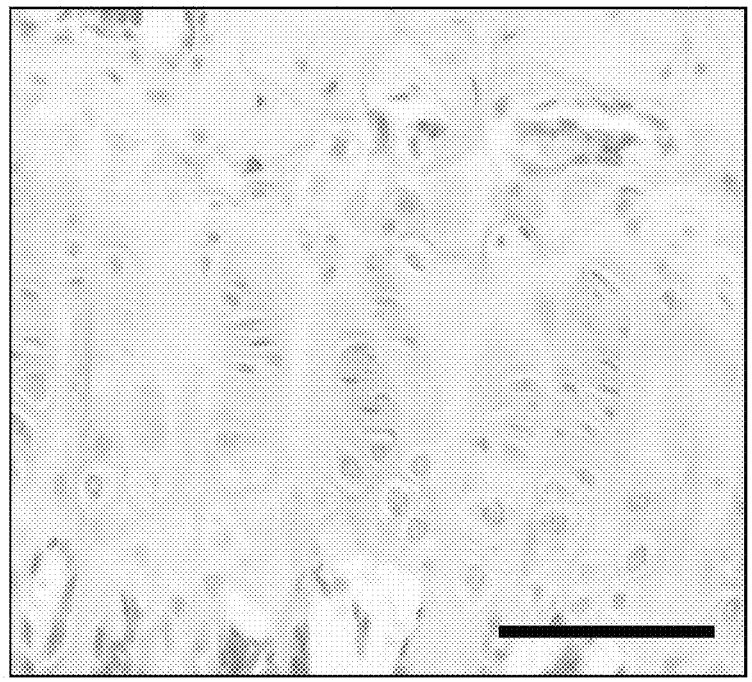
Figure 1G:
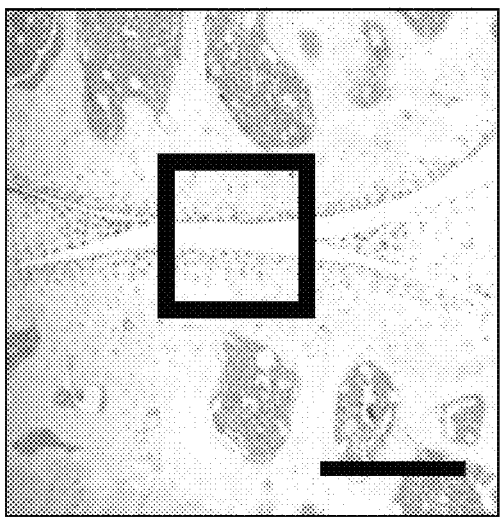
Figure 1G:
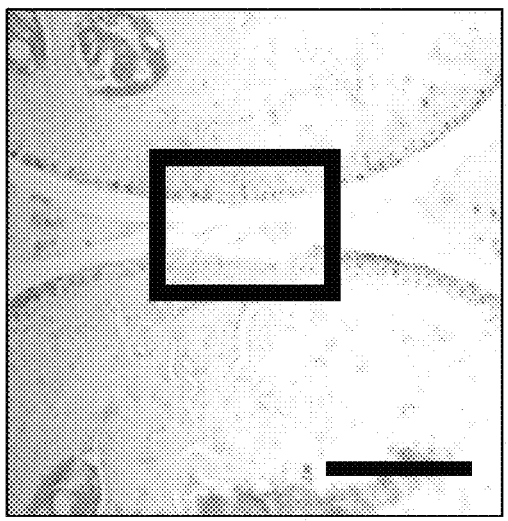
Figure 1G:
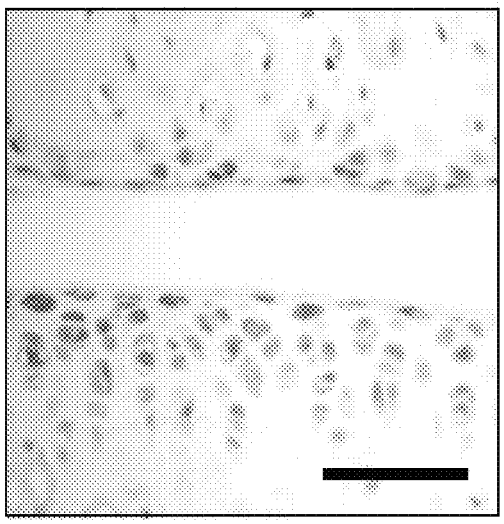
Figure 1G:
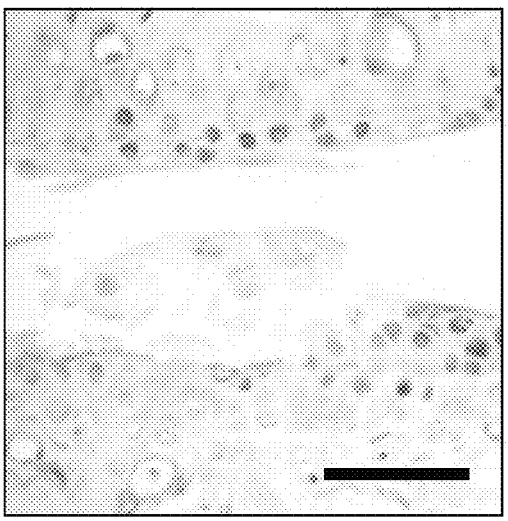
Figure 1H:
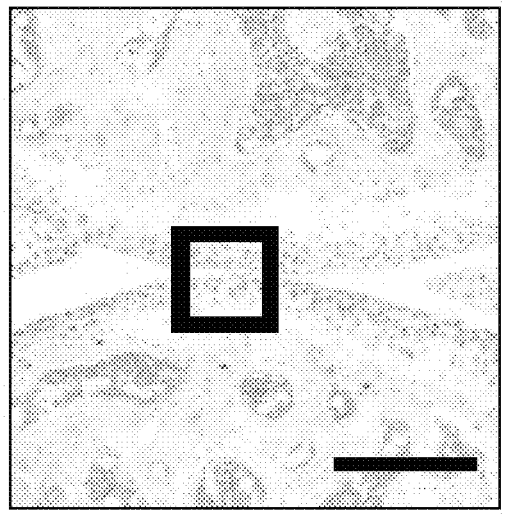
Figure 1H:
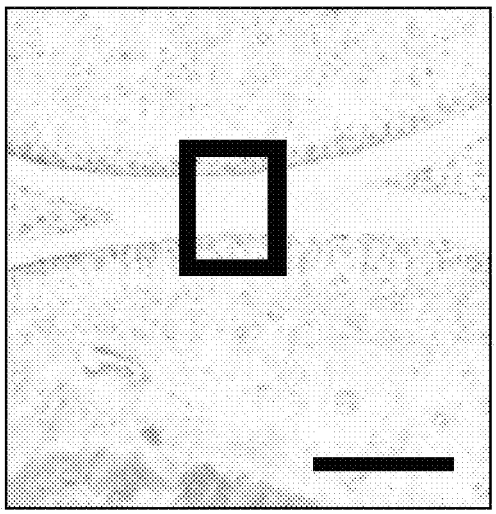
Figure 1H:
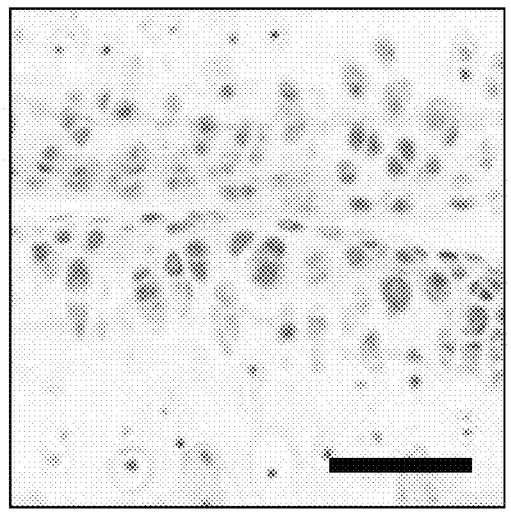
Figure 1H:
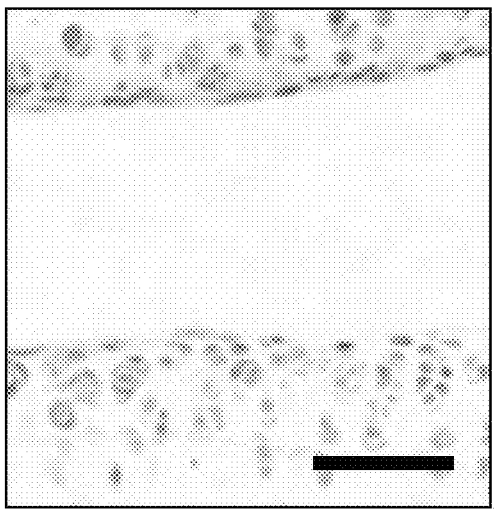
Figure 1I:
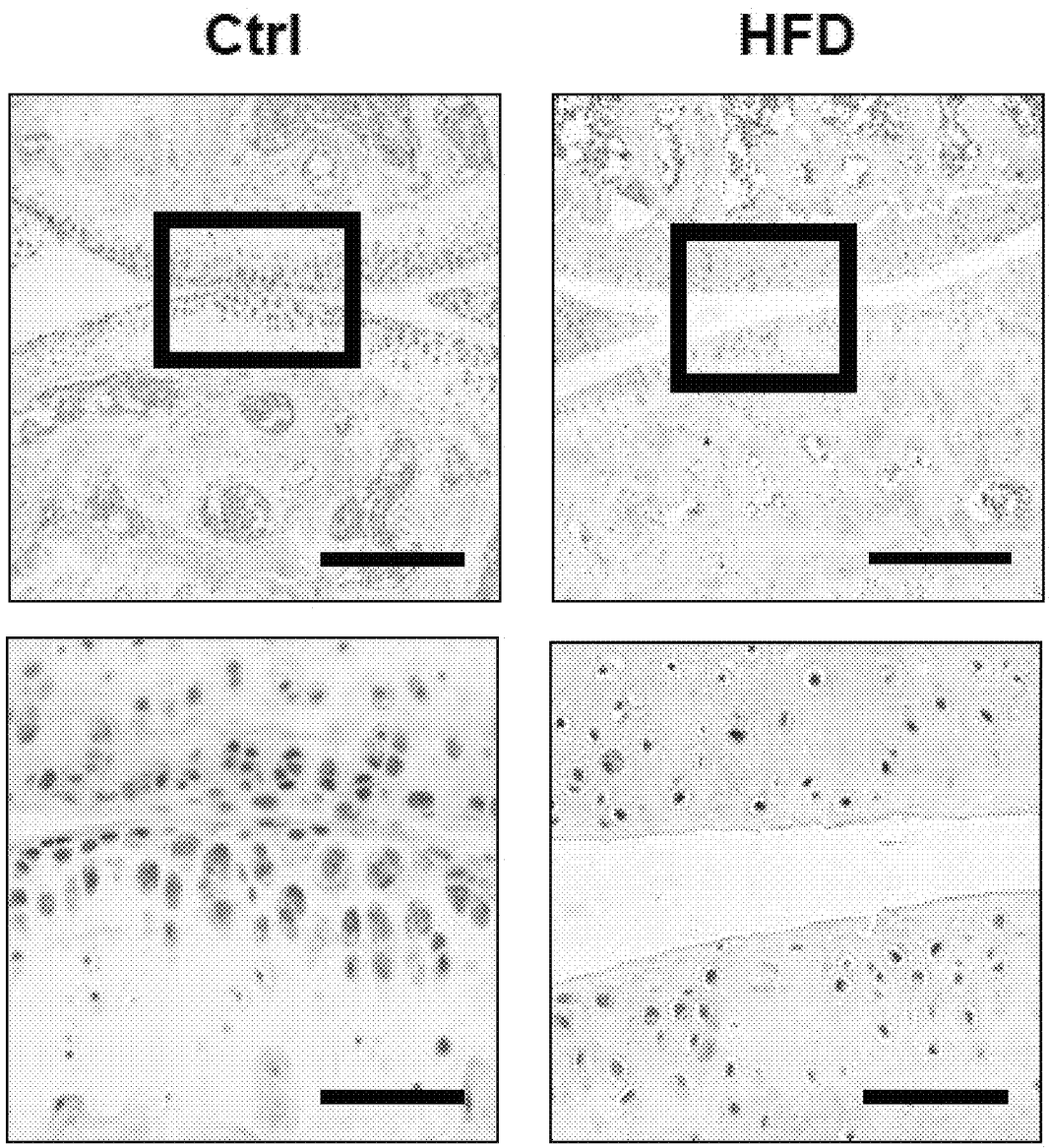
Figure 2:
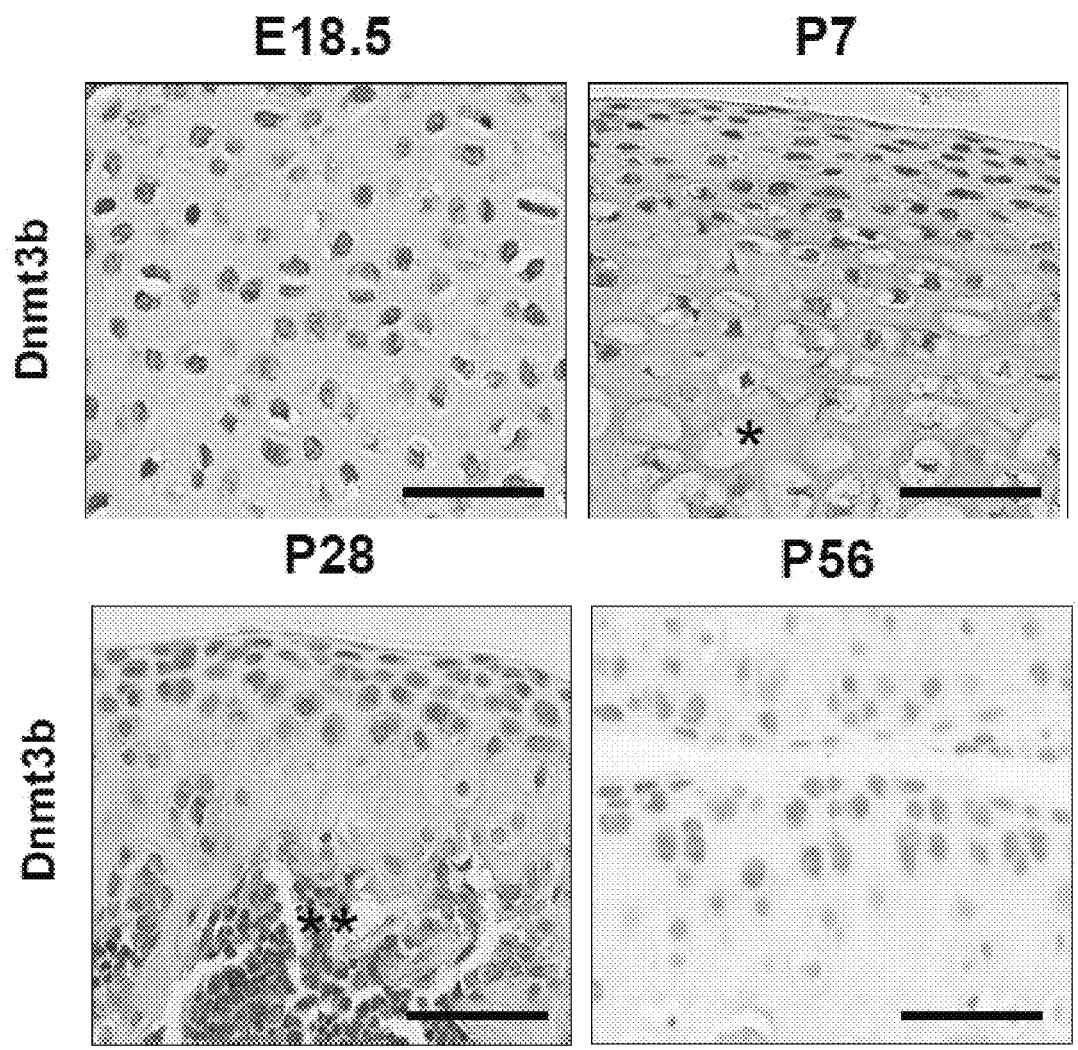
FIG. 2 depicts images showing Dnmt3b expression in embryonic and adult murine knee joint cartilage. Immunohistochemical staining shows Dnmt3b protein expression in chondrocytes from C57BL/6 WT murine articular cartilage knee joints at embryonic time point E18.5 and post-natal time points P7, P28 and P56. *, hypertrophic chondrocyte; **, bone marrow cells. All scale bars, 100 μm.

Decreased Expression of Dnmt3b is Associated with a Murine and Human OA Phenotype Immunohistochemical (IHC) staining of 3 mo wild type (WT) murine knee joints shows low to undetectable levels of Dnmt3a in articular and growth plate cartilage (FIG. 1A, FIG. 1B). However, Dnmt3b was abundantly expressed in chondrocytes of articular cartilage (FIG. 1D, FIG. 1E) but was almost undetectable in chondrocytes of the underlying growth plate (FIG. 1F). During murine cartilage development, Dnmt3b was ubiquitously expressed in proliferating chondrocytes of developing limbs, with restricted expression to articular chondrocytes post-natally (FIG. 2). Interestingly, Dnmt3b expression decreased with age in murine articular cartilage (FIG. 1G). Induction of OA catabolic processes in cartilage by either destabilization of murine knee joints via meniscal ligament injury (MLI)[8] or via high fat diet[27] also resulted in reduced Dnmt3b expression. (FIG. 1H, FIG. 1I).

Figure 1J:
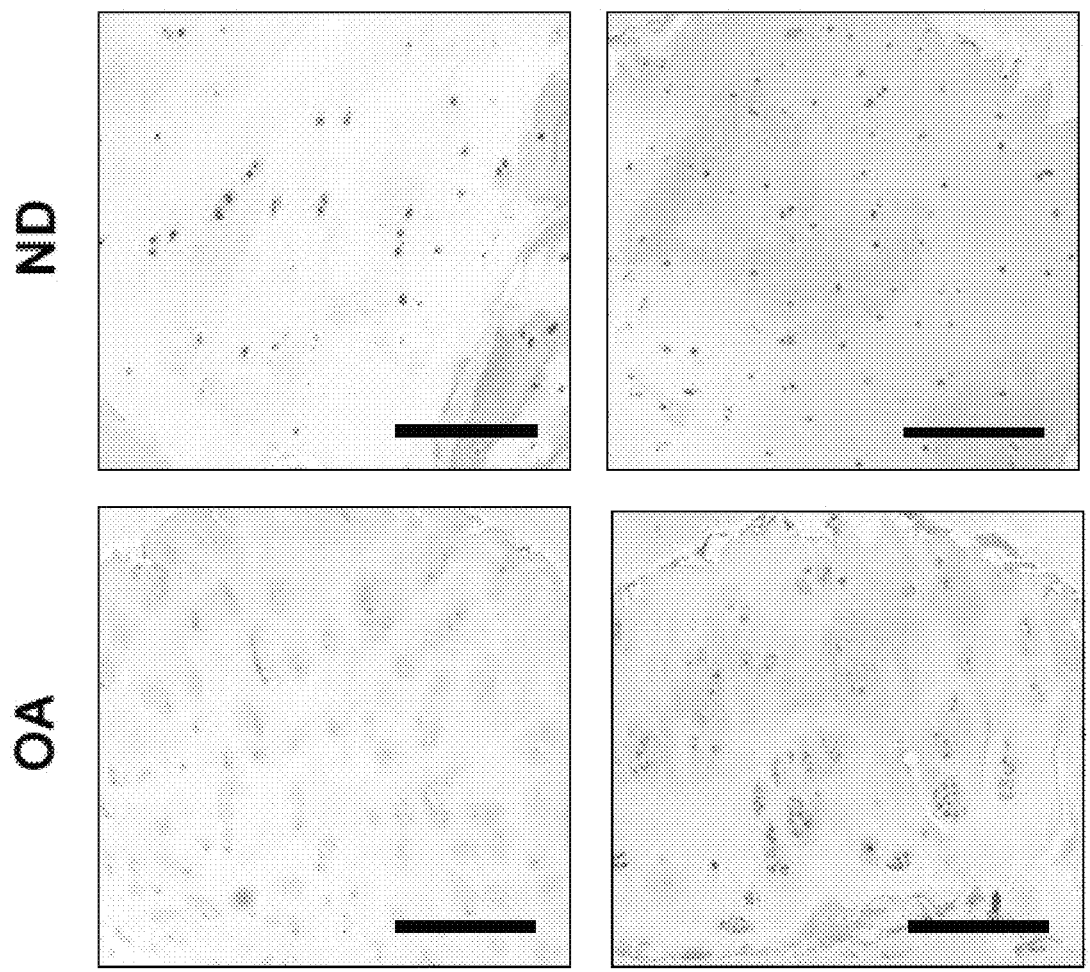
Figure 1K:
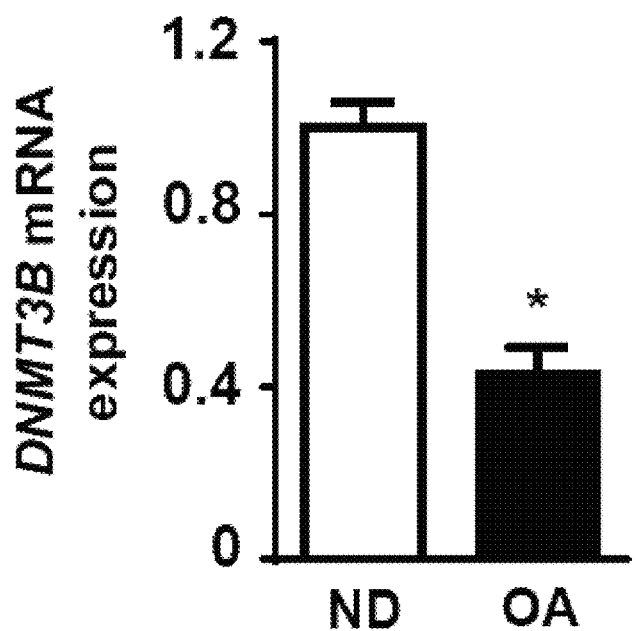
Figure 1L:
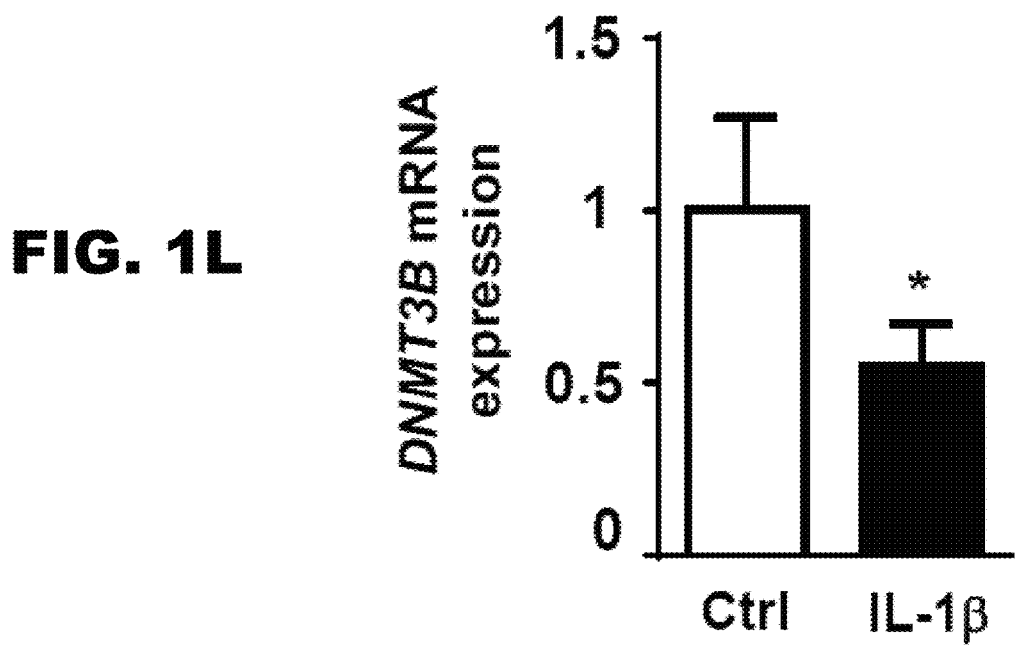
Figure 1M:
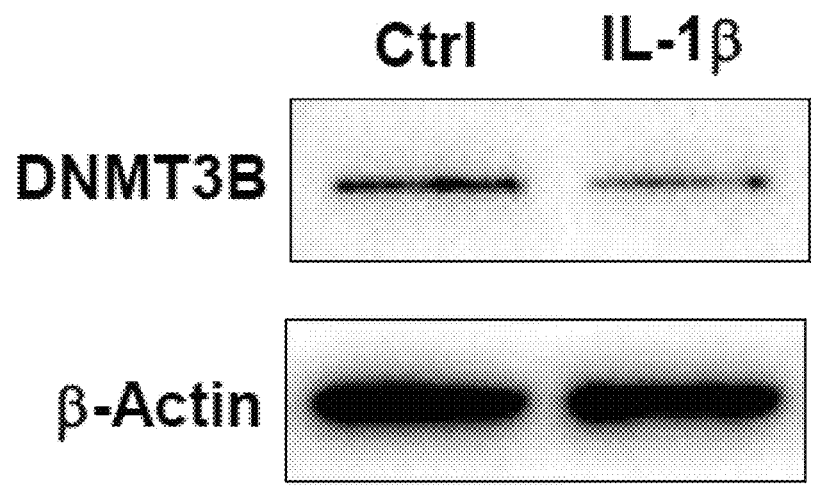
Figures 4A, 4B:
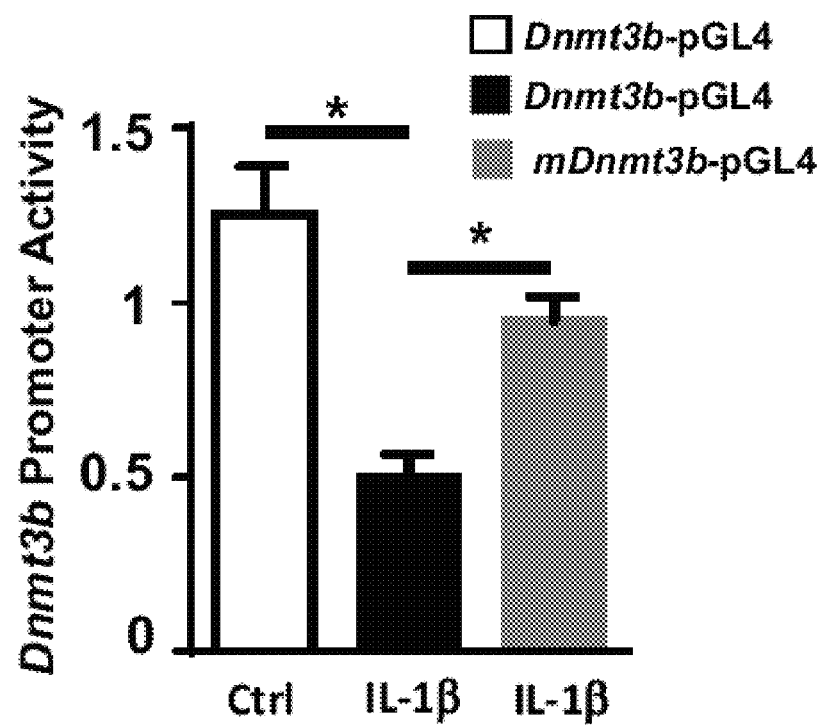
FIG. 4A, FIG. 4B, FIG. 4C, FIG. 4D, FIG. 4E and FIG. 4F depict sequences, graphs and a nucleic acid gel and immunoblot showing IL-1β regulation of Dnmt3b is mediated in part by NF-κB.
Figure 4C:
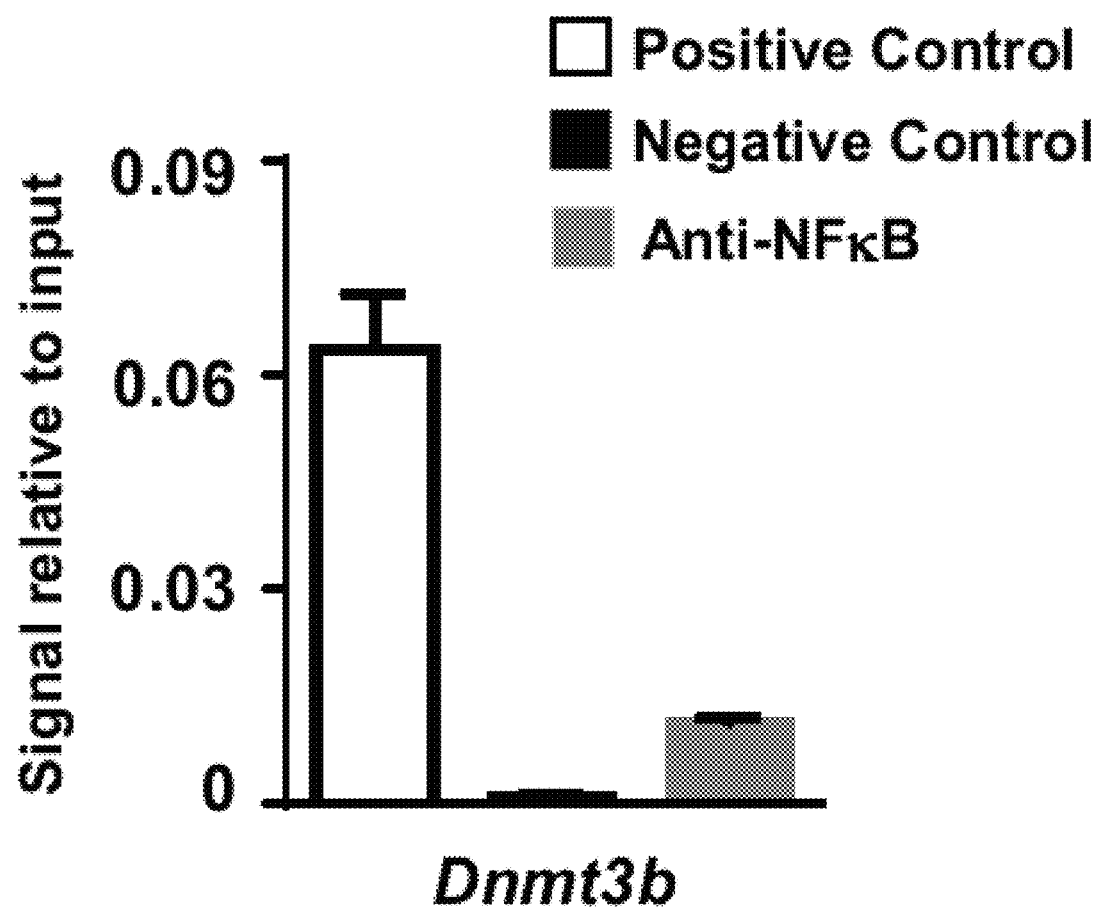
Figure 4D:
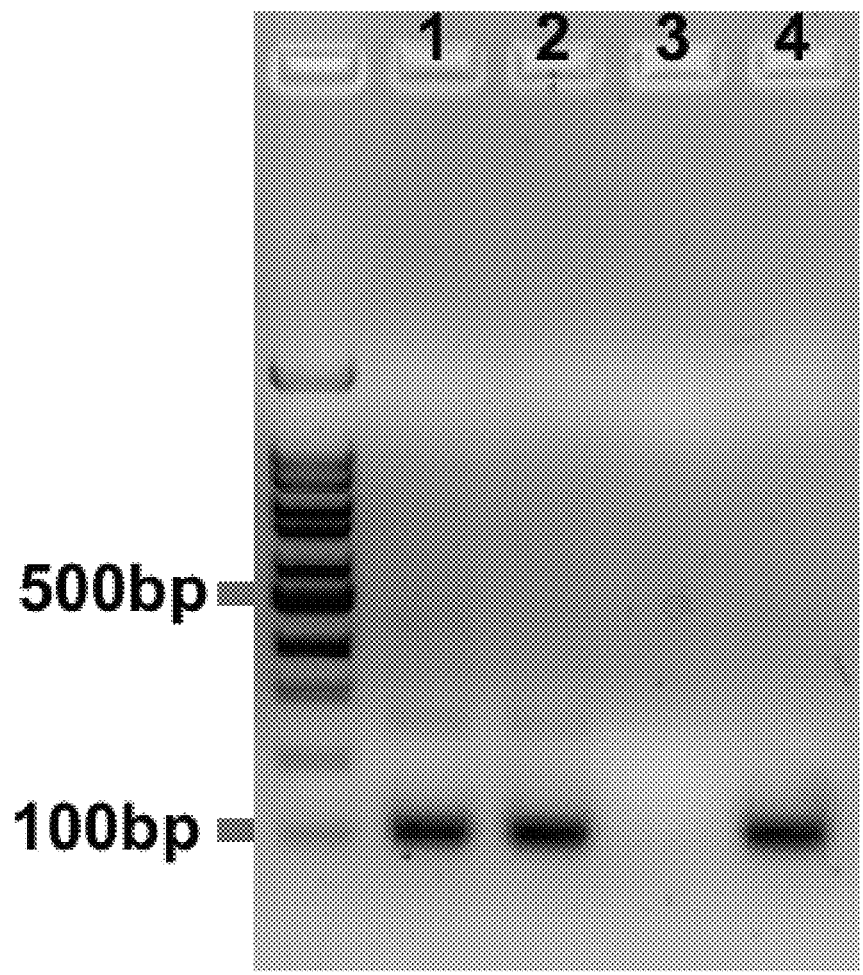
Figure 4E:
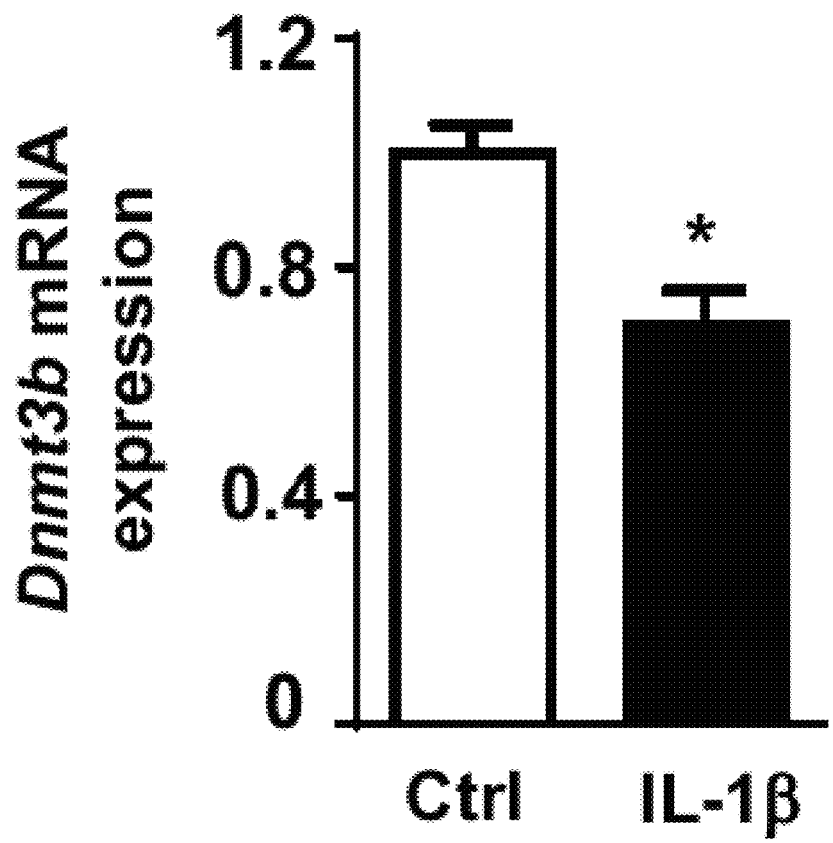
Figure 4F:
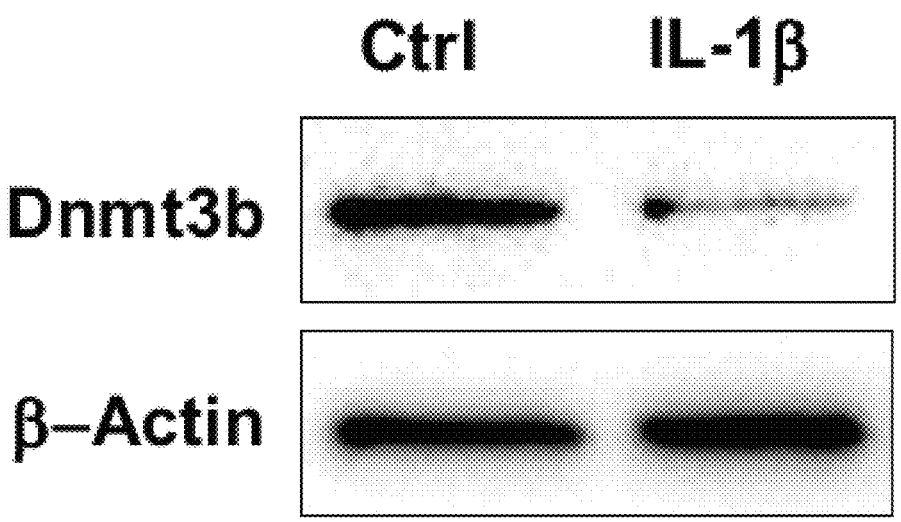

In human non-diseased articular cartilage tissue sections, abundant DNMT3B expression was consistently detected whereas expression was either undetectable or restricted to articular chondrocytes of the deep zone (FIG. 1J). DNMT3B gene expression was also found to be significantly lower in cells from OA cartilage and meniscal injured cartilage (FIG. 1K). Treatment of human primary articular chondrocytes (PACs) with the pro-inflammatory cytokine, IL-1β, resulted in decreased DNMT3B mRNA and protein expression (FIG. 1L, FIG. 1M). These PACs were obtained from knee joints following total knee replacement surgery and were found to be responsive to IL-1β based on the expected expression changes of COL2A1 and MMP-13 (FIG. 3A, FIG. 3B). Similarly, Dnmt3b expression was also decreased in murine primary chondrocytes in response to IL-1β (FIG. 4E, FIG. 4F). These data suggest that inflammatory mediators (known to increase in the context of OA) may regulate DNMT3B. In fact, the inventors identified an NF-κB binding site in the promoter region of the murine Dnmt3b gene (also present in the human DNMT3B promoter) (FIG. 4A). Luciferase reporter assays showed functional utilization of the NF-κB binding site following IL-1β treatment of murine ATDC-5 cells; this affect was attenuated following mutation of the binding site (FIG. 4B). NF-κB interaction with its binding site was also shown by chromatin immunoprecipitation assays (FIG. 4C, FIG. 4D).

Figure 5A:
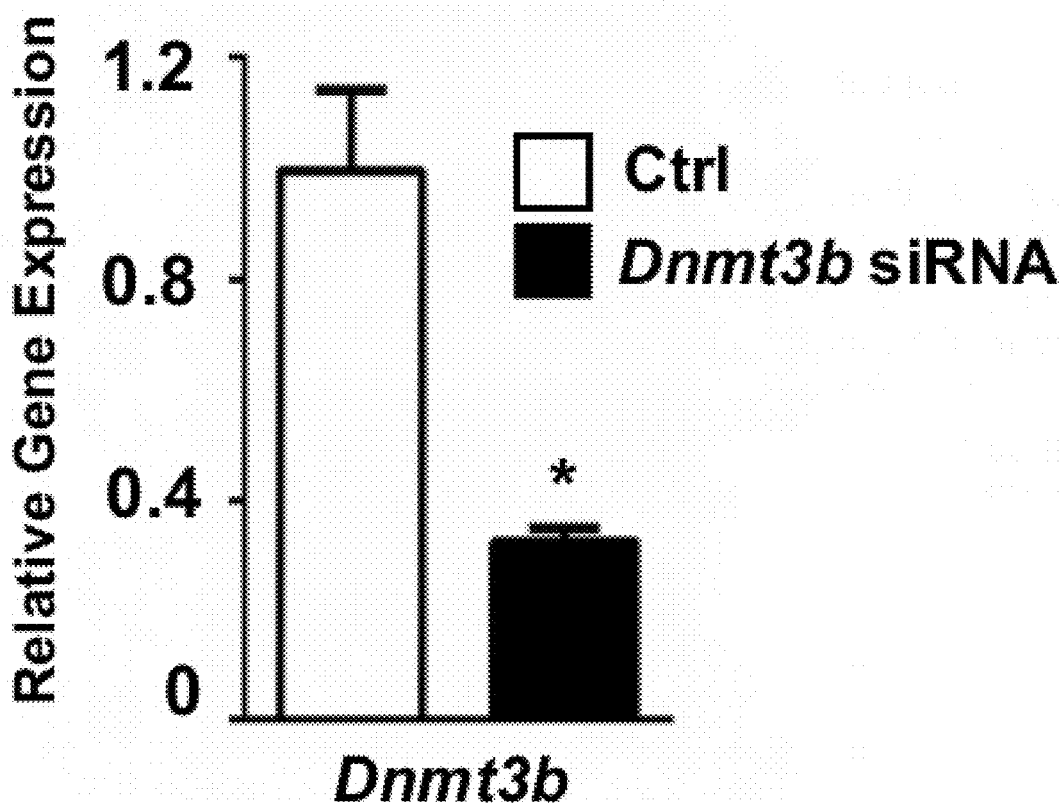
FIG. 5A, FIG. 5B, FIG. 5C, FIG. 5D, FIG. 5E and FIG. 5F depicts graphs, immunoblots and images showing that ablation of Dnmt3b in articular chondrocytes in vitro alters cell homeostasis. Reduced expression of (FIG. 5A) Dnmt3b mRNA and (FIG. 5B) Dnmt3b protein following transfection with 20 nM Dnmt3b si RNA for 48 h in murine primary chondrocytes isolated from 3 mo WT mice.
Figure 5B:
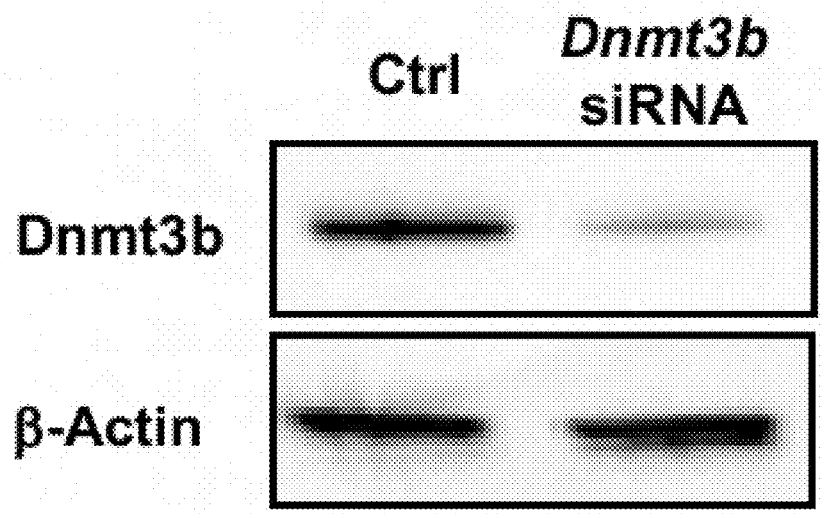
Figure 5C:
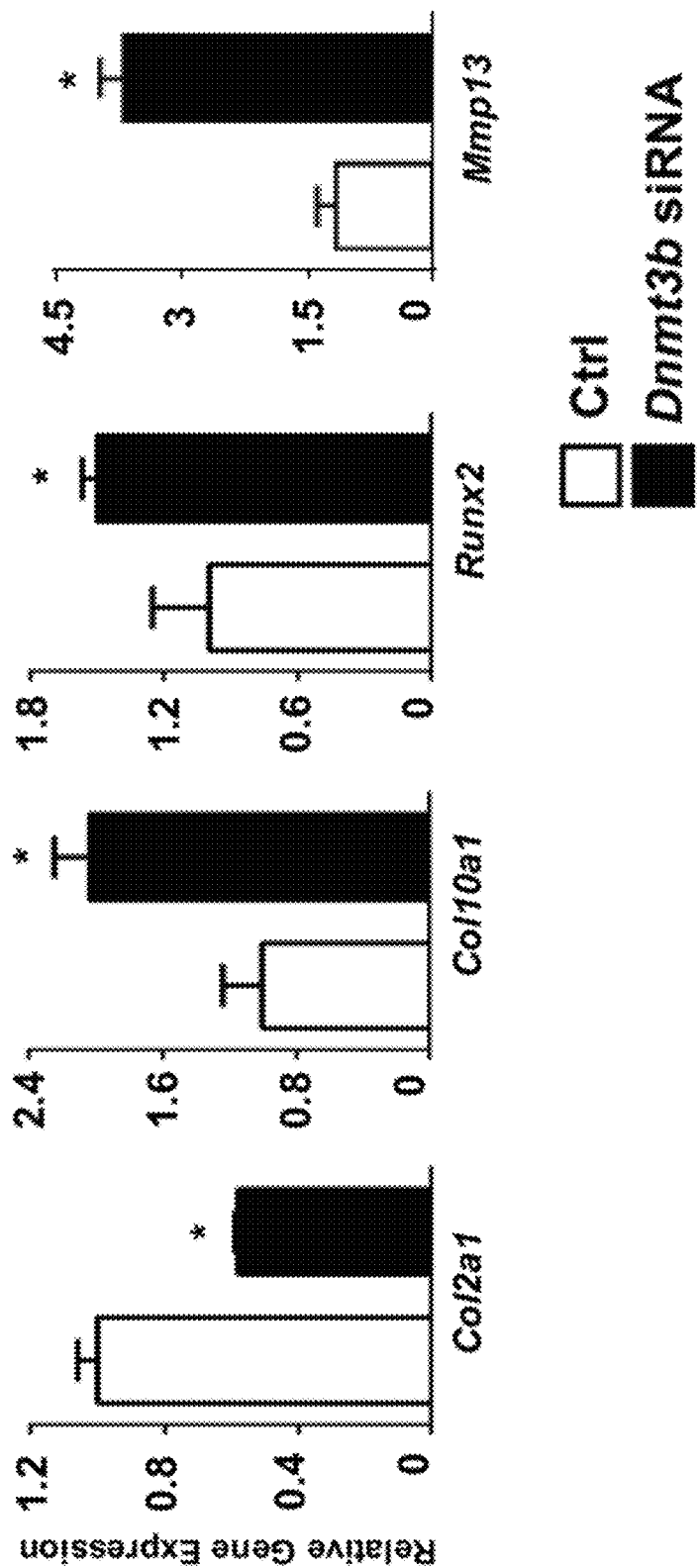
Figure 5D:
Figure 5E:
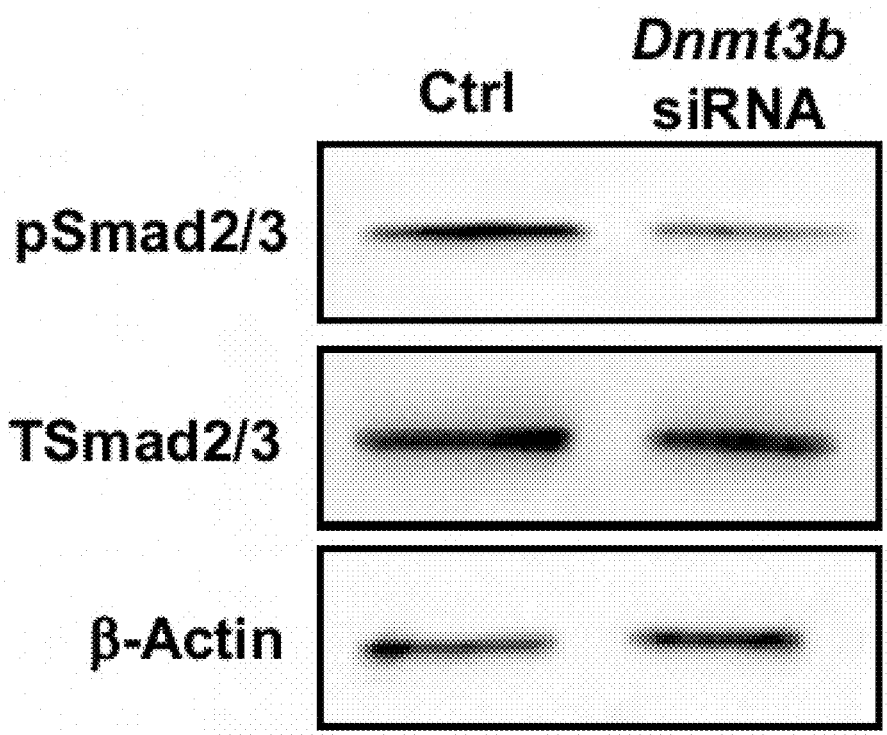
Figure 5F:
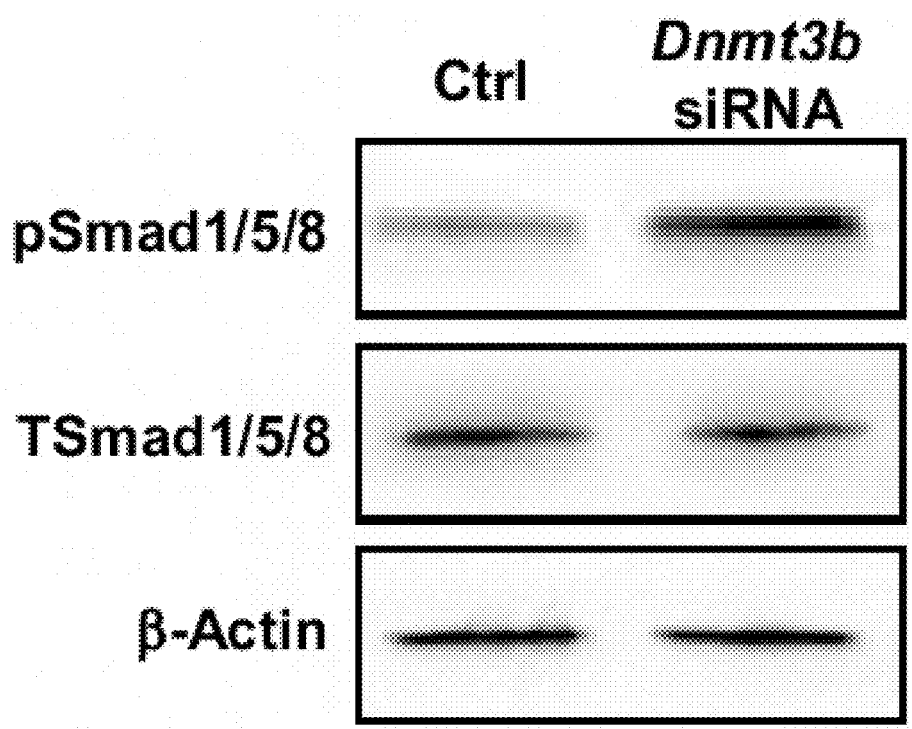

Given the trend toward decreased Dnmt3b expression with age and OA, the effect of Dnmt3b knock-down in murine PACs (FIG. 5A, FIG. 5B) was examined. Knockdown resulted in decreased expression of the anabolic cartilage gene, Col2a1, and increased expression of markers associated with catabolism or terminal hypertrophic chondrocyte differentiation (Col10a1, Runx2, Mmp13) (FIG. 5C). Alkaline phosphatase (ALP) activity also increased in PACs following Dnmt3b knock-down, albeit not to the level induced by BMP-2 (FIG. 5D). Since TGF-β and BMP signaling can have opposing effects on chondrocyte catabolism[28], Smad signaling was analyzed following Dnmt3b knock-down. Phospho-Smad (p-Smad)2/3 levels decreased while p-Smad1/5/8 levels increased following Dnmt3b siRNA treatment (FIG. 5E, FIG. 5F). This suggests that increased BMP-2 signaling may, in part, explain the increase in chondrocyte catabolism.

Example 2

Figure 7A:
FIG. 7A and FIG. 7B depict images and an immunoblot showing ablation of Dnmt3b in articular chondrocytes in vivo.
Figure 7A:
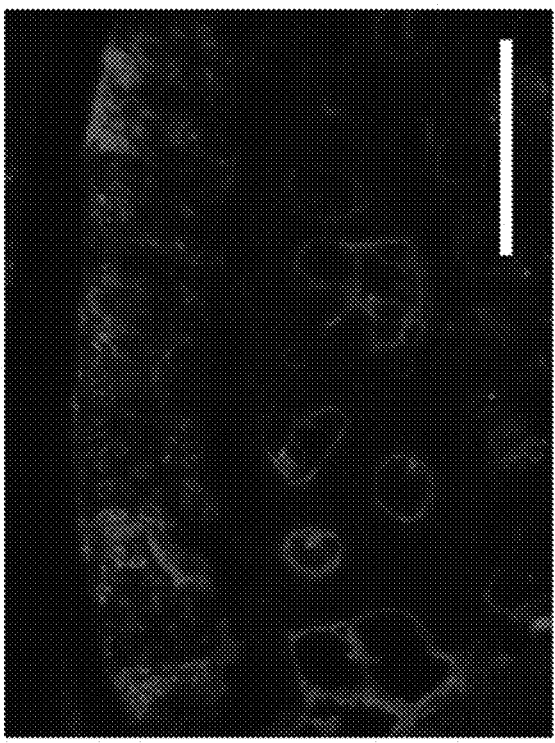
Figure 7B:
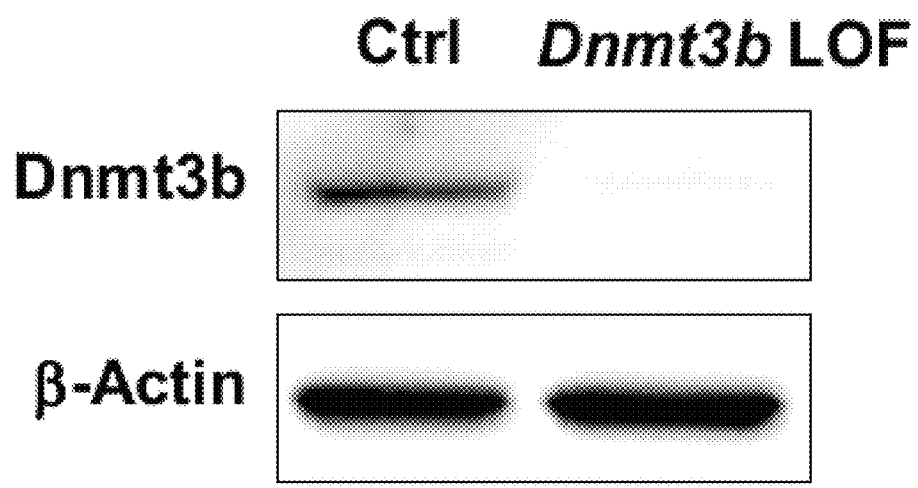
Figure 8A:
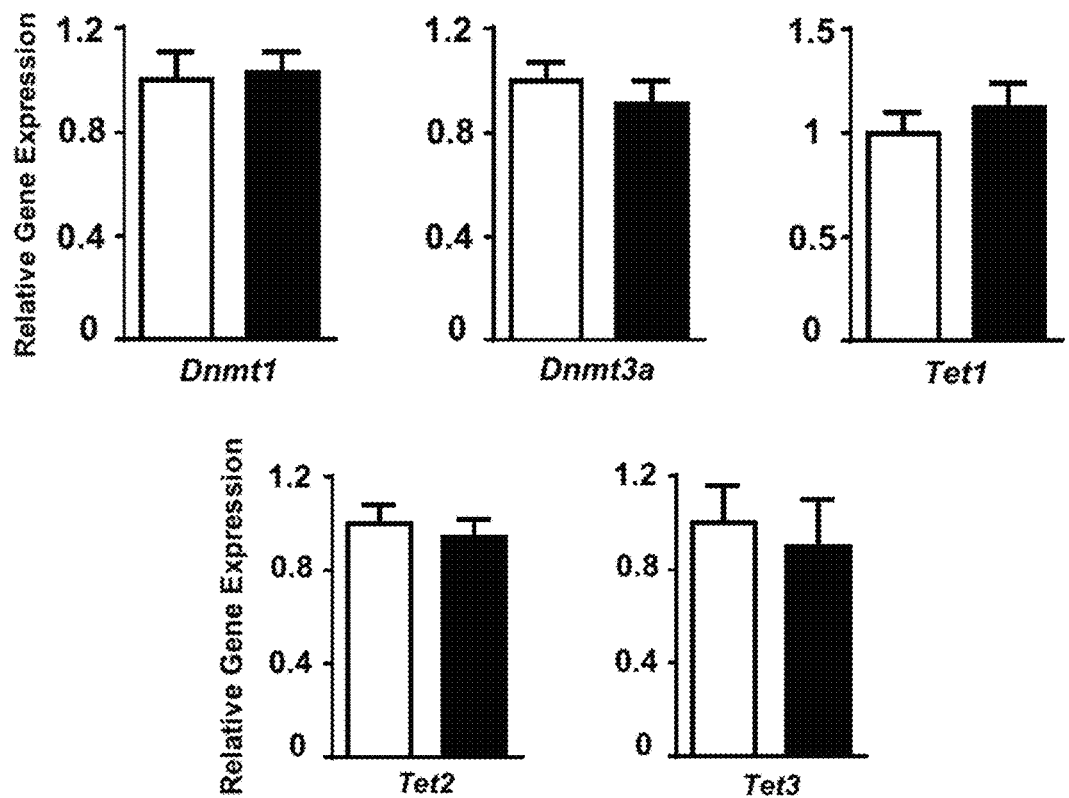
FIG. 8A and FIG. 8B depict graphs showing expression of Dnmt and Tet enzymes in Dnmt3b LOF cartilage tissue.
Figure 8B:
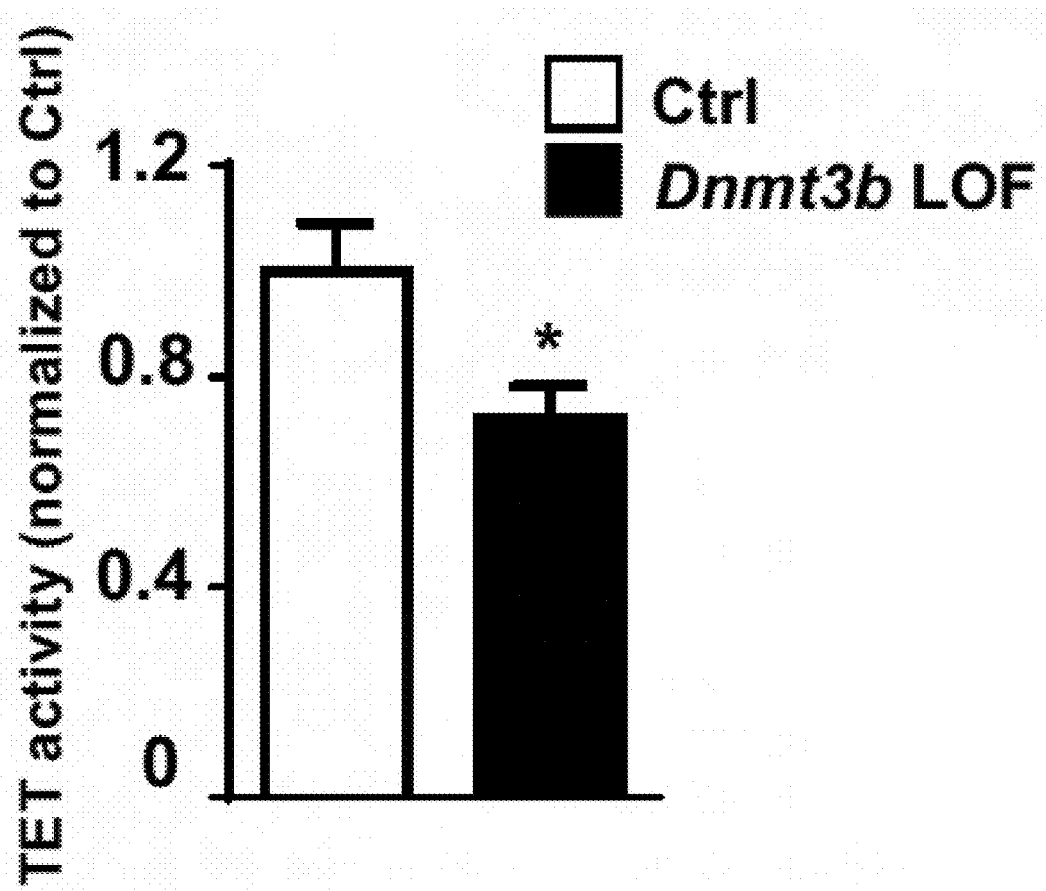
Figure 9:
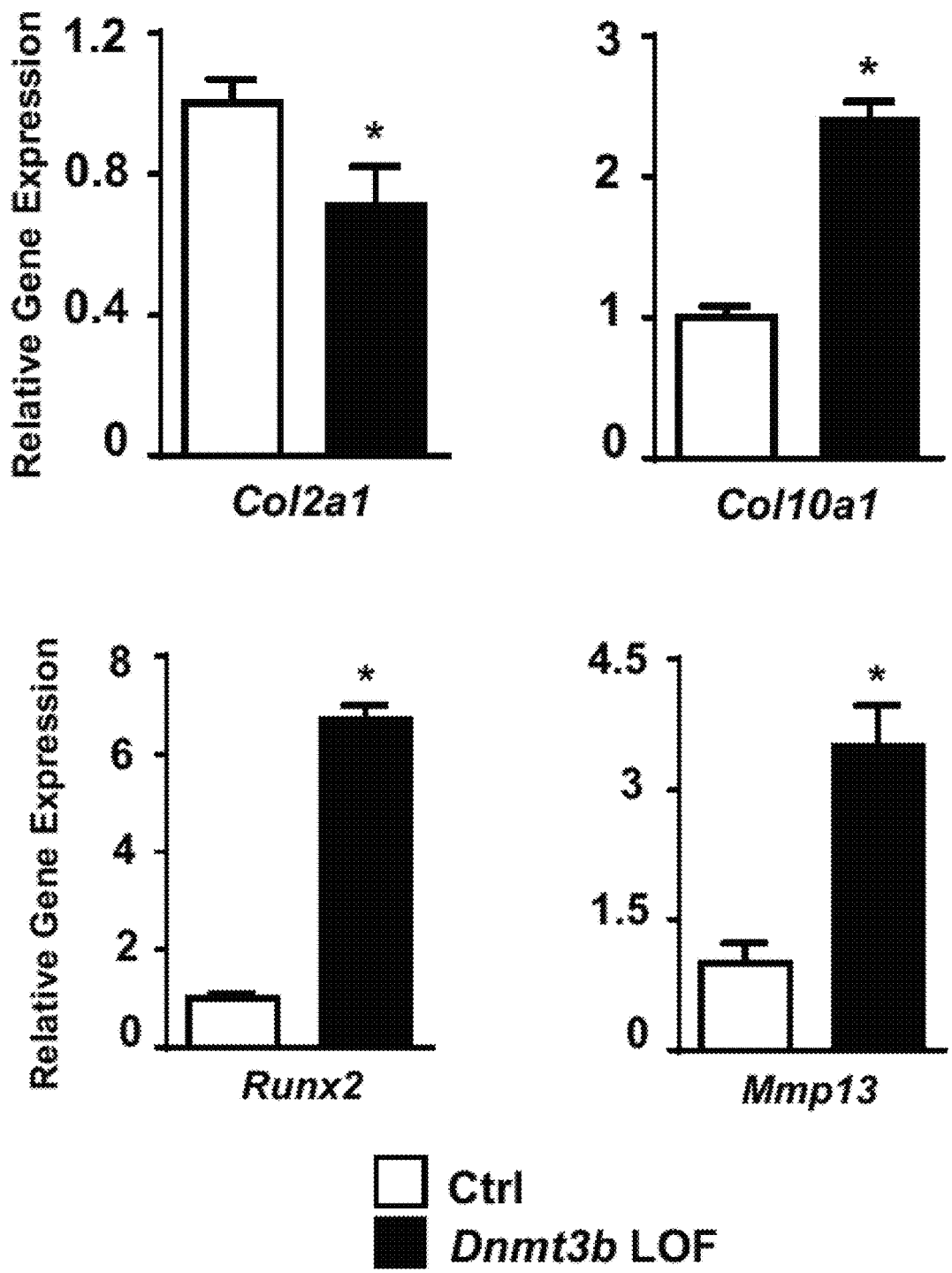
FIG. 9 depicts graphs showing anabolic and catabolic gene expression in Dnmt3b LOF cartilage tissue. Col2a1 (anabolic) and Col10a1, Runx2 and Mmp13 (catabolic/hypertrophic) marker expression in articular chondrocytes from 3 mo Dnmt3b LOF and Cre+ control (Ctrl) mice.

Dnmt3b Conditional Knock-down In Vivo Results in a Progressive OA-Like Pathology Conditional knock-down of Dnmt3b in cartilage was achieved by generating AgcCre$^{ERT2}$; Dnmt3b f/f (Dnmt3b loss-of-function; LOF) transgenic mice. The specificity of the AgcCre$^{ERT}$ driver line[29] to target chondrocytes was confirmed by crossing with Rosa-tomato (mT/mG) mice (FIG. 7A). Decreased Dnmt3b protein expression was confirmed in articular cartilage from Dnmt3b LOF mice (FIG. 7B). Analysis of the other Dnmts (Dnmt3a and Dnmt1) and the ten-eleven translocation (TET) DNA demethylation enzymes (Tet1, 2, 3) showed no significant changes in their expression in Dnmt3b LOF cartilage (FIG. 8A), while Tet activity was found to decrease (FIG. 8B). As expected, Col2a1 expression was decreased in Dnmt3b LOF chondrocytes while expression of Col10a1, Runx2 and Mmp13 increased (FIG. 9).

Figure 6A:
FIG. 6A, FIG. 6B, FIG. 6C, FIG. 6D, FIG. 6E, FIG. 6F, FIG. 6G, FIG. 6H, FIG. 6I, FIG. 6J and FIG. 6K depicts images and graphs showing that Dnmt3b loss-of-function mice develop accelerated OA. Tissue sections of knee joints harvested from 5 mo and 8 mo Dnmt3b loss-of-function (LOF) mice (FIG. 6B, FIG. 6C, FIG. 6E, FIG. 6F) and Cre+ control (Ctrl) mice (FIG. 6A, FIG. 6D) were analyzed by alcian blue/hematoxylin/orange G (ABH/OG) staining.
Figure 6B:
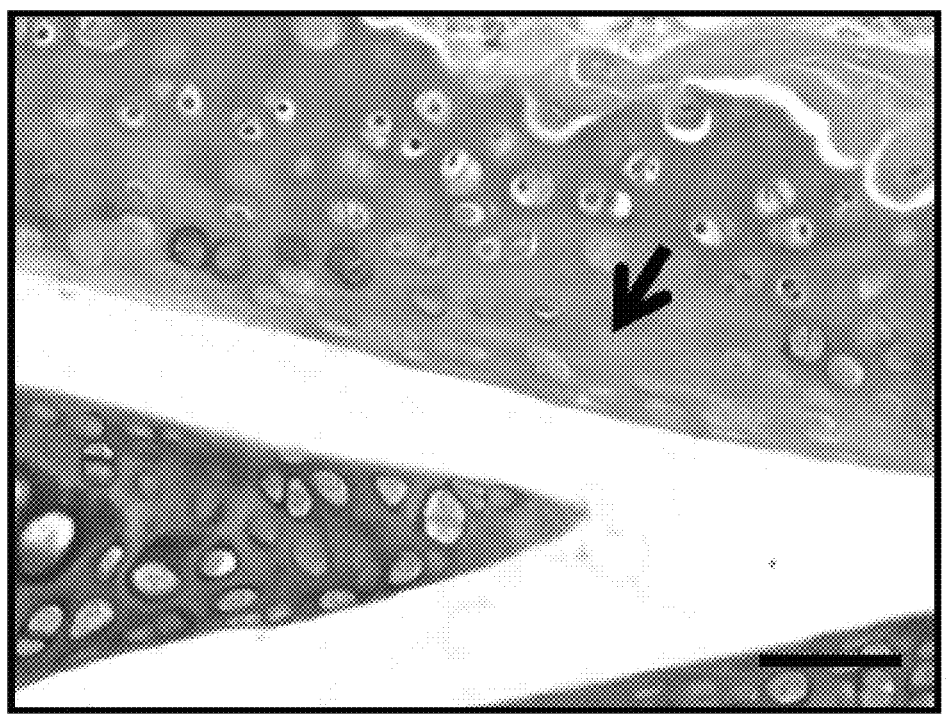
Figure 6C:
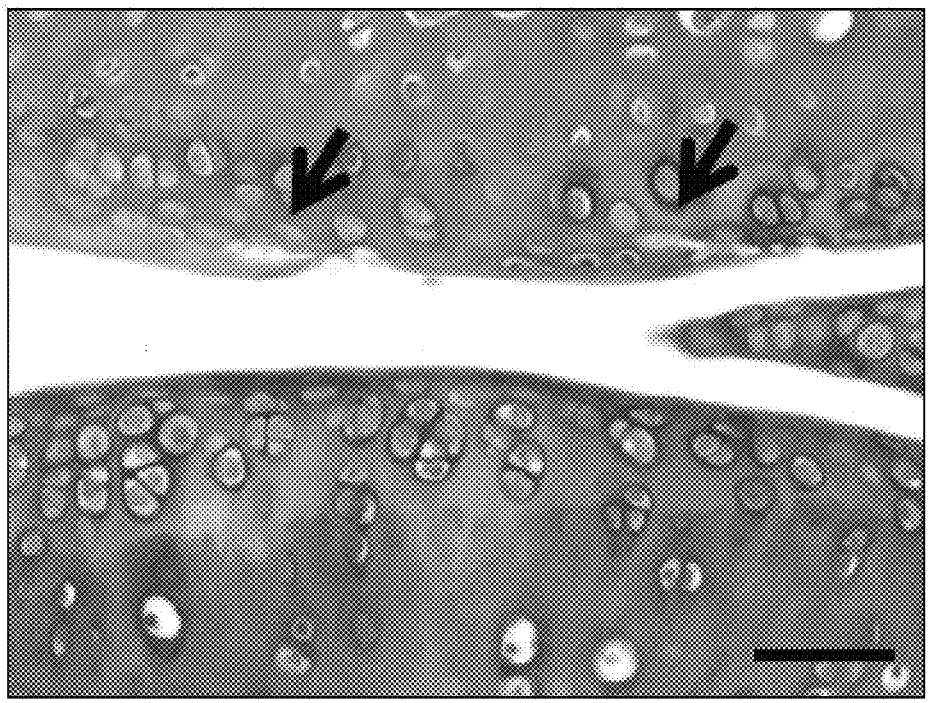
Figure 6D:
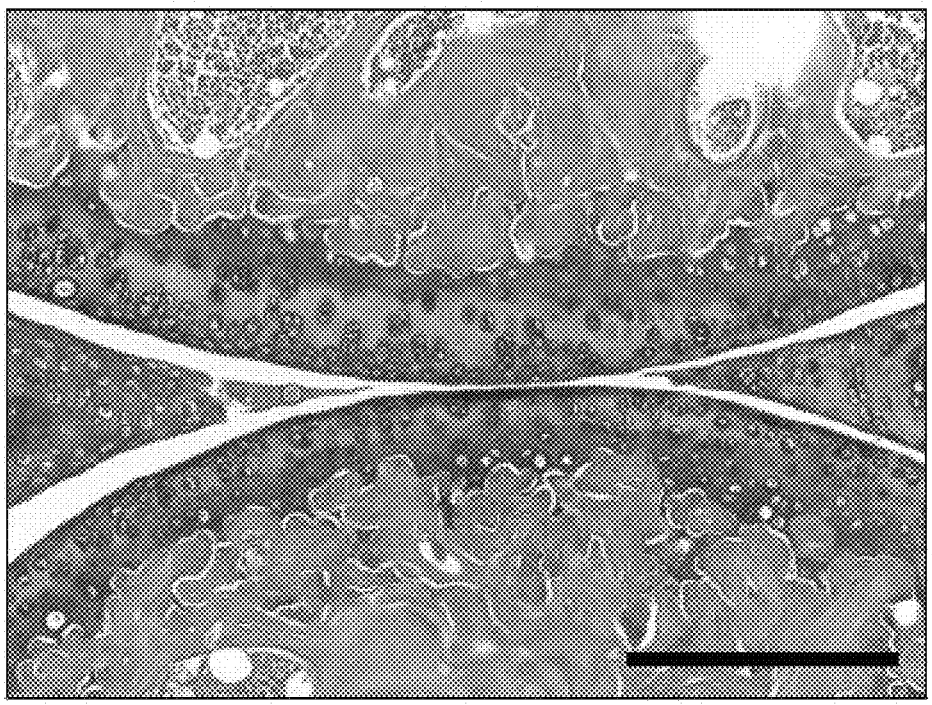
Figure 6E:
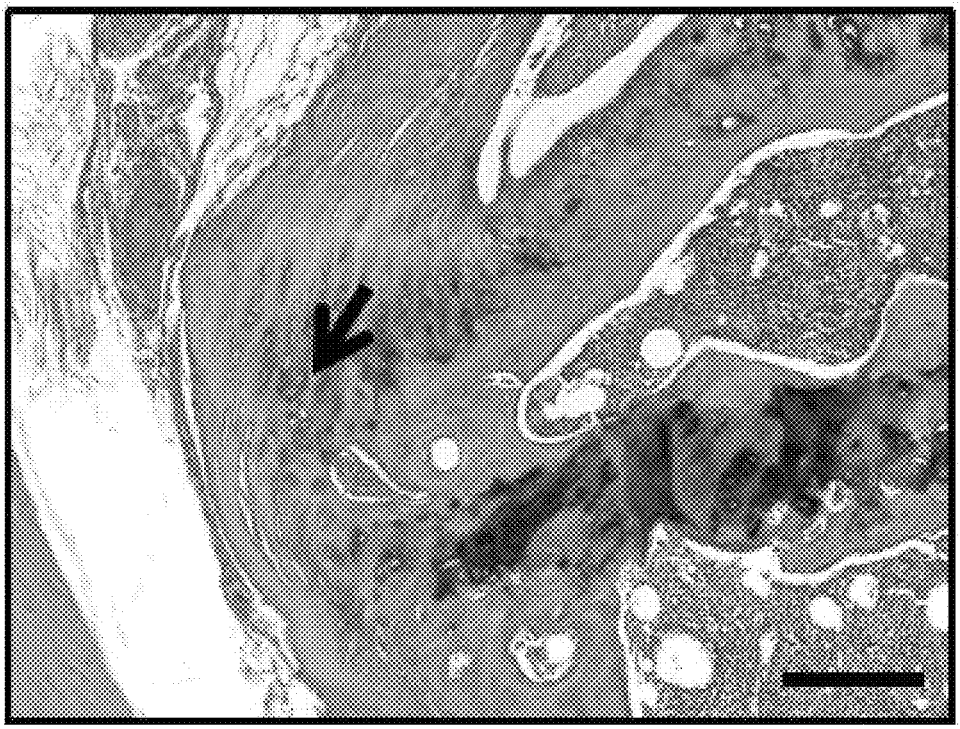
Figure 6F:
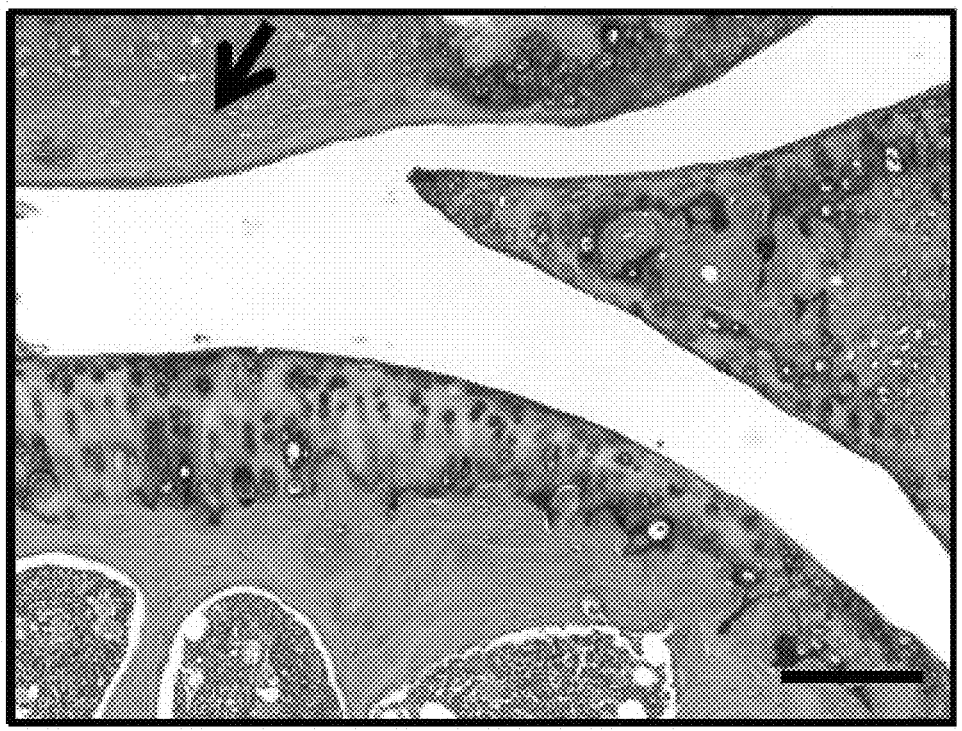
Figure 6G:
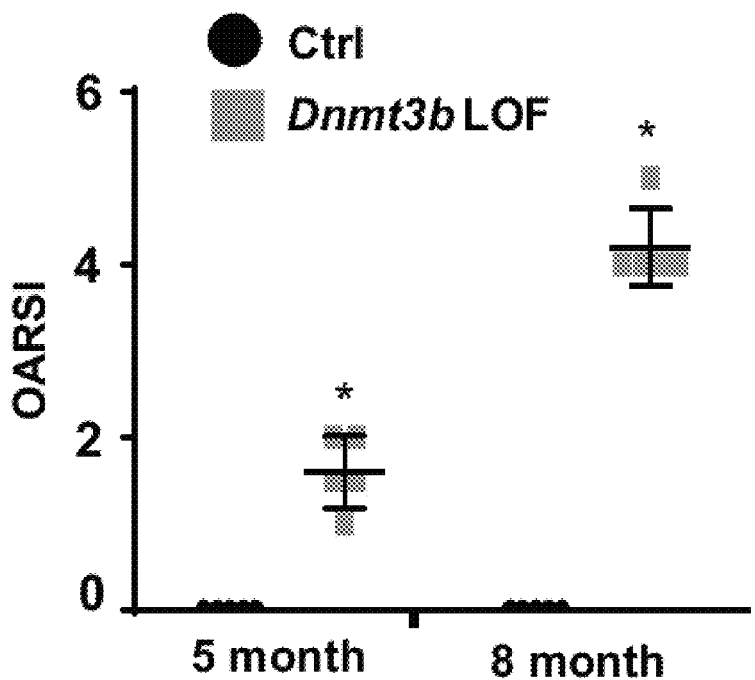
Figure 6H:
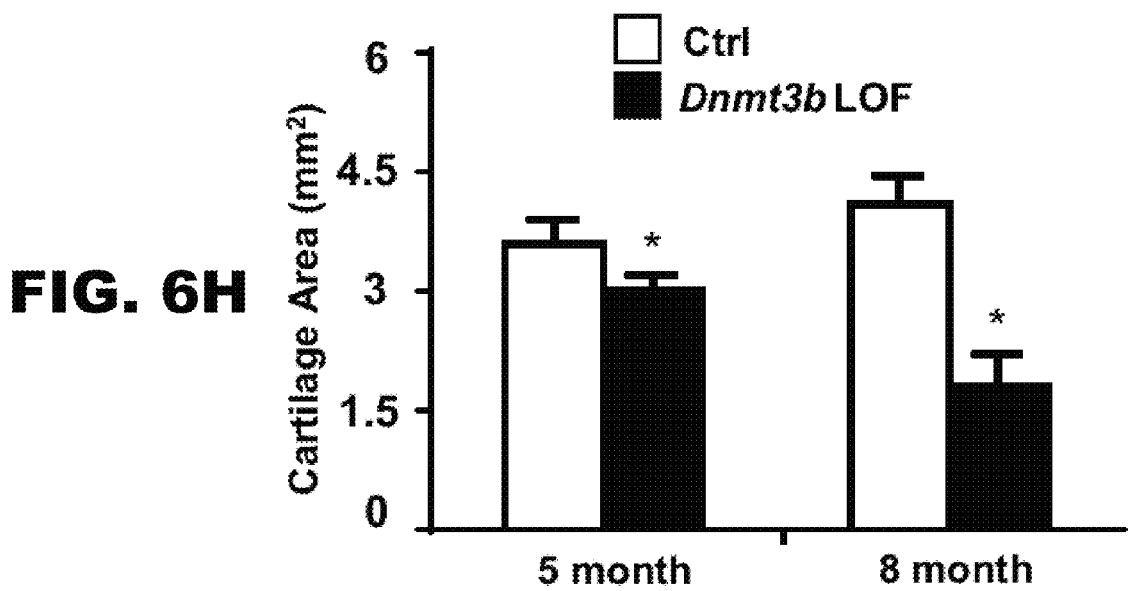
Figure 6I:
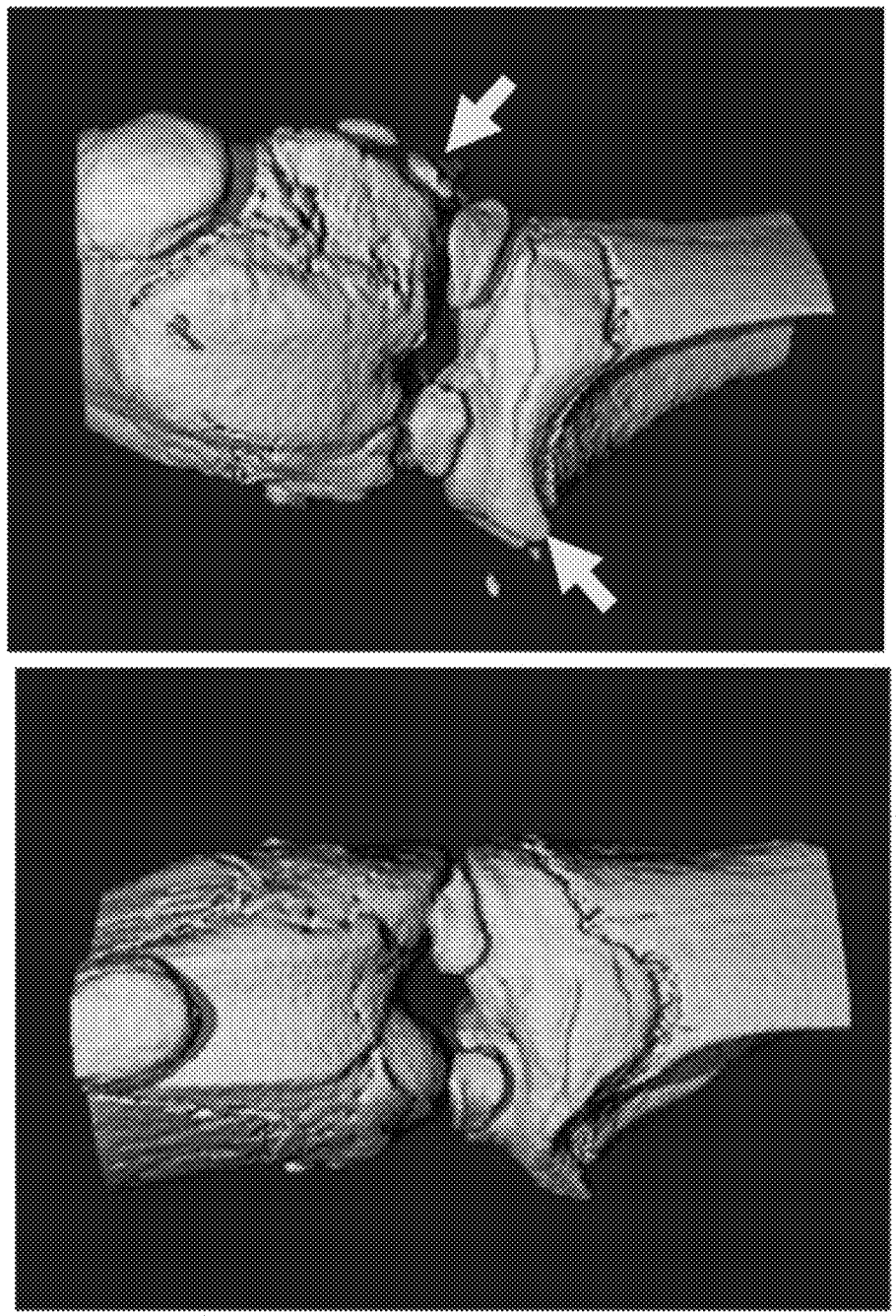
Figure 6J:
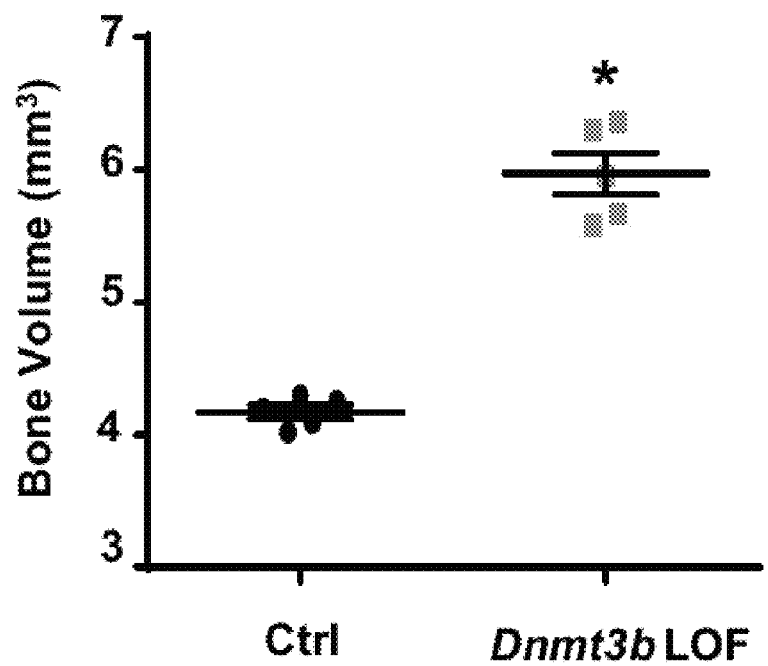
Figure 6K:
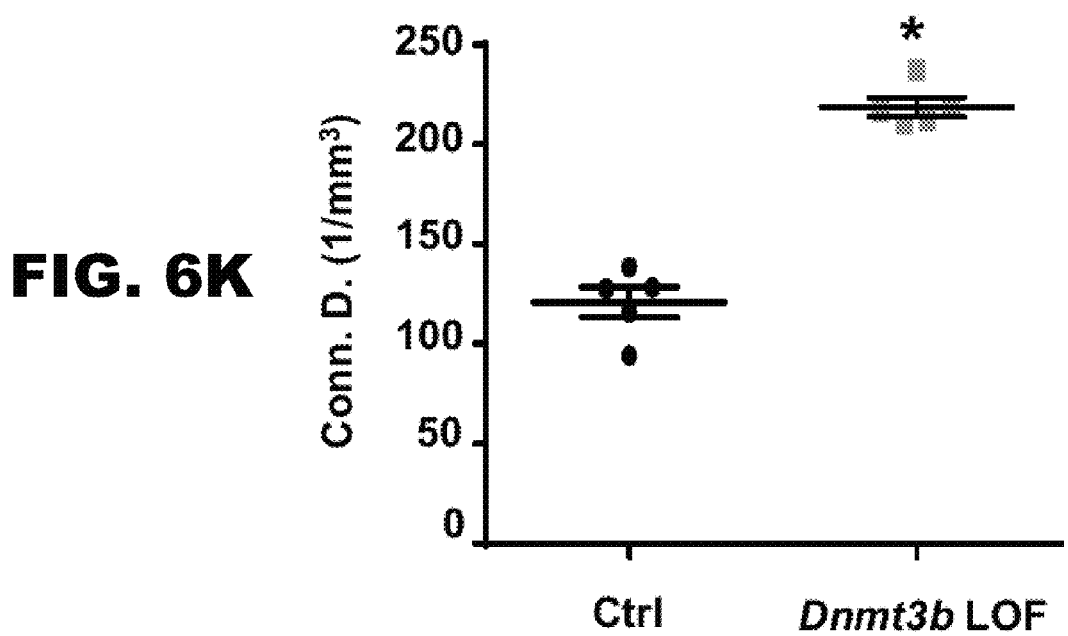
Figure 10A:
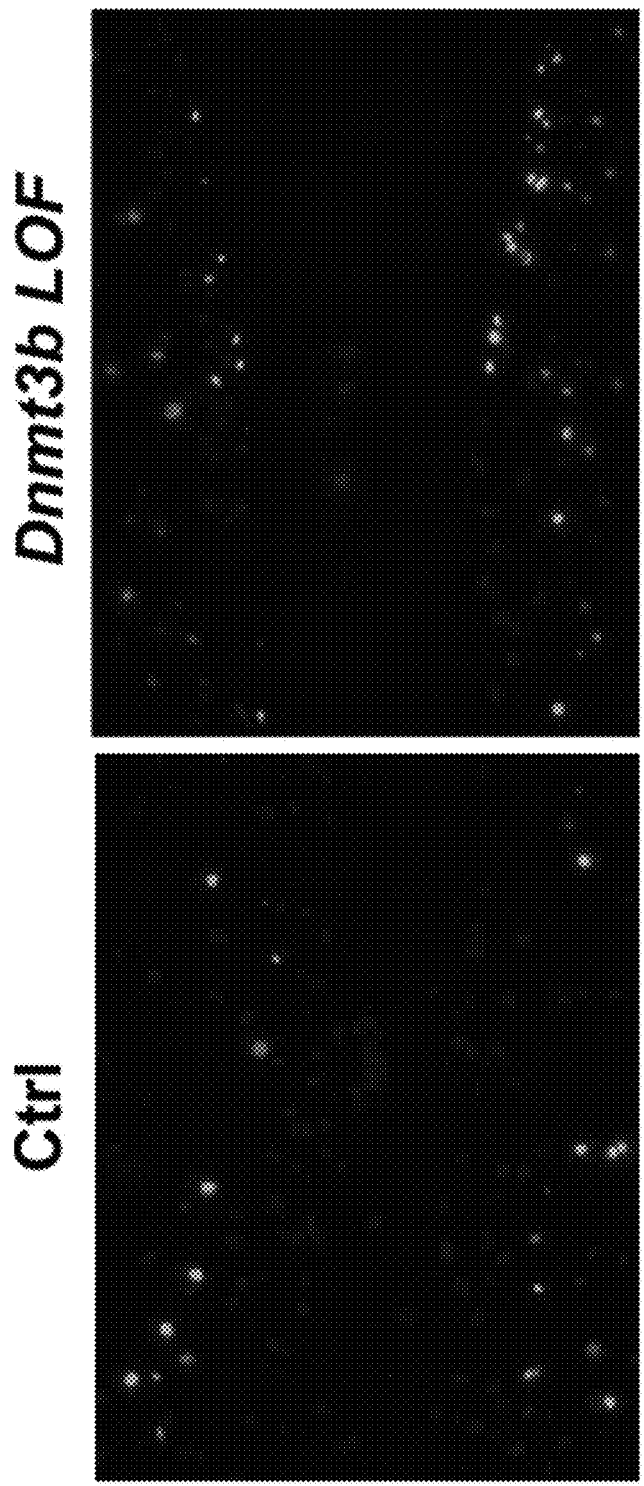
FIG. 10A, FIG. 10B and FIG. 10C depict images and graphs showing analysis of apoptosis and reactive oxygen species in Dnmt3b LOF cartilage.
Figure 10B:
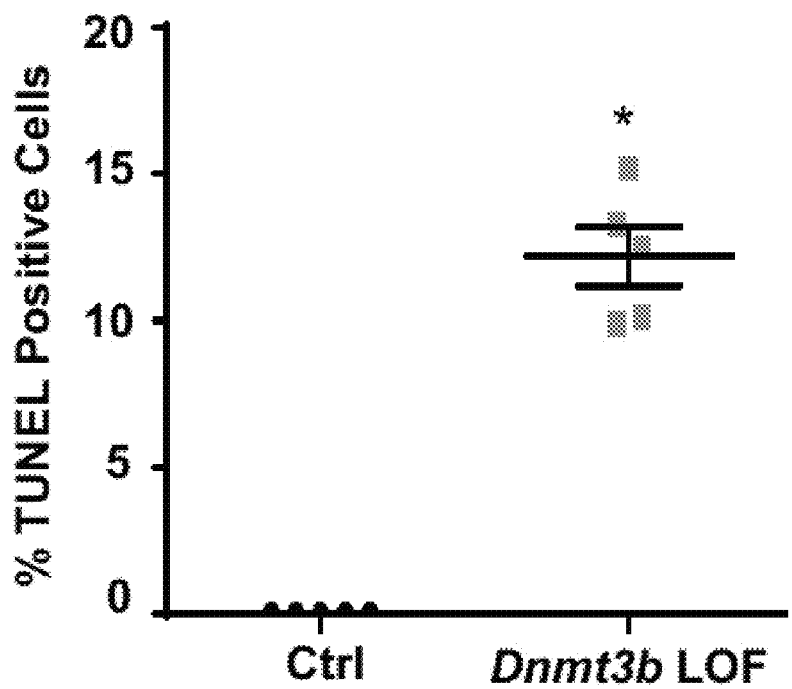
Figure 10C:
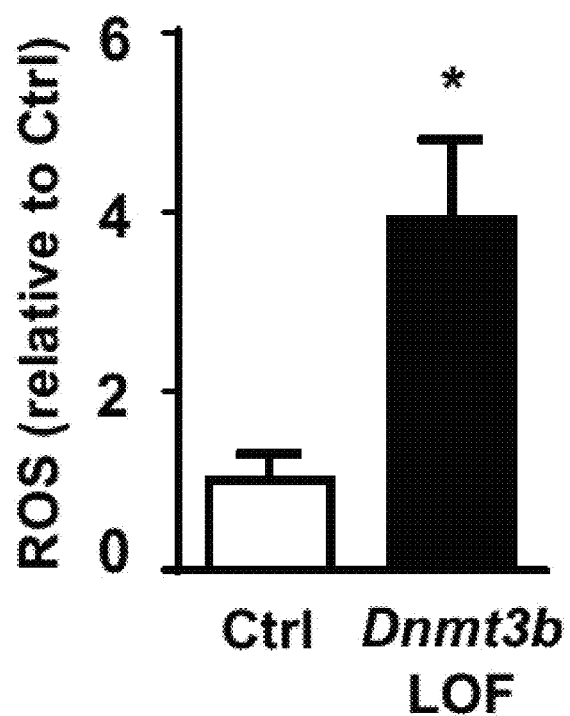

Histological and histomorphometric assessment of knee joints from aged male Dnmt3b LOF mice (compared to Cre+ controls) showed features of OA (proteoglycan loss, cartilage fibrillation and clefting, osteophyte production, increased OARSI score, decreased cartilage area) (FIG. 6A, FIG. 6B, FIG. 6C, FIG. 6D, FIG. 6E, FIG. 6F, FIG. 6G, FIG. 6H). MicroCT analysis showed the presence of osteophytes (FIG. 6I) and quantification of scanned images showed increased subchondral bone thickness in Dnmt3b LOF mice compared to age matched controls (FIG. 2J, FIG. 2K). Dnmt3b LOF cartilage also contained increased numbers of apoptotic cells and levels of reactive oxygen species (FIG. 10A, FIG. 10B, FIG. 10C).

Example 3

Transcriptomic and Epigenomic Alterations in Dnmt3b LOF Chondrocytes

Figure 11A:
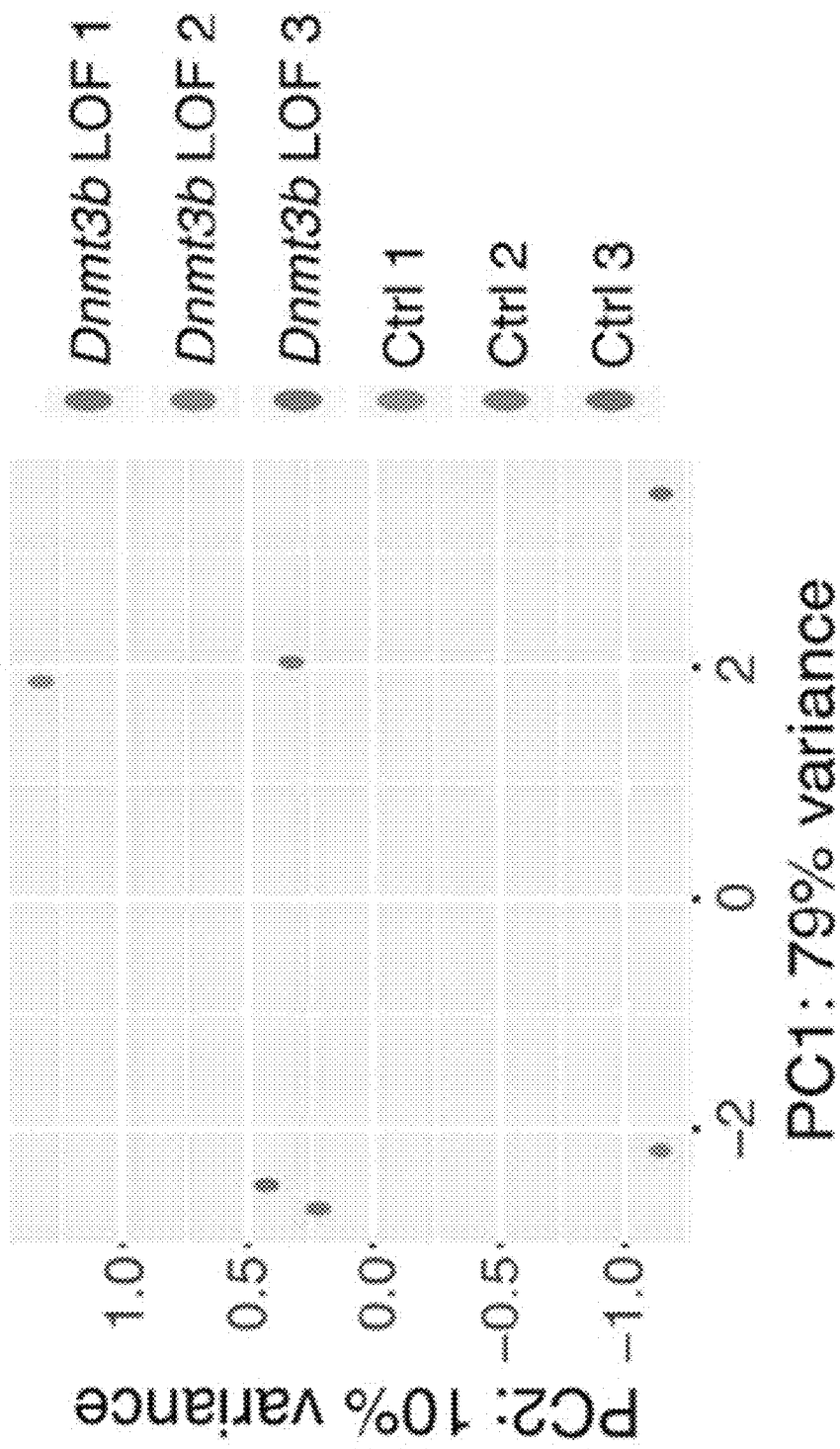
Figure 11B:
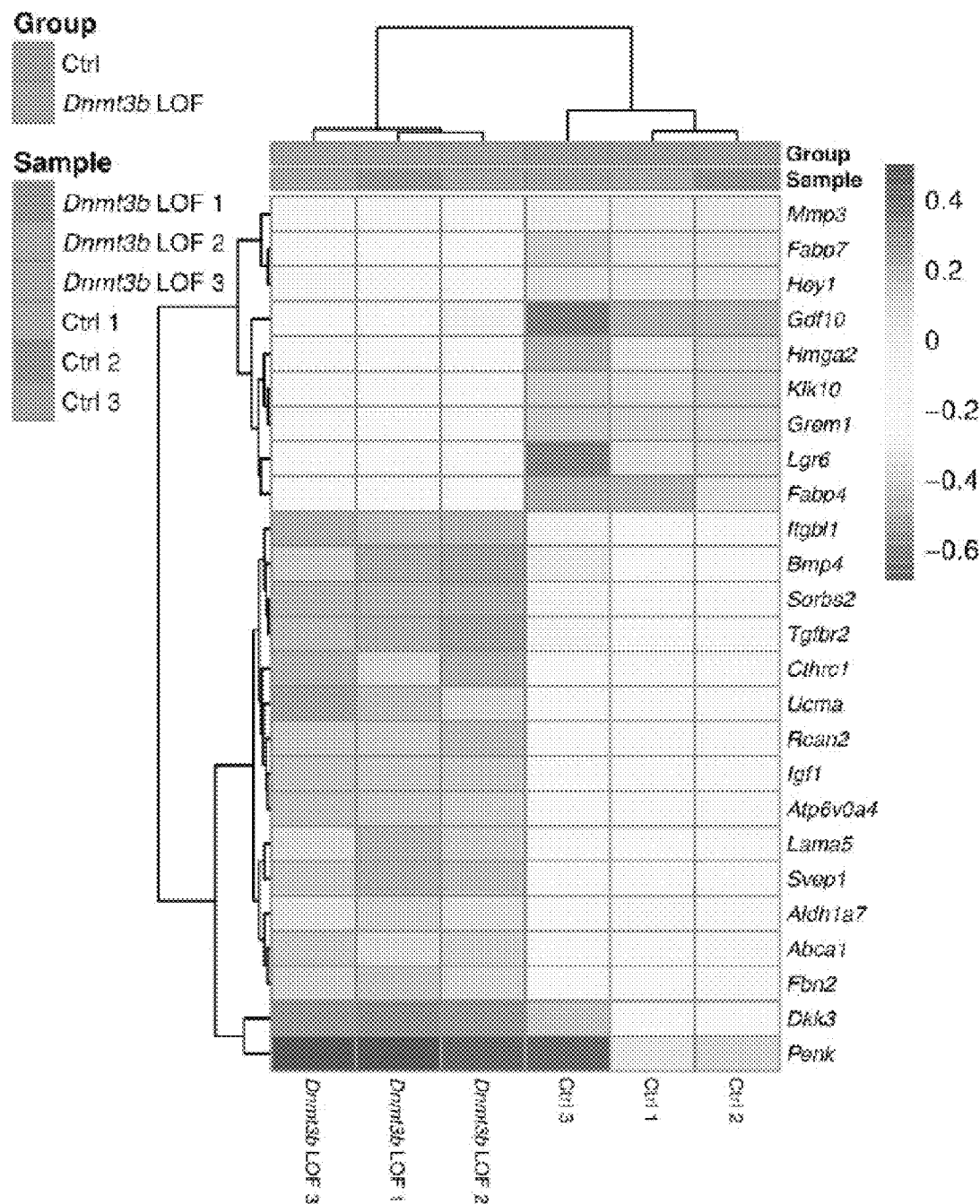
Figure 11C:
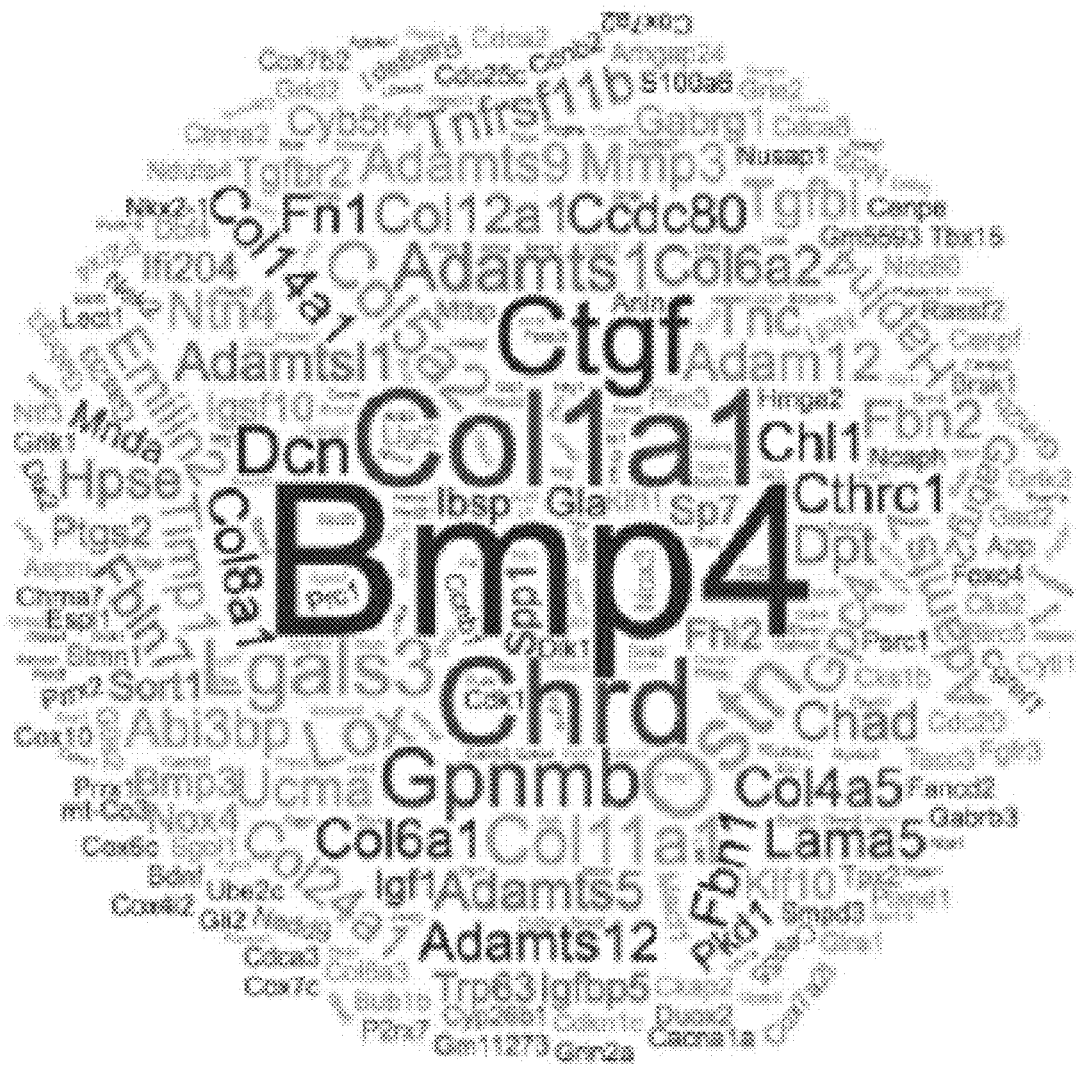

Dnmt3b LOF chondrocytes were generated in vitro followed by RNA-Seq and methylC-Seq analysis (see Methods) to examine genome wide gene transcription and DNA methylation alterations in LOF chondrocytes. Dnmt3b LOF was associated with subtle yet profound DNA methylation and gene expression changes (FIG. 11, FIG. 12). Global gene expression exhibited systematic differences between Dnmt3b LOF and control, as illustrated by their separation pattern in Principle Component Analysis (FIG. 11A) and in pairwise clustering analysis (FIG. 12A). Overall, 368 genes were significantly differentially expressed (FIG. 12B); the hierarchical clustering pattern of the top 25 differentially expressed genes is shown (FIG. 11B). These 368 genes include members of the BMP/TGF signaling pathways (e.g. Bmp4, Tgfbr2) as well as those involved in catabolic/ hypertrophic processes (e.g. Smad2/3, Runx2, Mmp13) (FIG. 11B, FIG. 11C, FIG. 12D). Overall, the RNA-Seq data showing alterations in BMP/TGF signaling and catabolic/ hypertrophic genes is in agreement with changes known to occur in OA as well as the in vitro and in vivo data presented here related to Dnmt3b LOF effects in vitro and in vivo. Gene ontology enrichment and Ingenuity Pathway analyses shows an enrichment in processes including cell death and survival, lipid metabolism, cell cycle as well as skeletal cells in arthritis (FIG. 11D, FIG. 11H).

Figure 11E:
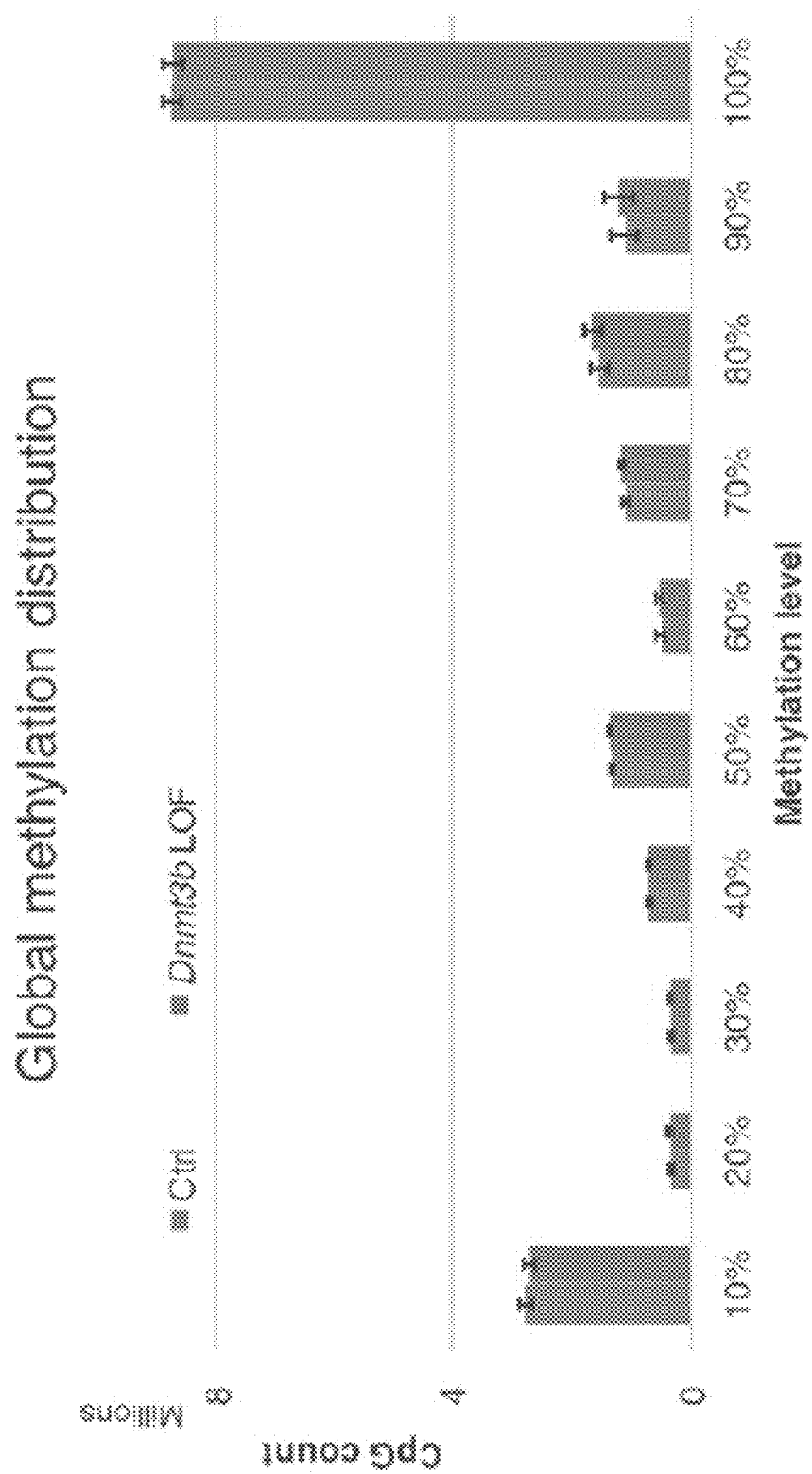
Figure 11F:
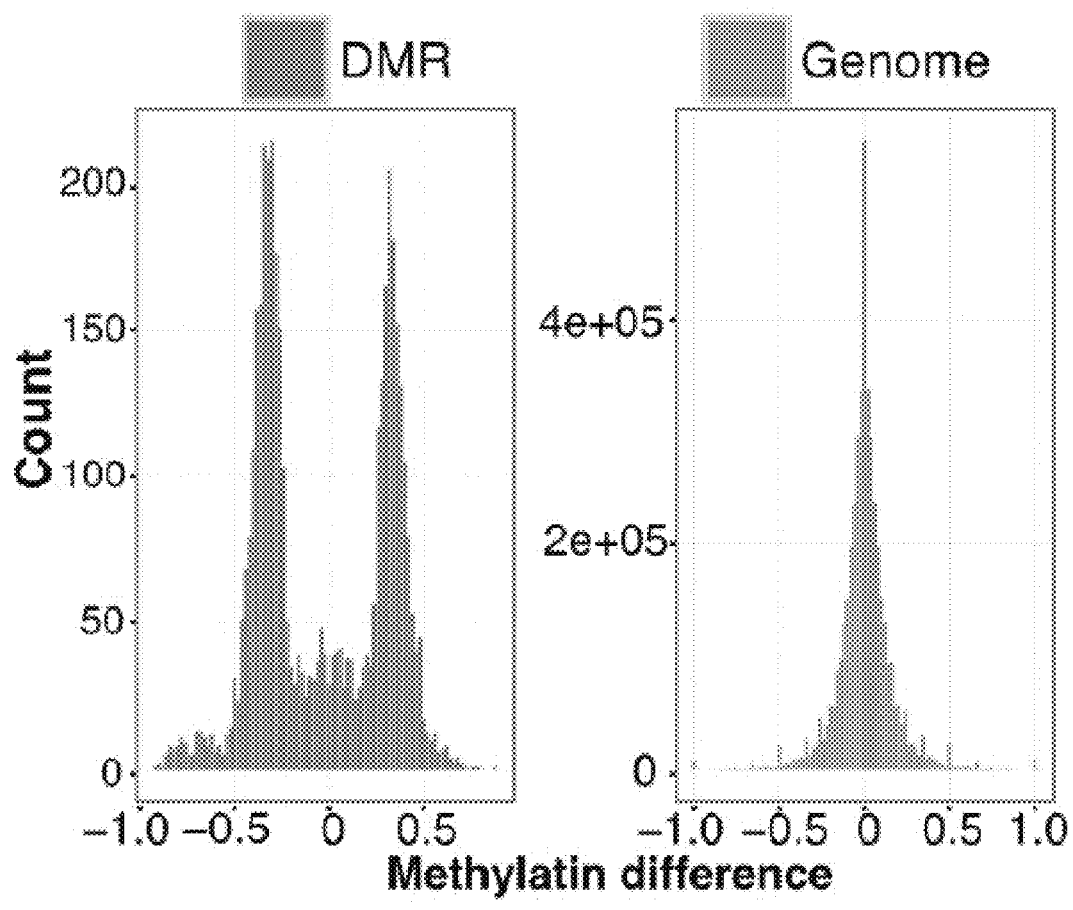
Figures 11G, 11H:
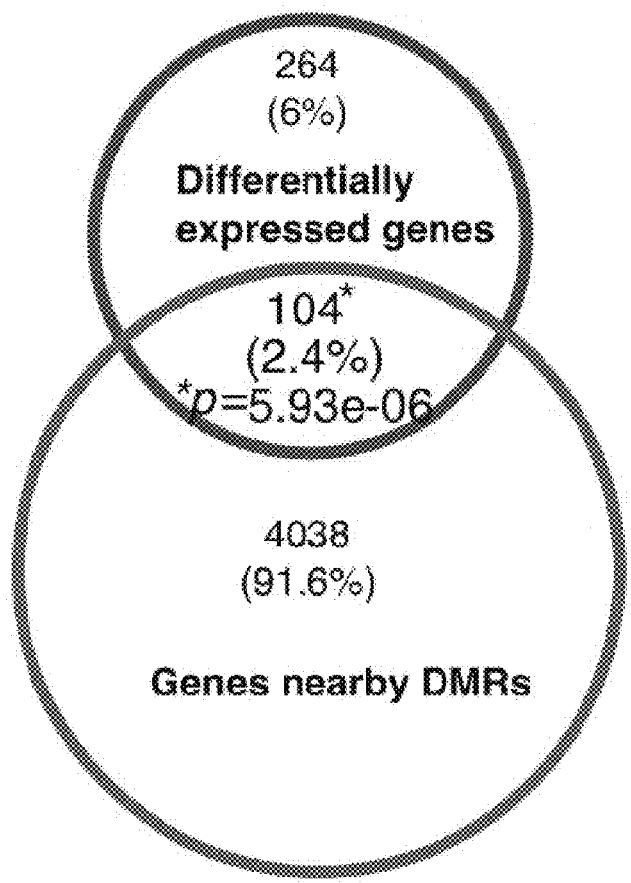
Figure 12A:
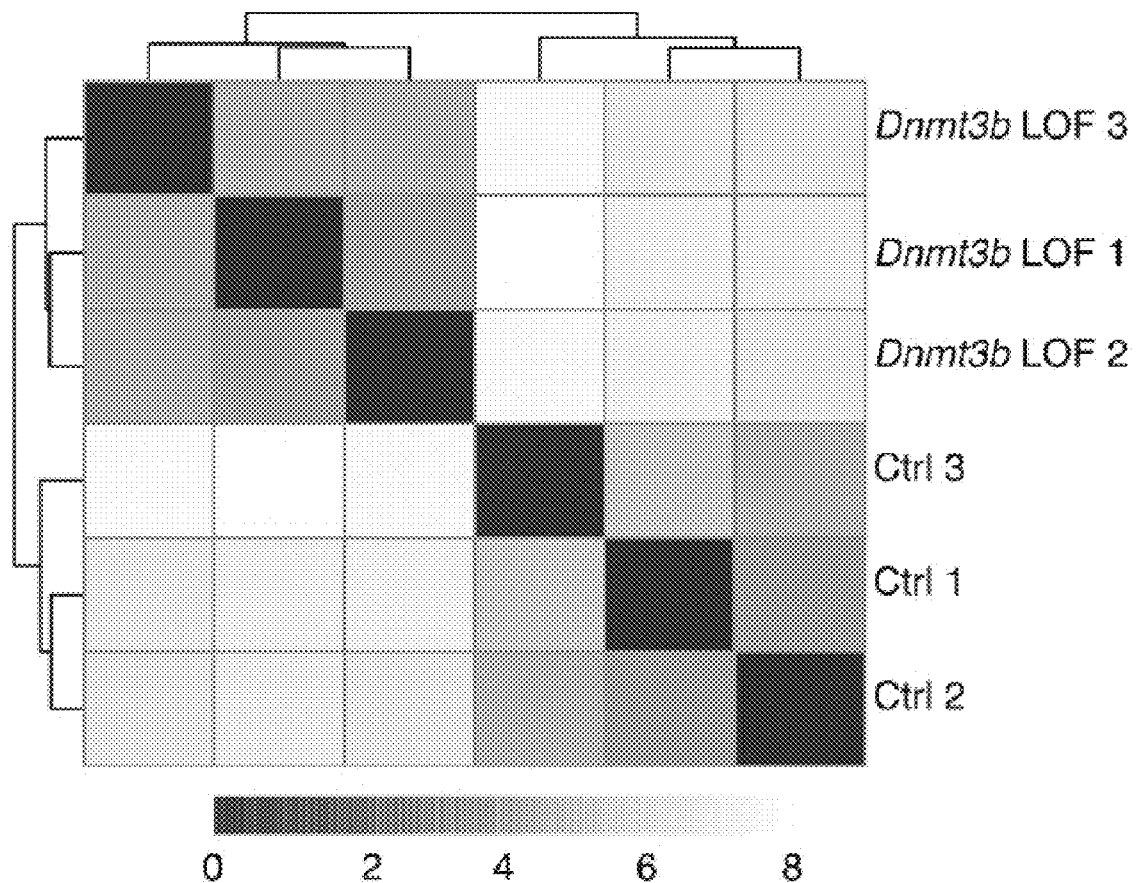
FIG. 12A, FIG. 12B, FIG. 12C, FIG. 12D, FIG. 12E and FIG. 12F depict graphs and images showing analysis of RNA-seq and methylC-seq data.
Figure 12B:
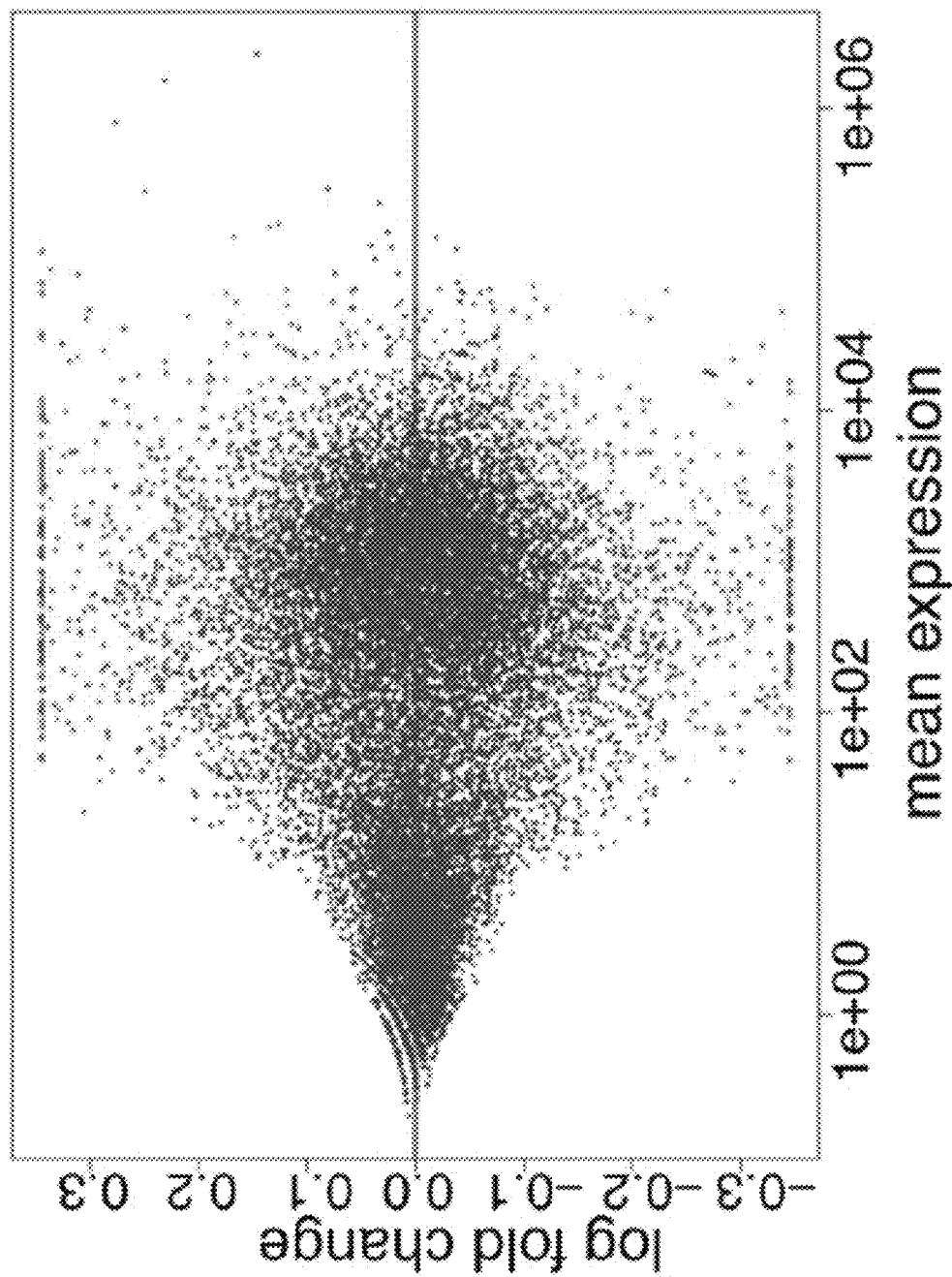
Figure 12C:
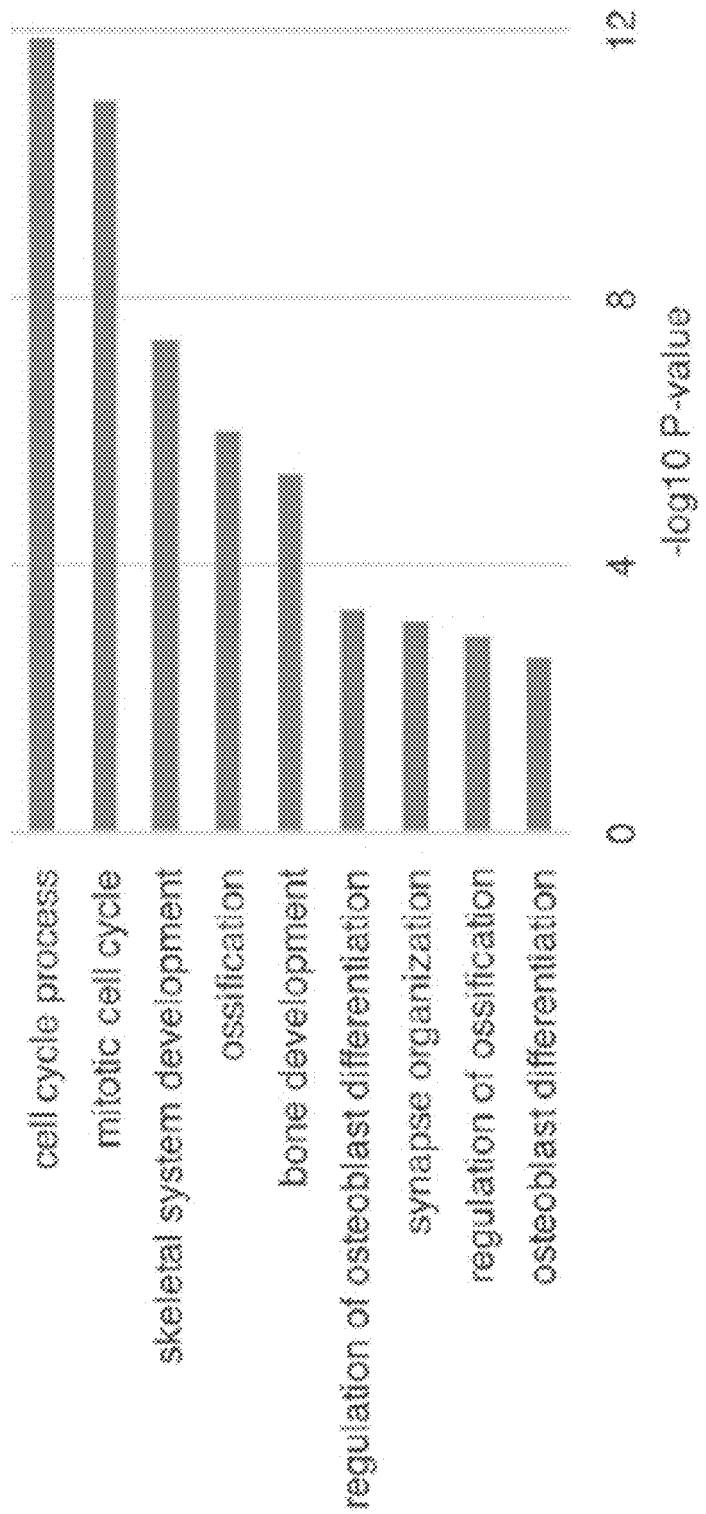
Figure 12D:
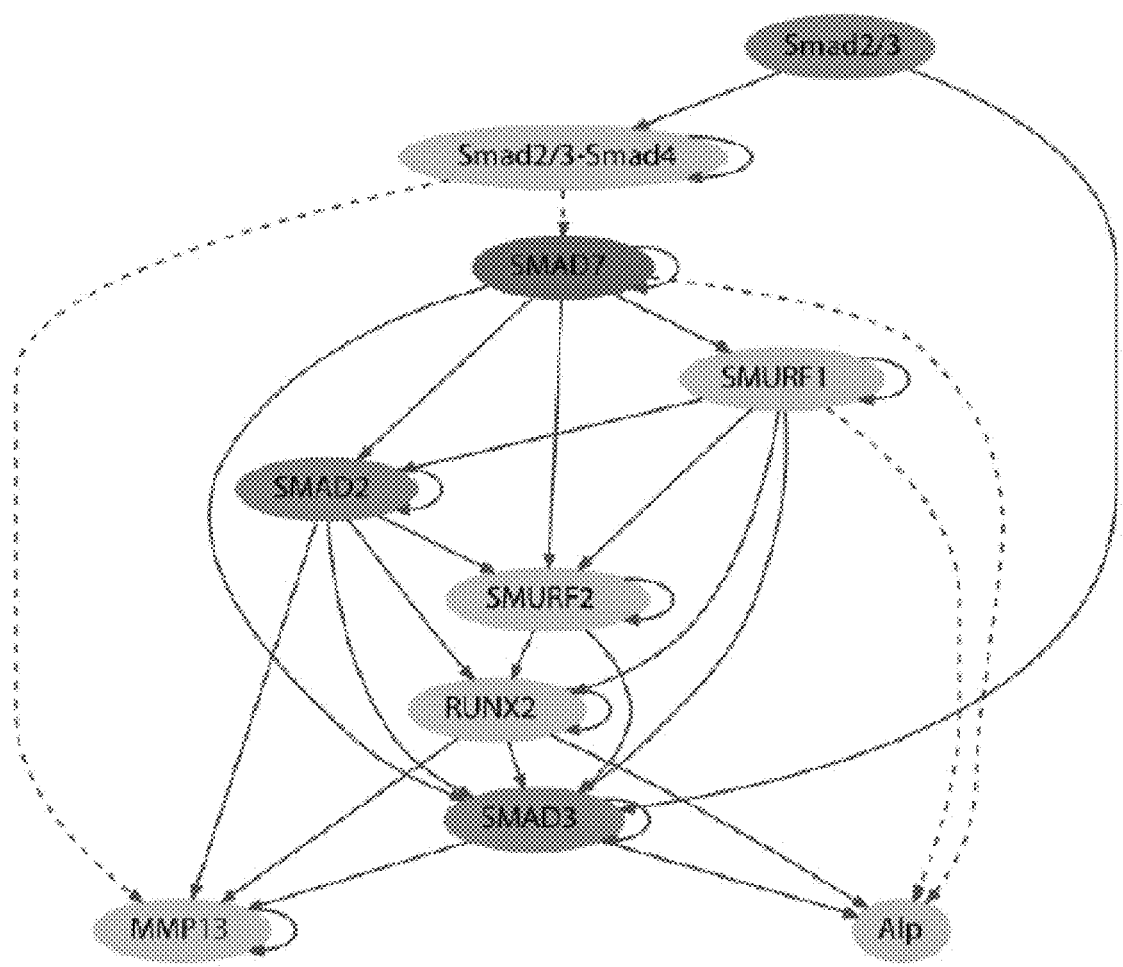
Figure 12E:
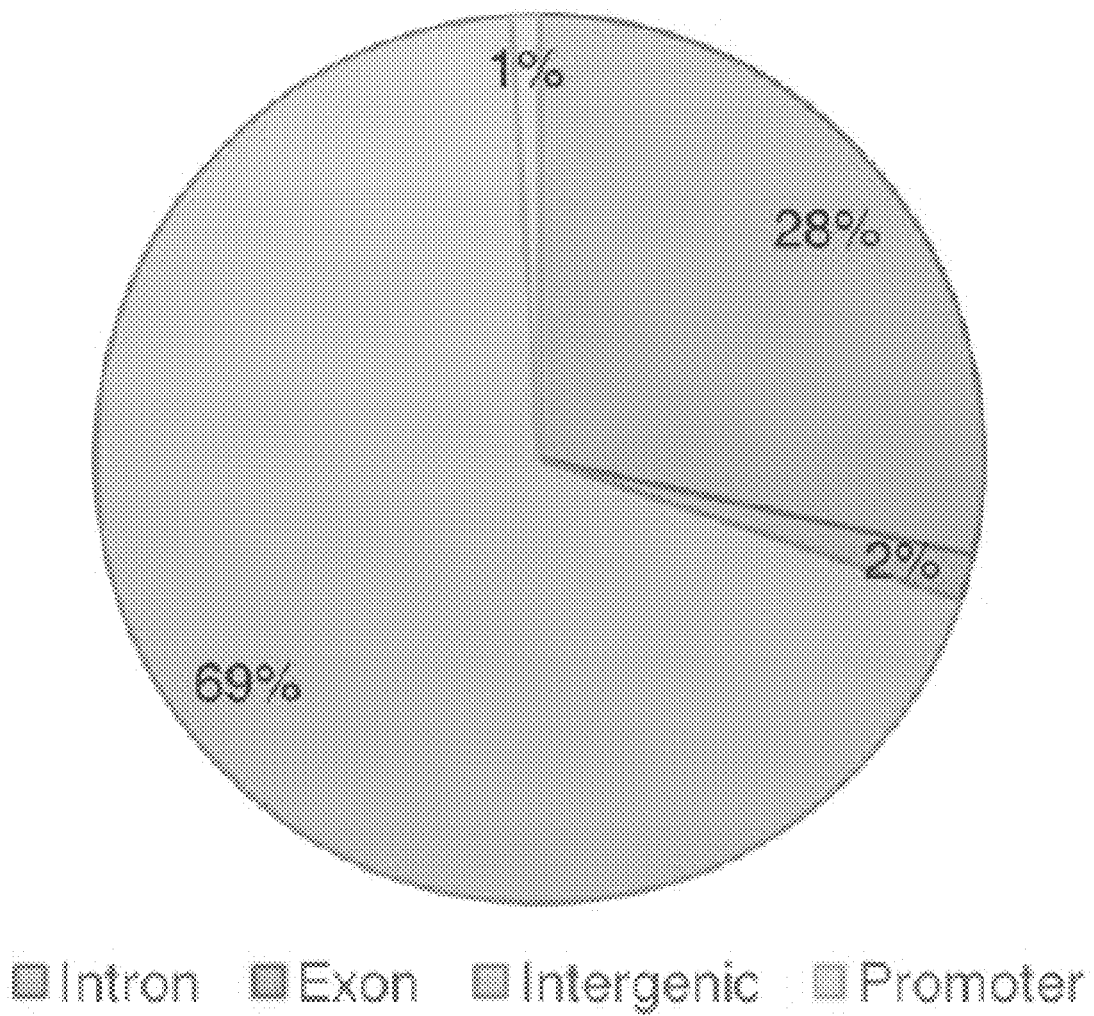
Figure 12F:
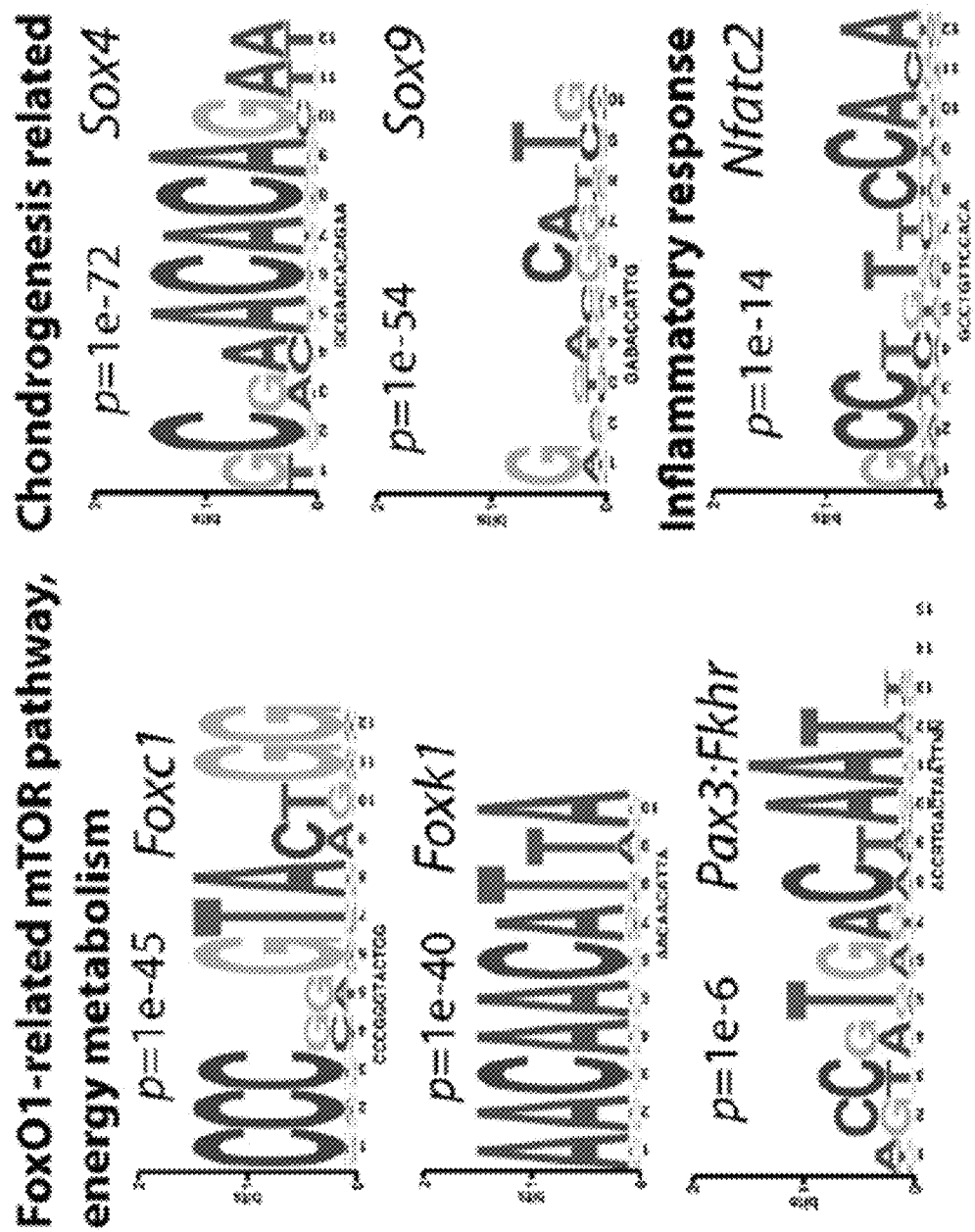

Global DNA methylation pattern followed classic bi-modal distribution and did not exhibit significant differences between Dnmt3b LOF and control (FIG. 11E). However, local differentially methylated regions (DMRs) were widespread. Overall 4,271 DMRs were identified, with a mean difference of methylation level of 32% (FIG. 11F, FIG. 11G). The large majority (97%) of these DMRs were located in introns and intergenic regions, with only 1% overlapping gene promoters (FIG. 12E). Of all the DMRs, 44% exhibited hypomethylation, and 56% hypermethylation. Using GREAT[30], DMRs were associated with nearby genes; these DMR-associated genes overlapped significantly with differentially expressed genes (p-value <6e-06), and they enriched for functions related to osteoblasts and chondrocytes (FIG. 11G, FIG. 12C). 104 genes exhibited changes in both expression and DNA methylation; two thirds of these were hypomethylated including cartilage genes that are known to be altered in OA Ucma[31], Bmp4, and Igf1 (FIG. 11B, FIG. 11C, FIG. 11G). In addition, binding sites of transcription factors including Fkhr, Foxc1, Foxk1, Sox4, Sox9 and Nfatc2 were significantly enriched in DMRs, highlighting functional connections with pathways related to chondrogenesis (Sox4, Sox9), inflammation (Nfatc2) and FOXO-related energy metabolism (Fkhr, Foxc1, Foxk1) (FIG. 12F).

Example 4

Increased Mitochondrial Metabolism in Dnmt3b LOF Chondrocytes

Figure 13A:
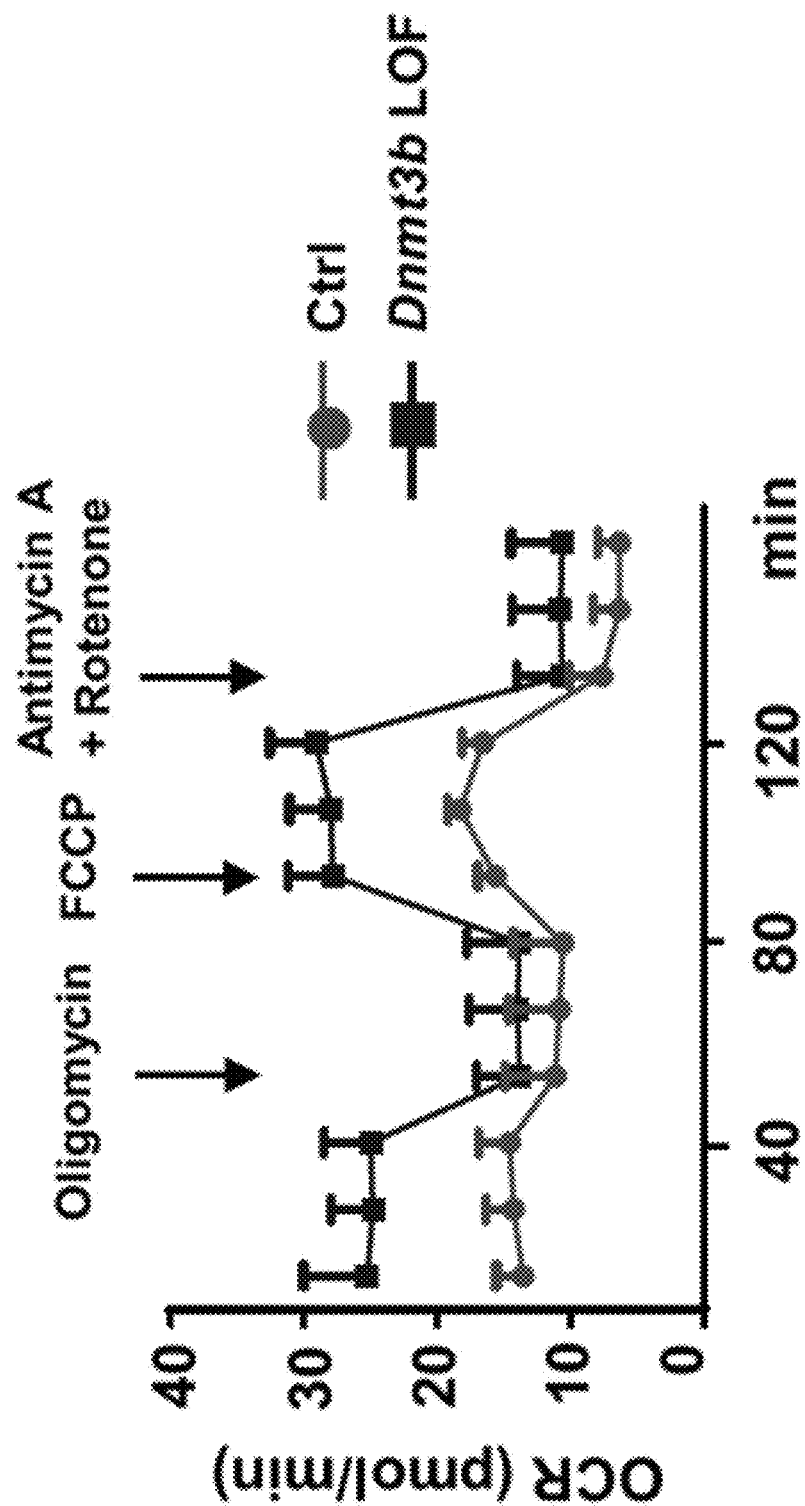
Figure 13D:
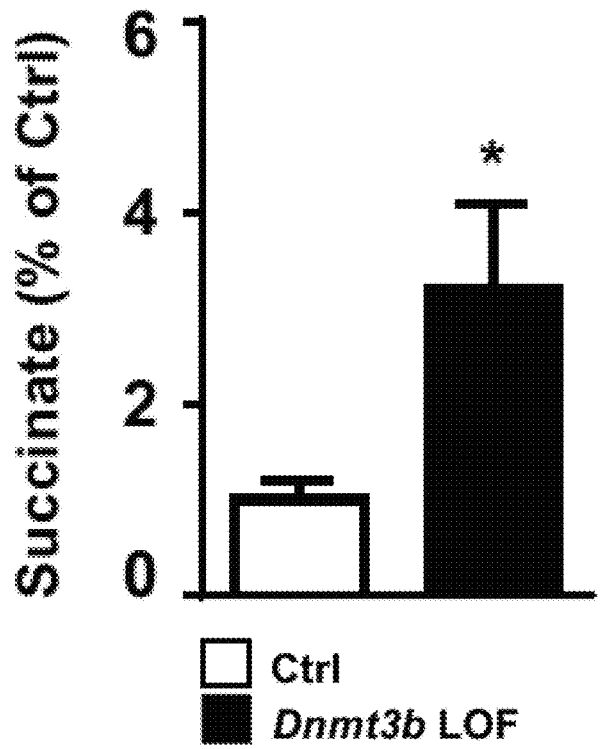
Figure 13E:
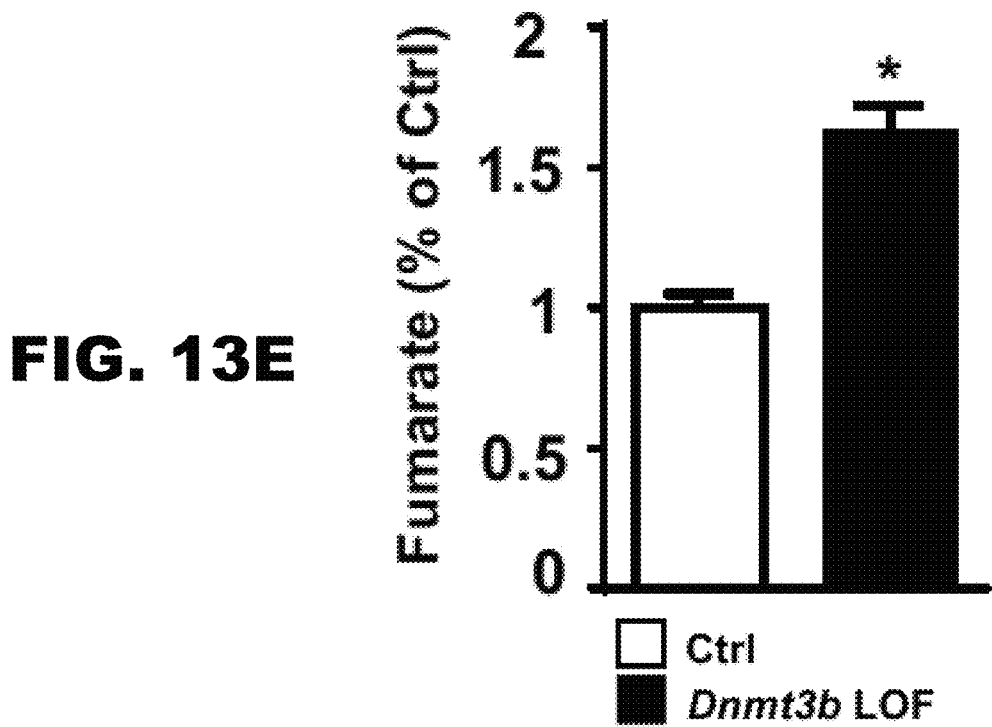
Figure 13F:
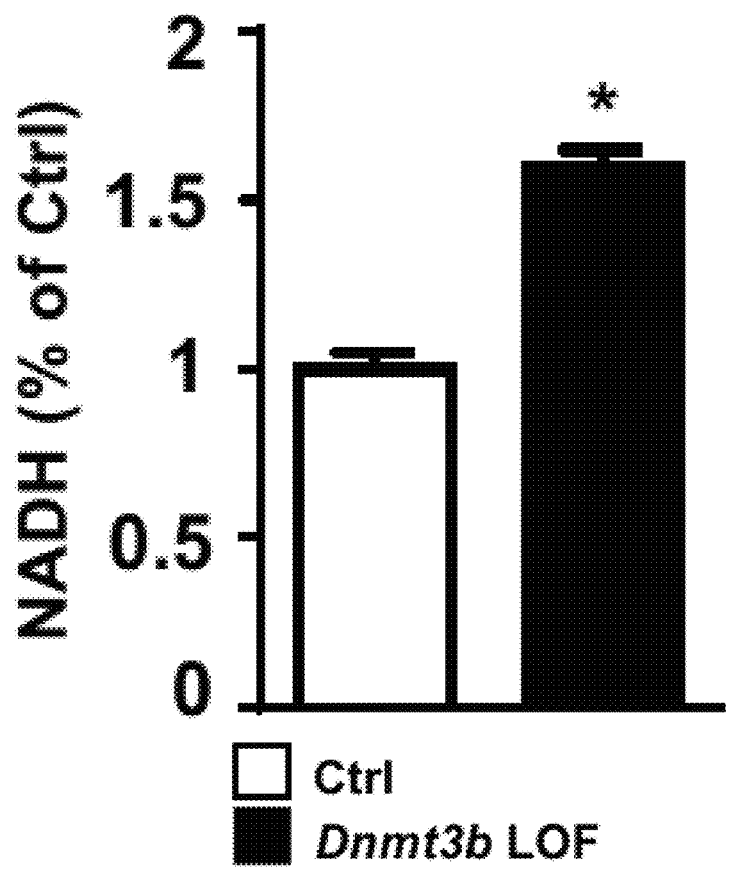
Figure 13G:
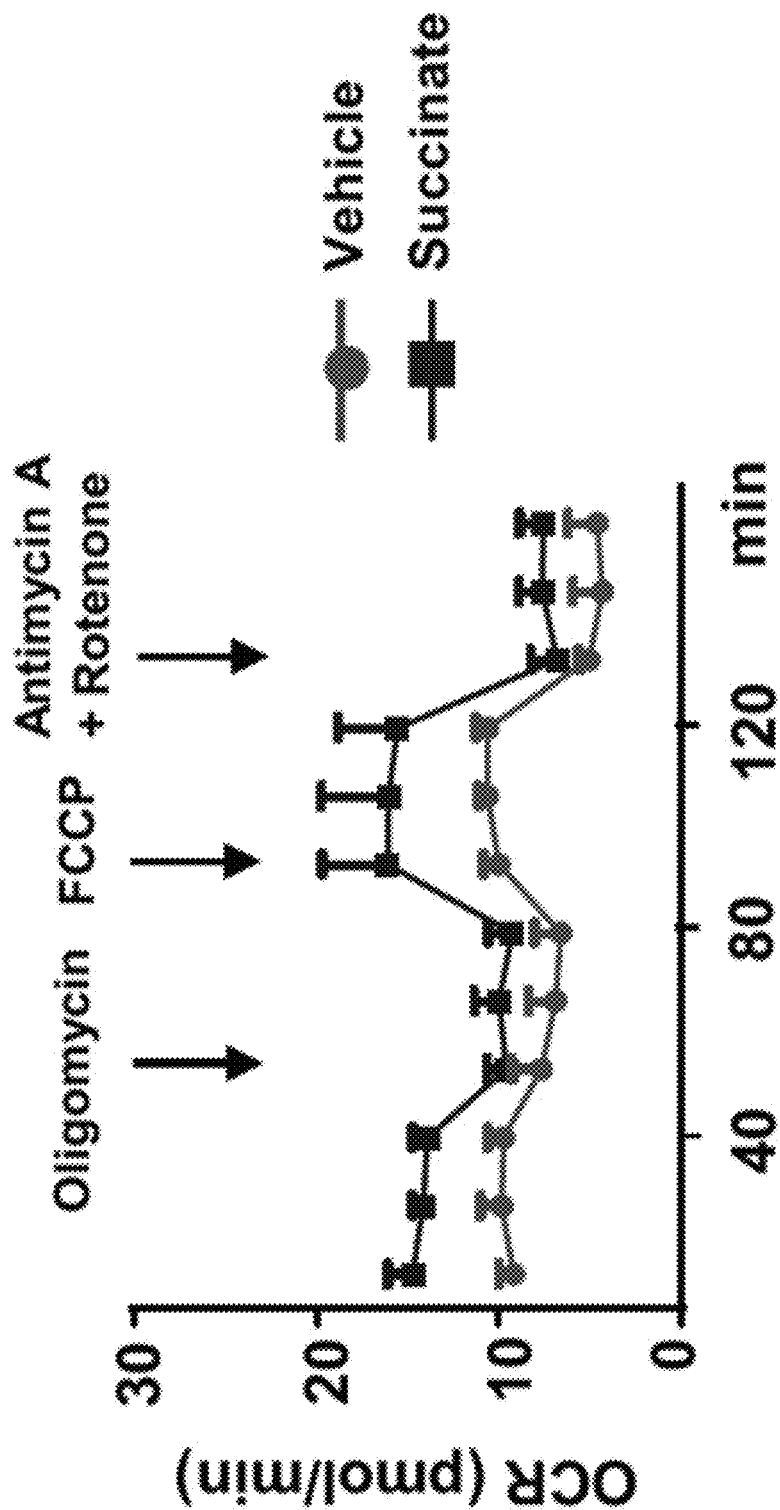
Figure 13H:
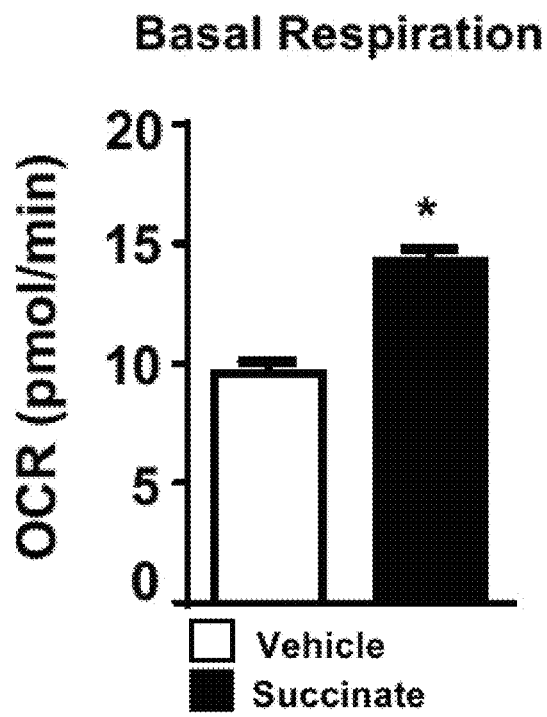
Figure 13I:
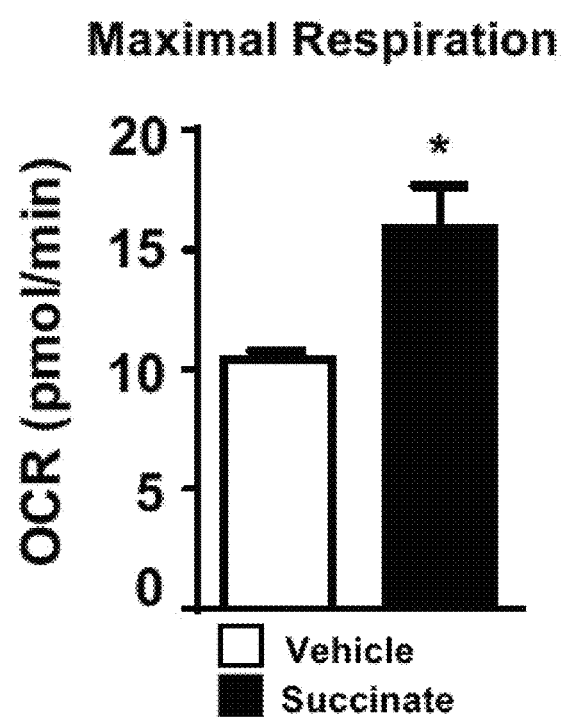
Figure 13J:
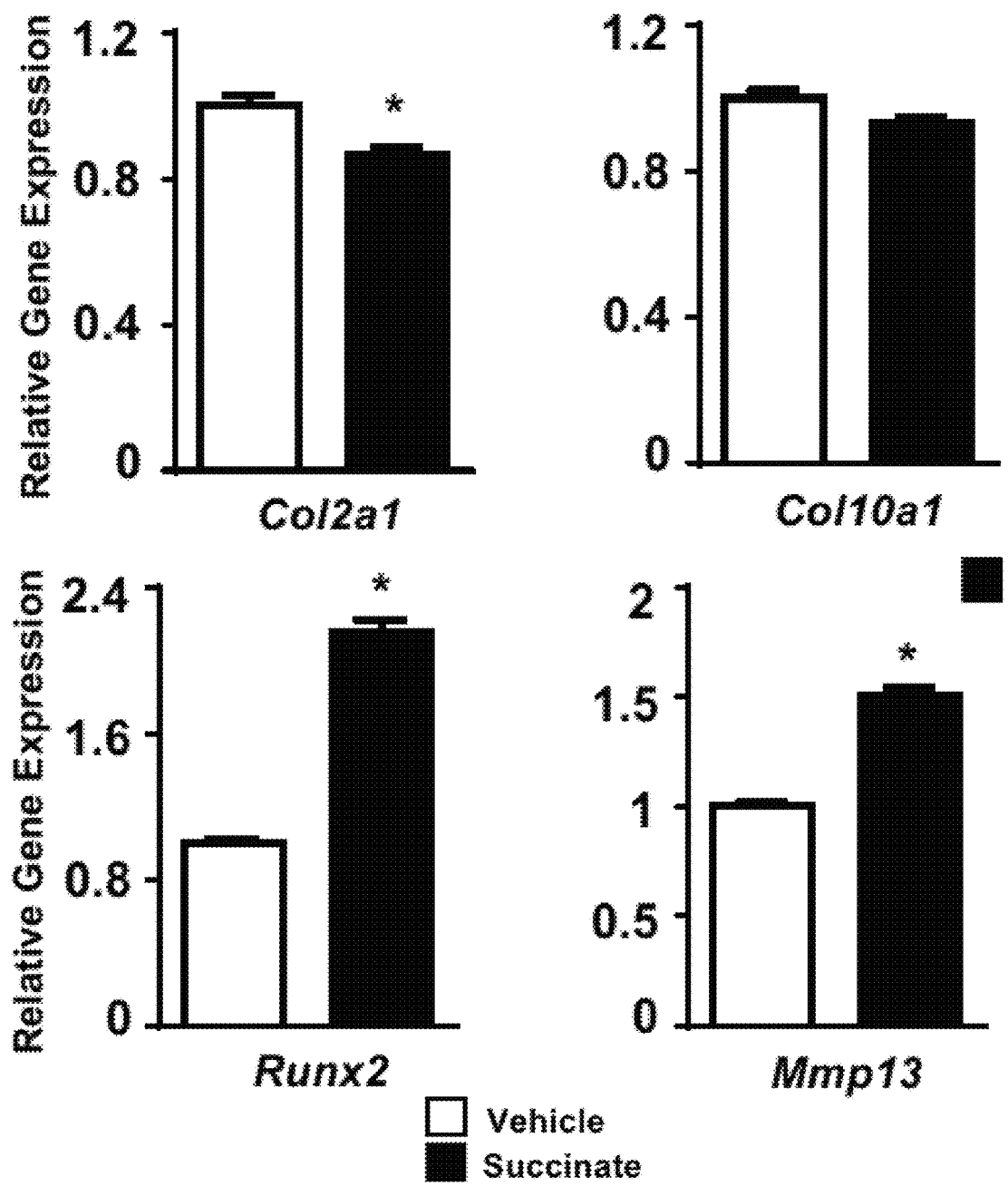
Figure 13K:
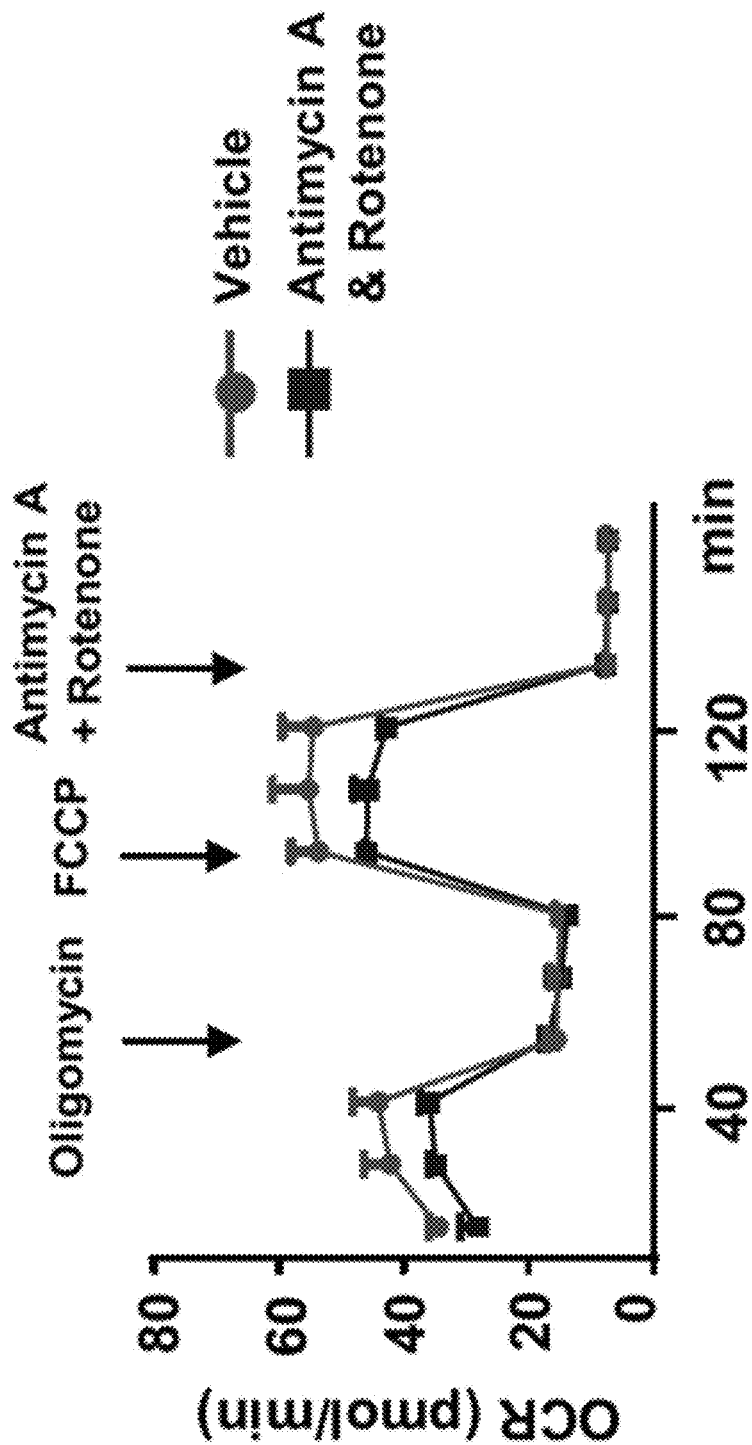
Figure 13L:
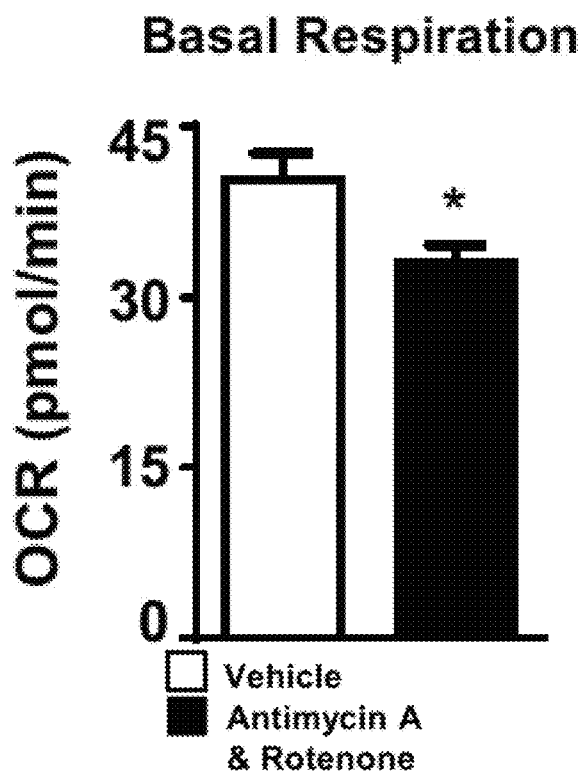
Figure 13M:
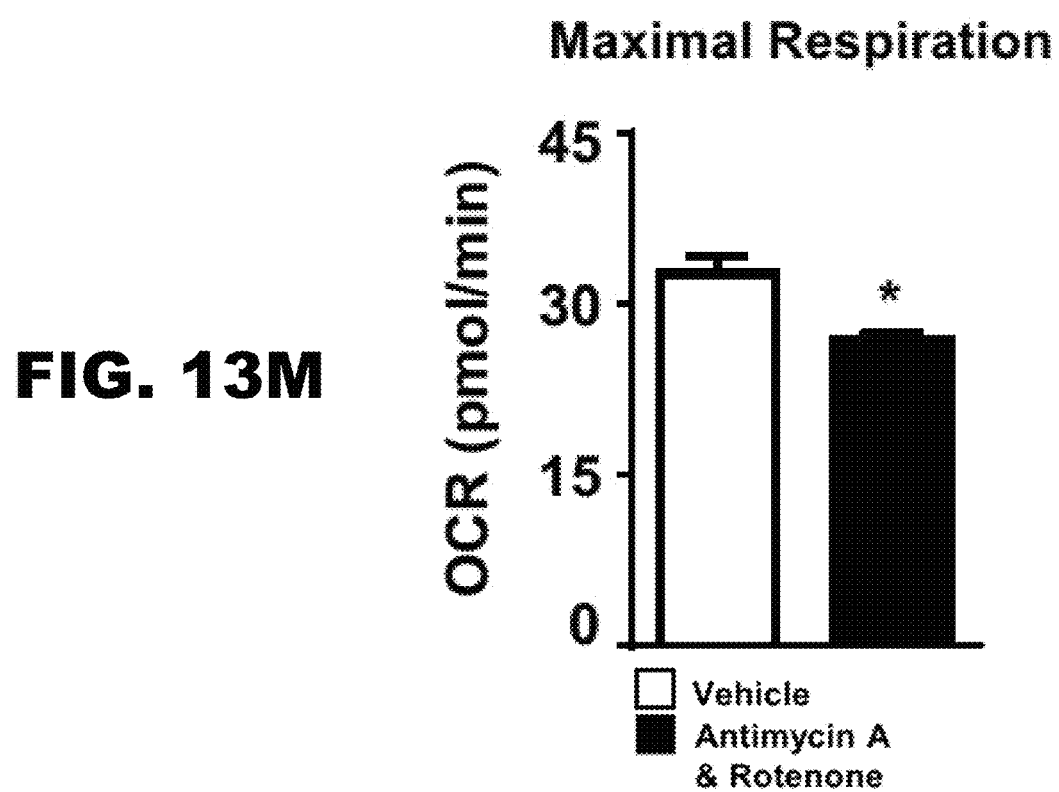
Figure 13N:
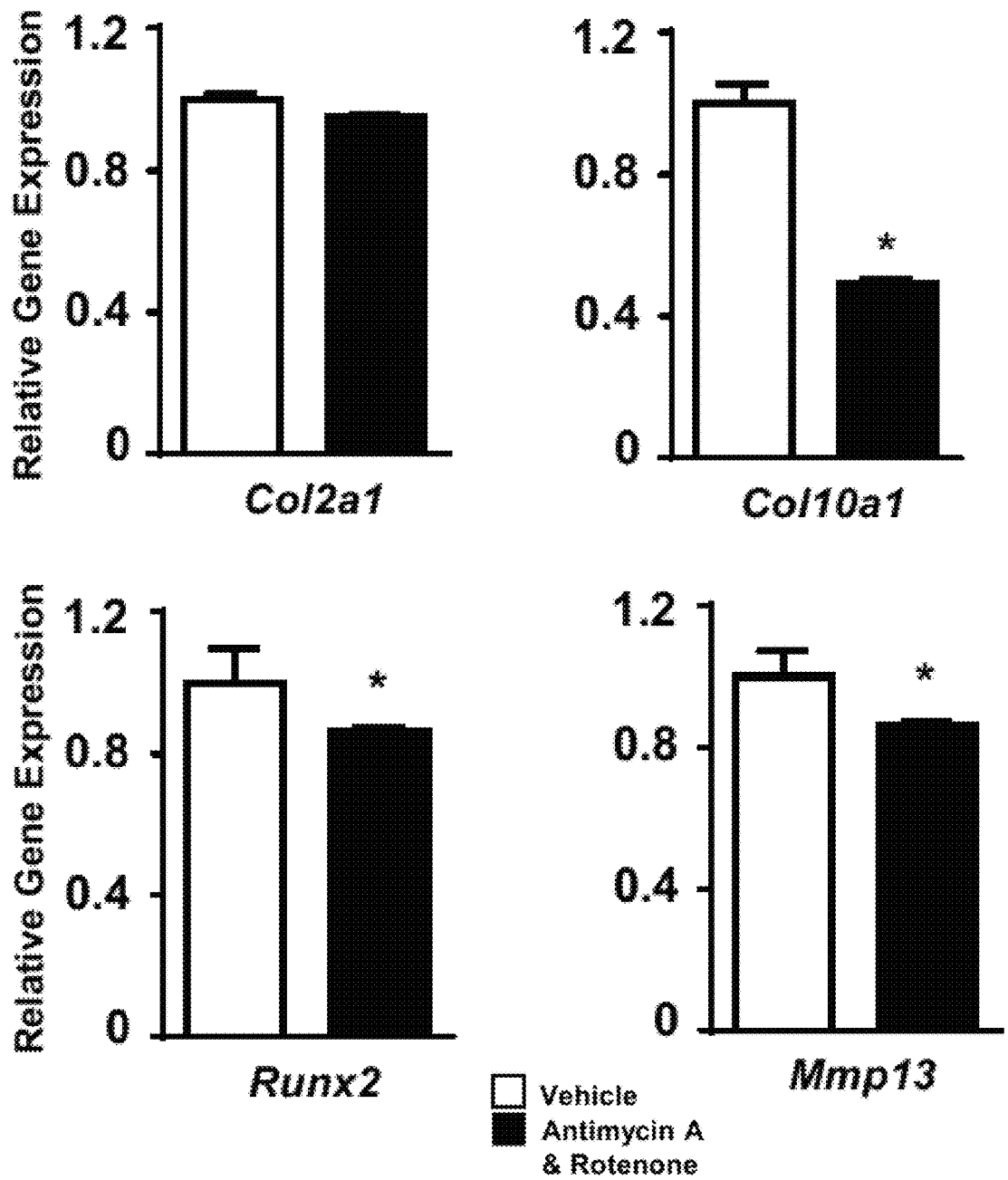
Figure 14:
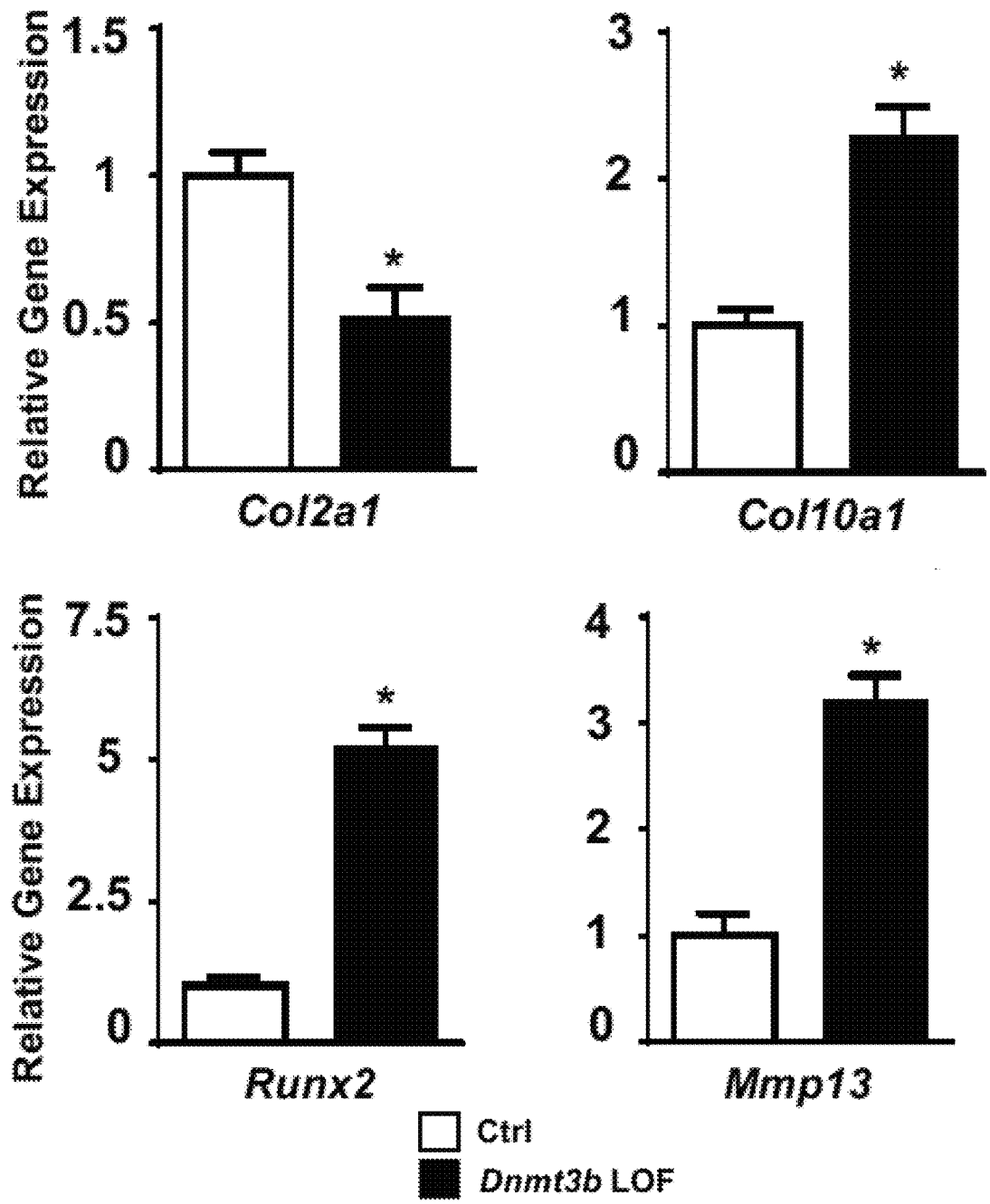
FIG. 14 depicts graphs showing chondrocyte gene expression in Dnmt3b LOF cells. Primary articular chondrocytes were isolated from 2 mo Dnmt3b$^{f/f}$ mice and infected with Ad5-Cre (Dnmt3b LOF) or Ad5-GFP (Ctrl) for 48 h. Expression of anabolic (Col2a1) or catabolic/hypertrophic genes (Col10a1, Runx2, Mmp13) is shown.
Figure 15:
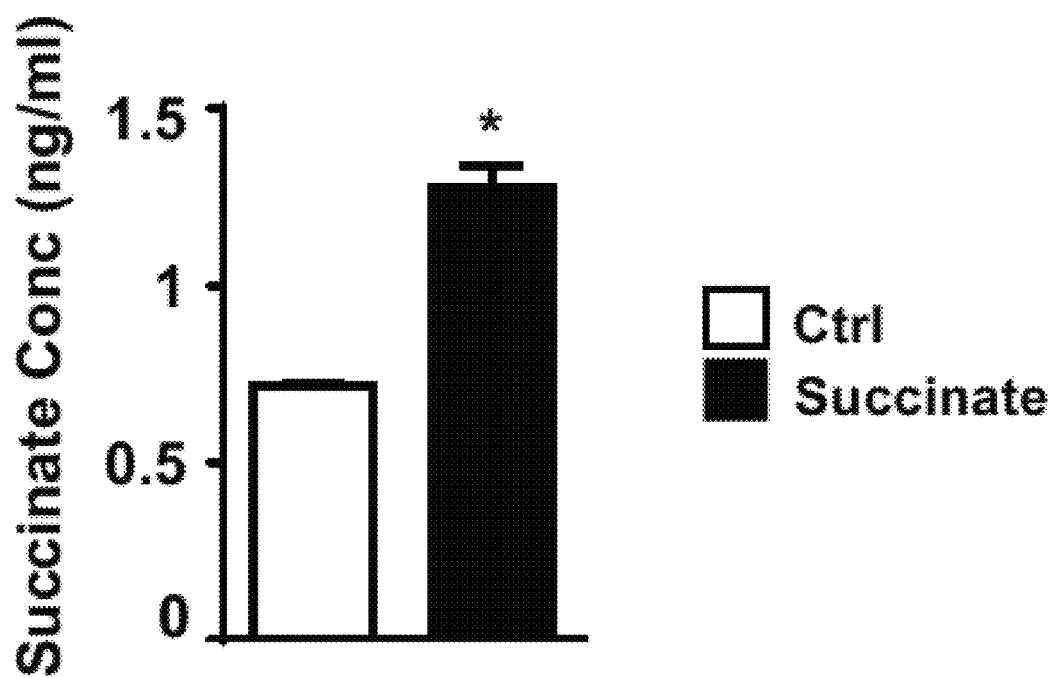
FIG. 15 depicts a graph showing cellular succinate levels in murine chondrocytes. Primary articular chondrocytes from 2 mo WT mice were treated with 1 mM diethyl succinate or vehicle for 48 h. Increased levels of cellular succinate in treated cells was confirmed.
Figure 16A:
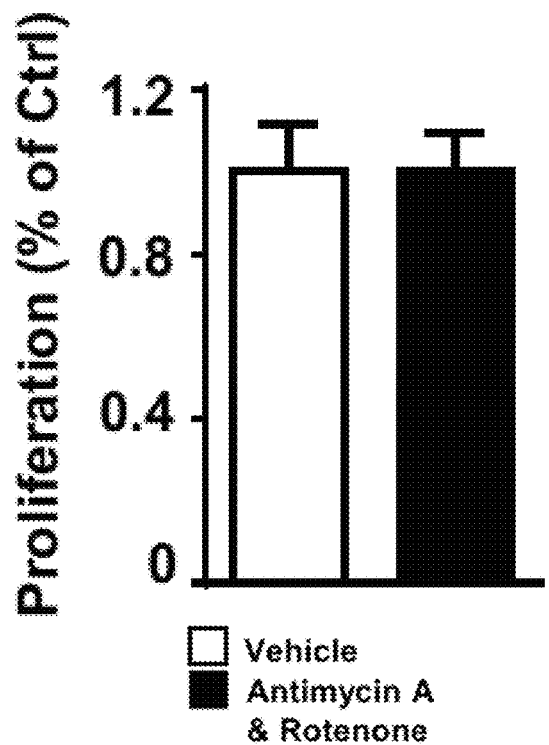
FIG. 16A and FIG. 16B depict graphs showing the effect of antimycin A and rotenone treatment on chondrocyte proliferation (FIG. 16A) and apoptosis (FIG. 16B). Primary articular chondrocytes form 2 mo WT mice were treated with 0.1 µM antimycin A and rotenone for 48 h. Proliferation and apoptosis were measured by ELISA kits and showed no difference following antimycin A and rotenone treatment.
Figure 16B:
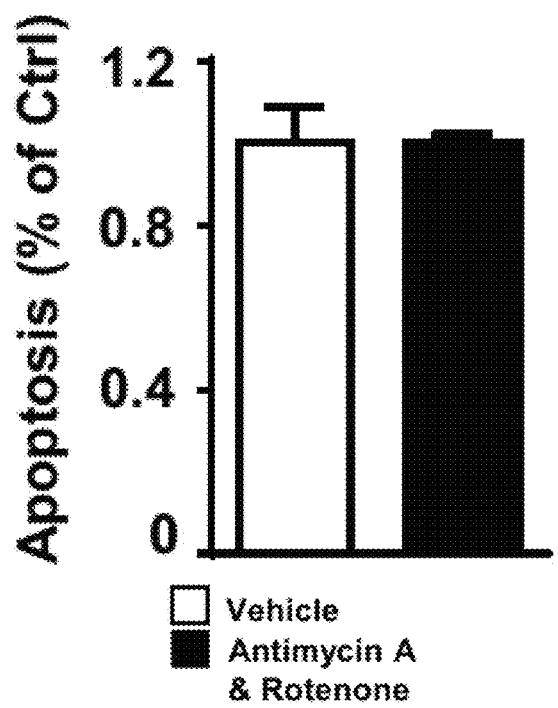

Since mitochondria are the major organelles for lipid metabolism and energy metabolism, the inventors investigated mitochondrial function within the context of Dnmt3b LOF. Basal and maximal mitochondrial respiration was higher in Dnmt3b LOF cells (FIG. 13A, FIG. 13B, FIG. 13C); these findings coincided with the expected alteration in anabolic and catabolic gene expression in LOF cells (FIG. 14). Given the alterations in mitochondrial function, levels of the TCA cycle metabolites, succinate and fumarate, were investigated and found to be increased in Dnmt3b LOF cells compared to control cells (FIG. 13D, FIG. 13E). Levels of reduced co-enzyme NADH, also generated by the TCA cycle and fed into the oxidative phosphorylation pathway, were increased in Dnmt3b LOF cells (FIG. 13F). The inventors then examined if increased mitochondrial respiration coincides with increased chondrocyte catabolism/hypertrophy. Addition of succinate to WT murine PACs (FIG. 15) resulted in increased basal and maximal respiration (FIG. 13G, FIG. 13H, FIG. 13I), decreased Col2a1 expression and an increase in the hypertrophic/catabolic chondrocyte markers, Runx2 and Mmp13 (FIG. 13J). The inventors then showed that antimycin A and rotenone (inhibitors of mitochondrial respiration) could attenuate the effects of BMP-2 induced hypertrophy of WT murine PACs (FIG. 13L, FIG. 13M, FIG. 13N, FIG. 13O). These inhibitors had no effect on cell proliferation or cell death (FIG. 16A, FIG. 16B). These data strongly suggest that mitochondrial metabolism can regulate chondrocyte hypertrophy and that decreased expression/function of Dnmt3b alters metabolic processes in chondrocytes to induce a catabolic-like phenotype.

Example 5

Figure 18A:
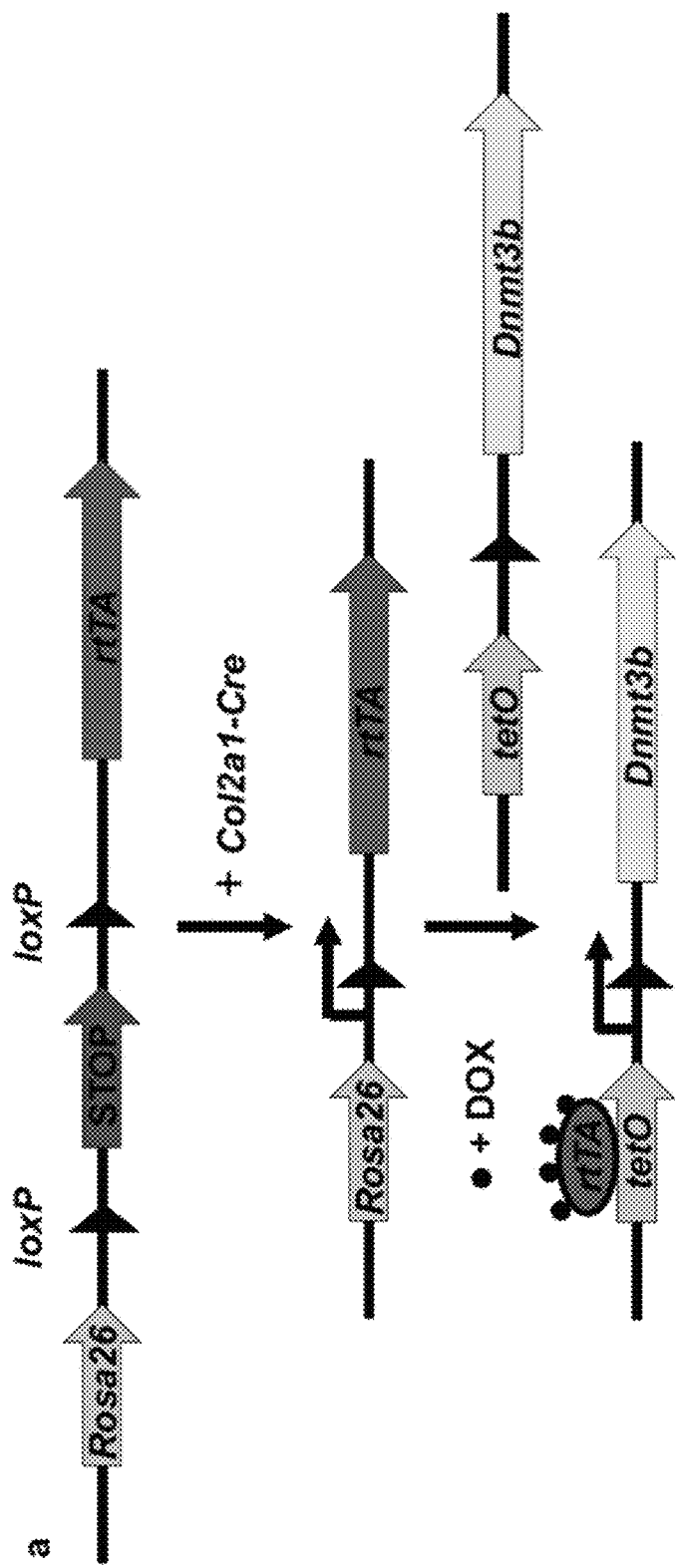
FIG. 18A, FIG. 18B, FIG. 18C and FIG. 18D depict a schematic and nucleic acid gels showing generation of Dnmt3b gain-of-function (GOF) transgenic mice.
Figure 18B:
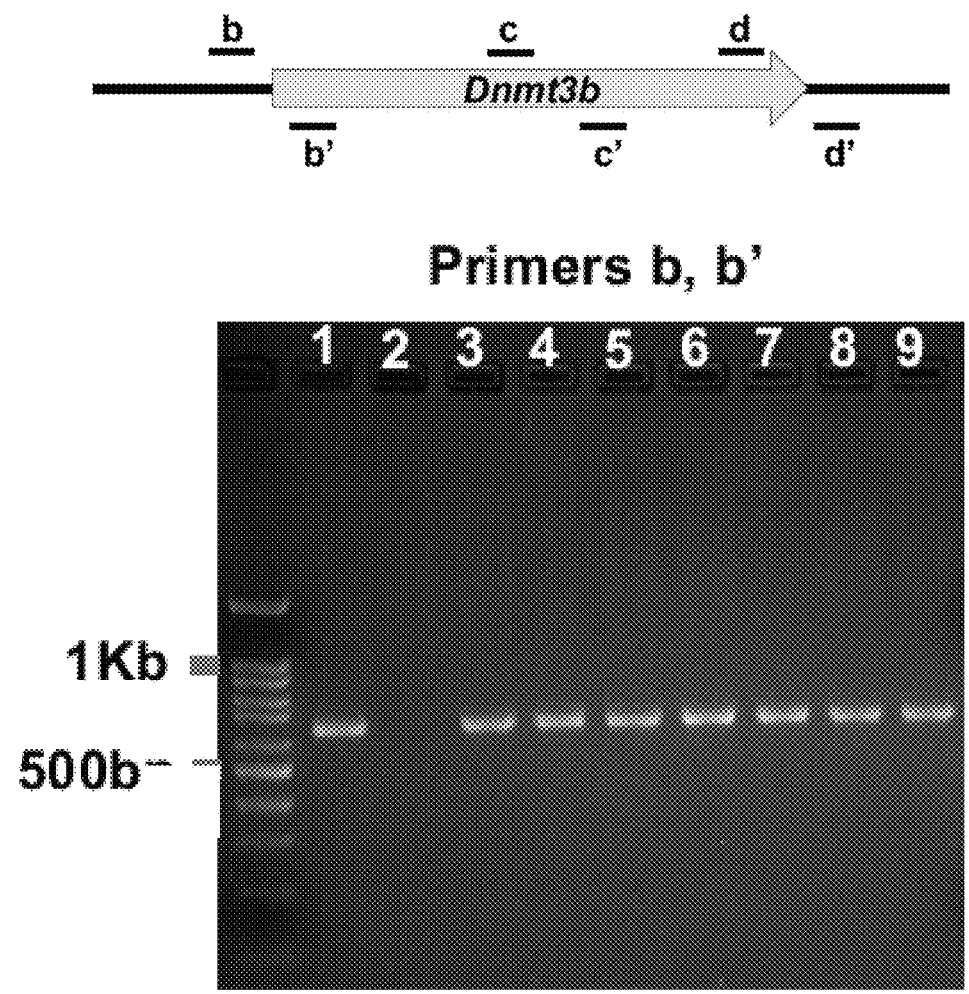
Figure 18C:
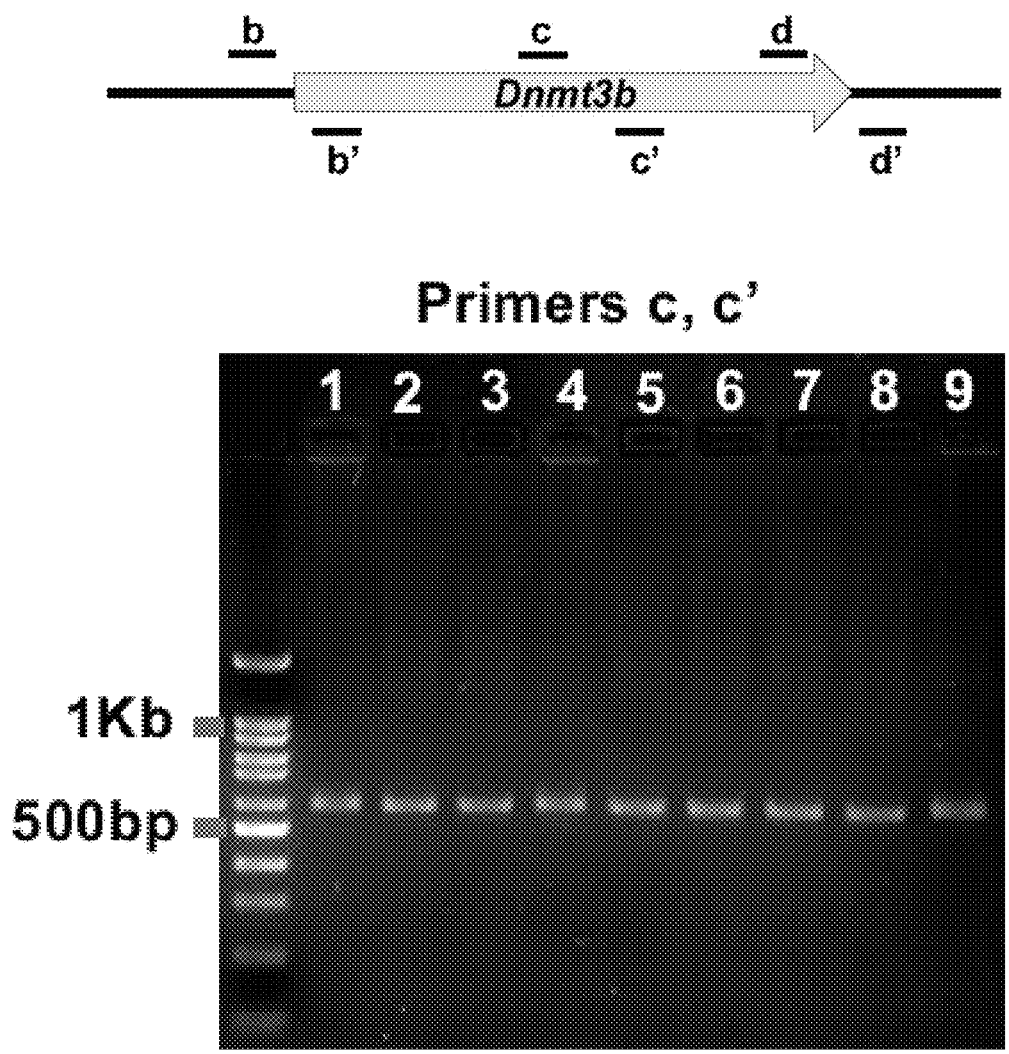
Figure 18D:
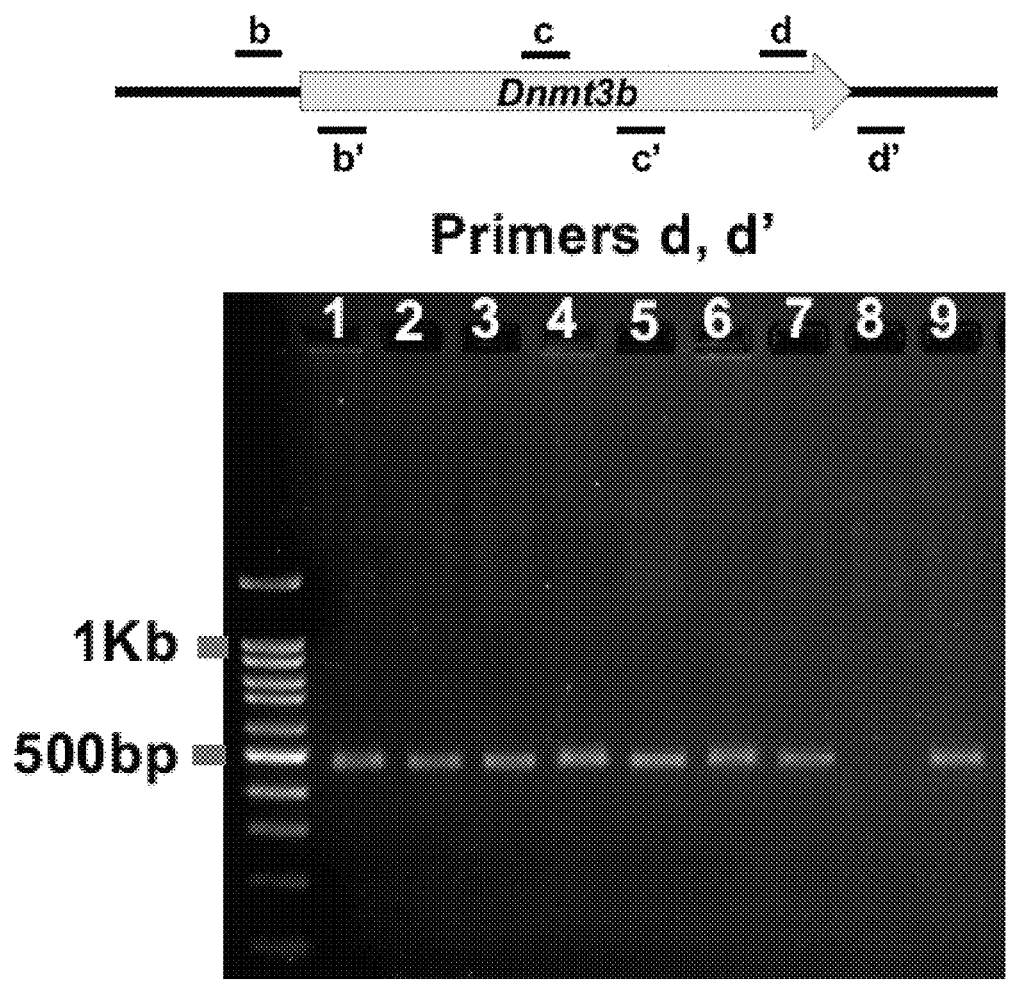
Figure 19A:
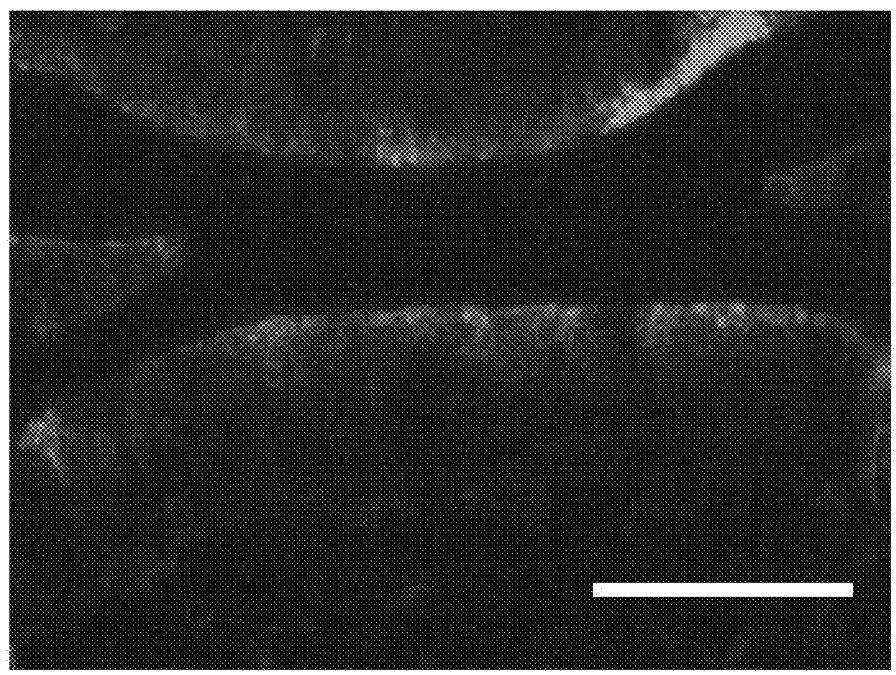
FIG. 19A and FIG. 19B depict an image and immunoblot showing over-expression of Dnmt3b in articular chondrocytes in vivo.
Figure 19B:
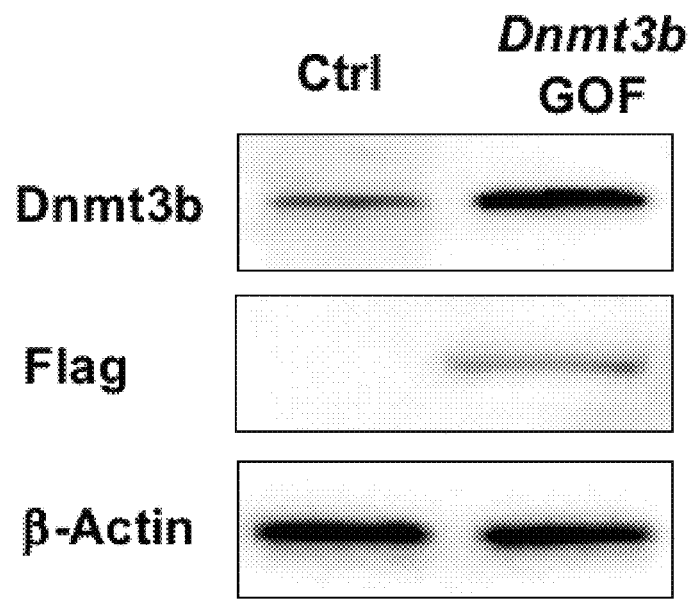

Dnmt3b Over-expression In Vivo Attenuates OA Progression and Alters Chondrocyte Metabolism Given that Dnmt3b LOF in vitro and in vivo induces hypertrophic/catabolic effects in chondrocytes, it was hypothesized that conditional over-expression of Dnmt3b in post-natal cartilage could be chondro-protective. FIG. 18 shows the strategy to generate Col2a1-Cre; Rosa-rtTA$^{f/+}$; Dnmt3b-tg (Dnmt3b GOF) mice. FIG. 19A shows the specificity of the Col2a1-Cre driver line in targeting chondrocytes in articular cartilage of Col2a1Cre; Rosa-rtTA$^{f/+}$; H2BGFP mice. FIG. 19B confirms Dnmt3b protein over-expression in articular chondrocytes from Dnmt3b GOF mice.

Figure 17A:
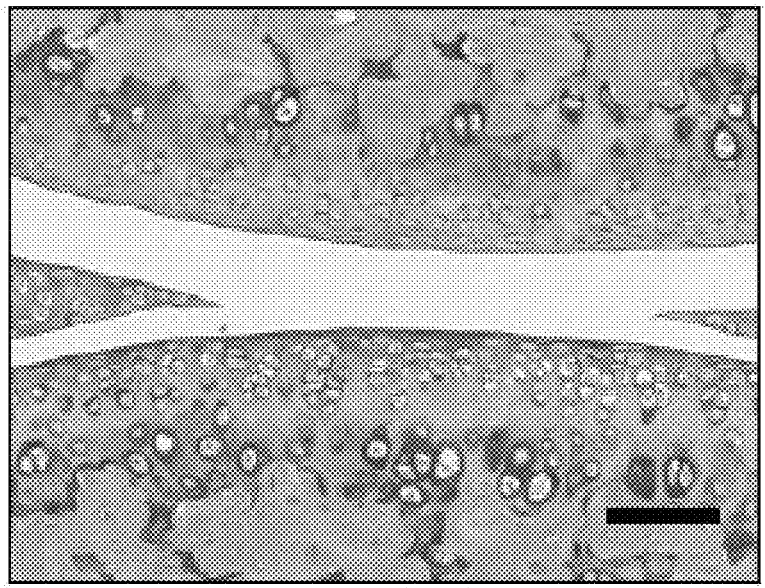
FIG. 17A, FIG. 17B, FIG. 17C, FIG. 17D, FIG. 17E, FIG. 17F, FIG. 17G, FIG. 17H, FIG. 17I, FIG. 17J, FIG. 17K, FIG. 17L, FIG. 17M, FIG. 17N, FIG. 17O and FIG. 17P depict images and graphs showing that Dnmt3b gain-of-function mice are protected from cartilage degeneration following surgical induction of OA. MLI or sham surgeries were performed on Dnmt3b gain-of-function (GOF) mice or Cre+ control (Ctrl) mice.
Figure 17B:
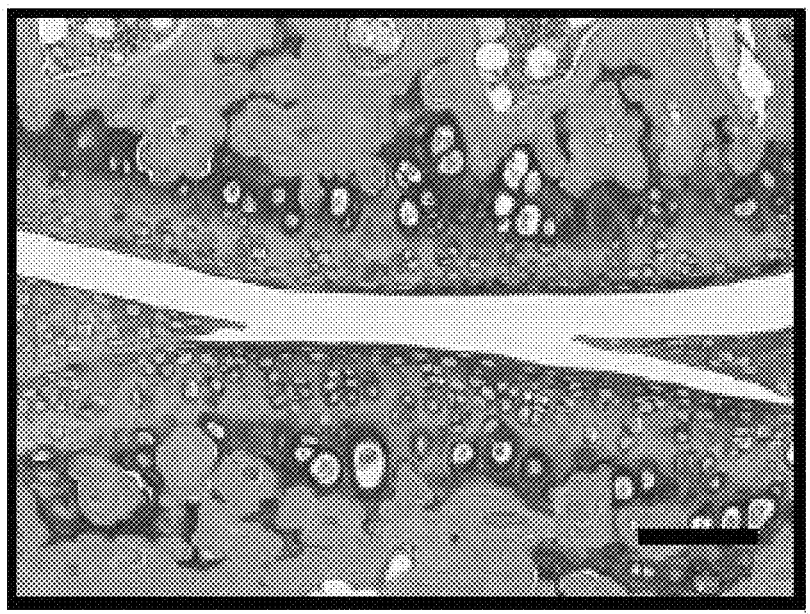
Figure 17C:
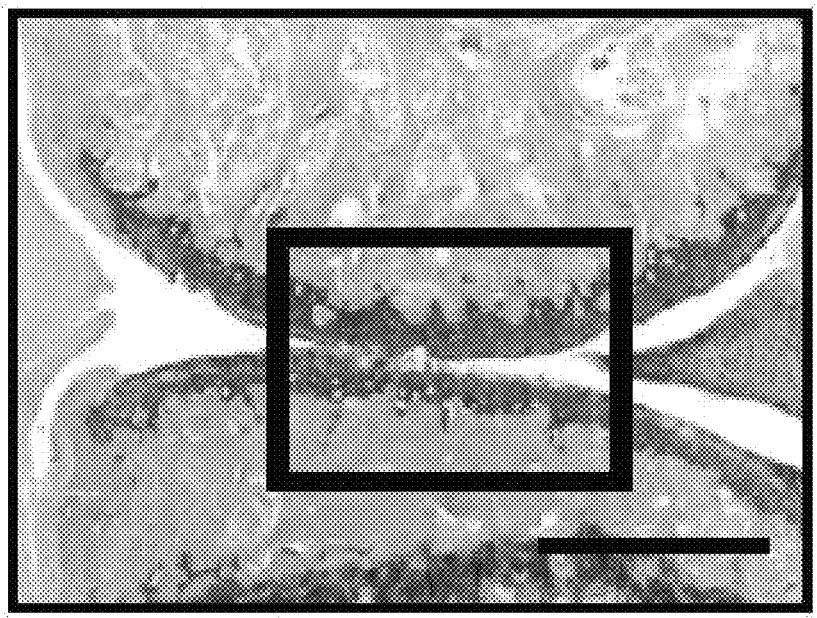
Figure 17D:
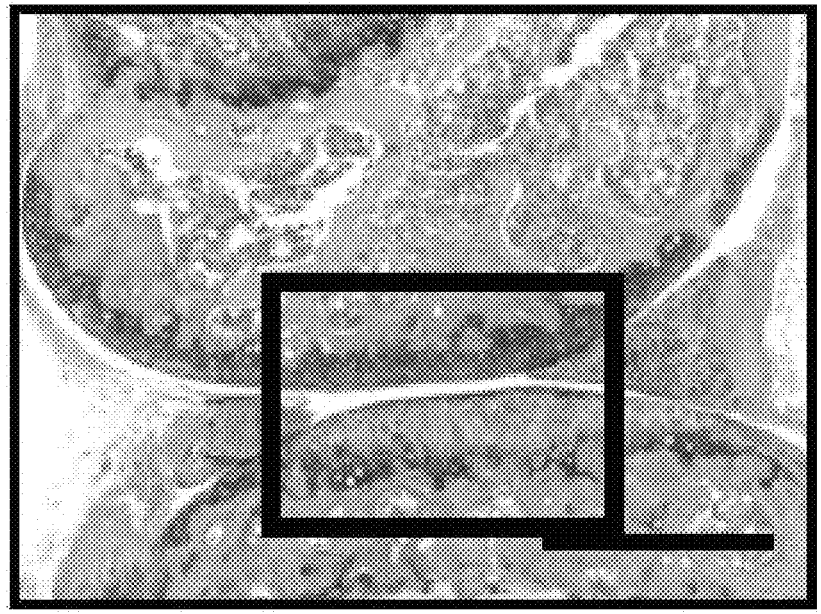
Figure 17E:
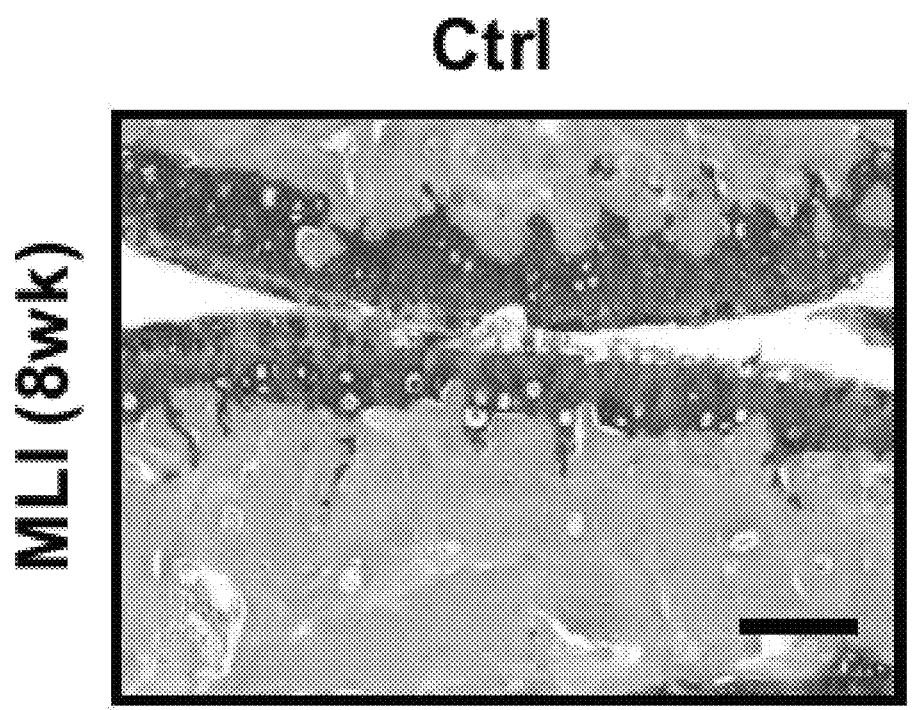
Figure 17F:
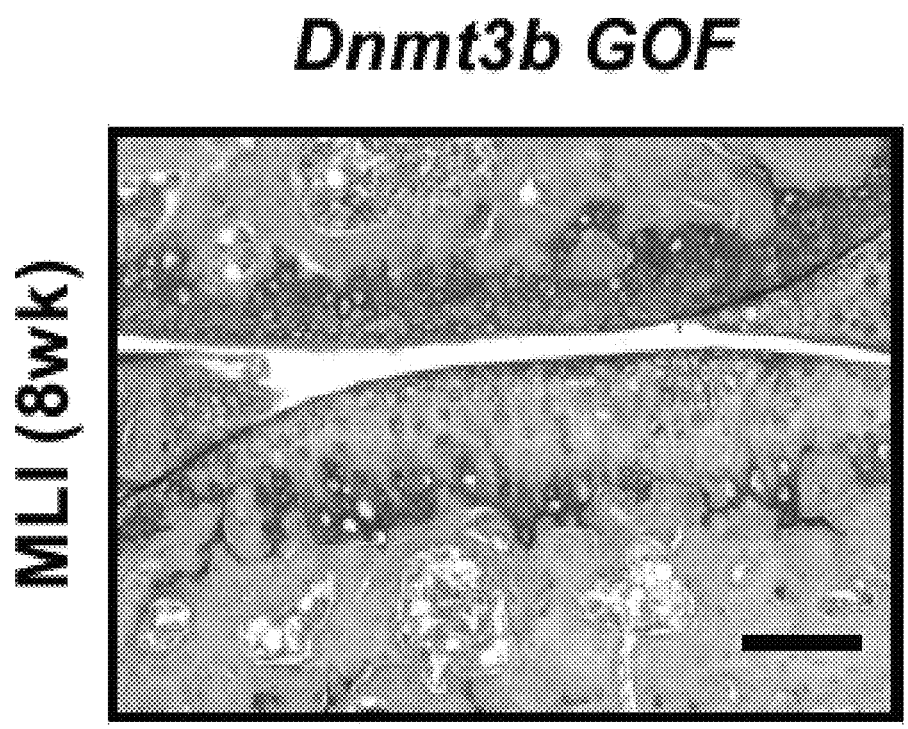
Figure 17G:
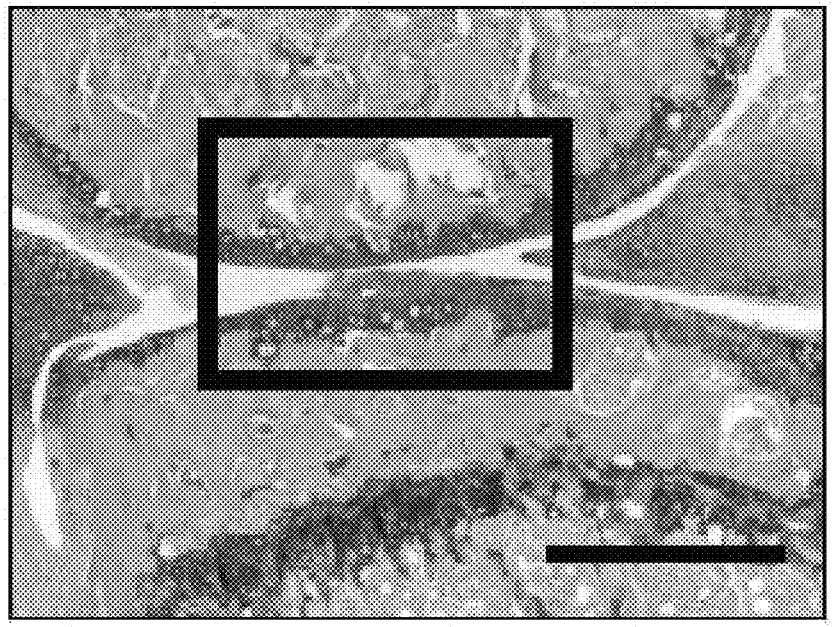
Figure 17H:
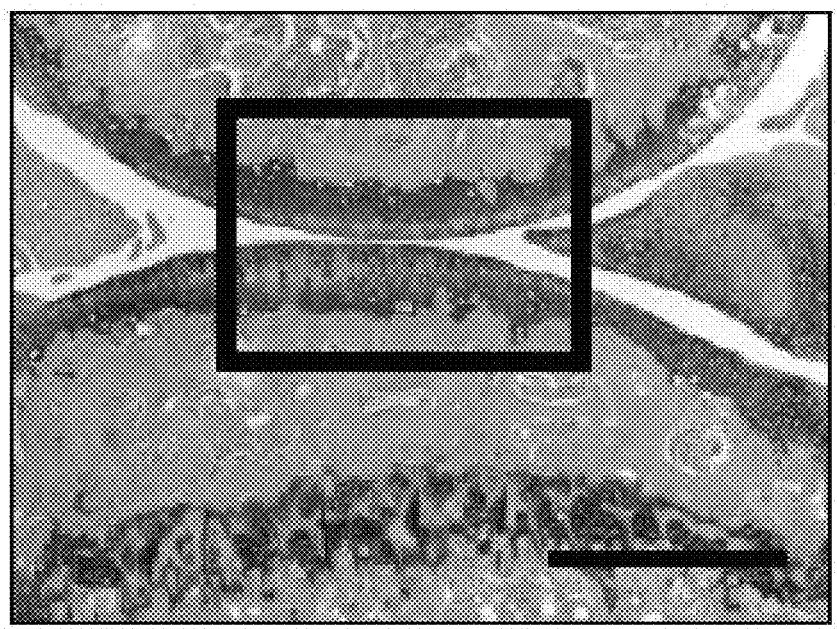
Figure 17I:
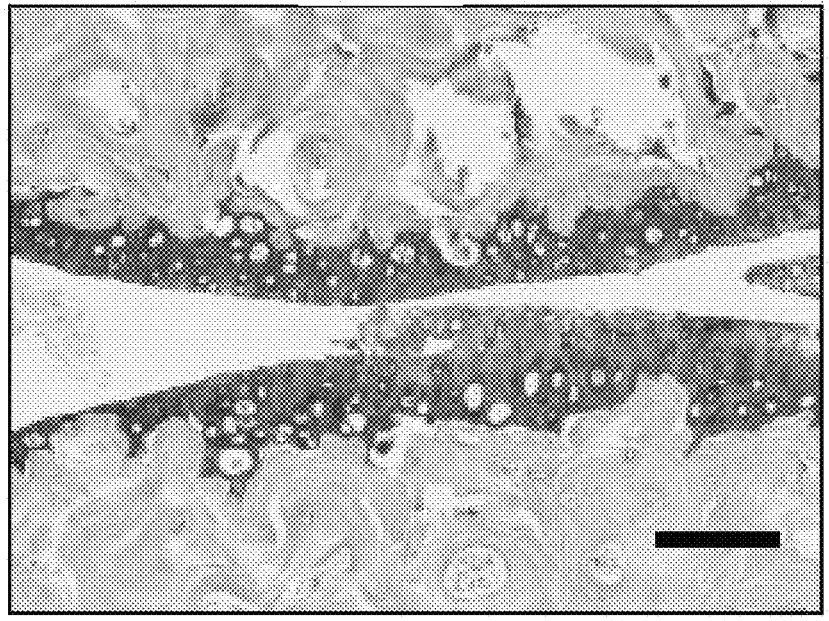
Figure 17J:
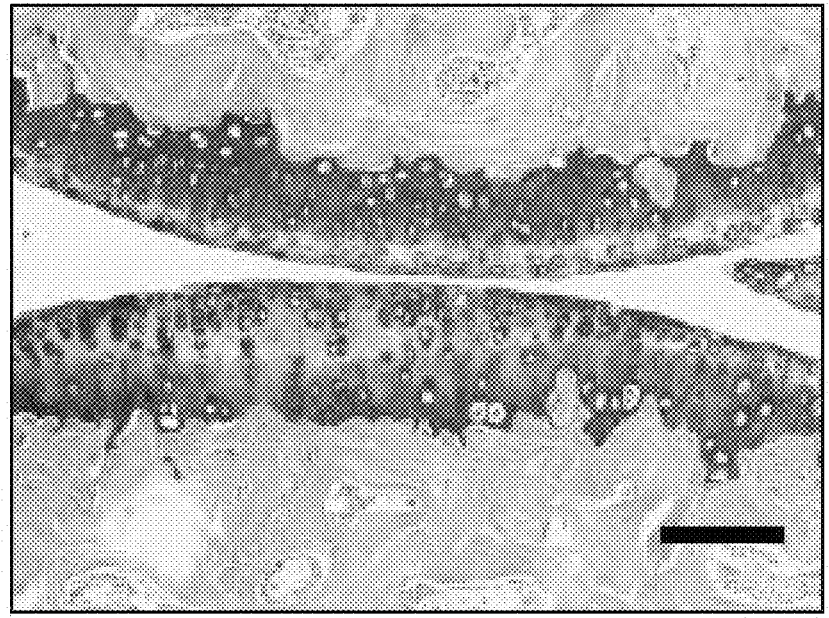
Figure 17K:
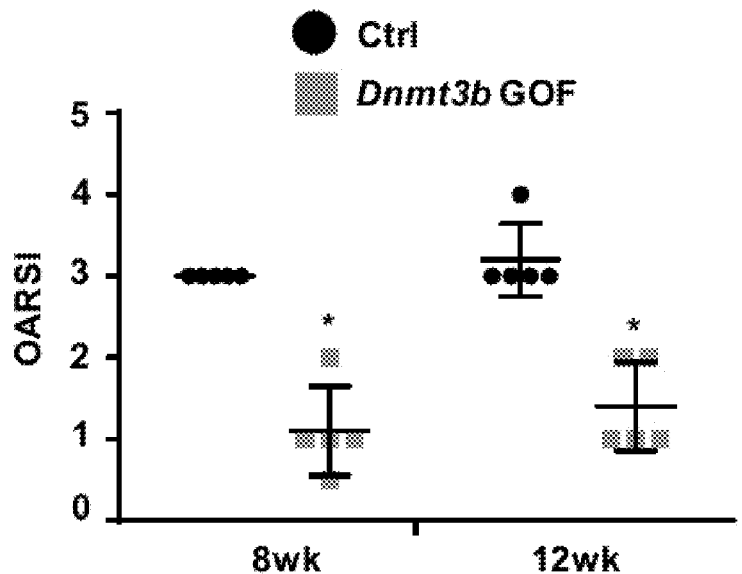
Figure 17L:
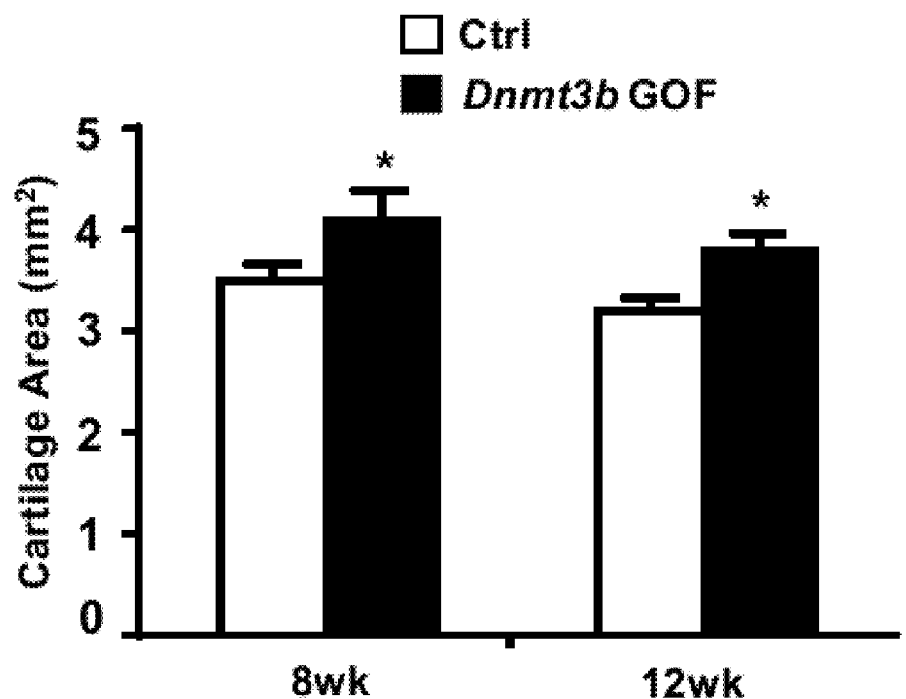
Figure 17M:
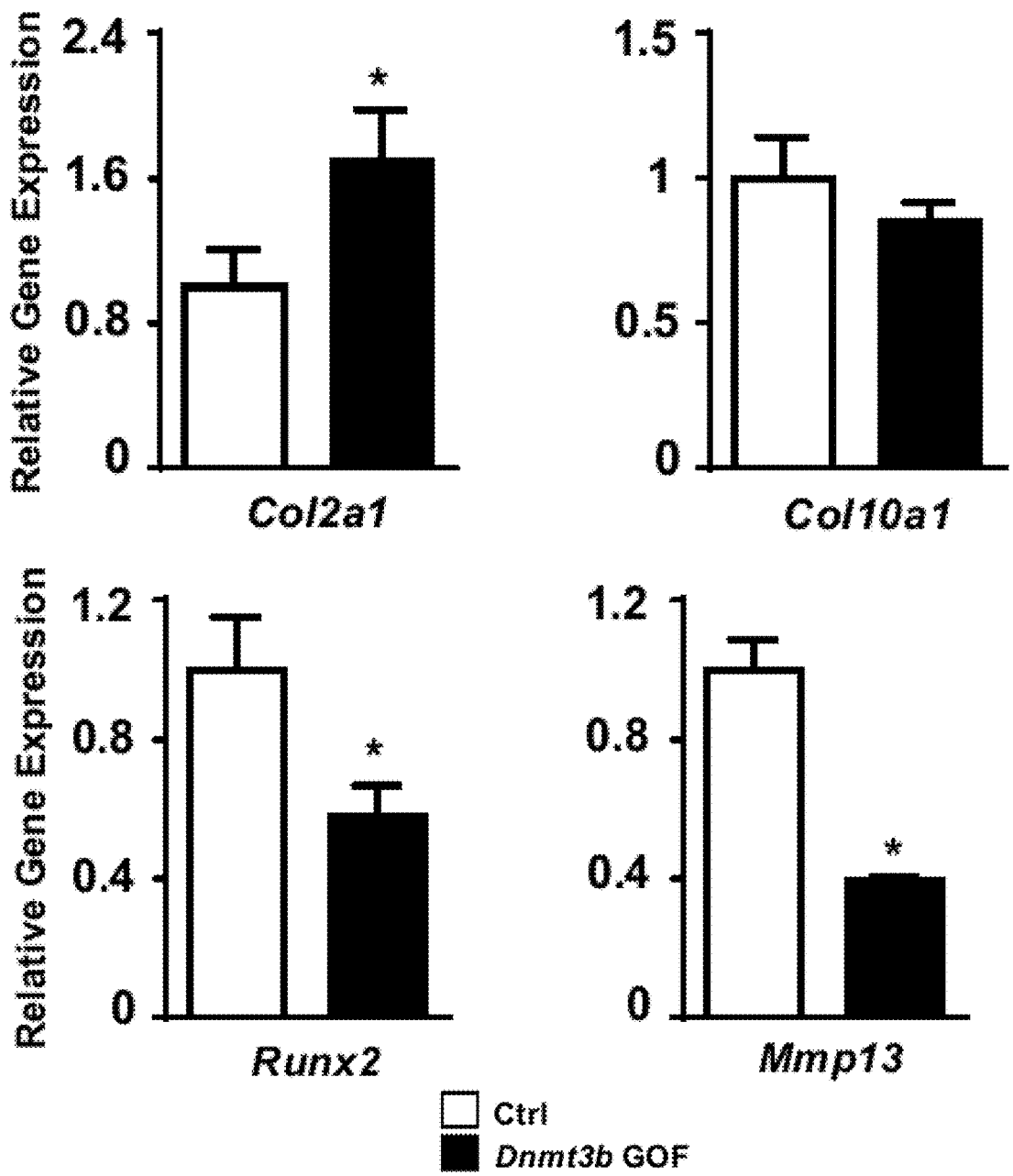
Figure 17N:
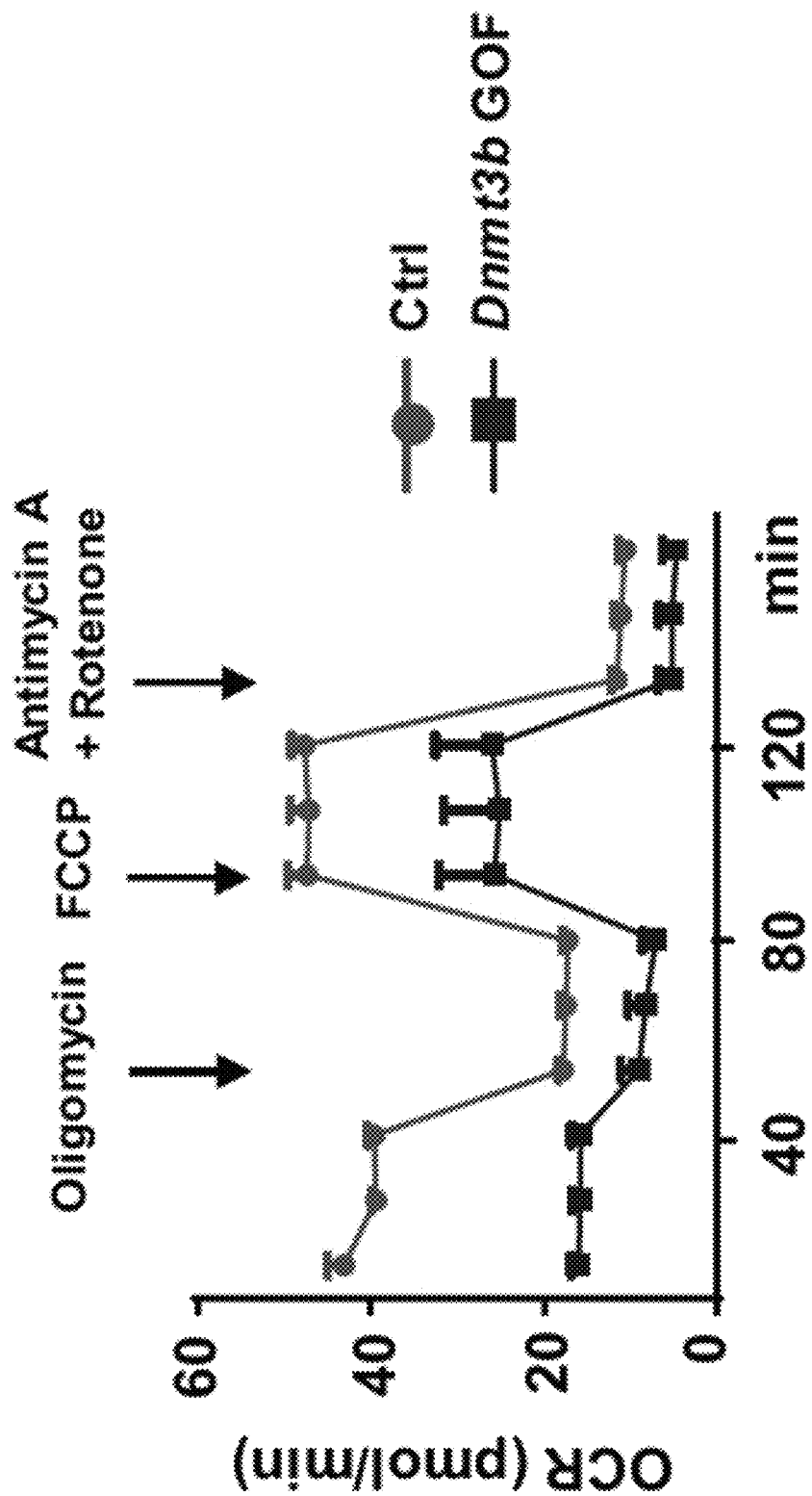
Figure 17O:
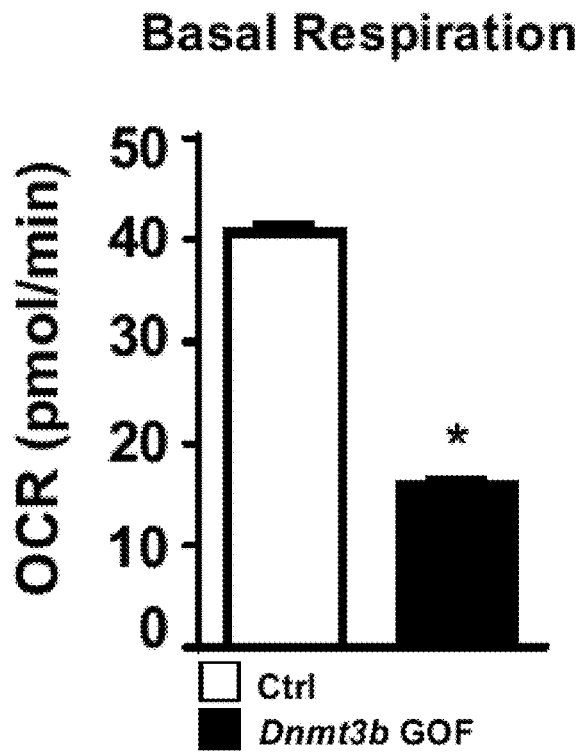
Figure 17P:
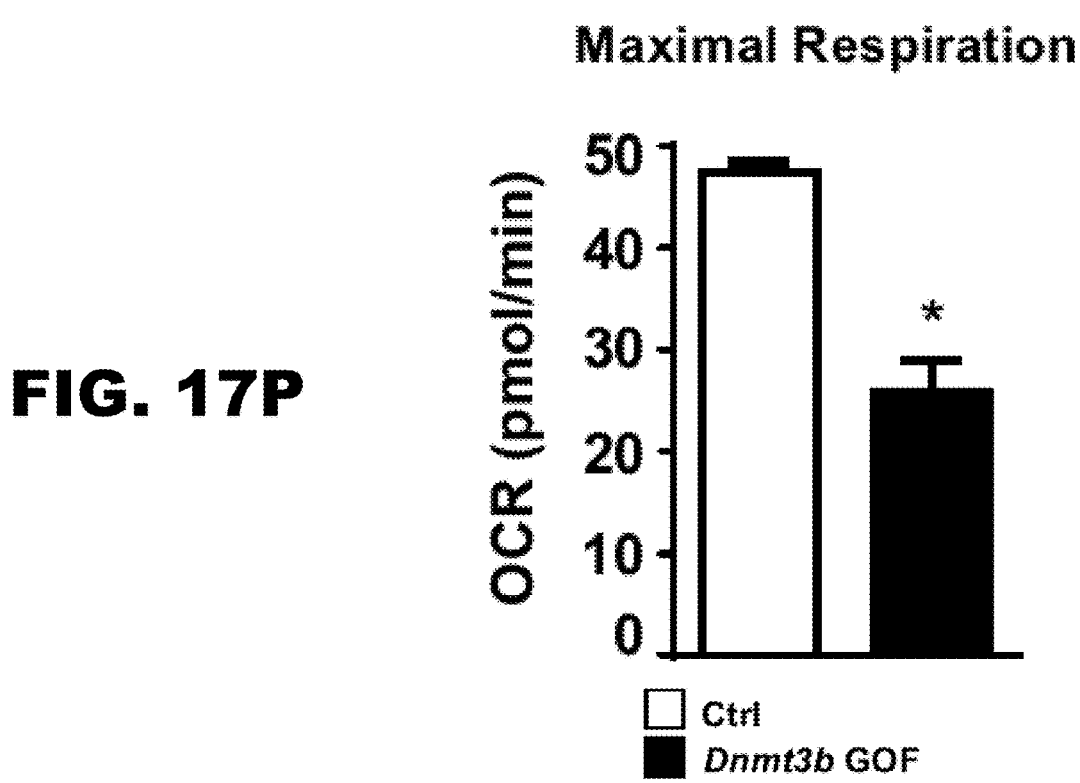

Histological examination of knee joints from Dnmt3b GOF mice following induction of OA by meniscal ligamentous injury (MLI) surgery showed chondro-protection compared to joints from Cre+ controls (FIG. 17A, FIG. 17B, FIG. 17C, FIG. 17D, FIG. 17E, FIG. 17F, FIG. 17G, FIG. 17H, FIG. 17I, FIG. 17J). In general, the apparent loss of articular cartilage tissue induced by MLI was not observed in Dnmt3b GOF mice; in fact articular cartilage thickness was increased in these mice (FIG. 17D, FIG. 17F, FIG. 17H, FIG. 17I). Further analysis of knee joint tissue sections showed a decrease in OARSI score (FIG. 17K) and an increase in articular cartilage area (FIG. 17L) due to Dnmt3b GOF. Expression of Col2a1 was significantly higher in Dnmt3b GOF cartilage while expression of hypertrophic markers Runx2 and Mmp13 was reduced compared to control articular cartilage (FIG. 17M).

To determine if mitochondrial metabolism was altered in Dnmt3b GOF chondrocytes, PACs from Dnmt3b GOF mice or Cre+ control mice were treated with BMP-2 to induce hypertrophy. Following treatment with antimycin A and rotenone, it was found that the basal and maximal respiration rates of GOF cells were significantly lower than in control cells. This data strongly suggests that modulation of Dnmt3b levels within the context of joint injury can alter mitochondrial metabolic processes to maintain articular chondrocyte homeostasis and attenuate the progression of articular cartilage degradation.

Discussion for Examples 1-5

This study focused on the de novo Dnmts and showed that decreased Dnmt3b expression is associated with aging and osteoarthritic murine and human articular cartilage. To further explore the effects of decreased Dnmt3b levels at the cell and tissue level, a loss-of-function (LOF) approach was pursued in vitro and in vivo. Interestingly, Dnmt3b LOF appeared to enhance expression of markers associated with chondrocyte catabolism and terminal hypertrophic differentiation (Mmp13, Runx2, Col10a1, Alp) and alter the balance of BMP and TGF-β signaling, favoring the BMP pathway. These cellular changes are well-known to occur in chondrocytes from cartilage at various stages of OA[35]. In agreement with these findings, conditional knock-down of Dnmt3b in murine cartilage in vivo was found to result in accelerated OA-like changes including cartilage fibrillation, osteophyte formation, increased reactive oxygen species and increased apoptosis. Importantly, over-expression of Dnmt3b in murine articular cartilage following surgical induction of OA appeared to be chondro-protective. Collectively, the data provide strong evidence that Dnmt3b-driven epigenetic mechanisms can regulate homeostasis of mature articular cartilage tissue.

Chronic inflammation is thought to contribute to age-related diseases such as OA[36,37]. These studies show that the pro-inflammatory cytokine, IL-1β, down-regulates Dnmt3b in murine and human chondrocytes and that these effects may be mediated via NF-κB. Whether canonical and/or non-canonical NF-κB signaling mechanisms play a role in regulating Dnmt3b expression has yet to be determined. In addition, IL-1β has also been shown to down-regulate TET1 in chondrocytes[38,39]. TET1 belongs to the ten-eleven translocation (TET) family proteins that catalyze DNA de-methylation and there is growing interest in how these TET-mediated epigenetic processes control cartilage homeostasis. Recent studies have shown that TET proteins can inhibit inflammatory signals in other systems[40,41]. It will be interesting to elucidate if the chondro-protective effects of Dnmt3b may be due, in part, to attenuating inflammatory processes.

In addition to the changes in catabolic and hypertrophic gene expression due to Dnmt3b LOF, in-depth bioinformatic analyses of RNA-Seq and methylC-seq data provided insights into other genes and pathways that may also be affected. Interestingly, analysis of differentially-expressed genes in Dnmt3b LOF chondrocytes showed an enrichment in pathways involved in lipid metabolism. Lipids are important nutrients in chondrocyte metabolism and reports have shown a potential link between OA and disruptions in lipid metabolic processes[42-44]. MethylC-Seq analysis also identified a number of transcription factor binding sites that were enriched in DMRs in Dnmt3b LOF cells. Among these included binding sites for Fhkr, Foxc1 and Foxl1 which are known to be involved in regulating a number of metabolic processes[45-47]. Future studies are focused on identifying downstream metabolic targets of Dnmt3b. For the purposes of this study, it was investigated if cellular metabolism was altered in Dnmt3b LOF cells by analysis of mitochondrial function. It was found that mitochondrial respiration was increased, as were levels of TCA cycle metabolites (succinate, fumarate) and NADH (generated by the TCA cycle and fed into the oxidative phosphorylation pathway). Since it was shown that Dnmt3b LOF chondrocytes express higher levels of catabolic genes, including hypertrophic chondrocyte markers, then this may be one explanation for why mitochondrial respiration appears to increase in these cells.

In conclusion, this novel body of research has established that Dnmt3b-mediated mechanisms are important in maintaining post-natal cartilage homeostasis. These findings show that inflammatory signals may play a role in decreasing Dnmt3b levels which then leads to the disruption of a number of cellular pathways including those involved in metabolic processes. Future studies will involve deciphering what specific metabolic pathways are disrupted in a Dnmt3b LOF scenario. Interestingly, succinate levels were found to be elevated in Dnmt3b LOF cells and recent reports have shown that succinate itself is an inflammatory signal that can induce IL-1β[49]. It remains to be determined whether or not a vicious cycle may exist in OA chondrocytes whereby inflammation can modulate metabolic processes via downregulation of Dnmt3b, thereby leading to increased production of metabolic intermediates, such as succinate, which may then further enhance the inflammatory process. Overall, these studies will open up new avenues of research with respect to exploring alternative therapeutic strategies to treat OA. Such approaches may involve development of approaches to prevent loss of Dnmt3b activity in the OA joint or target intermediates of specific metabolic pathways that are regulated by this DNA methyltransferase.

Methods for Examples 1-5

Human cartilage tissue. Two separate Institutional Review Board-approved protocols were executed at the University of Rochester to collect articular cartilage from normal, OA, and injured joints. Normal cartilage was collected from amputation patients (talus or knee, n=11) and OA cartilage was harvested from total knee arthroplasty patients (n=57) under IRB ID # RSRB00042321. Injured cartilage, debrided from patients that underwent arthroscopic knee surgery to treat a recent meniscal injury (within 1 month, n=14), was collected under IRB ID # RSRB00014518. At harvest, tissues were immediately fixed in 10% neutral buffered formalin and processed for embedding in paraffin. After facing the cartilage blocks on a microtome, between 1 and 4 biopsy punches were recovered from each block (1 mm diameter, 3 mm deep) and transferred to a receiver block to create a tissue microarray containing 176 biopsies. Human knee articular cartilage tissue was also obtained from surgeons at Washington University Department of Orthopaedic Surgery following total knee replacement surgery. All studies involving this tissue, which was used to generate primary articular chondrocytes for in vitro experiments, were approved by Washington University Human Research Protection Office (IRB ID #: 201104119).

Transgenic mice. All studies involving mice were approved by the University of Rochester Committee on Animal Resources. All mouse strains including Agc1CreERT2 29, Col2a1Cre [50], Dnmt3bf/f[51], and Rosa-rtTA f/f52 have been previously described. Dnmt3b$^{f/f}$ mice were generated by Dr. En Li and were obtained from the Mutant Mouse Regional Resource Center supported by the NIH. The Agc1Cre$^{ERT2}$ mouse line was a generous gift from the laboratory of Dr. Benoit de Crombrugghe (MD Anderson Cancer Center, University of Texas, USA). The efficiency of the Agc1Cre$^{ERT2}$ driver line in targeting chondrocytes of knee joint articular cartilage was confirmed by generation of Agc1Cre$^{ERT2}$; Rosa-tomato (mT/mG) mice and analysis of knee joint tissue sections by fluorescence microscopy. Agc1Cre; Dnmt3b$^{f/f}$ (Dnmt3b$^{Agc1ER}$) mice were viable, fertile, and produced in expected Mendelian ratios. Tamoxifen (1 mg/10 g body weight/day) was delivered i.p. to all Dnmt3b$^{Agc1ER}$ mice and Cre+ littermate controls for 5 continuous days starting at 2 mo of age to permanently delete the Dnmt3b gene in adult cartilage tissue. Western blot analysis of proteins extracted from articular cartilage of 3 mo Dnmt3b$^{Agc1ER}$ or control mice was carried out to confirm Dnmt3b knock-down in the conditional knock-out mice following tamoxifen injection. Knee joints from Dnmt3b conditional knock-out and Cre+littermate control mice were harvested at 5 mo and 8 mo for histological and micro-CT analyses.

For production of Dnmt3b gain-of-function (GOF) mice, a construct was generated by cloning full-length Flag-tagged murine Dnmt3b cDNA into pBI-3 vector[53]. The pBI-3 vector contains an rtTA promoter binding site upstream of Dnmt3b. Upon recombination, Dnmt3b is expressed with addition of doxycycline (Dox). Thus, the model provides both cell specific and temporal regulation for Dnmt3b overexpression (FIG. S13). Dnmt3b transgenic mice (Dnmt3b-tg) were subsequently generated by Cyagen Biosciences Inc (Santa Clara, Calif.). We obtained 68 Dnmt3b-tg mice, 7 of which were founder mice. Dnmt3b-tg mice were crossed with Col2a1Cre; Rosa-rtTA$^{f/+}$ mice to generate Dnmt3b GOF mice. These mice were viable, fertile, and produced in expected Mendelian ratios. The efficiency of the Col2a1Cre driver line in targeting chondrocytes of articular cartilage was confirmed by analysis of knee joint tissue sections of Col2a1Cre; Rosa-rtTA$^{f/+}$; H2BGFP mice by fluorescence microscopy. Dox (2.5 mg/kg body weight) was administrated i.p. to 10 wk old male Dnmt3b GOF mice and littermate controls one day prior to the meniscus ligament surgery (MLI). Dox injections continued twice a week following MLI surgery for 8 wk or 12 wk, at which point mice were sacrificed and knee joint specimens harvested for downstream histological analyses.

Murine knee joint analysis. Murine hind limbs were harvested, followed by removal of skin and soft tissues before fixation in 10% neutral-buffered formalin for 3 days and decalcification in 14% EDTA for 7 days. Limbs were then processed, embedded in paraffin and sectioned (5 μm). Alcian Blue Hematoxylin/Orange G (ABH/OG) staining was performed to analyze knee joint tissue architecture and proteoglycan localization. Quantitative histomorphometry was performed on ABH/OG stained sections using the Osteomeasure Analysis System (Osteometrics). The tidemark was used to differentiate between un-mineralized and mineralized articular cartilages. The OARSI score was evaluated as previously described[54]. Immunohistochemistry (IHC) was performed on sections using traditional antigen retrieval and colorimetric development methodologies. Briefly, paraffin slides were baked at 60° C. overnight and after re-equilibration to room temperature, slides were de-paraffined through three changes in xylene, 100% ethanol, 95% ethanol, one change in 70% ethanol and final rehydration in distilled water. Heat-induced antigen retrieval was performed with citric acid buffer (pH 6.0). Rabbit anti-mouse antibodies against COL2A1 (Thermo Scientific, #M5235-P, 1:1000), DNMT3A (LSBio, #LS-B7420, 1:1000) and DNMT3B (LSBio, #LS-B1191, 1:1000) were used. Impact NovaRed (Vector Laboratories) was used for peroxidase substrate reaction. Counterstaining were performed using hematoxylin.

MicroCT analyses were performed on 2, 4, 6, and 8 mo mouse knee joints prior to decalcification using a VivaCT 40 scanner (Scanco USA, Inc.). Briefly, the tibia was scanned from knee to the connection at the fibula using a protocol consisting of high-resolution (10.5 microns) X-ray energy settings of 55 kVp, 145 µA and 300 ms integration time. Parameters of subchondral bone volume, bone mineral density (BMD) and bone connective density were measured as previously described using the Scanco analysis software[55].

Primary articular chondrocyte isolation and culture. Articular cartilage was isolated from the knee joints of 3 mo Dnmt3b$^{f/f}$ mutant mice as previously described, with modifications[56]. Briefly, articular cartilage was excised from femoral condyles and tibial plateaus with a scalpel and placed in 1×PBS. Cartilage fragments were digested using 3 mg/ml Collagenase D in 10 ml high glucose DMEM (Invitrogen, #11965-092) for 12 hours at 37° C. Murine articular chondrocyte cell suspensions were filtered through 0.4 µM filters and seeded at a density of 500,000 cells/well in 6-well tissue culture plates in DMEM high glucose medium supplemented with 10% Fetal Bovine Serum (FBS) (Sigma) and 1% Penicillin/Streptomycin (Life Technologies, #15140-122).

Full thickness sections of human articular cartilage were removed from the femoral condyles and tibial plateaus of specimens obtained following total knee replacement surgery, diced into 2 mm cubes and digested in sterile spinner flasks for 90 min at 37° C. in pronase digestion buffer [DMEM/F12 (Gibco); 5% FBS (Atlanta Biologicals), 2% penicillin/streptomycin (Gibco) and 0.4% pronase (Roche)]. Following washes in HBSS (Gibco), tissue was further digested in collagenase digestion buffer at 37° C. [DMEM/F12; 5% FBS; 2% penicillin/streptomycin; 0.035% collagenase P (Roche)] for 14-16 hr. Cells were collected, filtered through 70 µm cell strainers (VWR) and plated at a density of 100,000 cells/cm². After 24 hr, chondrocytes were treated with IL-1β (10 ng/ml; Gibco) for 48 hr. Total RNA was collected using the Total RNA prep kit (Norgen Biotek) and cDNA was synthesized using Superscript RT II (Life Technologies).

Next generation RNA sequencing and data analysis. Primary articular chondrocytes were isolated from Dnmt3b$^{f/f}$ mice and treated with either Adeno-Cre or Adeno-GFP (MOI=100) for 72 hr. Total RNA was collected using the AllPrep DNA/RNA Mini Kit (Qiagen, #80204). Total RNA concentration was determined with the NanoDrop 1000 spectrophotometer (NanoDrop, Wilmington, Del.) and RNA quality was assessed with the Agilent Bioanalyzer (Agilent, Santa Clara, Calif.). The TruSeq RNA Sample Preparation Kit V2 (Illumina, San Diego, Calif.) was used for next generation sequencing library construction (as per the manufacturer's protocol) at the Genomics Research Center (GRC) at University of Rochester Medical School (URMC). Briefly, mRNA was purified from 100 ng total RNA with oligo-dT magnetic beads and fragmented. First-strand cDNA synthesis was performed with random hexamer priming followed by second-strand cDNA synthesis. End repair and 3′ adenylation was then performed on the double stranded cDNA. Illumina adaptors were ligated to both ends of the cDNA, purified by gel electrophoresis and amplified with PCR primers specific to the adaptor sequences to generate amplicons of approximately 200-500 bp in size. The amplified libraries were hybridized to the Illumina single end flow cell and amplified using the cBot (Illumina, San Diego, Calif.) at a concentration of 8 pM per lane. Single end reads of 100 nt were generated for each sample and aligned to the organism specific reference genome. Sequences reads were submitted to NCBI Gene Expression Omnibus (GEO; ncbi.nlm.nih.gov/geo/) under Accession Number GSE85148. Raw reads generated from the Illumina HiSeq2500 sequencer were be de-multiplexed using configurebcl2fastq.pl version 1.8.4. Low complexity reads and vector contamination were removed using sequence cleaner ("seqclean") and the NCBI univec database, respectively. The FASTX toolkit (fastq_quality_trimmer) was applied to remove bases with quality scores below Q=13 from the end of each read. Processed reads were then mapped to the UCSC *Mus musculus* reference genome (mm10) with SHRiMP version 2.2.3 and differential expression analysis was performed using Cufflinks version 2.0.2; specifically, cuffdiff2 and usage of the general transfer format (GTF) annotation file for the given reference genome. Heatmap of sample-to-sample distances using the rlog-transformed values, MA plot of expression changes and heatmap of significantly expressed genes were analyzed by DEseq2 package using R/Bioconductor platform[57]. Network analysis of differentially expressed genes was generated by GeneMania tool (genemania.org/). Significantly differentially-expressed genes were further analyzed for statistically enriched pathways using IPA (Ingenuity Systems, ingenuity.com) and categorized for biological function using DAVID (Functional Annotation Bioinformatics, david.abcc.ncifcrf.gov/).

Whole genome bisulfite sequencing and data analysis. Following treatment of murine articular chondrocytes (isolated from Dnmt3b$^{f/f}$ mice), with either Adeno-Cre or Adeno-GFP (MOI=100) for 72 h, genomic DNA was isolated using the AllPrep DNA/RNA Mini Kit (Qiagen, #80204). Genomic DNA was quantified using the Qubit fluorometer (Life Technologies, Grand Island, N.Y.) and DNA integrity was determined using the TapeStation with genomics DNA tape reagents (Agilent, Santa Clara, Calif.). Methylation libraries were generated with Epicentre's Epinome Methyl-seq library kit in collaboration with the Genomics Research Center (GRC) at URMC. Briefly, bisulfite conversion was carded out on 100 ng of genomics DNA using Zymo EZ DNA Methylation Gold as per manufacturer's recommendations (Zymo Research, Irvine, Calif.) and conversion efficiency was determined with the Bioanalyzer 2100 (Agilent, Santa Clara, Calif.). Single-stranded cDNA was generated and tagged from bisulfite converted DNA using random hexamers containing a 5′ tag followed by terminal tagging to mark the 3′ end of the DNA. Illumina specific adaptors were added during PCR amplification. DNA libraries were purified with AmpureXP beads and quantified with the Bioanalyzer 2100 and Qubit fluorometer. The amplified libraries were hybridized to the Illumina pair end flow cell and amplified using the cBot (Illumina, San Diego, Calif.) at a concentration of 8 pM per lane. Pair end reads of 100 nt were generated for each sample and aligned to the organism specific reference genome. Sequences reads were also submitted to NCBI Gene Expression Omnibus (GEO; ncbi.nlm.nih.gov/geo/) under Accession Number GSE85148. Raw reads generated from the Illumina HiSeq2500 sequencer were de-multiplexed using configurebcl2fastq.pl version 1.8.4. Pre-processing of the data will be performed using Trimmomatic-0.32 for stringent adapter removal and quality filtering. Alignment of the processed read data to the NCBI build 37.2 of the *Mus musculus* genome was then performed using Bismark version 0.9.0 which made use of bowtie version 2.1.0 and samtools version 0.1.19. Methylation extraction was also performed using Bismark version 0.9.0 with the following parameters: "- - - cutoff 5- - - ignore 3- - - ignore_r2 3". A Python program was written to combine the methylation information in the form of an average percent methylation for each locus that was called by Bismark for all three replicates within a group and convert the format which DSS package[58] required for differentially methylation analysis. The differentially methylated regions (DMRs) were chosen using cutoffs with delta methylation level as 0.1, p-value as 0.01 and minimum length as 200 bp (the average size of DMRs is 560 bp, data not shown). A customized Python script was used to assign methylation values to the 500 bp windows among genome, and methylation difference between Dnmt3b LOF and control group at genome background or DMRs were plotted using ggplot2 package (ggplot2.org/). DMRs were further annotated to genomic regions based on refGene annotation from UCSC Genome Browser (genome.ucsc.edu/) using customized scripts. Motif search within DMRs was done using Homer software[59] with default parameters.

Metabolite analysis and mitochondria stress test. Proteins were isolated from primary articular chondrocytes and 10 μl samples were injected into an LC-20 AD HPLC system (Shimadzu), which was coupled to a triple-quadrupole mass spectrometer (Thermo Fisher Scientific). Metabolites were analyzed by LC-MS/MS as previously described[60]. Briefly, articular chondrocytes were plated in XF96 plates at 50,000 cells per well with XF Assay Medium Modified DMEM (Seahorse, #101022-100). Oligomycin and FCCP (Seahorse Stress Kit) were prepared in XF assay medium at a final concentration of 5 μM and 1 μM, respectively, and were injected during the measurements. At the end of the assays, protein concentrations were measured for normalization.

Dnmt3b promoter luciferase assay. ATDC-5 cells were transfected with a pGL4 luciferase plasmid containing cDNA encoding 1 kb of the murine Dnmt3b promoter using X-tremeGENE transfection reagents (Roche, #06366236001). A Dnmt3b promoter construct containing mutations in the predicted NFκB binding site was also transfected into an additional set of ATDC-5 cells. All transfected cells were then treated with IL-1β (1 ng/ml) for 24 h before performing the luciferase assay.

Chromatin immunoprecipation (ChIP) assay. ATDC-5 cells (1×10⁷) were harvested for ChIP assays following the manufacturer's protocol (Cell Signaling, #9003). Briefly, cells were fixed with formaldehyde and chromatin was fragmented by Micrococcal Nuclease to 200-900 bp. Chromatin immunoprecipitations were performed using NFκB1 antibody (Cell Signaling, #13586, 1:50) while Histone H3 and IgG antibodies were used as positive and negative controls, respectively. After reversal of protein-DNA crosslink, the enrichment of Dnmt3b DNA fragment during immunoprecipitation was analyzed by standard PCR and quantitative real-time PCR. Dnmt3b primer sequences used for PCR were Forward: 5'-CTG GTC ATC TAG GAG GGT GA-3' (SEQ ID NO:6); and Reverse: 5'-CGG GCG AGG GAG ATT TG-3' (SEQ ID NO:7).

Tet activity assay. Nuclear extracts were prepared from the Dnmt3b LOF chondrocytes or WT control chondrocytes using a cell nuclear extraction preparation kit (Active Motif, Carlsbad, Calif.). These nuclear extracts (containing 5 μg protein) extracts were then used to assess total Tet activity according to the manufacturer's instructions (Abcam, Cambridge, Mass.).

Real-time PCR and western blot. RNA was isolated from ATDC-5 chondrocytes or primary articular chondrocytes using RNeasy Mini kit (Qiagen). cDNA synthesis and real-time RT-PCR was performed according to manufacturer's instructions. Primer sequences for Col2a1, Runx2, Mmp13, Col10a1, Dnmt1, Dnmt3a, Dnmt3b, Tet1, Tet2, Tet3 and β-actin are shown in Table 1. Western blot analyses were conducted on the protein of lysates from either ATDC-5 cells or primary (murine or human) articular chondrocytes. The following primary antibodies were used: pSmad1/5 (Cell Signaling technology Inc., 1:500), pSmad2 (Cell Signaling technology Inc., 1:1000), Smad1/5/8 (Cell Signaling technology Inc., 1:1000), Smad2 (Cell Signaling technology Inc., 1:1000), DNMT3A (LSBio, 1:1000), DNMT3B (LSBio, 1:1000), FLAG (Life technology, 1:1000) and β-actin (Sigma, 1:2000).

Cell proliferation and cell death detection. BMP-2 treated primary articular chondrocytes isolated from 2 mo WT (C57BL/6) mice were treated with vehicle or Rotenone and Antimycin A for 48 hr. Cell proliferation and cell death were detected by Roche Proliferation ELISA Kit (Roche, #11647229001) and Cell Death Detection ELISA Kit (Roche, #11774425001).

Succinate concentration assay. Primary articular chondrocytes isolated from 2 mo WT mice were treated with vehicle or diethylsuccinate (1 mM) for 48 h. Intracellular succinate concentration was measured using the succinate colorimetric assay kit following the manufacturer's instruction (Sigma, #MAK184-1KT).

Statistical analyses. Data (in vitro experiments and histomorphometry) are presented as mean±standard deviation. The comparisons for OARSI scores, bone mass and micro-architecture among different groups were performed using multiple-factorial analysis of variance (ANOVA). When ANOVA testing indicated overall significance of main effects and without interaction between them, the difference between individual time points and sites was assessed by post hoc tests. The level of significance was set at P<0.05. Statistic tests for RNA-seq and methylC-seq data analysis were performed using the R environment (r-project.org/).

TABLE 1

Primer Sequences.

| Genes | Sequences | SEQ ID NO |
|---|---|---|
| Col2a1 | 5'-GCA GAG ATG GAG AAC CTG GTA-3' | 8 |
|  | 5'-AGC CTT CTC GTC ATA CCCT-3' | 9 |
| Col10a1 | 5'-ATG CCT TGT TCT CCT CTT ACT G-3' | 10 |
|  | 5'-TGC TGA ACG GTA CCA AAC G-3' | 11 |
| Runx2 | 5'-CGT CCA CTG TCA CTT TAA TAG CTC-3' | 12 |
|  | 5'-GTA GCC AGG TTC AAC GAT CTG-3' | 13 |
| Mmp13 | 5'-AGA CTG GTA ATG GCA TCA AGG-3' | 14 |
|  | 5'-GCC ATT TCA TGC TTC CTG ATG-3' | 15 |

TABLE 1 -continued

Primer Sequences.

| Genes | Sequences | SEQ ID NO |
|---|---|---|
| Dnmt1 | 5'-CCT GCC AGG GCT TCA GTG GC-3' | 16 |
| | 5'-CAG GCA GCG CAG TGT GAG CT-3' | 17 |
| Dnmt3a | 5'-GCC GAA TTG TGT CTT GGT GGA TGA CA-3' | 18 |
| | 5'-CCT GGT GGA ATG CAC TGC AGA AGG A-3' | 19 |
| Dnmt3b | 5'-AAT ACC CAA CTC CTT GAG CAC-3' | 20 |
| | 5'-TCT TCA CTA CTG ATC CTG ACC T-3' | 21 |
| Tet1 | 5'-GAG CCT GTT CCT CGA TGT GG-3' | 22 |
| | 5'-CAA ACC CAC CTG AGG CTG TT-3' | 23 |
| Tet2 | 5'-TGTTGTTGTCAGGGTGAGAATC-3' | 24 |
| | 5'-TCTTGCTTCTGGCAAACTTACA-3' | 25 |
| Tet3 | 5'-CCGGATTGAGAAGGTCATCTAC-3' | 26 |
| | 5'-AAGATAACAATCACGGCGTTCT-3' | 27 |
| β-actin | 5'-AGA TGT GGA TCA GCA AGC AG-3' | 28 |
| | 5'-GCG CAA GTT AGG TTT TGT CA-3' | 29 |
| DNMT3B | 5'-TTG ATA TTC CCC TCG TGC TTC-3' | 30 |
| | 5'-CGA GTC CTG TCA TTG TTT GAT G-3' | 31 |
| COL2A1 | 5'-GGC AAT AGC AGG TTC ACG TAC A-3' | 32 |
| | 5'-CGA TAA CAG TCT TGC CCC ACT T-3' | 33 |
| MMP13 | 5'-CTTGACCACTCCAAGGACCC-3' | 34 |
| | 5'-CCTGGACCATAGAGAGACTGGA-3' | 35 |
| GAPDH | 5'-TGT AGT TGA GGT CAA TGA AGG G-3' | 36 |
| | 5'-ACA TCG CTC AGA CAC CAT G-3' | 37 |

REFERENCES FOR EXAMPLES 1-5

1. Felson, D. T. Clinical practice. Osteoarthritis of the knee. The New England journal of medicine 354, 841-848 (2006).
2. Felson, D. T. Clinical practice. Osteoarthritis of the knee. N Engl J Med 354, 841-848 (2006).
3. Wang, M., et al. Recent progress in understanding molecular mechanisms of cartilage degeneration during osteoarthritis. Ann N Y Acad Sci 1240, 61-69 (2011).
4. Bijlsma, J. W., Berenbaum, F. & Lafeber, F. P. Osteoarthritis: an update with relevance for clinical practice. Lancet 377, 2115-2126 (2011).
5. Anderson, D. D., et al. Post-traumatic osteoarthritis: improved understanding and opportunities for early intervention. J Orthop Res 29, 802-809 (2011).
6. van den Berg, W. B. Osteoarthritis year 2010 in review: pathomechanisms. Osteoarthritis Cartilage 19, 338-341 (2011).
7. Glasson, S. S., Blanchet, T. J. & Morris, E. A. The surgical destabilization of the medial meniscus (DMM) model of osteoarthritis in the 129/SvEv mouse. Osteoarthritis Cartilage 15, 1061-1069 (2007).
8. Kamekura, S., et al. Osteoarthritis development in novel experimental mouse models induced by knee joint instability. Osteoarthritis and cartilage/OARS, Osteoarthritis Research Society 13, 632-641 (2005).
9. Goldring, M. B. & Berenbaum, F. Emerging targets in osteoarthritis therapy. Curr Opin Pharmacol 22, 51-63 (2015).
10. Valdes, A. M., et al. Genetic variation in the SMAD3 gene is associated with hip and knee osteoarthritis. Arthritis and rheumatism 62, 2347-2352 (2010).
11. Valdes, A. M., et al. The GDF5 rs143383 polymorphism is associated with osteoarthritis of the knee with genome-wide statistical significance. Annals of the rheumatic diseases 70, 873-875 (2011).
12. Panoutsopoulou, K. & Zeggini, E. Advances in osteoarthritis genetics. J Med Genet 50, 715-724 (2013).
13. Reynard, L. N. & Loughlin, J. Insights from human genetic studies into the pathways involved in osteoarthritis. Nat Rev Rheumatol 9, 573-583 (2013).
14. Evangelou, E., et al. A meta-analysis of genome-wide association studies identifies novel variants associated with osteoarthritis of the hip. Ann Rheum Dis 73, 2130-2136 (2014).
15. Rodriguez-Fontenla, C., et al. Assessment of osteoarthritis candidate genes in a meta-analysis of nine genome-wide association studies. Arthritis Rheumatol 66, 940-949 (2014).
16. Goldring, M. B. & Marcu, K. B. Epigenomic and microRNA-mediated regulation in cartilage development, homeostasis, and osteoarthritis. Trends Mol Med 18, 109-118 (2012).
17. Barter, M. J., Bui, C. & Young, D. A. Epigenetic mechanisms in cartilage and osteoarthritis: DNA methylation, histone modifications and microRNAs. Osteoarthritis and cartilage/OARS, Osteoarthritis Research Society 20, 339-349 (2012).
18. Loughlin, J. & Reynard, L. N. Osteoarthritis: Epigenetics of articular cartilage in knee and hip OA. Nature reviews. Rheumatology 11, 6-7 (2015).
19. Maunakea, A. K., et al. Conserved role of intragenic DNA methylation in regulating alternative promoters. Nature 466, 253-257 (2010).
20. Gu, J., et al. Mapping of Variable DNA Methylation Across Multiple Cell Types Defines a Dynamic Regulatory Landscape of the Human Genome. G3 (Bethesda) 6, 973-986 (2016).
21. Smith, Z. D. & Meissner, A. DNA methylation: roles in mammalian development. Nature reviews. Genetics 14, 204-220 (2013).
22. Fernandez-Tajes, J., et al. Genome-wide DNA methylation analysis of articular chondrocytes reveals a cluster of osteoarthritic patients. Ann Rheum Dis 73, 668-677 (2014).
23. Rushton, M. D., et al. Characterization of the cartilage DNA methylome in knee and hip osteoarthritis. Arthritis Rheumatol 66, 2450-2460 (2014).
24. Jeffries, M. A., et al. Genome-wide DNA methylation study identifies significant epigenomic changes in osteoarthritic cartilage. Arthritis Rheumatol 66, 2804-2815 (2014).
25. Rushton, M. D., Young, D. A., Loughlin, J. & Reynard, L. N. Differential DNA methylation and expression of inflammatory and zinc transporter genes defines subgroups of osteoarthritic hip patients. Annals of the rheumatic diseases (2015).
26. Rushton, M. D., et al. Methylation quantitative trait locus analysis of osteoarthritis links epigenetics with genetic risk. Hum Mol Genet 24, 7432-7444 (2015).
27. Mooney, R. A., Sampson, E. R., Lerea, J., Rosier, R. N. & Zuscik, M. J. High-fat diet accelerates progression of osteoarthritis after meniscal/ligamentous injury. Arthritis Res Ther 13, R198 (2011).

28. Wang, M., et al. Recent progress in understanding molecular mechanisms of cartilage degeneration during osteoarthritis. *Annals of the New York Academy of Sciences* 1240, 61-69 (2011).
29. Henry, S. P., et al. Generation of aggrecan-CreERT2 knockin mice for inducible Cre activity in adult cartilage. *Genesis* 47, 805-814 (2009).
30. McLean, C. Y., et al. GREAT improves functional interpretation of cis-regulatory regions. *Nature biotechnology* 28, 495-501 (2010).
31. Lorenzo, P., Bayliss, M. T. & Heinegard, D. Altered patterns and synthesis of extracellular matrix macromolecules in early osteoarthritis. *Matrix Biol* 23, 381-391 (2004).
32. Kim, K. I., Park, Y. S. & Im, G. I. Changes in the epigenetic status of the SOX-9 promoter in human osteoarthritic cartilage. *J Bone Miner Res* 28, 1050-1060 (2013).
33. Imagawa, K., et al. Association of reduced type IX collagen gene expression in human osteoarthritic chondrocytes with epigenetic silencing by DNA hypermethylation. *Arthritis Rheumatol* 66, 3040-3051 (2014).
34. Barter, M. J. & Young, D. A. Epigenetic mechanisms and non-coding RNAs in osteoarthritis. *Curr Rheumatol Rep* 15, 353 (2013).
35. Blaney Davidson, E. N., et al. Increase in ALK1/ALK5 ratio as a cause for elevated MMP-13 expression in osteoarthritis in humans and mice. *J Immunol* 182, 7937-7945 (2009).
36. Greene, M. A. & Loeser, R. F. Aging-related inflammation in osteoarthritis. *Osteoarthritis and cartilage/OARS, Osteoarthritis Research Society* 23, 1966-1971 (2015).
37. Wang, X., Hunter, D., Xu, J. & Ding, C. Metabolic triggered inflammation in osteoarthritis. *Osteoarthritis and cartilage/OARS, Osteoarthritis Research Society* 23, 22-30 (2015).
38. Taylor, S. E., Smeriglio, P., Dhulipala, L., Rath, M. & Bhutani, N. A global increase in 5-hydroxymethylcytosine levels marks osteoarthritic chondrocytes. *Arthritis Rheumatol* 66, 90-100 (2014).
39. Haseeb, A., Makki, M. S. & Haqqi, T. M. Modulation of ten-eleven translocation 1 (TET1), Isocitrate Dehydrogenase (IDH) expression, alpha-Ketoglutarate (alpha-KG), and DNA hydroxymethylation levels by interleukin-1 beta in primary human chondrocytes. *The Journal of biological chemistry* 289, 6877-6885 (2014).
40. Neves-Costa, A. & Moita, L. F. TET1 is a negative transcriptional regulator of IL-1 beta in the THP-1 cell line. *Mol Immunol* 54, 264-270 (2013).
41. Zhang, Q., et al. Tet2 is required to resolve inflammation by recruiting Hdac2 to specifically repress IL-6. *Nature* 525, 389-393 (2015).
42. Villalvilla, A., Gomez, R., Largo, R. & Herrero-Beaumont, G. Lipid transport and metabolism in healthy and osteoarthritic cartilage. *Int J Mol Sci* 14, 20793-20808 (2013).
43. Tsolis, K. C., et al. Comparative proteomic analysis of hypertrophic chondrocytes in osteoarthritis. *Clin Proteomics* 12, 12 (2015).
44. Thijssen, E., van Caam, A. & van der Kraan, P. M. Obesity and osteoarthritis, more than just wear and tear: pivotal roles for inflamed adipose tissue and dyslipidaemia in obesity-induced osteoarthritis. *Rheumatology (Oxford)* 54, 588-600 (2015).
45. Gross, D. N., van den Heuvel, A. P. & Birnbaum, M. J. The role of FoxO in the regulation of metabolism. *Oncogene* 27, 2320-2336 (2008).
46. Eijkelenboom, A. & Burgering, B. M. FOXOs: signalling integrators for homeostasis maintenance. *Nat Rev Mol Cell Biol* 14, 83-97 (2013).
47. Kousteni, S. FoxO1, the transcriptional chief of staff of energy metabolism. *Bone* 50, 437-443 (2012).
48. Pollesello, P., et al. Energy state of chondrocytes assessed by 31 P-NMR studies of preosseous cartilage. *Biochem Biophys Res Commun* 180, 216-222 (1991).
49. Tannahill, G. M., et al. Succinate is an inflammatory signal that induces IL-1 beta through HIF-1 alpha. *Nature* 496, 238-242 (2013).
50. Ovchinnikov, D. A., Deng, J. M., Ogunrinu, G. & Behringer, R. R. Col2a1-directed expression of Cre recombinase in differentiating chondrocytes in transgenic mice. *Genesis* 26, 145-146 (2000).
51. Dodge, J. E., et al. Inactivation of Dnmt3b in mouse embryonic fibroblasts results in DNA hypomethylation, chromosomal instability, and spontaneous immortalization. *The Journal of biological chemistry* 280, 17986-17991 (2005).
52. Belteki, G., et al. Conditional and inducible transgene expression in mice through the combinatorial use of Cre-mediated recombination and tetracycline induction. *Nucleic acids research* 33, e51 (2005).
53. Baron, U., Freundlieb, S., Gossen, M. & Bujard, H. Co-regulation of two gene activities by tetracycline via a bidirectional promoter. *Nucleic acids research* 23, 3605-3606 (1995).
54. Glasson, S. S., Chambers, M. G., Van Den Berg, W. B. & Little, C. B. The OARSI histopathology initiative—recommendations for histological assessments of osteoarthritis in the mouse. *Osteoarthritis and cartilage/OARS, Osteoarthritis Research Society* 18 Suppl 3, S17-23 (2010).
55. Sampson, E. R., et al. Establishment of an index with increased sensitivity for assessing murine arthritis. *Journal of orthopaedic research: official publication of the Orthopaedic Research Society* 29, 1145-1151 (2011).
56. Gosset, M., Berenbaum, F., Thirion, S. & Jacques, C. Primary culture and phenotyping of murine chondrocytes. *Nat Protoc* 3, 1253-1260 (2008).
57. Love, M. I., Huber, W. & Anders, S. Moderated estimation of fold change and dispersion for RNA-seq data with DESeq2. *Genome Biol* 15, 550 (2014).
58. Park, Y. & Wu, H. Differential methylation analysis for BS-seq data under general experimental design. *Bioinformatics* 32, 1446-1453 (2016).
59. Heinz, S., et al. Simple combinations of lineage-determining transcription factors prime cis-regulatory elements required for macrophage and B cell identities. *Molecular cell* 38, 576-589 (2010).
60. Munger, J., et al. Systems-level metabolic flux profiling identifies fatty acid synthesis as a target for antiviral therapy. *Nature biotechnology* 26, 1179-1186 (2008).

Example 6

Identification of Abat as a Downstream Target of Dnmt3b

Figure 20A:
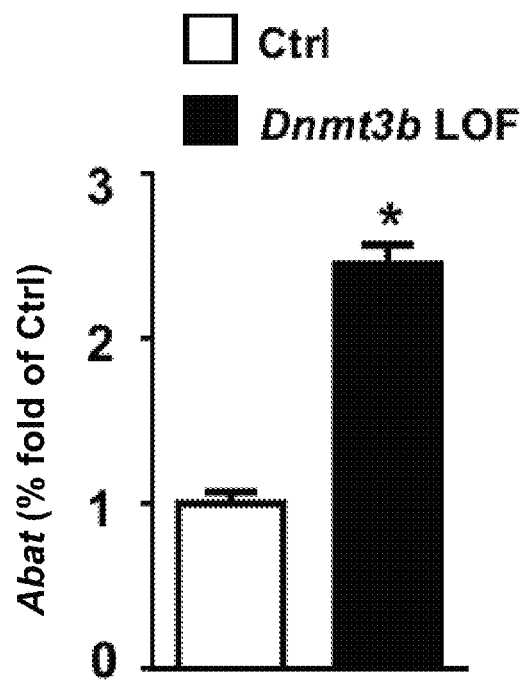
FIG. 20A and FIG. 20B depict graphs showing integrative analysis of Methyl-seq and RNA-seq.
Figure 20B:
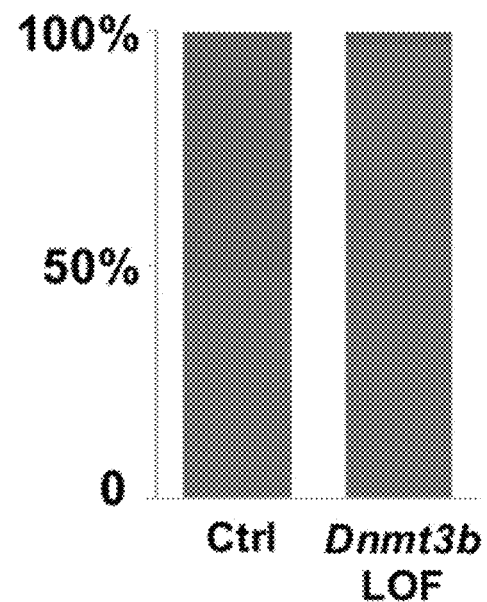

Primary chondrocytes were isolated from 2 mo Dnmt3b$^{f/f}$ mice and infected with either Ad5-CMV-Cre (Dnmt3b LOF cells) or Ad5-CMV-GFP (control cells) followed by RNA-Seq and Methyl-Seq analyses. The data showed that global 5-methylcytosine (5mC) levels, representing overall methylation, was similar in control and Dnmt3b LOF chondrocytes, which is consistent with methylation profiling data in human OA patients. However, differentially methylated loci (DML) were identified between LOF and control groups, some of which were present in cartilage regulatory genes (i.e. Smad3, Runx2, Mmp13, Adam12). Integrative analysis of RNA-Seq and Methyl-Seq data revealed that 44 genes had both altered methylation and an altered gene expression pattern. One of these genes, encoding the enzyme 4-aminobutyrate aminotransferase (Abat) (1), was found to be significantly hypomethylated and also over-expressed in Dnmt3b LOF cells. Gene ontology analysis (Ingenuity Pathway Analysis) of the 44 differentially-expressed genes revealed an enrichment in pathways regulating glutamate metabolism. Since Abat is known to be involved in glutamate metabolism (2), this enzyme was investigated further. Validation qPCR analysis showed that Abat expression was indeed increased in Dnmt3b LOF cells and enzymatic methylation qPCR confirmed hypomethylation in the Abat promoter region (FIG. 20A, FIG. 20B).

Since Abat is known to regulate cellular metabolism (2), it was hypothesized that levels of succinate, (the product of Abat's catalytic action on gamma-aminobutyric acid; GABA), and other downstream TCA cycle metabolites (fumarate, NADH) would be increased in Dnmt3b LOF cells. This was shown (FIG. 13D, FIG. 13E, FIG. 13F), as was the expected increase in mitochondrial metabolism (e.g. increased basal respiration and ATP production) in Dnmt3b LOF cells compared to control cells (FIG. 13B, FIG. 13C).

Figure 21:
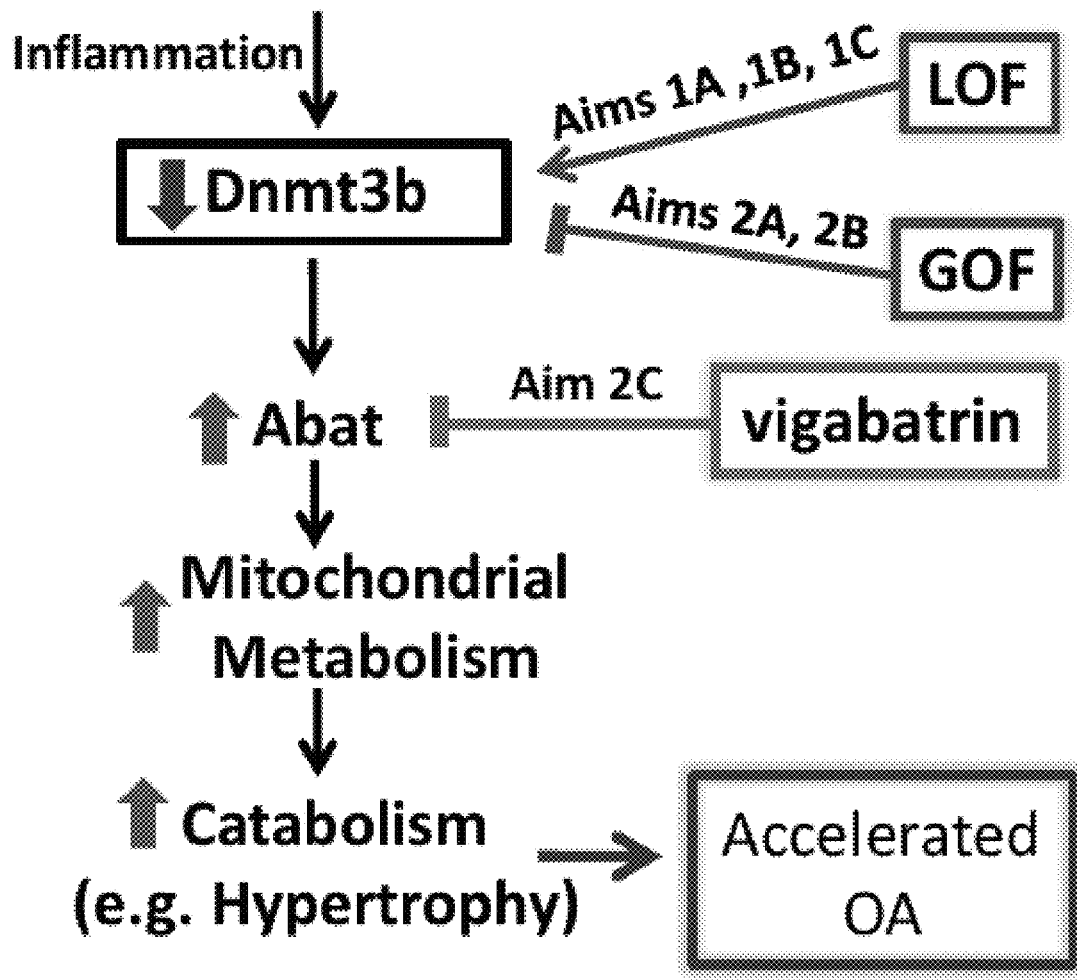
FIG. 21 depicts proposed Dnmtb3/Abat axis in chondrocytes following joint injury/aging.

Based on these findings, it is hypothesized that joint injury/inflammation results in alteration of a Dnmt3b/Abat signaling axis (FIG. 21). Complementary in vitro and in vivo approaches will be used to study the downstream effects of modulating Dnmt3b expression by using Dmnt3b LOF and GOF genetic models. The hypotheses will be tested that: i) LOF leads to induction of Abat, increased mitochondrial metabolism, development of a catabolic/hypertrophic phenotype, and OA; and ii) GOF maintains reduced Abat expression, low levels of mitochondrial metabolism, maintenance of a stable articular chondrocyte phenotype, and protection against the development and progression of OA. Mechanistic studies will be performed using Abat LOF and GOF approaches to explore the hypothesis that Abat acts as a key target of Dnmt3b in the regulation of articular chondrocyte homeostasis. As Abat is a targetable enzyme, the FDA approved Abat inhibitor drug, vigabatrin, will be used for in vivo studies in mice to demonstrate potential chondroprotection. This innovative work will provide new insights toward understanding the role of specific enzymes that control epigenetic and metabolic pathways in cartilage health and disease. Identification of new targets for the design of novel strategies to treat OA is expected.

Example 7

MLI Surgery Results in Increased Abat Expression in Articular Cartilage

Figure 22A:
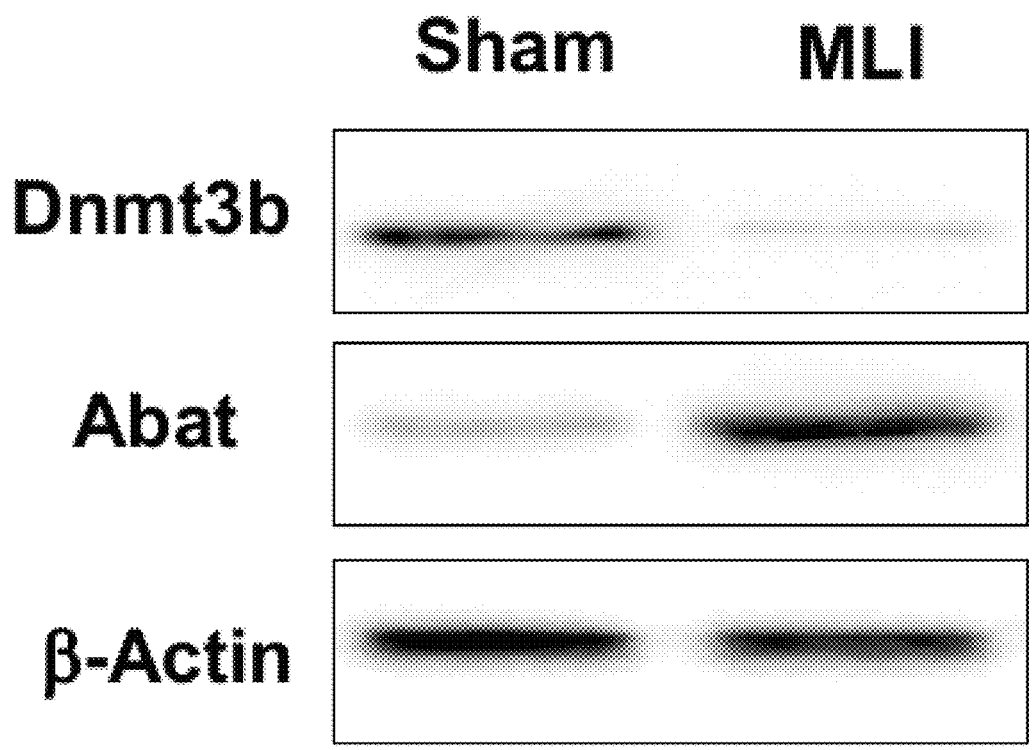
FIG. 22A and FIG. 22B depict Abat expression in chondrocytes and cartilage tissue.
Figure 22B:
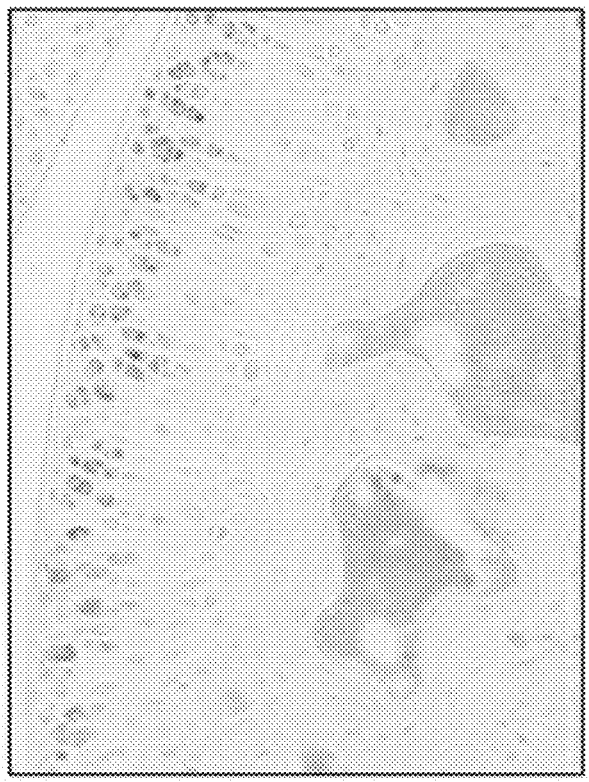

To determine if the expression of Dnmt3b and Abat are coordinately regulated in OA, MLI or sham surgery was performed on 10-wk-old male WT mice. Knee joint tissues and isolated articular chondrocytes were obtained 4 weeks later for protein analysis. Western blot showed decreased Dnmt3b expression and increased Abat expression in articular chondrocytes following MLI (FIG. 22A). IHC confirmed increased Abat expression in cartilage tissue from joints that had undergone MLI (FIG. 22B).

Example 8

Figure 23A:
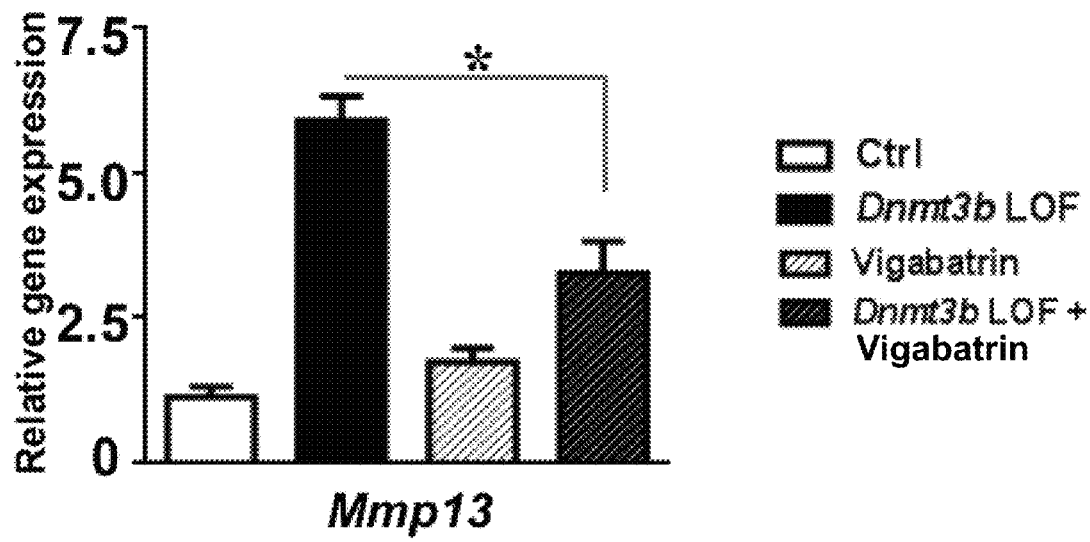
FIG. 23A, FIG. 23B and FIG. 23C depict ablation of Dnmt3b in articular chondrocytes (ACs). Primary Acs from Dnmt3b$^{f/f}$ mice were infected with Ad5-Cre or Ad-GFP for 48 hr and cultured for a further 48 hr with or without vigabatrin (500µM). Vigabatrin treatment partially attenuated hypertrophic gene expression induced by Dnmt3b LOF.
Figure 23B:
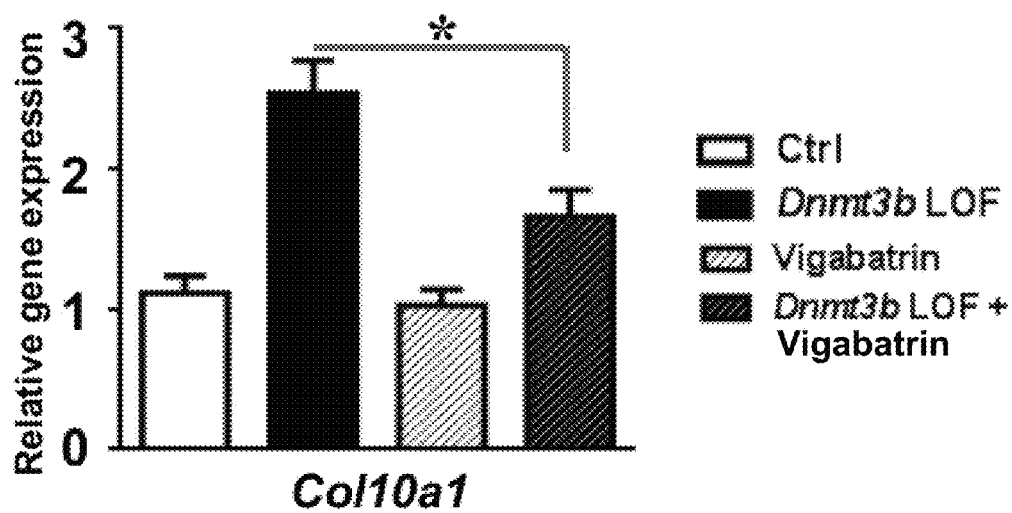
Figure 23C:
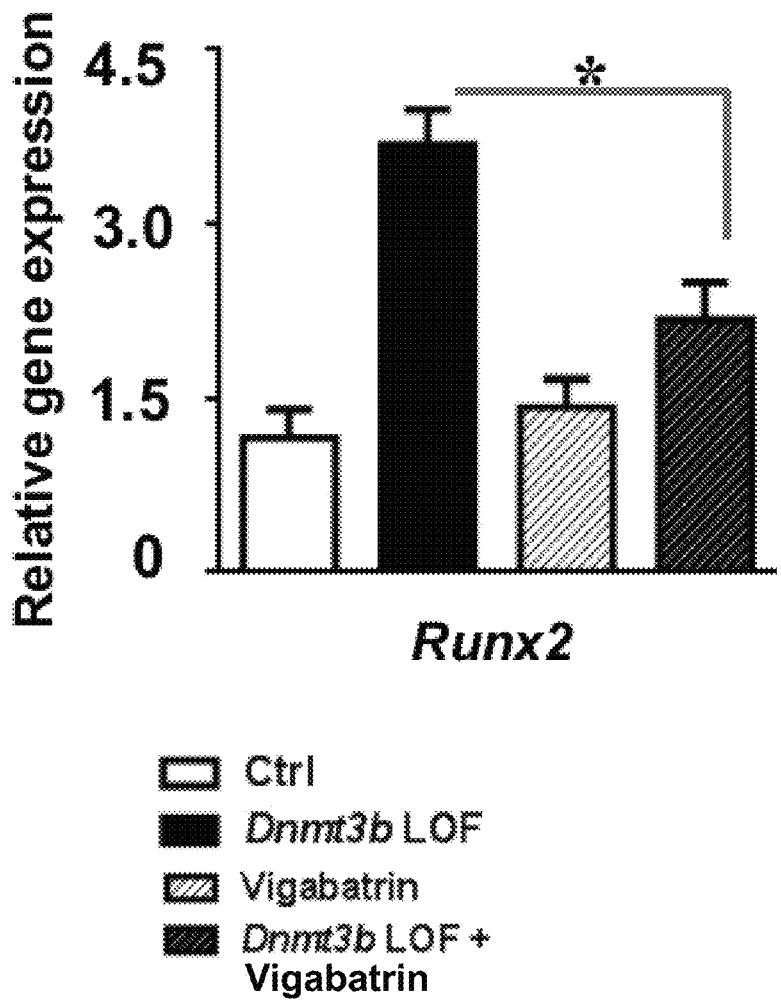

Vigabatrin, a Pharmacological Inhibitor of Abat Enzyme Activity, Attenuates Hypertrophy in Dnmt3b LOF Chondrocytes FIG. 23 shows that Dnmt3b LOF is associated with an increase in hypertrophic chondrocyte marker expression. To determine if this effect is dependent upon increased Abat expression, experiments were performed using vigabatrin to inhibit Abat activity in articular chondrocytes. FIG. 23 shows that Abat inhibition attenuates the increased expression of Mmp13, Col10a1 and Runx2 observed in Dnmt3b LOF chondrocytes. Work will comprehensively investigate the role of Abat in controlling both metabolism and hypertrophic/catabolic responses in articular chondrocytes, and define its role in the development of OA.

Example 9

Dnmt3b over-expression attenuates cytokine-induced chondrocyte hypertrophy

Figure 24:
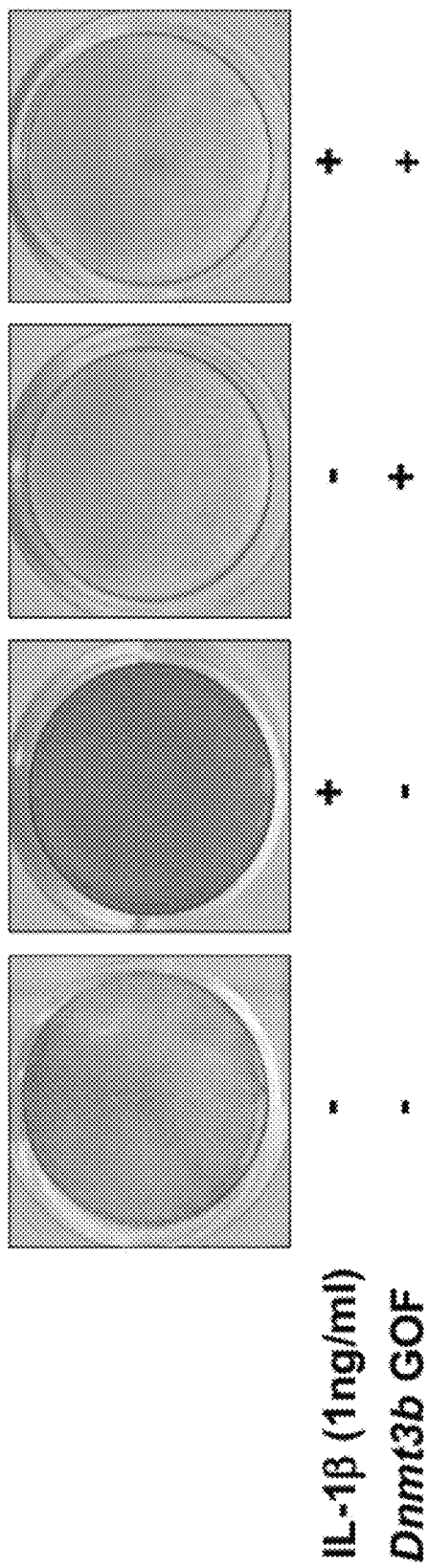
FIG. 24 depicts Dnmt3b gain-of-function attenuates IL-1β-induced chondrocyte hypertrophy. Primary ACs from 2 mo Dnmt3b GOF mice were treated with vehicle or doxycycline (10 µg/ml) for 24 hr. Medium without or with IL-1β (1 ng/ml) was added for 48 hr and ALP staining performed using NBT/BCIP substrate solution.

Hypertrophic characteristics, as measured by ALP activity, were induced in primary articular chondrocytes by treatment with either IL-1β or TNF-α. Dnmt3b GOF was induced by transfecting a plasmid expressing full-length Flag-tagged Dnmt3b cDNA. Western blot confirmed protein over-expression (data not shown). FIG. 24 shows that over-expression of Dnmt3b blocked the increase in ALP observed in IL-1β-treated primary articular chondrocytes. Similar results were shown in the TNF-α experiment (results not shown)

Example 10

The Effects of Post-natal Ablation of Dnmt3b During Murine Aging and Following MLI Surgery in Mice Preliminary data has established that Dnmt3b protein, but not Dnmt3a, is highly expressed in cells of healthy murine and human articular cartilage (FIG. 1A-FIG. 1F). Importantly, reduced expression of Dnmt3b in articular cartilage from WT aged mice that naturally develop signs of OA was detected (FIG. 1G). Reduced Dnmt3b expression was also noted in articular cartilage of WT mice following MLI (FIG. 1H). It was also shown that: i) in vitro inhibition of Dnmt3b in articular chondrocytes induces expression of terminal hypertrophic markers (FIG. 5C), and ii) post-natal deletion of Dnmt3b in murine articular cartilage results in early development of an OA phenotype (FIG. 6A-FIG. 6G). It will be determined if cartilage breakdown and chondrocyte phenotypic changes are accelerated due to the loss of Dnmt3b. The MLI surgical approach to induce OA was chosen since published data has shown that MLI surgery results in progressive OA over a period of 8 weeks (77, 78).

Generation of Dnmt3b loss-of-function (LOF) mice: Agc1Cre$^{ERT2}$; Dnmt3b$^{f/f}$ (Dnmt3b LOF) mutant mice will be generated by crossing Agc1Cre$^{ERT2}$; Dnmt3b$^{f/+}$ males with Dnmt3b$^{f/f}$ females. Prior to the aging or MLI surgery experiments, tamoxifen (TM) (1 mg/10 g body weight/day) will be administered to 2 mo old mice for 5 consecutive days. It has been confirmed that Agc1-Cre targets articular cartilage in LOF mice and leads to efficient recombination and deletion of Dnmt3b expression in articular chondrocytes (FIG. 7A, FIG. 7B).

Analysis of OA in aged mice: Dnmt3b LOF mice and Cre+ control mice will be aged to 5, 12 or 20 mo of age. Since gender has been shown to affect epigenetic profiles in rodents, male and female mice will be analyzed separately to determine if gender leads to differences in joint pathology due to Dnmt3b LOF. Hindlimbs of Dnmt3b LOF and Cre+ control mice for each of the three time points will be analyzed.

Induction of OA via meniscal ligament injury (MLI) surgery: For MLI surgery, since male mice are more severely affected than females following surgical induction of OA, only male mice will be used in our studies. MLI surgery will be performed on the right knee and a sham surgery on the left knee of 10 wk male Dnmt3b LOF or Cre+ control mice as has been previously described. Briefly, after administration of anesthesia, a 5-mm-long incision is made on the medial aspect of the joint. The medial collateral ligament is transected, the joint space opened, and a 25-gauge needle used to detach the medial meniscus from its anterior attachment to the tibia. A portion of the detached meniscus is removed. Sham surgery involves a similar incision to open the joint, but tissues are not manipulated. Hindlimbs will be harvested from all mice at 2, 4, 8 or 12 weeks post-surgery. The 2 wk time point is included since we predict more rapid cartilage degradation in Dnmt3b LOF mice.

(Immuno)histologic and histomorphometric analyses of knee joints: Hindlimbs from Dnmt3b LOF mice (or Cre+ control mice) following aging or MLI surgery will be harvested and skin/muscle will be removed. Limbs will then be fixed in 10% neutral buffered formalin overnight, decalcified in 14% EDTA for 10 days and processed in paraffin. Paraffin sections (5 μm) stained with Alcian Blue/Hematoxylin/Orange G (ABH) will be prepared for quantitative histomorphometric analysis using Osteomeasure software. Cartilage thickness will be measured from the middle of the femoral and tibial condyles. Cartilage area will be traced from both articular cartilage surfaces. The tidemark will be used to delineate upper zone and deep zone articular cartilage. Histomorphometry will be performed on 3 sagittal sections of the medial joint from each mouse, with five mice used per group.

Joint pathology will also be quantified using the OARSI scoring system. Sagittal sections obtained every 80 μm across the medial femoral-tibial joint will be used to determine the maximal scores and cumulative scores. For each group, 10 mice will be analyzed, and 13-16 slides will be examined by two blinded scorers per sample. Phenotypic changes in the meniscus, ligaments and the presence of osteophytes will also be noted. If we see signs of synovitis, then we will quantify this using the scoring system as described recently. ANOVA will be used to assess significance (n=10; p<0.05).

Protein expression will be assessed semi-quantitatively via IHC and include antibodies to detect Col2a1, Prg4, Comp, Col1a1, Col3a1, Col10a1, Mmp13, Runx2, Abat, as well as Dnmt3a and Dnmt3b. Proteoglycan catabolism will be assessed via IHC detection of the C-terminal aggrecan cleavage product (i.e. C-terminal neoepitope, NITEGE). Cell proliferation (PCNA kit; Santa Cruz) and apoptosis (cleaved caspase 3 Ab; Roche), will also be assessed.

Micro-CT subchondral bone imaging and analyses: Hindlimbs collected from aged mice or at specific time points following MLI will first be imaged using a micro-CT system (VivaCT 40, Scanco Medical). The tibia will be scanned from knee to lower fibula using a protocol that utilizes high-resolution (10.5 microns) x-ray energy settings of 55kVp, 145 μA and 300 ms integration time. Parameters of subchondral bone volume, bone mineral density (BMD) and bone connective density will be measured as previously described using the Scanco analysis software. Limbs will then be fixed in formalin, decalcified and used for (immuno) histologic and histomorphometric analysis as described above. ANOVA will be used to assess significance (n=10; p<0.05).

Example 11

Determine the Catabolic Changes in Dnmt3b LOF Chondrocytes and Elucidate if these Effects are Mediated by the Metabolic Enzyme, Aba Data shows that chondrocytes with Dnmt3b LOF have elevated expression of hypertrophic differentiation markers (Col10a1, Runx2, Mmp13) (FIG. 5C). RNA-Seq and Methyl-Seq approaches were used to define potential mechanisms and targets in a Dnmt3b LOF scenario. Integrated analysis of this RNA-Seq and Methyl-Seq data showed that the metabolic enzyme, Abat, may be a critical downstream target of Dnmt3b (FIG. 20) and potentially mediate the catabolic processes and altered metabolic state (FIG. 13B-FIG. 13F) induced by Dnmt3b LOF.

Figure 25C:
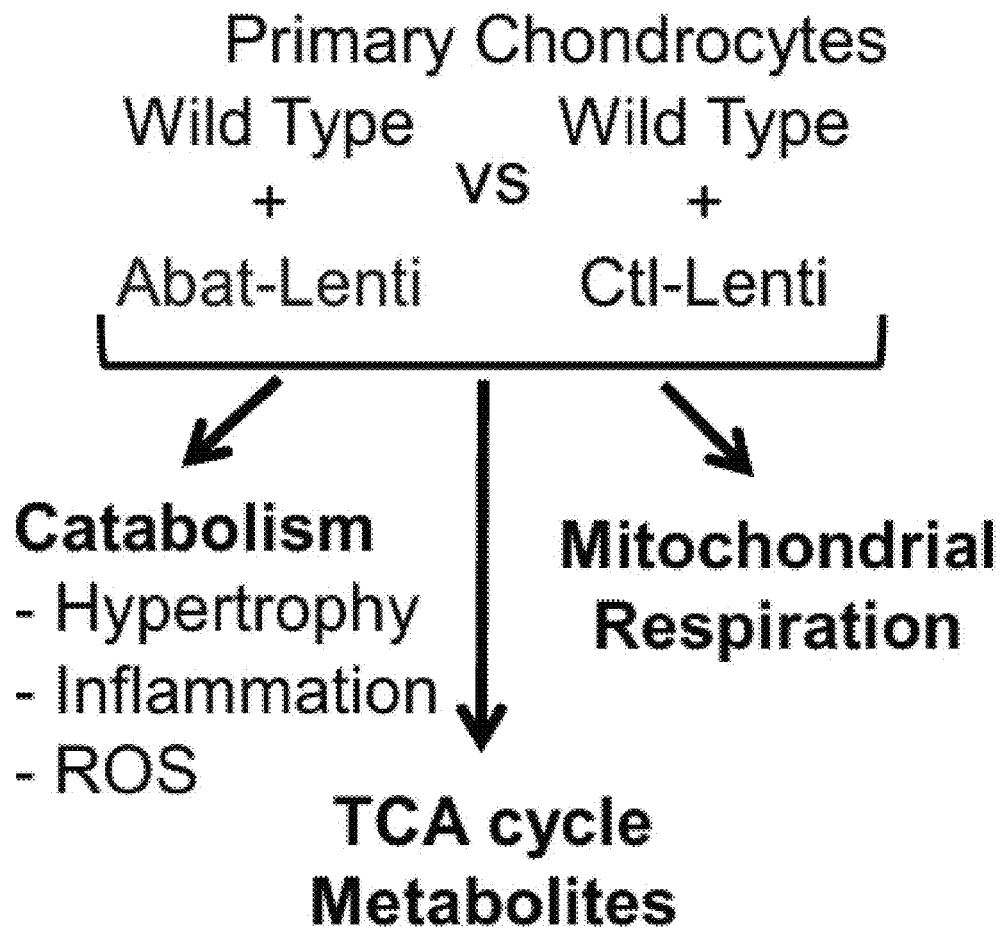

FIG. 25 summarizes the experimental plan to study the effects of Dnmt3b knock-down on altering chondrocyte homeostasis. It is hypothesized that Dnmt3b LOF will lead to a catabolic phenotype as shown by chondrocyte hypertrophy and increased production of inflammatory cytokines, chemokines, and reactive oxygen species (ROS). (FIG. 25A). Experiments will also be performed to alter the activity and/or expression of Abat in primary chondrocytes to define its role in controlling chondrocyte catabolism (FIG. 25B, FIG. 25C). It is expected that modulation of Abat will affect production of succinate and alter the concentration of other TCA cycle metabolites as well as affect mitochondrial function. Therefore, these parameters will also be investigated as outlined in FIG. 25B, FIG. 25C.

Primary articular chondrocyte isolation and culture: Articular chondrocytes will be isolated from the knee joints of 2 mo WT or Dnmt3b$^{f/f}$ mutant mice as previously described. Briefly, articular cartilage will be excised from femoral condyles and tibial plateaus and placed in 1×PBS. Cartilage fragments are then digested using 3 mg/ml Collagenase D in 10 ml high glucose DMEM (HG-DMEM) for 12 hr at 37° C. Primary cell suspensions will be passed through 0.4 μM filters and seeded at a density of 500,000 cells/well in 6-well tissue culture plates in HG-DMEM medium supplemented with 10% FBS.

Chondrogenic hypertrophy assays: Primary articular chondrocytes will be seeded at a density of 500,000 cells/well in HG-DMEM medium containing 50 μg/mL ascorbic acid, 10 mM β-glycerophosphate and Insulin-Transferrin-Selenium (ITS-G, Life Technologies, Grand Island, N.Y.) for 7, 14, and 21 days. Following formalin fixation, cell cultures will be stained with alcian blue, alizarin red or NBT/BCIP substrate solution (to detect ALP). RNA will be isolated from chondrocyte cultures for qPCR to examine the expression of various anabolic and catabolic (hypertrophic) genes, including Col2a1, Comp, Agc, Runx2, Mmp13, Col10, Hif1a, Hif2a, Alp. Protein expression of Runx2, Hif1a, Hif2a, and phosphorylated and non-phosphorylated Smad 2/3 and Smad 1/5/8 will be examined by Western blot. Significant differences will be determined using ANOVA (p<0.05; n=4). Western blots will be quantified by Image Lab™ software (Bio-rad, Hercules, Calif.).

Inflammatory response analyses: Gene expression of the pro-inflammatory cytokines including Il-1, Il-6, Tnf-a, chemokines such as 11-8, and Mcp-1 as well as chemokine receptors including Cxcr3, Cxcr4, and Cxcr5 will be assessed by qPCR analyses using RNA isolated from the chondrocyte cultures. ELISA will be performed to determine the cellular concentration for pro-inflammatory cytokines and chemokines. Western blot will be performed to determine the protein expression level of chemokine receptors. ANOVA will be used to assess significance (n=4; $p<0.05$).

Production of ROS: Primary articular chondrocytes will be seeded at a density of 500,000 cells/well in HG-DMEM. Cellular luminescent assay for detection of ROS will be performed 48 hr after treatment as per manufacturer's protocol (Promega, Madison, Wis.). ANOVA will be used to assess significance (n=4; $p<0.05$).

Inhibition or overexpression of Abat: Primary articular chondrocytes isolated from Dnmt3b$^{f/f}$ mice will be infected with Ad5-CMV-Cre (Dnmt3b LOF) or Ad5-CMV-GFP (Ctrl) at an MOI of 100 for 48 hr. Vigabatrin (500 μM) will be added to inhibit Abat function (3). To over-express Abat, a lentivirus expressing murine Abat will be generated by using a lentiviral construct containing a CMV promoter and an RFP reporter as previously reported. Vigabatrin efficacy will be examined by the GABA ELISA KIT ((# LS-F4121, LSBio, Seattle, Wash.). Abat over-expression efficiency will be validated by qPCR and Western blot.

Analyses of TCA cycle metabolites and mitochondria respiration: Primary articular chondrocytes will be seeded at a density of 500,000 cells/well in HG-DMEM. Total protein lysates will be isolated following treatments as indicated in FIG. 25B and FIG. 25C, and 10 μl samples will be injected into an LC-20 AD HPLC system (Shimadzu), which is coupled to a triple-quadrupole mass spectrometer (Thermo Fisher Scientific). TCA cycle metabolites will be analyzed by LC-MS/MS as previously described. Briefly, articular chondrocytes will plated in XF96 plates at 20,000 cells per well with XF Assay Medium Modified DMEM (Seahorse, #101022-100). The Seahorse Stress Kit will be used per manufacturer's instructions to measure the oxygen consumption rate (OCR). Total protein concentrations will be measured for normalization. ANOVA will be used to assess significance (n=4; $p<0.05$).

It is anticipated that Dnmt3b LOF mice will display an accelerated OA-like phenotype during aging and following MLI, with loss of cartilage tissue, subchondral bone thickening and osteophyte formation. It is expected that increased Abat expression in Dnmt3b LOF chondrocytes in vivo during aging and following MLI surgery. It is expected that in vivo histological and IHC analyses of Dnmt3b LOF knee joints will be consistent with the cellular and molecular changes observed in our in vitro preliminary findings (i.e. reduced anabolic protein expression and increased markers of catabolism/hypertrophy). In vitro mechanistic experiments will demonstrate that Dnmt3b LOF chondrocytes will produce higher levels of inflammatory mediators, and inhibition of Abat in Dnmt3b LOF chondrocytes will attenuate TCA metabolism, mitochondria respiration and hypertrophic differentiation. It is predicted that over-expression of Abat will stimulate a chondrocyte catabolic phenotype, including increased expression of inflammatory cytokines, ROS, and hypertrophic differentiation markers. In the unlikely event of cell toxicity caused by the Abat inhibitor, vigabatrin, or even insufficient knock-down in Abat activity by this drug in vitro, then we will use Abat shRNA (Dharmacon) or utilize the CRISPR/Cas9 approach to knock-down Abat in primary chondrocytes.

Example 12

The Effect of Post-natal Over-Expression of Dnmt3b in Articular Cartilage Following Knee Joint Injury Data show that Dnmt3b expression in cartilage is reduced following mouse joint injury (FIG. 1H) and in human OA (FIG. 1J). It is also shown that Dnmt3b LOF in vitro induces a catabolic gene response in chondrocytes (FIG. 5C) and spontaneous OA in vivo (FIG. 6A-FIG. 6G). Therefore, the hypothesis is that over-expression of Dnmt3b in chondrocytes of post-natal articular cartilage will induce a chondroprotective effect in a murine joint injury model. Toward this end, a new cartilage-specific, inducible Dnmt3b gain-of-function (GOF) mouse model has been generated (FIG. 18A) and recombination efficiency and Dnmt3b over-expression in articular cartilage has been confirmed (FIG. 19A, FIG. 19B). Creating joint injury in these transgenic animals via MLI will allow us to directly address the hypothesis that these mice will be protected from developing OA.

Generation of Dnmt3b gain-of-function (GOF) Mice: Col2-Cre; Rosa-rtTA$^{f/+}$; Dnmt3b (Dnmt3b GOF) transgenic mice will be generated by crossing Col2-Cre; Rosa-rtTA$^{f/f}$ mice with Dnmt3b transgenic mice. Doxycycline (2.5 mg/kg body weight, twice per week) will be administrated by IP injection one day prior to MLI surgery to ensure Dnmt3b over-expression following surgery (FIG. 18A, FIG. 19A, FIG. 19B).

Induction of OA via meniscal ligament injury (MLI) surgery: 10 wk male Dnmt3b GOF or Cre+ control mice will be used for MLI surgeries. The surgical procedure will be carried out as described above. Hindlimbs will be harvested from all mice at either 2, 4, 8, 12 or 16 wk post-surgery.

Phenotypic analyses of murine knee joints: For in vivo analyses, hindlimbs will be harvested at the afore-mentioned time points and micro-CT analysis performed to determine subchondral bone thickness as described above. Hindlimbs will then be processed for paraffin embedding and resulting tissue sections will be stained with ABH/OG. A range of other analyses (i.e. OARSI scoring, synovium scoring, identification of osteophytes, IHC analysis of cartilage and histomorphometric analyses) will be performed as also described.

Example 13

Determine the Effects of Dnmt3b, Abat and Mitochondria Metabolism on Regulating Catabolic Responses in Articular Chondrocytes Data has shown that over-expression of Dnmt3b in articular chondrocytes attenuates ALP activity following cytokine treatment (FIG. 24), suggesting that increased Dnmt3b expression may protect against catabolic effects. It has also been shown that methylation of the Abat gene promoter is decreased in Dnmt3b LOF chondrocytes, which is consistent with increased Abat gene expression in Dnmt3b LOF cells (FIG. 20).

Figure 26A:
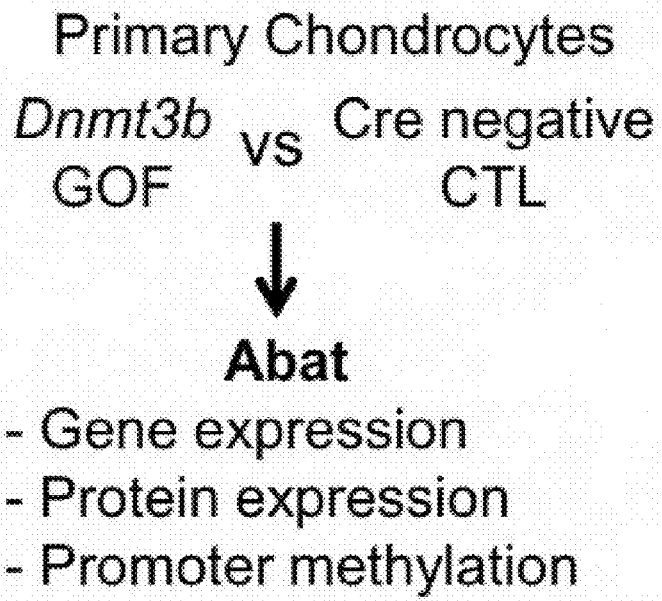
FIG. 26A, FIG. 26B and FIG. 26C depict the experimental design to determine the Abat expression and methylation in Dnmt3b gain of function (GOF) cells at basal level (FIG. 26A) as well as following BMP2 or IL-1β treatment (FIG. 26B). Experiments are also included to address the effects Abat over-expression in reversing the effects of Dnmt3b GOF (FIG. 26C).
Figure 26B:
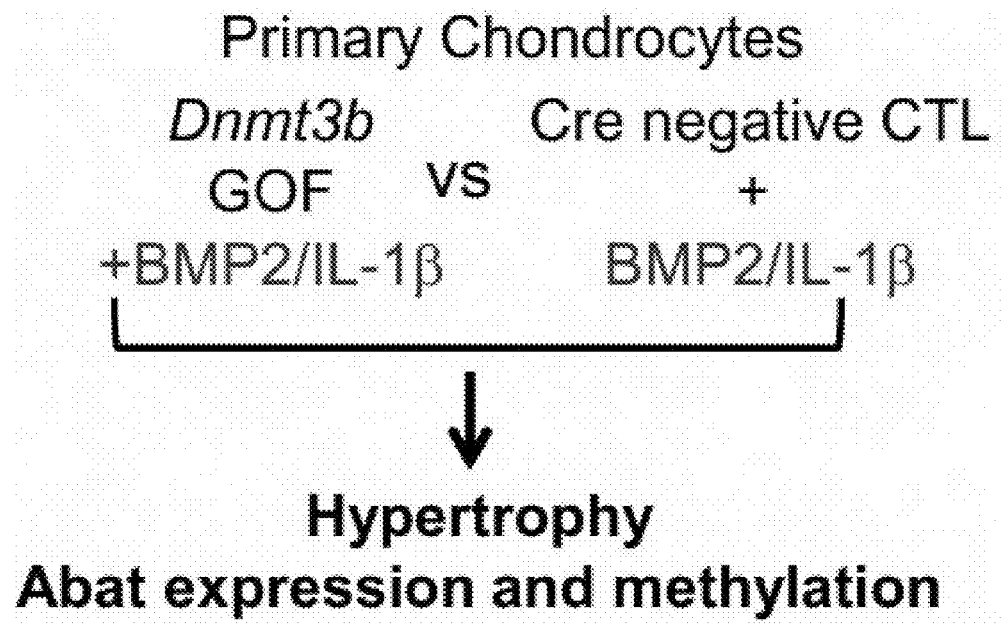
Figure 26C:
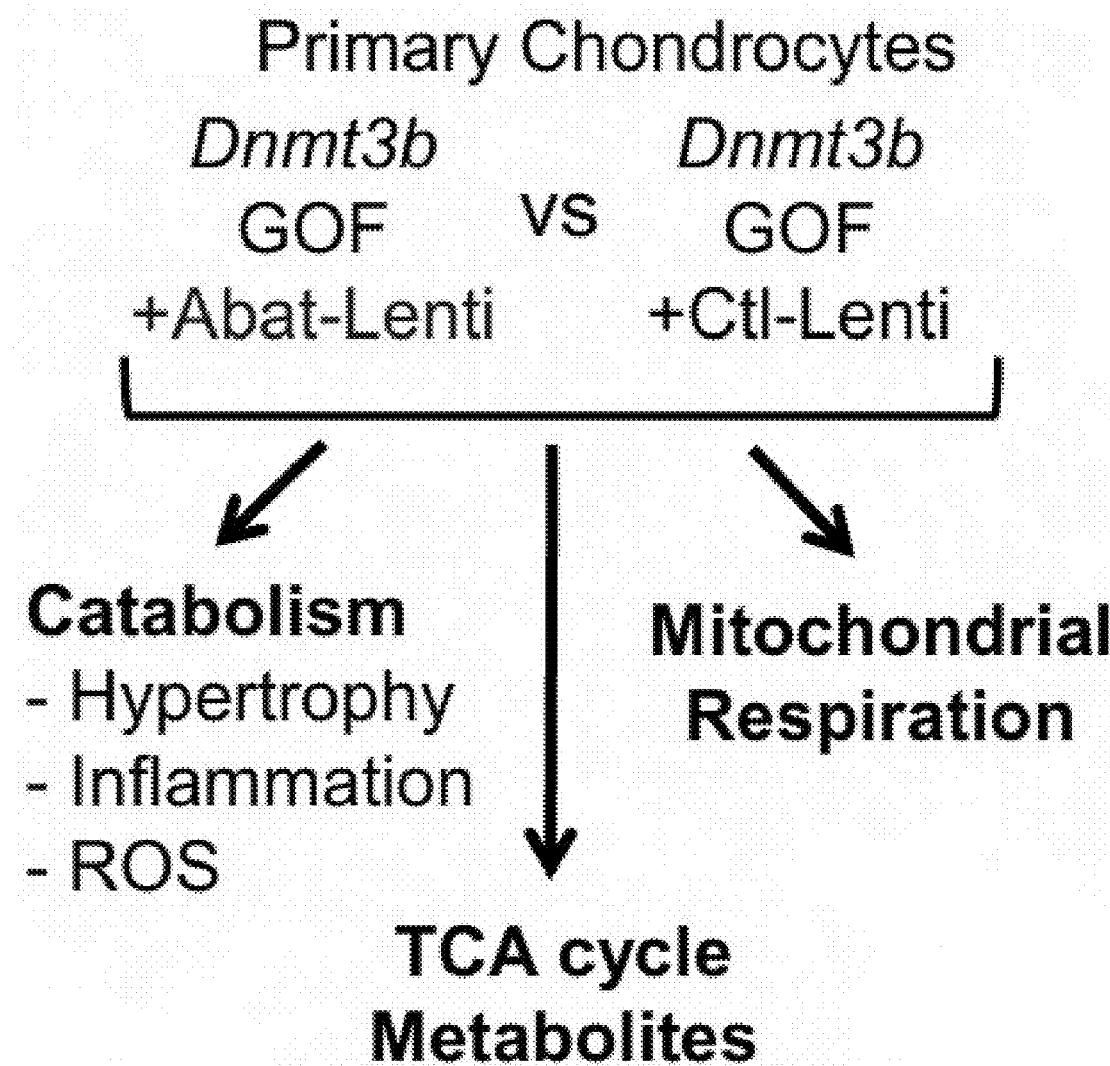

FIG. 26 outlines the experimental approach used to determine a key role for Dnmt3b in controlling chondrocyte homeostasis and to define Abat and mitochondrial metabolism as mechanisms involved in this process. Initial experiments will examine baseline differences in Abat gene methylation patterns as well as Abat gene/protein expression levels in Dnmt3b GOF chondrocytes compared to control cells (FIG. 26A). Subsequently, expression of markers of chondrocyte hypertrophy (via BMP-2 or IL-1β) will be induced to determine if Dnmt3b over-expression can ameliorate these effects (FIG. 26B). Finally, Abat in Dnmt3b GOF cells will be overexpressed to determine if Abat can reverse the anti-catabolic effects of Dnmt3b.

Figure 27A:
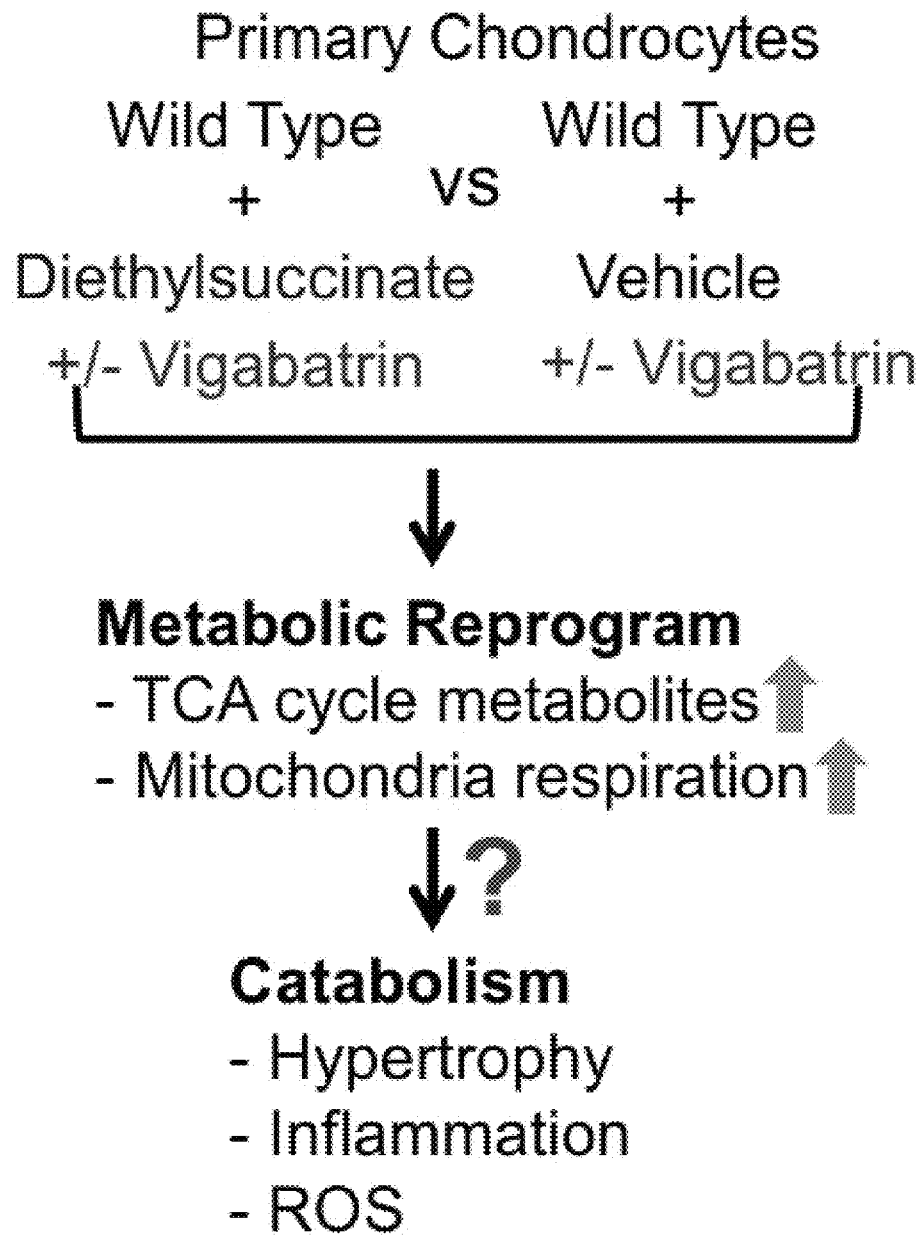
FIG. 27A and FIG. 27B depict the experimental design to determine the potential role of cellular metabolic reprogramming on chondrocyte catabolism.

FIG. 27 summarizes the experiments performed to determine the potential role of articular chondrocyte metabolic reprogramming in shifting cells toward a more or less catabolic/hypertrophic state. Further rationale to carry out these studies comes from a publication showing that hypertrophic chondrocytes rely more on mitochondrial respiration than resting chondrocytes. Experiments have been designed to increase succinate levels which will subsequently increase TCA metabolism and mitochondrial respiration, and determine if increased cellular metabolism leads to up-regulation of catabolic markers. It will also be determined if vigabatrin can reverse the effects of increased succinate (FIG. 27). Catabolism in WT cells will also be induced via BMP-2 or IL-1 and then it will be determined if these effects can be reversed by addition of rotenone and antimycinA, which are mitochondria complex I and III inhibitors.

Primary articular chondrocyte isolation and culture: Articular cartilage will be isolated from the knee joints of 2 mo Dnmt3b GOF mice or Cre+ control littermates. Primary articular chondrocytes will be seeded at a density of 500,000 cells/well in 6-well tissue culture plates in HG-DMEM. Doxycycline (10 μg/ml) will be added to cell culture for 24 hr to activate Dnmt3b expression. Gene and protein expression level of Dnmt3b will be measured by qPCR and Western blot.

Abat gene promoter methylation assay: Primary articular chondrocytes will be seeded at a density of 500,000 cells/well in 6-well tissue culture plates in HG-DMEM and stimulated with BMP-2 (100 ng/ml) or IL-1β (1 ng/ml) for 48 hr. Genomic DNA will be isolated for enzymatic methylation qPCR analysis (Qiagen, Valencia, Calif.) by using EpiRect II DNA Methylation Enzyme Kit and EpiTect Methyl II PCR Primer Assay for Mouse Abat (CpG Island 104232).

Figure 27B:
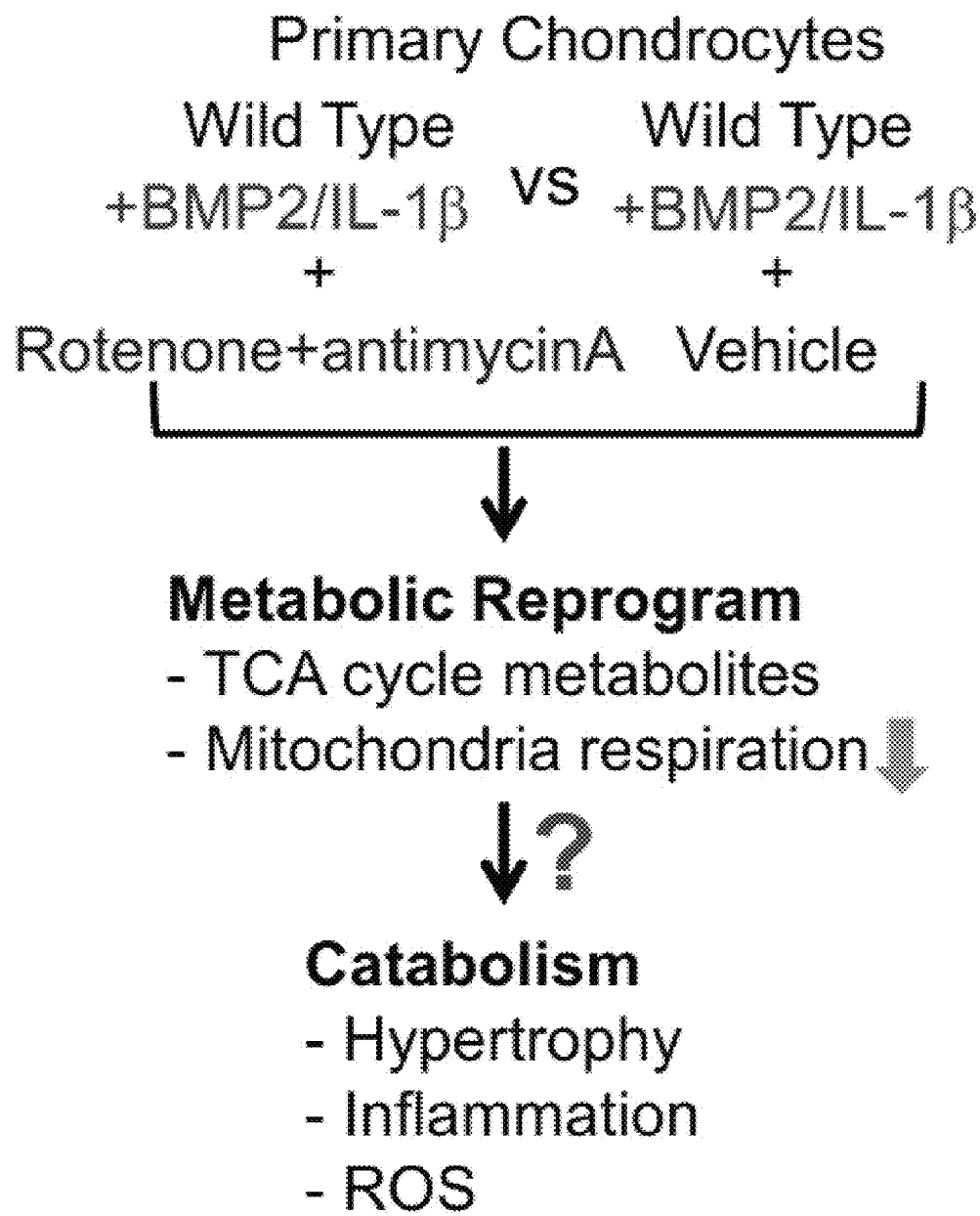

Metabolic reprogramming of chondrocytes to determine changes in homeostasis: Primary articular chondrocytes will be seeded at a density of 500,000 cells/well in 6-well tissue culture plates in HG-DMEM, and treated with either diethylsuccinate (1-5 mM) or rotenone+antimycinA cocktail (10-50 μM) to alter cell metabolism (FIG. 27, FIG. 27B). TCA cycle metabolites, mitochondria respiration, and hypertrophic differentiation will be assessed by HPLC-MS, Seahorse XF Extracellular Flux Analyzer, and staining/qPCR/Western blot respectively.

Example 14

Figure 22B:
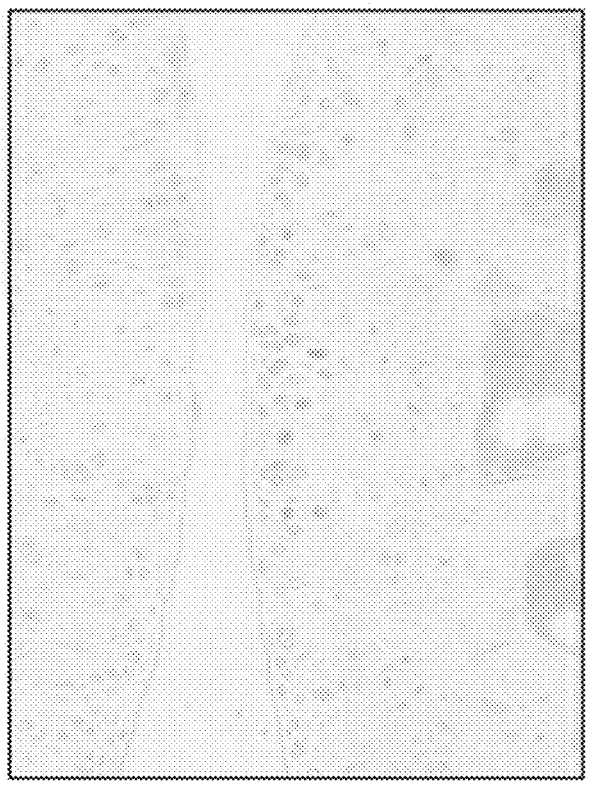

Determine the Effect of In Vivo Inhibition of Abat Following Surgical Induction of OA Data shows that MLI surgery in WT C57BL/6J mice results in increased expression of Abat in articular chondrocytes (FIG. 22) and that in vitro administration of the Abat inhibitor, vigabatrin, can block catabolic responses in chondrocytes (FIG. 23). In vivo studies will be used to determine the efficacy of vigabatrin to inhibit or ameliorate cartilage breakdown following MLI surgery. Vigabatrin is an FDA-approved specific inhibitor of Abat (4) and is currently used clinically to treat refractory complex partial seizures and infantile spasms (5). These studies have high clinical and translational significance, and the potential to yield exciting results that could lead to the design of future human clinical trials to treat OA.

In vivo knock-down of Abat activity using vigabatrin: Vigabatrin will be given by IP administration to 10 wk male mice once per week at three dosage levels: 50,100 or 200 mg/kg body weight. Articular cartilage tissue and serum will be isolated 2 wk later. To determine Abat activity, GABA concentration from articular cartilage homogenates and serum will be measured by GABA EIA kit (# LS-F4121, LSBio, Seattle, Wash., sensitivity: 24.69-2000 pg/ml). Western blotting will be conducted to determine if vigabatrin affects Abat protein levels.

Induction of OA via MLI surgery in vigabatrin-treated and vehicle-treated mice: Once adequate knock-down of Abat activity has been determined, then MLI surgery will be performed on 10 wk male C57BL/6J WT mice. Hindlimbs will be harvested from all mice at 2, 4, 8, 12 or 16 weeks post-surgery.

Phenotypic analyses of murine knee joints: For in vivo analyses, hindlimbs will be harvested at the afore-mentioned time points and micro-CT analysis performed to determine subchondral bone thickness. Hindlimbs will then be processed for paraffin embedding and resulting tissue sections will be stained with ABH/OG. OARSI scoring, synovium scoring, identification of osteophytes and other joint changes, IHC analysis of cartilage and histomorphometric analyses will be performed.

It is anticipated that both in vitro and in vivo assays will establish that Dnmt3b over-expression has a positive effect on maintaining normal articular chondrocyte homeostasis. It is expected that vigabatrin will inhibit Abat activity in vivo, but not affect Abat protein levels. It is predicted that inhibiting Abat activity will result in amelioration or blockage of catabolic responses in chondrocytes. It is expected that experiments proposed in FIG. 27 will enhance the understanding of how directly controlling metabolism can affect chondrocyte catabolic responses. One study using vigabatrin in rodents within the proposed dosage range did not report any side effects (99) so toxicity is not anticipated. If adverse side effects occur, intra-articular injection of vigabatrin will be explored rather than systemic delivery.

In summary, it will be established that Dnmt3b plays a critical role in regulating cartilage homeostasis via the metabolic enzyme, Abat. It will also be determined if targeting Abat in vivo could be a promising new therapy to treat OA. Future studies will include developing Agc1Cre$^{ERT2}$; Dnmt3b$^{f/f}$; Abat$^{f/f}$ mice to elucidate if deletion of Abat can decelerate OA under a Dnmt3b LOF background. Other future studies will involve deciphering the upstream factors and signaling events that lead to the decrease in Dnmt3b expression in aging/OA chondrocytes (e.g. inflammatory cytokines, growth factors, and chemokines).

REFERENCES FOR EXAMPLES 6-14

1. Osei Y D, Churchich J E. Screening and sequence determination of a cDNA encoding the human brain 4-aminobutyrate aminotransferase. Gene. 1995; 155(2): 185-7.
2. Sarup A, Larsson O M, Schousboe A. GABA transporters and GABA-transaminase as drug targets. Current drug targets CNS and neurological disorders. 2003; 2(4):269-77.
3. Tannahill G M, Curtis A M, Adamik J, Palsson-McDermott E M, McGettrick A F, Goel G, Frezza C, Bernard N J, Kelly B, Foley N H, Zheng L, Gardet A, Tong Z, Jany S S, Corr S C, Haneklaus M, Caffrey B E, Pierce K, Walmsley S, Beasley F C, Cummins E, Nizet V, Whyte M, Taylor C T, Lin H, Masters S L, Gottlieb E, Kelly V P, Clish C, Auron P E, Xavier R J, O'Neill L A. Succinate is an inflammatory signal that induces IL-1 beta through HIF-1 alpha. Nature. 2013; 496(7444):238-42.

4. Tolman J A, Faulkner M A. Vigabatrin: a comprehensive review of drug properties including clinical updates following recent FDA approval. Expert opinion on pharmacotherapy. 2009; 10(18):3077-89.

5. Pellock J M. Balancing clinical benefits of vigabatrin with its associated risk of vision loss. Acta neurologica *Scandinavica* Supplementum. 2011(192):83-91.

What is claimed is:

1. A method to reduce cartilage degradation in a human subject, the method comprising administering to the subject a composition comprising a compound that increases the expression of Dmnt3b and/or a compound that inhibits aminobutyrate aminotransferase.

2. The method of claim 1, wherein the compound that increases the expression of Dmnt3b is a vector comprising the Dnmtb3nucleotide sequence.

3. The method of claim 1, wherein the compound that inhibits aminobutyrate aminotransferase is selected from the group consisting of vigabatrin, L-2,4-diaminobutyric acid dihydrochloride, gamma-acetylenic GABA, S(+)-gamma-vinyl-GABA, 3-methyl-GABA, 4-amino-5-hexynoic acid, gabaculine, aminooxyacetic acid, phenelzine, phenylethylidenehydrazine (PEH),rosmarinic acid and valproic acid.

4. The method of claim 3, wherein the compounds that inhibits aminobutyrate aminotransferase is vigabatrin.

5. The method of claim 1, wherein the subject is at risk of developing osteoarthritis (OA).

6. The method of claim 5, wherein the subject is obese or has had joint surgery.

7. The method of claim 1, wherein the composition is administered orally or via intra-articular injection.

8. A method to increase cartilage area, the method comprising administering a composition comprising a compound that increases the expression of Dmnt3b and/or a compound that inhibits aminobutyrate aminotransferase.

9. The method of claim 8, wherein the compound that increases the expression of Dmnt3b is a vector comprising the Dnmtb3nucleotide sequence.

10. The method of claim 8, wherein the compound that inhibits aminobutyrate aminotransferase is selected from the group consisting of vigabatrin, L-2,4-diaminobutyric acid dihydrochloride, gamma-acetylenic GABA, S(+)-gamma-vinyl-GABA, 3-methyl-GABA, 4-amino-5-hexynoic acid, gabaculine, aminooxyacetic acid, phenelzine, phenylethylidenehydrazine (PEH), rosmarinic acid and valproic acid.

11. The method of claim 10, wherein the compounds that inhibits aminobutyrate aminotransferase is vigabatrin.

12. The method of claim 8, wherein the subject is at risk of developing osteoarthritis (OA).

13. The method of claim 8, wherein the composition is administered orally or via intra-articular injection.

14. A method of treating osteoarthritis (OA) in a subject, the method comprising administering to the subject a composition comprising a compound that increases the expression of Dmnt3b and/or a compound that inhibits aminobutyrate aminotransferase.

15. The method of claim 14, wherein the compound that increases the expression of Dmnt3b is a vector comprising the Dnmtb3nucleotide sequence.

16. The method of claim 14, wherein the compound that inhibits aminobutyrate aminotransferase is selected from the group consisting of vigabatrin, L-2,4-diaminobutyric acid dihydrochloride, gamma-acetylenic GABA, S(+)-gamma-vinyl-GABA, 3-methyl-GABA, 4-amino-5-hexynoic acid, gabaculine, aminooxyacetic acid, phenelzine, phenylethylidenehydrazine (PEH), rosmarinic acid and valproic acid.

17. The method of claim 16, wherein the compounds that inhibits aminobutyrate aminotransferase is vigabatrin.

18. The method of claim 14, wherein the subject is at risk of developing OA.

19. The method of claim 14, further comprising administering standard treatments for OA.

20. The method of claim 14, wherein the composition is administered orally or via intra-articular injection.

21. A method to reduce cartilage degradation, the method comprising administering a composition comprising a compound that increases the expression of Dmnt3b and/or a compound that inhibits aminobutyrate aminotransferase, wherein the compound is selected from the group consisting of vigabatrin, L-2,4-diaminobutyric acid dihydrochloride, gamma-acetylenic GABA, S(+)-gamma-vinyl-GABA, 3-methyl-GABA, 4-amino-5-hexynoic acid, gabaculine, aminooxyacetic acid, phenelzine, phenylethylidenehydrazine (PEH) and valproic acid.

* * * * *